(12) United States Patent
Bavetsias et al.

(10) Patent No.: US 8,088,761 B2
(45) Date of Patent: Jan. 3, 2012

(54) ENZYME INHIBITORS

(75) Inventors: Vassilios Bavetsias, Sutton (GB);
Edward McDonald, Sutton (GB);
Spyridon Linardopoulos, Sutton (GB)

(73) Assignee: Cancer Research Technology Limited (GB)

( * ) Notice: Subject to any disclaimer, the term of this patent is extended or adjusted under 35 U.S.C. 154(b) by 454 days.

(21) Appl. No.: 12/158,339

(22) PCT Filed: Dec. 21, 2006

(86) PCT No.: PCT/GB2006/004854
§ 371 (c)(1),
(2), (4) Date: Sep. 12, 2008

(87) PCT Pub. No.: WO2007/072017
PCT Pub. Date: Jun. 28, 2007

(65) Prior Publication Data
US 2009/0247507 A1    Oct. 1, 2009

(30) Foreign Application Priority Data

Dec. 22, 2005  (GB) ................................. 0526169.8
Oct. 20, 2006  (GB) ................................. 0620884.7

(51) Int. Cl.
*A61K 31/437*  (2006.01)
*A61K 31/496*  (2006.01)
*A61K 31/551*  (2006.01)
*A61P 37/08*  (2006.01)
*C07D 471/04*  (2006.01)

(52) U.S. Cl. ........ 514/218; 540/575; 544/357; 544/121; 544/127; 544/295; 544/362; 544/212; 546/118; 514/234.2; 514/235.8; 514/252.18; 514/253.04; 514/303; 514/252.11

(58) Field of Classification Search .................. None
See application file for complete search history.

(56) References Cited

U.S. PATENT DOCUMENTS 6,187,778 B1 *   2/2001   Dow et al. ................. 514/265.1
2006/0189617 A1   8/2006   Pelletier

FOREIGN PATENT DOCUMENTS

WO    01-96336 A    12/2001
WO    2004016611 A    2/2004

OTHER PUBLICATIONS

Vippagunta et al. Advanced Drug Delivery Reviews, vol. 48, pp. 3-26 (2001).*
Bavetsias et al. Bioorganic & Medicinal Chemistry Letters, vol. 17, p. 6567-6571 (2007).*

* cited by examiner

*Primary Examiner* — Emily Bernhardt
(74) *Attorney, Agent, or Firm* — Banner & Witcoff, Ltd.

(57) ABSTRACT

Compounds of formula (I), are aurora kinase inhibitors: wherein X is —N—, —CH2-N—, —CH2-CH—, or —CH—; R1 is a radical of formula (IA) wherein Z is —CH2-, —NH—, -0-, —S(O)— —S—, —S(O)2 or a divalent monocyclic carbocyclic or heterocyclic radical having 3-7 ring atoms; Alk is an optionally substituted divalent C1-C6 alkylene radical; A is hydrogen or an optionally substituted monocyclic carbocyclic or heterocyclic ring having 5-7 ring atoms; r, s and t are independently 0 or 1, provided that when A is hydrogen then at least one of r and s is 1; R2 is halogen, —CN, —CF3, —OCH3, or cyclopropyl; and R3 is a radical of formula (IB) wherein Q is hydrogen or an optionally substituted phenyl or monocyclic heterocyclic ring with 5 or 6 ring atoms; Z<1> is —S—, —S(O)—, —S(O)2-, —O—, —SO2NH—, —NHSO2-, NHC(=O)NH, —NH(C=S)NH—, Or —N(R4)— wherein R4 is hydrogen, C1-C3 alkyl, cycloalkyl, or benzyl; and Alk<1> and Alk<2> are, independently, optionally substituted divalent C1-C3 alkylene radicals; and m, n and p are independently 0 or 1.

27 Claims, No Drawings

ENZYME INHIBITORS

CROSS REFERENCE TO RELATED APPLICATIONS

This application is a National Stage application of co-pending PCT application PCT/GB2006/004854 filed Dec. 21, 2006, which claims the benefit of Great Britain application number 0526169.8 filed Dec. 22, 2005 and Great Britain application number 0620884.7 filed Oct. 20, 2006. These applications are incorporated herein by reference in their entireties.

This invention relates to imidazopyridine compounds which inhibit members of the aurora kinase family of enzymes and to their use in the treatment of cell proliferative diseases, including cancer, and inflammation.

BACKGROUND TO THE INVENTION

In eukaryotic cells DNA is packaged with histones, to form chromatin. Approximately 150 base pairs of DNA are wrapped twice around an octamer of histones (two each of histones 2A, 2B, 3 and 4) to form a nucleosome, the basic unit of chromatin. The ordered structure of chromatin needs to be modified in order to allow transcription of the associated genes. Transcriptional regulation is key to differentiation, proliferation and apoptosis, and is, therefore, tightly controlled. Control of the changes in chromatin structure (and hence of transcription) is mediated by covalent modifications to histones, most notably of the N-terminal tails. Covalent modifications (for example methylation, acetylation, phosphorylation and ubiquitination) of the side chains of amino acids are enzymatically mediated (A review of the covalent modifications of histones and their role in transcriptional regulation can be found in Berger S L 2001 Oncogene 20, 3007-3013; See Grunstein, M 1997 Nature 389, 349-352; Wolffe A P 1996 Science 272, 371-372; and Wade P A et al 1997 Trends Biochem Sci 22, 128-132 for reviews of histone acetylation and transcription).

The aurora kinases are a family of serine/threonine kinases which have been identified as key regulators of the mitotic cell division process (Bischoff and Plowman, 1999 Trends Cell Biol 9, 454-459) which may become deregulated in cancer and other hyperproliferative diseases (Warner et al, 2003, Mol Can Ther 2, 589-595). The three members of this family identified so far are referred to as Aurora-A, Aurora-B and Aurora-C. Higher eukaryotic cells typically express two or more Aurora kinases. It has been shown that inhibition of Aurora B affects several facets of mitosis including histone H3 phosphorylation, chromosome segregation and cytokinesis. Aurora A and C localise to spindle poles with Aurora A being required for bipolar spindle formation in a number of systems (Giet and Prigent, 1999, J. Cell. Sci 11, 3591-3601). Aurora A and B have been shown to be overexpressed in a number of human cancers and their overexpression in cells in vitro leads to transformation, centrosome abnormalities and aneuploidy (Bischoff et al, 1998, EMBO J. 17, 3052). Cells which overexpress Aurora A have been shown to form tumours in athymic mice. The observations contained in these manuscripts suggest that increase in Aurora kinase activity may serve to promote tumour development by providing growth advantage or by inducing genetic instability and that Aurora Kinase inhibition should have therapeutic benefit in cancer.
Aurora Kinase Inhibitors.

Several structural classes of aurora kinase inhibitors are known, see for example WO 02/00649, WO 2004/000833, WO 03/055491, WO 2004/058752, WO 2004/058781, WO 04105765, WO 05004872, WO 04113324, U.S. Pat. No. 6,143,764 and US 2004/0049032, but the foregoing is by no means an exhaustive list.

BRIEF DESCRIPTION OF THE INVENTION

This invention makes available another class of aurora kinase inhibitors, and provides for their use in treatment of cell proliferative diseases, including cancer and rheumatoid arthritis. The compounds of the invention are substituted imidazopyridines.

International patent Application No. WO 2004/016611 relates to imidazopyridine derivatives which are said to be inhibitors of Indicible T cell Kinase (ItK) and therefore to be of value in the treatment of conditions in which inhibition of ItK activity is beneficial. The aurora kinase inhibitors of the present invention have combinations of substitution in the fused pyridine ring of the imidazopyridine scaffold, which combinations are not specifically disclosed in WO 2004/016611.

Published US patent application 20060189617 also relates to imidazopyridines which are antagonists of the Gonadotropin Releasing Hormone (GnRH), and said to be useful in the treatment of sex hormone related disorders including hormone-related cancers. The aurora kinase inhibitors of the present invention differ in structure from those of 20060189617 inter alia in the identity of the substituents in the fused pyridine ring.

DETAILED DESCRIPTION OF THE INVENTION

According to the present invention there is provided a compound of formula (I), or a salt, hydrate, solvate, or N-oxide thereof:

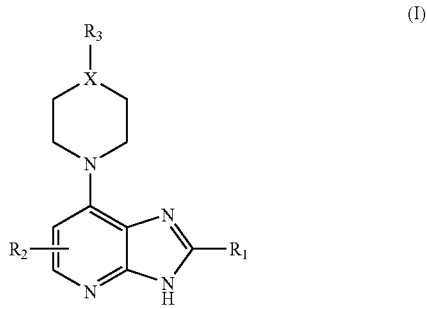

(I)

wherein
X is —N—, —CH$_2$—N—, —CH$_2$—CH—, or —CH—;
R$_1$ is a radical of formula (IA)

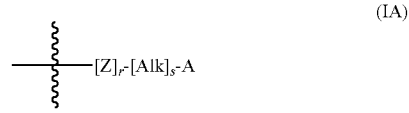

(IA)

wherein
Z is —CH$_2$—, —NH—, —O—, —S(O)—S, SO$_2$ or a divalent monocyclic carbocyclic or heterocyclic radical having 3-7 ring atoms;
Alk is an optionally substituted divalent C$_1$-C$_6$ alkylene radical;

A is hydrogen or an optionally substituted monocyclic carbocyclic or heterocyclic ring having 5-7 ring atoms;

r, s and t are independently 0 or 1, provided that when A is hydrogen then at least one of r and s is 1;

$R_2$ is halogen, —CN, —$CF_3$, —$OCH_3$, or cyclopropyl; and $R_3$ is a radical of formula (IB)

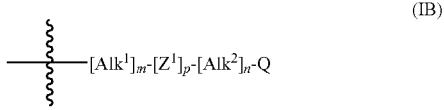

wherein

Q is hydrogen or an optionally substituted phenyl or monocyclic heterocyclic ring with 5 or 6 ring atoms;

$Z^1$ is —S—, —S(O)—, —S(O)$_2$—, —O—, —SO$_2$NH—, —NHSO$_2$—, NHC(=O)NH, —NH(C=S)NH—, or —N(R$_4$)— wherein $R_4$ is hydrogen, $C_1$-$C_3$ alkyl, cycloalkyl, or benzyl; and $Alk^1$ and $Alk^2$ are, independently, optionally substituted divalent $C_1$-$C_3$ alkylene radicals; and m, n and p are independently 0 or 1.

The compounds (I) of the invention exist in two tautomeric forms one of which is shown in formula (I), the other being shown in formula (II):

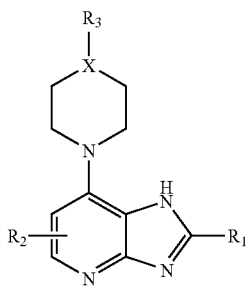

A third possible tautomeric form is shown in formula (III:

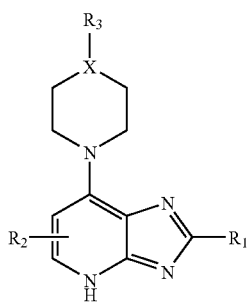

The present invention includes compounds of formula (I) and all tautomers thereof, as well as mixtures thereof in any proportions. References to compounds of formula (I) herein are to be taken as including references to compounds of formula (II) and (III) and mixtures thereof.

Although the above definition potentially includes molecules of high molecular weight, it is preferable, in line with general principles of medicinal chemistry practice, that the compounds with which this invention is concerned should have molecular weights of no more than 600, and the substituents $R_1$-$R_3$ may be selected accordingly.

In another broad aspect the invention provides the use of a compound of formula (I) as defined above, or an N-oxide, salt, hydrate or solvate thereof in the preparation of a composition for inhibiting the activity of an aurora kinase enzyme, aurora-A and/or aurora-B and/or Aurora C.

The compounds with which the invention is concerned may be used for the inhibition of aurora kinase activity, such as aurora-A and/or aurora-B, and/or aurora C activity, ex vivo or in vivo.

In one aspect of the invention, the compounds of the invention may be used in the preparation of a composition for the treatment of cell-proliferation disease, for example cancer cell proliferation and autoimmune diseases.

In another aspect, the invention provides a method for the treatment of the foregoing disease types, which comprises administering to a subject suffering such disease an effective amount of a compound of formula (I) as defined above.

TERMINOLOGY

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent ($C_a$-$C_b$)alkylene radical" wherein a and b are integers refers to a saturated hydrocarbon chain having from a to b carbon atoms and two unsatisfied valences.

As used herein the unqualified term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, $(C_1-C_6)$ alkyl, $(C_3-C_6)$ cycloalkyl, $(C_1-C_6)$alkoxy including methylenedioxy and ethylenedioxy, hydroxy, hydroxy$(C_1-C_6)$alkyl, mercapto, mercapto $(C_1-C_6)$alkyl, $(C_1-C_6)$alkylthio, phenyl, monocyclic heterocyclic, benzyl, phenoxy, halo (including fluoro, bromo and chloro), trifluoromethyl, trifluoromethoxy, nitro, nitrile (—CN), oxo, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$—, —NHR$^A$, —NR$^A$R$^B$, —OCONH$_2$, —OCONHR$^A$—OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a $(C_1-C_6)$alkyl, $(C_3-C_6)$ cycloalkyl, phenyl, benzyl or monocyclic heterocyclic having 5 or 6 ring atoms, or R$^A$ and R$^B$ when attached to the same nitrogen may, together with that nitrogen, form a 4- to 6-membered ring containing that nitrogen, such as a morpholine, thiomorpholine, piperidine or piperazine ring. An "optional substituent" may be one of the foregoing substituent groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like.

Compounds of the invention which contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

Variable Substituents

In the compounds with which the invention is concerned the following structural characteristics may be present, in any compatible combination:

The Ring Containing X

As defined above, X is —N—, —CH$_2$—N—, —CH$_2$—CH—, or —CH—, ie the ring containing X is selected from radicals A-D:

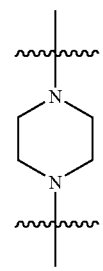

A

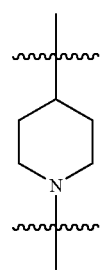

B

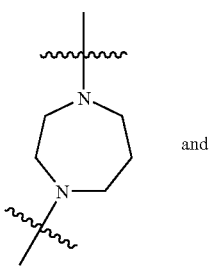

C and

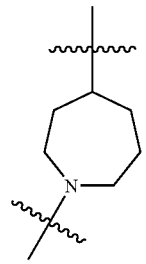

D

Presently, it is preferred that X be —N— (ie the ring containing X is a piperazine ring A).

The Group $R_1$

The group $R_1$ is a radical of formula (IA)

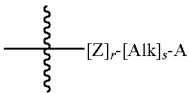

(IA)

In $R_1$, Z (when present) may be, for example, a divalent radical selected from:

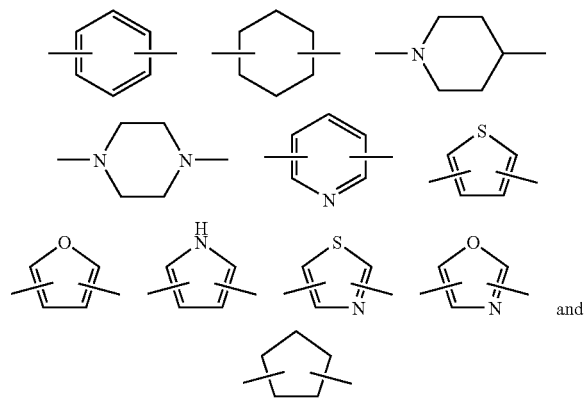

Also in $R_1$, Alk (when present) may be, for example, optionally substituted —$CH_2$—, —$CH_2CH_2$— or —$CH_2CH_2CH_2$—. Optional substituents in Alk include a primary, secondary or cyclic amino group.

In one subset of compounds (I), in the substituent $R_1$, r is 0 or 1, s is 1 and A is hydrogen. In this subset, Alk may be substituted on a terminal carbon by a primary, secondary or cyclic amino group. For example, Alk may be substituted by —$NR_5R_6$ wherein $R_5$ and $R_6$ are independently hydrogen or $C_1$-$C_3$ alkyl, or $R_5$ and $R_6$ taken together with the nitrogen to which they are attached form a 3-7 membered ring. In the latter case $R_5$ and $R_6$ taken together with the nitrogen to which they are attached may form a piperidine, piperazine, N-methylpiperazine, or morpholine ring.

In another subset of compounds (I), in the substituent $R_1$, r and s are both 0, and A is optionally substituted phenyl, or optionally substituted heteroaryl having 5 or 6 ring atoms. In this subset, the phenyl or heteroaryl ring A may be substituted, for example, by a group —$(CH_2)_vNR_5R_6$ wherein v is 0, 1, 2, 3 or 4, especially 1 or 2, and $R_5$ and $R_6$ are independently hydrogen or $C_1$-$C_3$ alkyl such as methyl or ethyl, or $R_5$ and $R_6$ taken together with the nitrogen to which they are attached form a 3-7 membered ring. In the latter case, $R_5$ and $R_6$ taken together with the nitrogen to which they are attached may form a piperidine, piperazine, N-methylpiperazine, morpholine or pyrazole ring. Alternatively, the phenyl or heteroaryl ring A may be substituted by a group —$O(CH_2)_v$ $NR_5R_6$ wherein v is 0, 1, 2, 3 or 4, and $R_5$ and $R_6$ are independently hydrogen or $C_1$-$C_3$ alkyl, such as methyl or ethyl, or $R_5$ and $R_6$ taken together with the nitrogen to which they are attached may form a piperidine, piperazine, N-methylpiperazine, morpholine or pyrazole ring. In other alternatives within this subset, the phenyl or heteroaryl ring A may be substituted by a group —$OCH_3$, or —$O(CH_2)_2OH$. In general in this subset, the phenyl or heteroaryl ring A may be substituted by an optional substituent which is recognised as a solubilising substituent in medicinal chemistry.

The Group $R_2$

In one subset of compounds (I) according to the invention $R_2$ is attached to the non-bridging carbon atom adjacent the group:

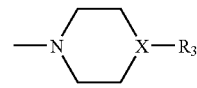

In the compounds (I), including the above identified subsets, $R_2$ may be selected from —CN, —$CF_3$, —$OCH_3$, cyclopropyl, and halogen, in particular Cl and Br.

The Group $R_3$

The substituent $R_3$ in the compounds of the invention is a radical of formula (IB) as defined above:

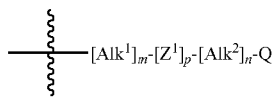

In the group $R_3$:

Q may be, for example, optionally substituted phenyl, pyridyl, pyrimidinyl, triazinyl, thienyl, furanyl, thiazolyl, oxazolyl, thiadiazolyl, or oxadiazolyl. $Alk^1$ and $Alk^2$ may be independently selected from optionally substituted —$CH_2$—, —$CH_2CH_2$— and —$CH_2CH_2CH_2$— is a radical of formula (IB).

$Z^1$ may be —$N(R_4)$— wherein $R_4$ is hydrogen, $C_1$-$C_3$ alkyl for example methyl or ethyl, cycloalkyl for example cyclopropyl, or benzyl and an adjacent carbon atom of $Alk^1$ or $Alk^2$ may be substituted by oxo, whereby $R_3$ includes an amido or reverse amido link.

In one currently preferred subset of compounds of the invention $R_3$ has formula (IB):

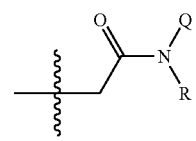

wherein Q is as defined in relation to formula (I), and R is hydrogen or methyl. In another currently preferred subset of compounds of the invention radical $R_3$ has formula (IC):

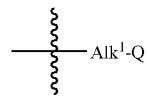

wherein $Alk^1$ and Q as defined in relation to formula (I). In this latter subset, $Alk^1$ may be, for example —CH(R)—, —CH(R)CH(R)—, or —CH(R)CH(R)CH(R)— wherein each R is independently hydrogen or methyl. Specific examples of $Alk^1$ are —$CH_2$— or —CH($CH_3$)—. In both subsets, Q may be selected from, for example, optionally substituted phenyl, thiazolyl, isothiazolyl, oxazolyl, isoxazolyl, pyrimidinyl and pyridyl. In the subset where $R_3$ has formula (IB), the cases where Q is thiazol-2-yl, 3-methylisoxazol-5-yl, 4-methylthiazol-2-yl, phenyl or 3-chlorophenyl are currently preferred. In the case where $R_3$ has formula (IC), the cases where Q is phenyl, 4-chlorophenyl, 5-methyl-isoxazol-3-yl, pyrid-3-yl, pyrid-4-yl, pyrimidin-5-yl or 2-methylthiazol-4-yl are currently preferred.

Thus, taking the structural preferences discussed above into account, one class of compounds of the invention has formula (ID):

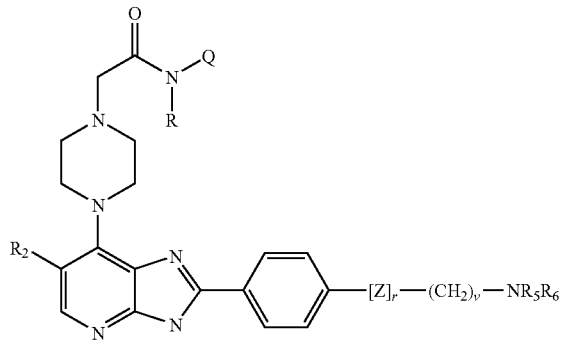

wherein R is hydrogen or methyl; $R_2$ is chloro or bromo; Q is thiazol-2-yl, 3-methylisoxazol-5-yl, 4-methylthiazol-2-yl, phenyl or 3-chlorophenyl; Z is —O—; r is 0 or 1; v is 1, 2, or 3; and $R_5$ and $R_6$ are independently hydrogen, methyl or ethyl, or $R_5$ and $R_6$ taken together with the nitrogen to which they are attached form a piperidinyl, morpholinyl, pyrazolyl or piperazinyl ring, the latter being optionally substituted on the second nitrogen; and another class of compounds of the invention has formula (IE):

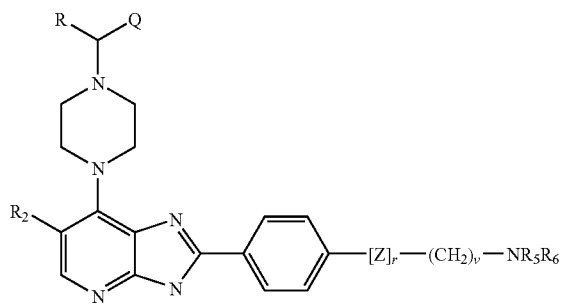

wherein R is hydrogen or methyl; $R_2$ is chloro or bromo; r is 0 or 1; v is 1, 2, or 3; and $R_5$ and $R_6$ are independently hydrogen, methyl or ethyl, or $R_5$ and $R_6$ taken together with the nitrogen to which they are attached form a piperidinyl, morpholinyl, pyrazolyl or piperazinyl ring, the latter being optionally substituted on the second nitrogen; and Q is phenyl, 4-chlorophenyl, 5-methyl-isoxazol-3-yl, pyrid-3-yl or pyrid-4-yl, pyrimidin-5-yl or 2-methylthiazol-4-yl.

Specific compounds of the invention include those of the Examples herein.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to those skilled in the art. Typical literature sources are "Advanced organic chemistry", $4^{th}$ Edition (Wiley), J March, "Comprehensive Organic Transformation", $2^{nd}$ Edition (Wiley), R. C. Larock, "Handbook of Heterocyclic Chemistry", $2^{nd}$ Edition (Pergamon), A. R. Katritzky), review articles such as found in "Synthesis", "Acc. Chem. Res.", "Chem. Rev", or primary literature sources identified by standard literature searches online or from secondary sources such as "Chemical Abstracts" or "Beilstein".

For example, one method of synthesis of the compounds involves reaction of a compound (IV) or (V) with an aldehyde $R_1CHO$, under conditions for formation of the fused imidazo ring of compounds (I). Details of such conditions appear, for example, in the Examples herein.

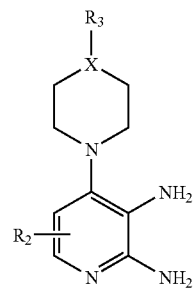

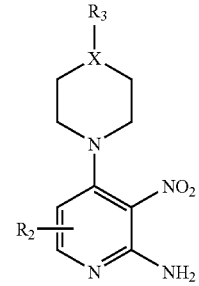

Utilities

As mentioned above, the compounds with which the invention is concerned are inhibitors of the Aurora kinase family, namely Aurora kinases A and/or B and/or C, and are therefore of use in the treatment of cell proliferative disease, such as cancer, and in treatment of inflammation, in humans and other mammals.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial as is required in the art.

The invention also includes pharmaceutical composition comprising a compound of the invention, together with a pharmaceutically acceptable carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The following examples illustrate methods for the preparation of compounds of the invention, make available specific compounds of the invention, and indicate their aurora kinase inhibitory activities:

General Experimental Comments

Commercially available starting materials, reagents and dry solvents were used as supplied. Flash column chromatography was performed using Merck silica gel 60 (0.025-0.04 mm). Column chromatography was also performed on a FlashMaster personal unit using isolute Flash silica columns or a Biotage SP1 purification system using Biotage Flash silica cartridges. Ion exchange chromatography was performed using acidic Isolute Flash SCX-II cartridges. $^1$H NMR spectra were recorded on a Bruker Avance dpx250 or a Bruker Avance-500. Samples were prepared as solutions in a deuterated solvent and referenced to the appropriate internal non-deuterated solvent peak or tetramethylsilane. Chemical shifts were recorded in ppm (δ) downfield of tetramethylsilane. LC-MS spectra were recorded on a Waters LCT with a Waters Alliance 2795 separations module, using a Phenomenex Gemini $C_{18}$ column and either of the following conditions:

Method A (10 mins)—nominal mass, LC injection with a 10 minute gradient (MeOH and 0.1% formic acid), positive ionisation and an injection volume of 3 μL. Column: Phenomenex Gemini $C_{18}$ column (5 micron, 50×4.6 mm)

Method B (6 mins)—nominal mass, LC injection with a 6 minute gradient (MeOH and 0.1% formic acid), positive ionisation and an injection volume of 2 μL. Column: Phenomenex Gemini $C_{18}$ column (3 micron, 30×4.6 mm). If method not stated, then Method A was followed.

High resolution mass spectra were obtained using the above instrumental set-up and the following conditions:

Accurate mass, LC injection with a 10 minute gradient (MeOH and 0.1% formic acid), +ve ionisation and an injection volume of 4 μL. Column: Phenomenex Gemini $C_{18}$ column (5 micron, 50×4.6 mm)

GC-MS: Instrument: Thermo Finnigan TraceGC with Polaris Q Mass spec Ionisation method: Cl (Methane); Carrier Gas: Helium; Column: Phenomenex Zebron (length: 15 m, i.d.: 0.25 mm, thickness: 0.25 uM); Operating temperatures: 80-300° C.

Example 1

Step 1

4-chloro-2-trimethylacetamidopyridine

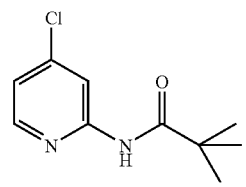

This compound was prepared as reported by K. S. Gudmundsson et al, *Synthetic Communications* 1997, 27 (5), 861-870: To a stirred solution of 2-amino-4-chloropyridine (0.723 g, 5.62 mmol) in anhydrous pyridine (2.8 ml) was dropwise added trimethylacetyl chloride (1.02 g, 8.46 mmol). The reaction mixture was stirred at room temperature for 4.5 h under argon, then partitioned between ethyl acetate (70 ml) and water (50 ml). The aqueous layer was extracted with ethyl acetate (2×30 ml), and the combined organics were washed with saturated aqueous $NaHCO_3$ (40 ml), brine (50 ml), dried ($Na_2SO_4$), and concentrated in vacuo. The residue was absorbed on silica gel and the free running powder was placed on a 50 g isolute silica column. Elution with 20% ethyl acetate in hexanes and 25% ethyl acetate in hexanes afforded the title compound as a white solid (0.880 g, 74%); $^1$H-NMR (250 Mz, DMSO-$d_6$) 1.24 (s, 9H, C(CH$_3$)$_3$), 7.25 (dd, J=1.91 Hz, 5.36 Hz, 1H, 5-H), 8.17 (d, J=1.87 Hz, 1H, 3-H), 8.34 (d, J=5.35 Hz, 1H, 6-H), 10.09 (s, 1H, CONH); LC-MS (ESI, m/z) 6.91 min—213, 215 [(M+H)$^+$, Cl isotopic pattern].

Step 2

4,5-dichloro-2-trimethylacetamido-pyridine

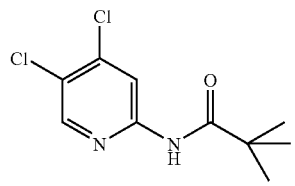

This compound was prepared as reported by K. S. Gudmundsson et al, *Synthetic Communications* 1997, 27 (5), 861-870: To a stirred solution of 4-chloro-2-trimethylacetamido-pyridine (0.870 g, 4.07 mmol) in anhydrous acetonitrile (11 ml) was added N-chlorosuccinimide (2.72 g, 20.37 mmol). The reaction mixture was heated at 100° C. for 3 h then more N-chlorosuccinimide (0.600 g) was added and stirring was continued at this temperature for 2 h. The mixture was then allowed to cool to room temperature, the solvent was removed in vacuo, and the residue was partitioned between ethyl acetate (170 ml) and 10% aqueous NaOH (60 ml). The organic layer was washed with 10% aqueous NaOH (60 ml), water (60 ml), saturated brine (60 ml), dried (Na$_2$SO$_4$), and concentrated in vacuo. The residue was absorbed on silica gel (2.3 g) and the free running powder was placed on a 50 g isolute silica column. Elution with 15% ethyl acetate in hexanes and 20% ethyl acetate in hexanes afforded the title compound as a white solid (0.500 g, 50%); $^1$H-NMR (250 Mz, CDCl$_3$) 1.35 (s, 9H, C(CH$_3$)$_3$), 8.05 (br s, 1H, CONH), 8.28 (s, 1H), 8.52 (s, 1H) (3-H, 6-H).

Step 3

2-amino-4,5-dichloropyridine

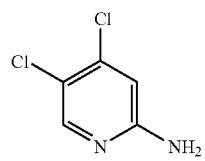

A mixture of 4,5-dichloro-2-trimethylacetamido-pyridine (0.500 g, 2.02 mmol) and aqueous HCl (6N; 9.5 ml) was heated was heated at 100° C. for 17 h. The reaction mixture was allowed to cool to room temperature, diluted with ice-water (~15 ml), and the pH of the mixture was adjusted to ~7.0 with 10% aqueous NaOH. The white precipitate was collected by filtration, washed with water (2×5 ml), and dried in vacuo over P$_2$O$_5$. The title compound was obtained as a white solid (0.284 g, 86%); $^1$H-NMR (500 Mz, DMSO-d$_6$) 6.44 (s, 2H, NH$_2$, exchangeable with D$_2$O), 6.64 (s, 1H), and 8.03 (s, 1H) (3-H, 6-H); LC-MS (ESI, m/z) 4.37 min—163, 165, 167 [(M+H)$^+$, Cl$_2$ isotopic pattern].

Step 4

2-amino-4,5-dichloro-3-nitropyridine

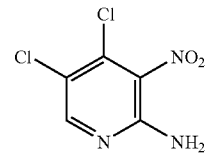

To a 50 ml round-bottomed flask containing 2-amino-4,5-dichloropyridine (0.275 g, 1.65 mmol) and cooled into an ice-bath was added conc. H$_2$SO$_4$ (2.79 g). The reaction mixture was stirred for 3 min and then HNO$_3$ (70%; 0.186 g) was dropwise added. The reaction mixture was stirred at 0° C. (ice-bath) for 7 min, then heated to 55° C. and stirred at this temperature for 1 h, allowed to cool to room temperature, diluted with ice-water (~15 ml) and the pH was adjusted to ~7.5 with 10% aqueous NaOH. The yellow precipitate was collected by filtration, washed with water and dried in vacuo over P$_2$O$_5$, then absorbed on silica gel and the free running powder was placed on a 10 g isolute silica column. Elution with 2% ethyl acetate in dichloromethane afforded the title compound as a yellow solid (0.090 g, 26%); $^1$H-NMR (250 Mz, DMSO-d$_6$) 7.39 (s, 2H, NH$_2$), 8.39 (s, 1H, 6-H); LC-MS (ESI, m/z) 6.54 min—208, 210, 212 [(M+H)$^+$, Cl$_2$ isotopic pattern].

Step 5

2-[4-(2-Amino-5-chloro-3-nitro-pyridin-4-yl)-piperazin-1-yl]-N-thiazol-2-yl-acetamide

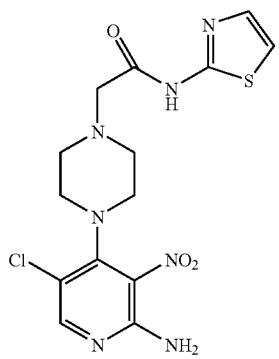

2-(piperazin-yl)-acetic acid N-(2-thiazolyl)-amide×2HCl (0.360 g) was partitioned between saturated aqueous NaHCO$_3$ (40 ml) and ethyl acetate (30 ml). The aqueous layer was extracted with ethyl acetate (2×30 ml), dichloromethane (5×25 ml) and the combined organics were dried (Na$_2$SO$_4$), and then concentrated in vacuo to give 0.165 g of the free base. A mixture of this free base (0.054 g, 0.24 mmol), isopropanol (4.3 ml), and 2-amino-4,5-dichloro-3-nitropyridine (0.040 g, 0.19 mmol) was heated at 45° C. for 22 h. The reaction mixture was allowed to cool to room temperature, absorbed on silica gel, and the free running powder was placed on a 10 g isolute silica column which was eluted with ethyl acetate/dichloromethane (v/v; 1:1) and then 5% methanol in ethyl acetate/dichloromethane (v/v; 1:1). The title compound was obtained as a yellow solid (0.041 g, 55%); $^1$H-NMR (250 Mz, DMSO-$d_6$) 2.68 (m, 4H, piperazine N(CH$_2$)$_2$), 3.12 (m, 4H, piperazine N(CH$_2$)$_2$), 3.38 (s, 2H, NCH$_2$CO), 6.98 (s, 2H, NH$_2$, exchangeable with D$_2$O), 7.23 (d, J=3.55 Hz, 1H) and 7.49 (d, J=3.54 Hz, 1H) (thiazole 4-H, 5-H), 8.08 (s, 1H, pyridine 6-H); 11.98 (s, 1H, CONH); LC-MS (ESI, m/z) 4.35 min—398, 400 [(M+H)$^+$, Cl isotopic pattern].

Step 6

2-{4-[6-Chloro-2-(4-dimethylamino-phenyl)-3H-imidazo[4,5-b]pyridin-7-yl]-piperazin-1-yl}-N-thiazol-2-yl-acetamide

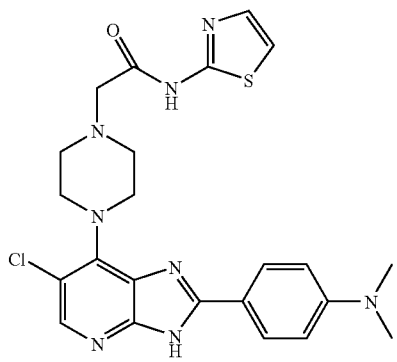

To a mixture of 2-[4-(2-Amino-5-chloro-3-nitro-pyridin-4-yl)-piperazin-1-yl]-N-thiazol-2-yl-acetamide (0.040 g, 0.10 mmol), ethanol (3 ml), and 4-dimethylamino-benzaldehyde (0.019 g, 0.13 mmol) was added a freshly prepared aqueous solution of Na$_2$S$_2$O$_4$ (1M; 0.4 ml, 0.4 mmol). The reaction mixture was heated at 70° C. for 3.5 h, then allowed to cool to room temperature and the solvents were removed in vacuo. The residue was absorbed on silica gel and the free running powder was placed on a 10 g isolute silica column which was eluted with ethyl acetate/dichloromethane (v/v; 1:1), 1.5% methanol in ethyl acetate/dichloromethane (v/v; 1:1) and finally 2% methanol in ethyl acetate/dichloromethane (v/v; 1:1). The title compound was obtained after trituration with diethyl ether as a pale yellow solid (0.005 g, 10%); $^1$H-NMR (250 Mz, DMSO-$d_6$) 2.78 (m, 4H, piperazine N(CH$_2$)$_2$), 3.01 (s, 6H, N(CH$_3$)$_2$), 3.40 (s, 2H, NCH$_2$CO), 3.72 (m, 4H, piperazine N(CH$_2$)$_2$), 6.83 (d, J=8.79 Hz, 2H, 3,5-ArH or 2,6-ArH), 7.25 (d, J=3.42 Hz, 1H) and 7.51 (d, J=3.53 Hz, 1H) (thiazole 4-H, 5-H), 8.03 (d, 3H, J=9.88 Hz, 3,5-ArH or 2,6-ArH, and imidazo[4,5-b]pyridine 5-H); 11.95 (s, 1H, CONH), 13.12 (s, 1H, imidazo[4,5-b]pyridine N—H); LC-MS (ESI, m/z) 6.17 min—497, 499 [(M+H)$^+$, Cl isotopic pattern]; ESI-HRMS Found: 497.1652, calculated for C$_{23}$H$_{26}$N$_8$ClOS (M+H)$^+$: 497.1633.

Example 2

Step 1

5-Bromo-4-chloro-pyridin-2-ylamine

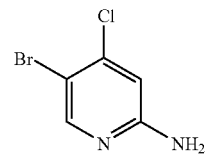

To a solution of 2-amino-4-chloropyridine (0.50 g, 3.9 mmol) in acetonitrile (20 ml) was added dropwise a solution of N-bromosuccinimide (0.730 g, 4.1 mmol) in acetonitrile (10 ml). The reaction mixture was stirred at room temperature for 16 h then concentrated in vacuo. The crude product was purified by chromatography on silica gel (hexane/ethyl acetate 6:4) to give the title compound as a white solid (0.65 g, 80%); $^1$H-NMR (250 MHz, CDCl$_3$) 6.63 (s, 1H) and 8.16 (s, 1H) (3-H, 6-H); LC-MS (ESI, m/z) Rt=4.8 min—206, 209 [(M+H$^+$), BrCl isotopic pattern, 100%];

Step 2

5-Bromo-4-chloro-3-nitro-pyridin-2-ylamine

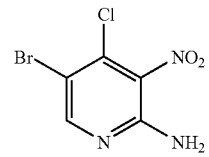

5-Bromo-4-chloro-pyridin-2-ylamine (0.640 g, 3.0 mmol) was added in portions to conc. H$_2$SO$_4$ (6 ml) while the temperature kept at −10° C. The reaction mixture was then stirred at −10° C. for 15 min. The resulting solution was then heated at 55° C. and HNO$_3$ (208 μL, 3.2 mmol) was added dropwise while the temperature was kept at 55° C.-60° C. maximum. The reaction mixture was stirred at 55° C. for 30 min then cooled to room temperature and poured slowly into ice (20 g). The pH was adjusted to 7 with 40% aqueous NaOH. The precipitated product was filtered, washed with water (20 ml) and dried in vacuo over P$_2$O$_5$ for 16 h to give the title compound as a yellow solid (0.580 g). 0.48 g was further purified by chromatography (hexane/ethyl acetate; v/v 7:3) to give the title compound as a yellow solid (0.287 g); ¹H-NMR (250 MHz, CDCl₃) 8.29 (s, 1H, 6-H).

Step 3

2-[4-(2-Amino-5-bromo-3-nitro-pyridin-4-yl)-piperazin-1-yl]-N-thiazol-2-yl-acetamide

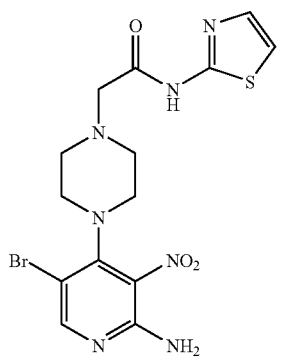

To a mixture of 5-bromo-4-chloro-3-nitro-pyridin-2-ylamine (0.100 g, 0.39 mmol) and isopropanol (4 ml) was added 2-(piperazin-1-yl)acetic acid N-2-thiazolyl)-amide.2HCl (0.124 g, 0.41 mmol) and dry DIPEA (275 µL, 1.58 mmol). The mixture was heated at 50° C. for 16 h, then allowed to cool to room temperature, and concentrated in vacuo. The crude product was purified by chromatography on silica gel (hexane/ethyl acetate v/v 1:1 to 5% methanol in ethyl acetate) to give the title compound as a yellow solid (0.144 g, 82%); ¹H-NMR (250 MHz, DMSO-d₆) 2.68 (broad t, J=4 Hz, 4H, piperazine N(CH₂)₂), 3.10 (broad t, J=4 Hz, 4H, piperazine N(CH₂)₂), 3.36 (s, 2H, NCH₂CO), 6.95 (broad s, 2H, NH₂), 7.22 (d, J=3.6 Hz, 1H) and 7.47 (d, J=3.6 Hz, 1H) (thiazole 4-H, 5-H), 8.16 (s, 1H, pyridine 6-H), 11.8 (broad s, 1H, CONH); LC-MS (ESI, m/z) Rt=4.69 min—442/444 [(M+H⁺), Br isotopic pattern, 100%].

Step 4

2-{4-[6-Bromo-2-(4-dimethylamino-phenyl)-3H-imidazo[4,5-b]pyridin-7-yl]-piperazin-1-yl}-N-thiazol-2-yl-acetamide

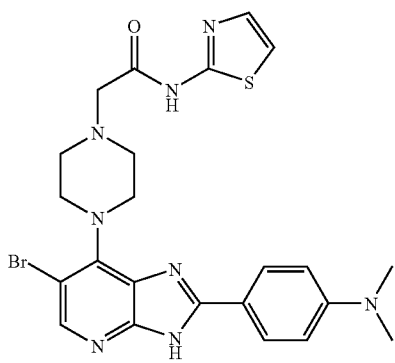

To a mixture 2-[4-(2-amino-5-bromo-3-nitro-pyridin-4-yl)-piperazin-1-yl]-N-thiazol-2-yl-acetamide (0.100 g, 0.22 mmol) and ethanol (3 ml) was added 4-dimethylamino benzaldehyde (0.044 g, 0.29 mmol) and 1M aq. Na₂S₂O₄ (900 µL, 0.9 mmol). The reaction mixture was stirred at reflux for 16 h then concentrated in vacuo. The crude product was purified by chromatography on silica gel (dichloromethane/ethyl acetate v/v 7:3, and then 0.5% to 2% methanol in ethyl acetate) to give the title compound as an off white solid (0.034 g, 27%); ¹H-NMR (250 MHz, DMSO-d₆) 2.77 (broad m, 4H, piperazine N(CH₂)₂), 2.99 (s, 6H, N(CH₃)₂), 3.40 (s, 2H, NCH₂CO), 3.67 (broad m, 4H, piperazine N(CH₂)₂), 6.82 (d, J=8.8 Hz, 2H) and 8.02 (d, J=8.8 Hz, 2H) 2,6-ArH and 3,5-ArH, 7.23 (d, J=3.5 Hz, 1H) and 7.49 (d, 1H, J=3.5 Hz) (thiazole 4-H, 5-H), 8.15 (s, 1H, imidazo[4,5-b]pyridine 5-H), 11.80 (broad s, 1H, CONH), 13.12 (broad s, 1H, imidazo[4,5-b]pyridine NH); LC-MS (ESI, m/z) Rt=6.0 min—541/543 [(M+H⁺), Br isotopic pattern, 100%]; ESI-HRMS Found: 541.1203, calculated for C₂₃H₂₆N₈OSBr (M+H⁺): 541.1134.

Example 3

Step 1

2-[4-(2-Amino-5-chloro-3-nitro-pyridin-4-yl)-piperazin-1-yl]-N-methyl-N-phenyl-acetamide

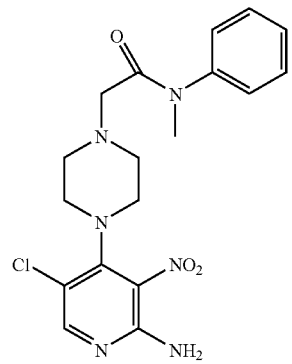

The method followed that used to prepare 2-[4-(2-amino-5-chloro-3-nitro-pyridin-4-yl)-piperazin-1-yl]-N-thiazol-2-yl-acetamide (Example 6, Steps 1 to 6), but using 2-amino-4,5-dichloro-3-nitropyridine (0.036 g, 0.17 mmol), isopropanol (4.0 ml), and N-methyl-N-phenyl-2-piperazin-1-yl-acetamide (0.056 g, 0.24 mmol). Work-up and purification as described for 2-[4-(2-amino-5-chloro-3-nitro-pyridin-4-yl)-piperazin-1-yl]-N-thiazol-2-yl-acetamide afforded the title compound as an orange solid (0.039 g, 57%), ¹H-NMR (500 Mz, DMSO-d₆) 2.50 (obscured by DMSO peak, piperazine N(CH₂)₂), 2.96 (br s, 4H, piperazine N(CH₂)₂), 3.18 (s, 3H, NCH₃), 6.94 (s, 2H, NH₂), 7.35 (m, 3H) and 7.42 (m, 2H)

(N-Ph), 8.05 (s, 1H, pyridine 6-H); LC-MS (ESI, m/z) 3.30 min—405, 407 [(M+H)+, Cl isotopic pattern].

Step 2

2-{4-[6-Chloro-2-(4-dimethylamino-phenyl)-3H-imidazo[4,5-b]pyridin-7-yl]-piperazin-1-yl}-N-methyl-N-phenyl-acetamide

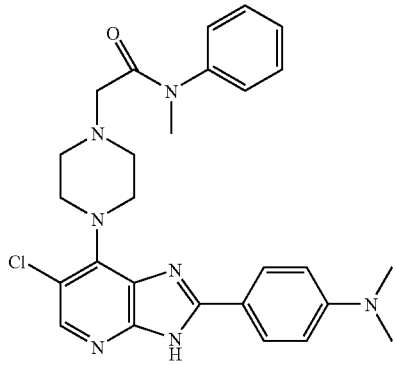

To a mixture of 2-[4-(2-amino-5-chloro-3-nitro-pyridin-4-yl)-piperazin-1-yl]-N-methyl-N-phenyl-acetamide (0.037 g, 0.09 mmol), ethanol (3 ml), and 4-dimethylamino-benzaldehyde (0.019 g, 0.13 mmol) was added a freshly prepared aqueous solution of $Na_2S_2O_4$ (1M; 0.4 ml, 0.4 mmol). The reaction mixture was heated at 70° C. for 6 h, then allowed to cool to room temperature and the solvents were removed in vacuo. The residue was absorbed on silica gel and the free running powder was placed on a 10 g isolute silica column which was eluted first with ethyl acetate/dichloromethane (v/v; 1:1), and then 1-2% methanol in ethyl acetate/dichloromethane (v/v; 1:1). The title compound was obtained after trituration with diethyl ether as a pale yellow solid (0.008 g, 18%); $^1$H-NMR (500 Mz, DMSO-$d_6$) 2.58 (br s, 4H, piperazine $N(CH_2)_2$), 3.00 (s, 6H, $N(CH_3)_2$), 3.21 (s, 3H, $NCH_3$), 3.61 (br s, 4H, piperazine $N(CH_2)_2$), 6.82 (d, J=9.87 Hz, 2H, 3,5-$C_6H_4$—$NMe_2$ or 2,6-$C_6H_4$—$NMe_2$), 7.30-7.50 (m, 5H, N-Ph), 8.00 (m, 3H, 3,5-$C_6H_4$—$NMe_2$ or 2,6-$C_6H_4$—$NMe_2$ and imidazo[4,5-b]pyridine 5-H); 13.09 (s, 1H, imidazo[4,5-b]pyridine N—H); LC-MS (ESI, m/z) 5.10 min—504, 506 [(M+H)+, Cl isotopic pattern]; ESI-HRMS Found: 504.2278, calculated for $C_{27}H_{31}N_7ClO$ (M+H)+: 504.2279.

Example 4

2-[4-(6-Chloro-2-phenyl-3H-imidazo[4,5-b]pyridin-7-yl)-piperazin-1-yl]-N-thiazol-2-yl-acetamide

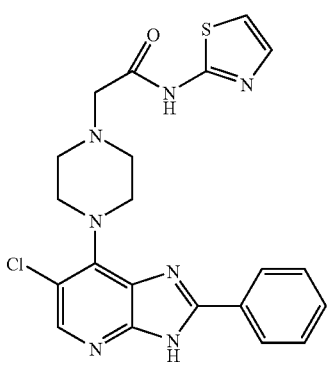

To a mixture of 2-[4-(2-amino-5-chloro-3-nitro-pyridin-4-yl)-piperazin-1-yl]-N-thiazol-2-yl-acetamide (0.040 g, 0.10 mmol), ethanol (3 ml), and benzaldehyde (0.015 g, 0.14 mmol) was added a freshly prepared aqueous solution of sodium dithionite ($Na_2S_2O_4$) (1M; 0.4 ml, 0.4 mmol). The reaction mixture was heated at 70° C. for 6 h, then allowed to cool to room temperature and the solvents were removed in vacuo. The residue was absorbed on silica gel and the free running powder was placed on a 10 g isolute silica column which was eluted with 70% dichloromethane in ethyl acetate and then 2% methanol in ethyl acetate/dichloromethane (v/v; 1:1). The title compound was obtained as an off white solid after trituration with diethyl ether (0.011 g, 24%); $^1$H-NMR (500 MHz, DMSO-$d_6$) 2.73 (br s, 4H, piperazine $N(CH_2)_2$), 3.40 (s, 2H, $CH_2CO$), 3.75 (br s, 4H, piperazine $N(CH_2)_2$), 7.23 (d, J=3.46 Hz, 1H) and 7.49 (d, J=3.46 Hz, 1H) (thiazole 4-H, 5-H), 8.12 (s, 1H, imidazo[4,5-b]pyridine 5-H), 7.60 (m, 3H) and 8.19 (d, J=7.00 Hz, 2H) (ArH), 11.92 (s, 1H, CONH), 13.49 (s, 1H, imidazo[4,5-b]pyridine N—H); LC-MS (ESI, m/z) Rt=6.16 min—454, 456 [(M+H)+, Cl isotopic pattern]. ESI-HRMS: Found: 454.1230, calculated for $C_{21}H_{21}N_7OSCl$ (M+H)+: 454.1217.

Example 5

2-[4-(6-Bromo-2-phenyl-3H-imidazo[4,5-b]pyridin-7-yl)-piperazin-1-yl]-N-thiazol-2-yl-acetamide

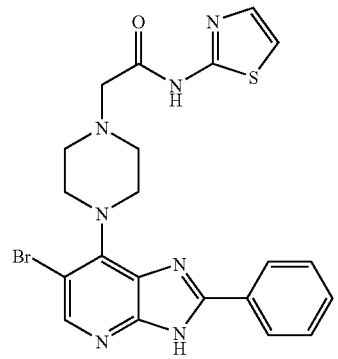

To a mixture 2-[4-(2-amino-5-bromo-3-nitro-pyridin-4-yl)-piperazin-1-yl]-N-thiazol-2-yl-acetamide (0.05 g, 0.11 mmol) and ethanol (3 ml) was added benzaldehyde (15 μL, 0.29 mmol) and a freshly prepared aqueous solution of $Na_2S_2O_4$ (1M; 450 μL, 0.45 mmol). The reaction mixture was stirred at 80° C. for 16 h then more benzaldehyde (15 μL, 0.29 mmol) and 1M aq. $Na_2S_2O_4$ (450 μL, 0.45 mmol) were added. The reaction mixture was stirred at 80° C. for another 16 h then concentrated in vacuo. The crude product was purified by chromatography on silica gel (100% dichloromethane to dichloromethane/ethyl acetate 6:4 to dichloromethane/ethyl acetate 1:1+0.5% methanol) to give the title compound as a pale yellow solid (0.033 g, 58%); $^1$H-NMR (500 MHz, DMSO-$d_6$) 2.80 (broad s, 4H, piperazine $N(CH_2)_2$), 3.42 (s, 2H, $CH_2$), 3.72 (broad s, 4H, piperazine $N(CH_2)_2$), 7.24 (d, 1H, J=3.4 Hz, thiazole 4-H or 5-H), 7.49 (d, 1H, J=3.4 Hz, Thiazole 4-H or 5-H), 7.54 (m, 3H, Ar—H), 8.20 (dd, 2H, J=1.5, 8.0 Hz, 2,6-Ar—H), 8.25 (s, 1H, imidazo[4,5-b]pyrazine 5-H), 11.92 (broad s, 1H, NHCO), 13.54 (broad s, 1H, imidazo[4,5-b]pyrazine NH); LC-MS (ESI, m/z) Rt=5.89 min—498/500 [(M+H⁺), Br isotopic pattern, 100%]; ESI-HRMS: Found: 498.0716, calculated for $C_{21}H_{21}BrN_7OS$ (M+H⁺): 498.0712.

Example 6

(4-{6-Bromo-7-[4-(thiazol-2-ylcarbamoylmethyl)-piperazin-1-yl]-3H-imidazo[4,5-b]pyridin-2-yl}-benzyl)-carbamic acid tert-butyl ester

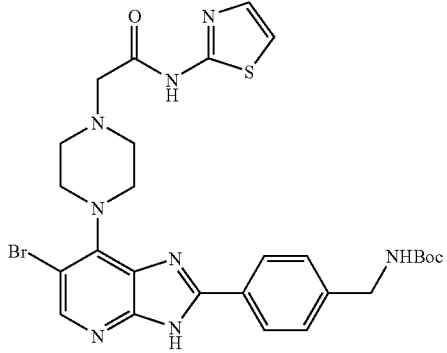

To a mixture of 2-[4-(2-amino-5-bromo-3-nitro-pyridin-4-yl)-piperazin-1-yl]-N-thiazol-2-yl-acetamide (0.1 g, 0.22 mmol) and ethanol (5 ml) was added tert-butyl N-(4 formyl-benzyl)carbamate (69 mg, 0.29 mmol) and a freshly prepared aqueous solution of $Na_2S_2O_4$ (1M; 900 µL, 0.9 mmol). The reaction mixture was stirred at 80° C. for 16 h then concentrated in vacuo. The crude product was purified by chromatography on silica gel (dichloromethane/ethyl acetate 7:3+ 0.5% methanol to 2% methanol in ethyl acetate). The isolated product was further triturated in ether/methanol 9:1, filtered, and dried in vacuo to give the title compound as a pale yellow solid (0.049 g, 34%);

¹H-NMR (500 MHz, CDCl₃/CD₃OD) 1.40 (s, 9H, (CH₃)₃ C Boc), 2.89 (broad s, 4H, piperazine N(CH₂)₂), 3.36 (s, 2H, CH₂), 3.86 (broad s, 4H, piperazine N(CH₂)₂), 4.31 (s, 2H, CH₂), 6.95 (d, 1H, J=3.6 Hz, thiazole 4-H or 5-H), 7.35 (d, 2H, J=8.0 Hz, 3,5-ArH), 7.41 (1H, d, J=3.6 Hz, thiazole 4-H or 5-H), 8.02 (d, 2H, J=8.0 Hz, 2,6-ArH), 8.15 (s, 1H, imidazo[4,5-b]pyrazine 5-H); LC-MS (ESI, m/z) Rt=6.83 min—627/629 [(M+H⁺), Br isotopic pattern, 100%]; ESI-HRMS Found: 627.1515, calculated for $C_{27}H_{32}BrN_8O_3S$ (M+H⁺): 627.1501.

Example 7

2-{4-[2-(4-Aminomethyl-phenyl)-6-bromo-3H-imidazo[4,5-b]pyridin-7-yl]-piperazin-1-yl}-N-thiazol-2-yl-acetamide

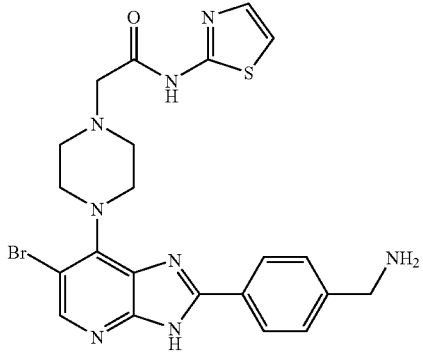

To (4-{6-bromo-7-[4-(thiazol-2-ylcarbamoylmethyl)-piperazin-1-yl]-3H-imidazo[4,5-b]pyridin-2-yl}-benzyl)-carbamic acid tert-butyl ester (0.053 g, 0.08 mmol) in dichloromethane (4 ml) was slowly added trifluoroacetic acid (0.5 ml) at 0° C. The reaction mixture was stirred at room temperature for 1 h then concentrated in vacuo. The crude product was run trough a 2 g SCX cartridge and eluted with 0.1M $NH_3$ in methanol to give the title compound as a pale yellow solid (0.046 g, 100%).

¹H-NMR (500 MHz, DMSO-d₆): 2.78 (broad t, 4H, piperazine N(CH₂)₂), 3.40 (s, 2H, CH₂), 3.70 (broad t, 4H, piperazine N(CH₂)₂), 3.81 (s, 2H, CH₂), 7.23 (d, 1H, J=3.4 Hz, Thiazole 4-H or 5-H), 7.49 (d, 1H, J=3.4 Hz, thiazole 4-H or 5-H), 7.50 (d, 2H, J=8.3 Hz, 2,6-ArH), 8.14 (d, 2H, J=8.3 Hz, 2,6-ArH), 8.23 (s, 1H, imidazo[4,5-b]pyrazine 5-H); LC-MS (ESI, m/z) Rt=3.29 min—527/529 [(M+H⁺), Br isotopic pattern, 100%]; ESI-HRMS: Found: 527.0977, calculated for $C_{22}H_{24}BrN_8OS$ (M+H⁺): 527.0977.

Example 8

2-{4-[6-Bromo-2-(4-dimethylaminomethyl-phenyl)-3H-imidazo[4,5-b]pyridin-7-yl]-piperazin-1-yl}-N-thiazol-2-yl-acetamide

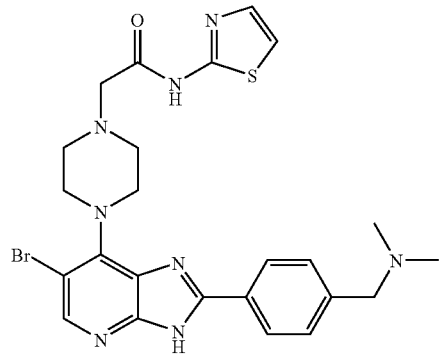

To a solution of 2-{4-[2-(4-aminomethyl-phenyl)-6-bromo-3H-imidazo[4,5-b]pyridin-7-yl]-piperazin-1-yl}-N-thiazol-2-yl-acetamide (0.042 g, 0.07 mmol) in THF (2 ml) and methanol (2 ml) was added 38% aq. formaldehyde (13 µL, 0.17 mmol) and NaBH₃CN (11 mg, 0.17 mmol). The reaction mixture was stirred at room temperature for 3 h then concentrated in vacuo. The crude product was purified by chromatography on silica gel (100% chloroform to chloroform/methanol 10:1). The isolated fraction was run through a 2 g SCX cartridge and the compound eluted with 0.1M $NH_3$ in methanol to give the title compound as a white solid (0.30 g, 68%);

¹H-NMR (500 MHz, DMSO-d₆) 2.17 (s, 6H, N(CH₃)₂), 2.78 (broad t, 4H, piperazine N(CH₂)₂), 3.40 (s, 2H, CH₂), 3.46 (s, 2H, CH₂), 3.70 (broad t, 4H, piperazine N(CH₂)₂), 7.23 (d, 1H, J=3.6 Hz, thiazole 4-H or 5-H), 7.45 (d, 2H, J=8.1 Hz, 3,5-ArH), 7.49 (d, 1H, J=3.6 Hz, thiazole 4-H or 5-H), 8.14 (d, 2H, J=8.1 Hz, 2,6-ArH), 8.24 (s, 1H, imidazo[4,5-b]pyrazine 5-H), 11.91 (broad s, 1H, CONH), 13.49 (s, 1H, imidazo[4,5-b]pyrazine NH); LC-MS (ESI, m/z) Rt=3.36 min—555/557 [(M+H⁺), Br isotopic pattern, 100%]; ESI-HRMS: Found: 555.1308, calculated for $C_{24}H_{28}BrN_8OS$ (M+H⁺): 555.1290.

Example 9

5-Chloro-3-nitro-4-[4-(2-phenoxy-ethyl)-piperazin-1-yl]-pyridin-2-ylamine

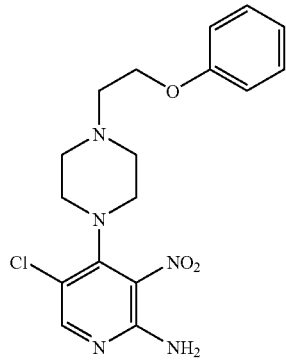

A mixture of 1-(2-phenoxy-ethyl)-piperazine (0.047 g, 0.23 mmol), isopropanol (4.0 ml), and 2-amino-4,5-dichloro-3-nitropyridine (0.034 g, 0.16 mmol) was heated at 45° C. for 18 h. The reaction mixture was allowed to cool to room temperature, absorbed on silica gel and the free running powder was placed on a 10 g isolute silica column which was eluted with 10% ethyl acetate in dichloromethane, 20% ethyl acetate in dichloromethane and finally 1% methanol in ethyl acetate/dichloromethane (v/v; 1:4). The title compound was obtained as a yellow solid (0.053 g, 88%); $^1$H-NMR (500 Mz, DMSO-$d_6$) 2.62 (br s, 4H, piperazine N(CH$_2$)$_2$), 2.76 (t, J=5.62 Hz, 2H, NCH$_2$CH$_2$O), 3.06 (br s, 4H, piperazine N(CH$_2$)$_2$), 4.09 (t, J=5.37 Hz, 2H, NCH$_2$CH$_2$O), 6.95 (m, 5H, 2-NH$_2$ and o-ArH and p-ArH), 7.27 (t, J=11.20 Hz, 2H, m-ArH), 8.06 (s, 1H, 6-H); LC-MS (ESI, m/z) 3.79 min—378, 380 [(M+H)⁺, Cl isotopic pattern].

(4-{6-Chloro-7-[4-(2-phenoxy-ethyl)-piperazin-1-yl]-3H-imidazo[4,5-b]pyridin-2-yl}-phenyl)-dimethyl-amine

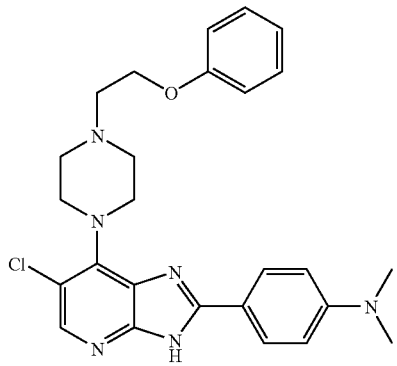

To a mixture of 5-chloro-3-nitro-4-[4-(2-phenoxy-ethyl)-piperazin-1-yl]-pyridin-2-ylamine (0.037 g, 0.10 mmol), ethanol (3 ml), and 4-dimethylamino-benzaldehyde (0.021 g, 0.14 mmol) was added a freshly prepared aqueous solution of Na$_2$S$_2$O$_4$ (1M; 0.4 ml, 0.4 mmol). The reaction mixture was heated at 70° C. for 5.5 h, then allowed to cool to room temperature and the solvents were removed in vacuo. The residue was absorbed on silica gel and the free running powder was placed on a 10 g isolute silica column, which was eluted with 1 to 2.5% gradient of methanol in ethyl acetate/dichloromethane (v/v; 1:1). The title compound was isolated as a pale yellow solid after trituration with diethyl ether (0.011 g, 23%); %); $^1$H-NMR (500 Mz, DMSO-$d_6$) 2.72 (br s, 4H, piperazine N(CH$_2$)$_2$), 2.79 (t, J=5.46 Hz, 2H, NCH$_2$CH$_2$O), 3.68 (br s, 4H, piperazine N(CH$_2$)$_2$), 4.15 (t, J=5.70 Hz, 2H, NCH$_2$CH$_2$O), 6.82 (d, J=10.17 Hz, 2H) and 8.00 (d, J=8.93 Hz, 2H) (3,5-C$_6$H$_4$—NMe$_2$ and 3,5-C$_6$H$_4$—NMe$_2$) 6.93 (t, J=6.7 Hz, 1H, p-ArH), 6.99 (d, J=8.92 Hz, 2H, o-ArH), 7.30 (t, J=8.16 Hz, 2H, m-ArH), 8.03 (s, 1H, imidazo[4,5-b]pyridine 5-H), 13.10 (s, 1H, imidazo[4,5-b]pyridine N—H); LC-MS (ESI, m/z) 5.57 min—477, 479 [(M+H)⁺, Cl isotopic pattern]; ESI-HRMS: Found: 477.2162, calculated for $C_{26}H_{30}N_6OCl$ (M+H)⁺: 477.2170.

Example 10

2-(4-(2,3-Diamino-5-bromopyridin-4-yl)piperazin-1-yl)-N-(thiazol-2-yl)acetamide

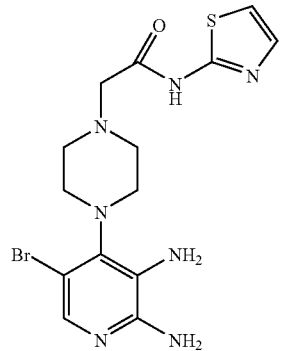

A mixture of 2-[4-(2-amino-5-bromo-3-nitro-pyridin-4-yl)-piperazin-1-yl]-N-thiazol-2-yl-acetamide (0.200 g, 0.47 mmol), ethanol (6 ml), and 1M aqueous Na$_2$S$_2$O$_4$ (1.8 ml) was stirred at 80° C. for 16 h. The reaction mixture was then allowed to cool to room temperature; the solvents were removed in vacuo, and the residue was absorbed on a silica gel. The free-running powder was placed on a 10 g isolute silica column, and elution of the column with a gradient of methanol (0 to 3%) in ethyl acetate gave the title compound (0.104 g, 54%); $^1$H-NMR (250 MHz, DMSO-$d_6$) 2.53, 2.70, 2.81, 3.50 (4×br s, 8H, piperazine N(CH$_2$)$_2$), 3.35 (s, 2H, NCH$_2$CO), 4.75 (s, 2H, NH$_2$), 5.60 (s, 2H, NH$_2$) 7.23 (d, J=3.46 Hz, 1H, thiazole 4-H or 5-H), 7.30 (s, 1H, 6-H), 7.48 (d, J=3.48 Hz, 1H, thiazole 4-H or 5-H);

LC-MS (ESI, m/z): Rt=1.75 min—412, 414 [(M+H⁺), Br isotopic pattern, 100%];

2-[4-(6-Bromo-3H-imidazo[4,5-b]pyridin-7-yl)-piperazin-1-yl]-N-thiazol-2-yl-acetamide

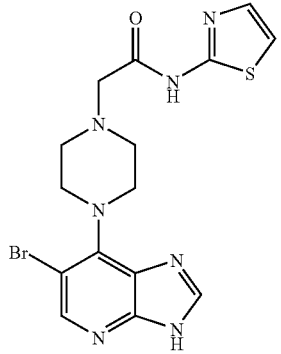

To 2-[4-(2,3-diamino-5-bromo-pyridin-4-yl)-piperazin-1-yl]-N-thiazol-2-yl-acetamide (0.1 g, 0.24 mmol) in trimethyl orthoformate (3 ml) was added conc. HCl (20 μL). The reaction mixture was stirred at room temperature for 8 h. Conc. HCl (20 μL) was added, and the reaction mixture was stirred at room temperature for another 16 h then concentrated in vacuo.

The crude product was purified by chromatography on silica gel (100% ethyl acetate to ethyl acetate/methanol 9:1 to chloroform/methanol 9:1). The isolated fraction was run through a 2 g SCX cartridge and the compound was eluted with 0.1M NH$_3$ in methanol to give the title compound as a glass solid (0.020 g, 20%);
$^1$H-NMR (250 MHz, DMSO-d$_6$) 2.78 (broad s, 4H, piperazine N(CH$_2$)$_2$), 3.42 (s, 2H, NCH$_2$CO), 3.66 (broad s, 4H, piperazine N(CH$_2$)$_2$), 7.23 (d, 1H, J=3.32 Hz, thiazole 4-H or 5-H), 7.49 (1H, d, J=3.97 Hz, thiazole 4-H or 5-H), 8.25 (s, 1H, imidazo[4,5-b]pyridine 5-H);
LC-MS (ESI, m/z): Rt=3.92 min—422, 424 [(M+H)⁺, Br isotopic pattern];
ESI-HRMS Found: 422.0392, calculated for C$_{15}$H$_{17}$BrN$_7$OS (M+H)⁺: 422.0398.

Example 11

(3-{6-Bromo-7-[4-(thiazol-2-ylcarbamoylmethyl)-piperazin-1-yl]-3H-imidazo[4,5-b]pyridin-2-yl}-benzyl)-carbamic acid tert-butyl ester

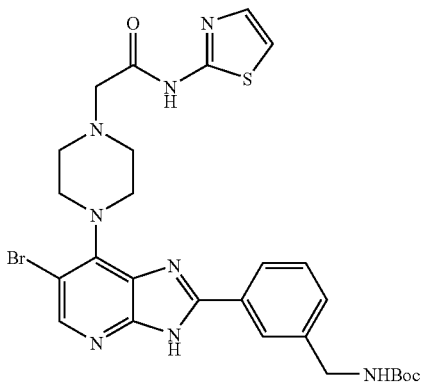

To 2-[4-(2-Amino-5-bromo-3-nitro-pyridin-4-yl)-piperazin-1-yl]-N-thiazol-2-yl-acetamide (0.1 g, 0.22 mmol) in ethanol (5 ml) was added tert-butyl N-(3 formylbenzyl)carbamate (69 mg, 0.29 mmol) and 1M aq. Na$_2$S$_2$O$_4$ (900 μL, 0.9 mmol). The reaction mixture was stirred at 80° C. for 16 h. tert-Butyl N-(3 formylbenzyl)carbamate (20 mg, 0.08 mmol) and 1M aq. Na$_2$S$_2$O$_4$ (200 μL, 0.2 mmol) were added and the reaction mixture was stirred for another 5 h. The reaction mixture was concentrated in vacuo. The crude product was purified by chromatography on silica gel (100% dichloromethane to dichloromethane/ethyl acetate 1:1+1% methanol to 2% methanol in ethyl acetate). The isolated product was further triturated in ether, filtered, and dried in vacuo to give the title compound as a pale yellow solid (0.038 g, 27%);
$^1$H-NMR (500 MHz, DMSO-d$_6$) 1.39 (s, 9H, CH$_3$ Boc), 2.78 (broad s, 4H, piperazine N(CH$_2$)$_2$), 3.40 (s, 2H, CH$_2$CO), 3.70 (broad s, 4H, piperazine N(CH$_2$)$_2$), 4.22 (d, J=6.23 Hz, 2H, CH$_2$NHBOC), 7.24 (d, 1H, J=3.60 Hz, thiazole 4-H or 5-H), 7.37 (d, J=7.21 Hz, 1H) and 8.02 (d, J=7.21 Hz, 1H) (4-ArH, and 6-ArH), 7.47 (m, 1H, 5-ArH), 7.49 (d, J=4.12 Hz, 1H, thiazole 4-H or 5-H), 8.11 (s, 1H, imidazo[4,5-b]pyridine 5-H), 11.89 (s, 1H, CONH), 13.54 (s, 1H, imidazo[4,5-b]pyridine NH);
LC-MS (ESI, m/z) Rt=6.92 min—627, 629 [(M+H⁺), Br isotopic pattern, 100%];
ESI-HRMS Found: 627.1513, calculated for C$_{27}$H$_{32}$BrN$_8$O$_3$S (M+H)⁺: 627.1501.

Example 12

2-{4-[2-(3-Aminomethyl-phenyl)-6-bromo-3H-imidazo[4,5-b]pyridin-7-yl]-piperazin-1-yl}-N-thiazol-2-yl-acetamide

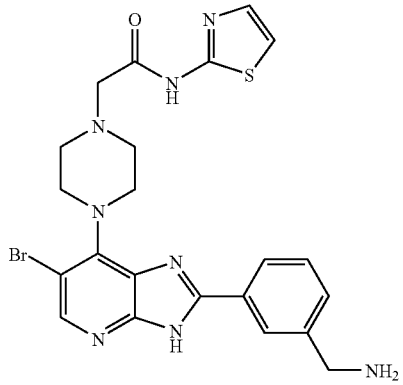

To (3-{6-Bromo-7-[4-(thiazol-2-ylcarbamoylmethyl)-piperazin-1-yl]-3H-imidazo[4,5-b]pyridin-2-yl}-benzyl)-carbamic acid tert-butyl ester (0.027 g, 0.04 mmol) in dichloromethane (5 mL) was slowly added trifluoroacetic acid (0.5 mL) at 0° C. trifluoroacetic acid (0.25 mL) was added and the reaction mixture was stirred for 1 h. The reaction mixture was stirred at room temperature for 1 h then concentrated in vacuo. The crude product was run trough a 2 g SCX cartridge and eluted with 0.1M NH$_3$ in methanol to give the title compound as a pale yellow solid (0.023 g, 100%);
$^1$H-NMR (250 MHz, DMSO-d$_6$) 2.78 (broad t, 4H, J=4.5 Hz, piperazine N(CH$_2$)$_2$), 3.41 (s, 2H, NCH$_2$CO), 3.70 (broad t, 4H, J=4.5 Hz, piperazine N(CH$_2$)$_2$), 3.83 (s, 2H, CH$_2$), 7.23 (d, 1H, J=3.6 Hz, thiazole 4-H or 5-H), 7.48 (m, 3H, thiazole 4-H or 5-H and 2 ArH), 8.03 (m, 1H, ArH), 8.18 (broad s, 1H, ArH), 8.18 (s, 1H, imidazo[4,5-b]pyridine 5-H);
LC-MS (ESI, m/z): Rt=3.39 min—527, 529 [(M+H⁺), Br isotopic pattern, 100%]; ESI-HRMS Found: 527.0964; calculated for C$_{22}$H$_{24}$BrN$_8$OS (M+H)⁺: 527.0977.

Example 13

2-{4-[6-Bromo-2-(3-dimethylaminomethyl-phenyl)-3H-imidazo[4,5-b]pyridin-7-yl]-piperazin-1-yl}-N-thiazol-2-yl-acetamide

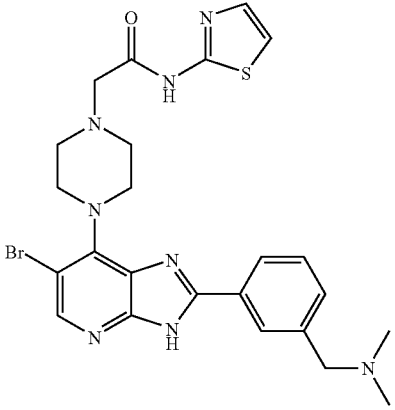

To 2-{4-[2-(3-Aminomethyl-phenyl)-6-bromo-3H-imidazo[4,5-b]pyridin-7-yl]-piperazin-1-yl}-N-thiazol-2-yl-acetamide (0.018 g, 0.03 mmol) in THF (1.5 mL) and methanol (1 mL) was added 38% aq. formaldehyde (10 μL, 0.07 mmol) and NaBH$_3$CN (5 mg, 0.07 mmol) in methanol (1 mL). The reaction mixture was stirred at room temperature for 2 h. 38% aq. formaldehyde (10 μL, 0.07 mmol) and NaBH$_3$CN (5 mg, 0.07 mmol) in methanol (1 mL) were added and the reaction mixture was stirred for 2 h then concentrated in vacuo. The crude product was purified by chromatography on silica gel (100% chloroform to chloroform/methanol 95:5) to give the title compound as a white solid (0.017 g, 93%);

$^1$H-NMR (250 MHz, DMSO-d$_6$) 2.18 (s, 6H, N(CH$_3$)$_2$), 2.78 (broad s, 4H, piperazine N(CH$_2$)$_2$), 3.41 (s, 2H, CH$_2$), 3.47 (s, 2H, CH$_2$), 3.70 (s, 4H, piperazine N(CH$_2$)$_2$), 7.24 (d, J=3.6 Hz, 1H, thiazole, 4-H or 5-H), 7.42 (broad d, J=7.5 Hz, Ar—H), 7.49 (m, 2H, thiazole 4-H or 5-H and Ar—H), 8.08 (broad d, J=7.5 Hz, 2H, Ar—H), 8.13 (broad s, Ar—H), 8.25 (s, 1H, imidazo[4,5-b]pyridine 5-H), 11.90 (broad s, 1H, CONH), 13.52 (broad s, 1H, imidazo[4,5-b]pyridine NH);

LC-MS (ESI, m/z): Rt=3.43 min—555, 557 [(M+H$^+$), Br isotopic pattern];

ESI-HRMS Found: 555.1300; calculated for C$_{24}$H$_{28}$BrN$_8$OS (M+H)$^+$: 555.1290.

Example 14 tert-Butyl 4-(2-amino-5-bromo-3-nitropyridin-4-yl)piperazine-1-carboxylate

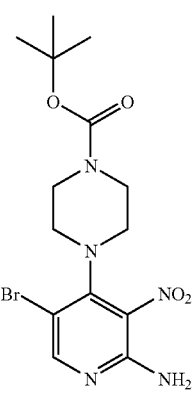

To a mixture of 5-bromo-4-chloro-3-nitro-pyridin-2-ylamine (0.126 g, 0.50 mmol) and isopropanol (9 ml) was added 1-BOC-piperazine (0.102 g, 0.55 mmol) followed by diisopropylethylamine (0.10 ml, 0.57 mmol). The reaction mixture was heated at 45° C. for 20 h, then allowed to cool to room temperature, and diluted with isopropanol (3 ml). The precipitate was collected by filtration and washed with isopropanol and diethyl ether. The title compound was thus obtained as a yellow solid (0.112 g, 56%). $^1$H-NMR (500 MHz, DMSO-d$_6$) 1.42 (s, 9H, C(CH$_3$)$_3$), 2.99 (br s, 4H, piperazine N(CH$_2$)$_2$), 3.45 (br s, 4H, piperazine N(CH$_2$)$_2$), 7.02 (s, 2H, NH$_2$), 8.20 (s, 1H, 6-H); LC (Method B)-MS (ESI, m/z): Rt=5.00 min—402, 404 [(M+H)$^+$, Br isotopic pattern].

4-[6-Bromo-2-(4-dimethylamino-phenyl)-3H-imidazo[4,5-b]pyridin-7-yl]-piperazine-1-carboxylic acid tert-butyl ester

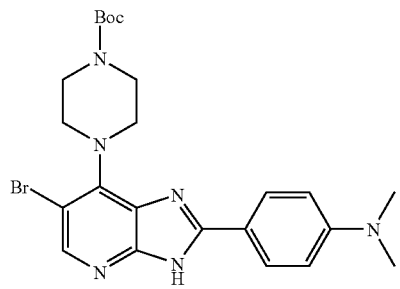

To tert-butyl 4-(2-amino-5-bromo-3-nitropyridin-4-yl)piperazine-1-carboxylate (0.5 g, 1.2 mmol) in EtOH (20 mL) was added 4-dimethylaminobenzaldehyde (0.241 g, 1.6 mmol), and 1M Na$_2$S$_2$O$_4$ (4.7 mL, 4.7 mmol) The reaction mixture was stirred at 80° C. for 16 h then concentrated in vacuo. The residue was purified by chromatography (100% dichloromethane to dichloromethane/ethyl acetate 1/1, 2% MeOH in dichloromethane/ethyl acetate 1/1, and 2% MeOH in CHCl$_3$). The compound is further triturated in dichloromethane/methanol 9/1, filtered and dried in vacuo to give the title compound as a solid (0.394 g, 63% yield).

$^1$H NMR (500 MHz, CDCl$_3$/CD$_3$OD) 1.45 (s, 9H, C(CH$_3$)$_3$), 3.00 (s, 6H, N(CH$_3$)$_2$), 3.62 (broad t, J=4.8 Hz, 4H, N(CH$_2$)$_2$), 3.72 (broad t, J=4.8 Hz, 4H, N(CH$_2$)$_2$), 6.73 (d, J=9.1 Hz, 2H, ArH), 7.93 (d, J=9.1 Hz, 2H, ArH), 8.07 (s, 1H, imidazo[4,5-b]pyridine 5-H);

LC-MS (ESI, m/z): Rt=9.24 min; 501, 503-[(M+H)$^+$, Br isotopic pattern];

ESI-HRMS Found: 501.1614, calculated for C$_{23}$H$_{30}$BrN$_6$O$_2$ (M+H)$^+$: 501.1613.

Example 15

[4-(6-Bromo-7-piperazin-1-yl-3H-imidazo[4,5-b]pyridin-2-yl)-phenyl]-dimethyl-amine

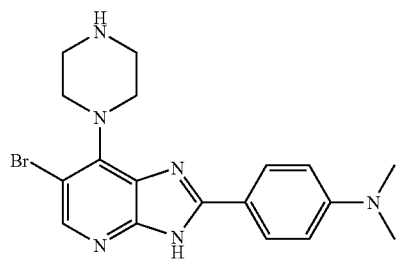

To 4-[6-Bromo-2-(4-dimethylamino-phenyl)-3H-imidazo[4,5-b]pyridin-7-yl]-piperazine-1-carboxylic acid tert-butyl ester (0.380 g, 0.75 mmol) in dichloromethane (20 mL) at 0° C. was added slowly TFA (2 mL) and the reaction mixture was stirred at rt for 30 mins. TFA (1 mL) was added and the reaction mixture was stirred at room temperature for 1 h. The reaction mixture was concentrated in vacuo and TFA was co-evaporated with $CH_3CN$. The crude product was run trough a 5 g SCX cartridge and eluted with 0.1M $NH_3$ in methanol. The compound was further triturated in ether/methanol 9/1 to give the title compound as a solid (0.228 g, 75%);

$^1$H NMR (500 MHz, DMSO-$d_6$) 2.95 (broad t, 4H, J=4.8 Hz, N($CH_2$)$_2$), 3.56 (broad t, 4H, J=4.8 Hz, N($CH_2$)$_2$), 6.82 (d, J=8.9 Hz, 2H, ArH), 8.01 (d, J=8.9 Hz, 2H, ArH), 8.15 (s, 1H, imidazo[4,5-b]pyridine 5-H).

LC-MS (ESI, m/z): Rt=4.08 min—401, 403 [(M+H)$^+$, Br isotopic pattern}; ESI-HRMS Found: 401.1085, calculated for $C_{18}H_{22}BrN_6$ (M+H$^+$): 401.1089.

Example 16

5-Chloro-4-(4-(2-chloro-6-fluorobenzyl)piperazin-1-yl)-3-nitropyridin-2-amine

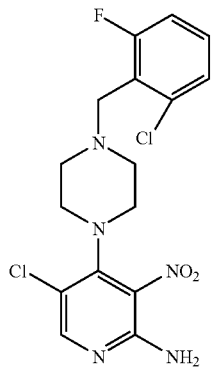

A mixture of 1-(2-chloro-6-fluorobenzyl)piperazine (0.063 g, 0.28 mmol), isopropanol (4.3 ml), and 2-amino-4,5-dichloro-3-nitropyridine (0.042 g, 0.20 mmol) was heated at 45° C. for 22 h. The reaction mixture was allowed to cool to room temperature, and concentrated in vacuo. The residue was absorbed on silica gel and the free running powder was placed on a 10 g isolute silica column which was eluted first with 30% petroleum ether 60-80° C., and then ethyl acetate. The title compound was obtained as a yellow solid (0.050 g, 62%); $^1$H-NMR (500 Mz, DMSO-$d_6$) 2.56 (br s, 4H, piperazine N($CH_2$)$_2$), 3.01 (br s, 4H, piperazine N($CH_2$)$_2$), 3.66 (s, 2H, NCH$_2$), 6.94 (s, 2H, 2-NH$_2$), 7.23 (t, J=8.91 Hz, 1H) and 7.38 (m, 2H) (ArH), 8.06 (s, 1H, 6-H); LC-MS (ESI, m/z) 4.85 min—400, 402, 404 [(M+H)$^+$, Cl$_2$ isotopic pattern].

4-(6-Chloro-7-(4-(2-chloro-6-fluorobenzyl)piperazin-1-yl)-3H-imidazo[4,5-b]pyridin-2-yl)-N,N-dimethylaniline

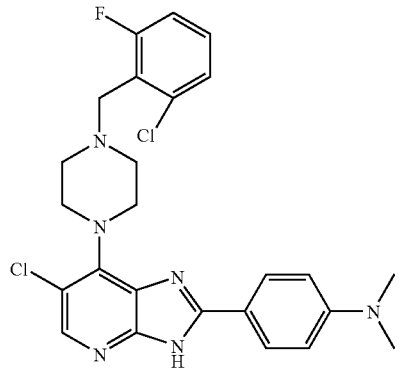

To a mixture of 5-chloro-4-(4-(2-chloro-6-fluorobenzyl)piperazin-1-yl)-3-nitropyridin-2-amine (0.045 g, 0.11 mmol), ethanol (3.2 ml), and 4-dimethylaminobenzaldehyde (0.022 g, 0.15 mmol) was added a freshly prepared aqueous solution of $Na_2S_2O_4$ (1M; 0.4 ml, 0.4 mmol). The reaction mixture was heated at 70° C. for 6 h, then allowed to cool to room temperature and the solvents were removed in vacuo. The residue was absorbed on silica gel and the free running powder was placed on a 10 g isolute silica column, which was eluted with diethyl ether/dichloromethane (v/v; 1:1). The title compound was isolated as a pale yellow solid after trituration with diethyl ether (0.09 g, 16%); $^1$H-NMR (500 Mz, DMSO-$d_6$) 2.68 (br s, 4H, piperazine N($CH_2$)$_2$), 2.99 (s, 6H, N($CH_3$)$_2$), 3.63 (br s, 4H, piperazine N($CH_2$)$_2$), 3.70 (s, 2H, NCH$_2$), 6.80 (d, J=8.56 Hz, 2H) and 8.00 (d, J=8.55 Hz, 2H) (3,5-$C_6H_4$—NMe$_2$ and 2,6-$C_6H_4$—NMe$_2$) 7.26 (t, J=9.78 Hz, 1H) and 7.40 (m, 2H) (ArH), 8.03 (s, 1H, imidazo[4,5-b]pyridine 5-H), 13.12 (s, 1H, imidazo[4,5-b]pyridine N—H);

LC-MS (ESI, m/z): 6.54 min—499, 501, 503 [(M+H)$^+$, Cl$_2$ isotopic pattern]; ESI-HRMS: Found: 499.1587, calculated for $C_{25}H_{26}N_6Cl_2F$ (M+H)$^+$: 499.1580.

Example 17

5-Chloro-3-nitro-4-(4-(1-phenylethyl)piperazin-1-yl)pyridin-2-amine

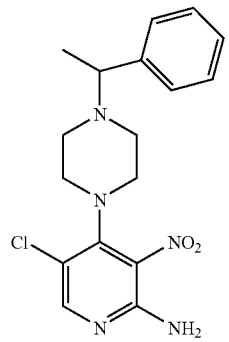

The method followed that used to prepare 2-[4-(2-amino-5-chloro-3-nitro-pyridin-4-yl)-piperazin-1-yl]-N-thiazol-2-yl-acetamide (Example 1, step 5), but using 2-amino-4,5-dichloro-3-nitropyridine (0.034 g, 0.16 mmol), isopropanol (3.5 ml), and 1-(1-phenylethyl)piperazine (0.048 g, 0.25 mmol). Purification of the crude product on a silica isolute column using a gradient of ethyl acetate in dichloromethane as eluant (10 to 20%) afforded the title compound as a yellow solid (0.047 g, 81%). $^1$H-NMR (500 Mz, DMSO-$d_6$) 1.30 (d, J=6.7 Hz, 3H, CH$_3$), 2.40 (br s), and 2.53 (br s, obscured by DMSO peak) (4H, piperazine N(CH$_2$)$_2$), 3.03 (br s, 4H, piperazine N(CH$_2$)$_2$), 3.45 (m, 1H, NCHCH$_3$), 6.98 (s, 2H, 2-NH$_2$), 7.25 (m, 1H) and 7.32 (m, 2H) (ArH), 8.06 (s, 1H, 6-H);

LC-MS (ESI, m/z): 3.37 min—362, 364 [(M+H)$^+$, Cl isotopic pattern].

4-(6-chloro-7-(4-(1-phenylethyl)piperazin-1-yl)-3H-imidazo[4,5-b]pyridin-2-yl)-N,N-dimethylaniline

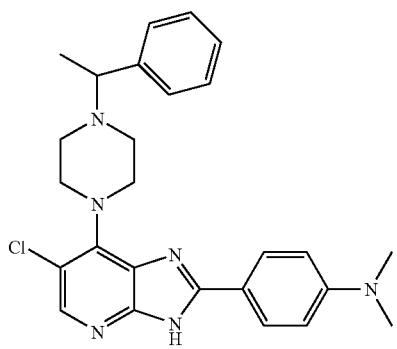

To a mixture of 5-chloro-3-nitro-4-(4-(1-phenylethyl)piperazin-1-yl)pyridin-2-amine (0.038 g, 0.10 mmol), ethanol (3 ml), and 4-dimethylamino-benzaldehyde (0.023 g, 0.15 mmol) was added a freshly prepared aqueous solution of Na$_2$S$_2$O$_4$ (1M; 0.44 ml, 0.44 mmol). The reaction mixture was heated at 70° C. for 6 h, then allowed to cool to room temperature and the solvents were removed in vacuo. The residue was absorbed on silica gel and the free running powder was placed on a 10 g isolute silica column, which was eluted with 2.5% methanol in ethyl acetate/dichloromethane (v/v; 1:1). The obtained yellow solid was suspended in dichloromethane (2 ml), and then a solution of HCl in methanol (1.25 M; 0.8 ml) was added. The mixture was stirred for approximately 1 min, and then diethyl ether was added. The yellow precipitate was collected by filtration, washed with ether to afford the title compound as a hydrochloride salt. (0.013 g); $^1$H-NMR (500 Mz, CD$_3$OD) 1.90 (d, J=5.43 Hz, 3H, CHCH$_3$), 3.43 (m), 3.96 (m), 4.12 (m) (8H, piperazine N(CH$_2$)$_2$), 3.21 (s, 6H, N(CH$_3$)$_2$), 4.65 (m, 1H, NCHCH$_3$), 7.14 (d, J=7.30 Hz, 2H) and 8.14 (d, J=7.32 Hz, 2H) (3,5-C$_6$H$_4$—NMe$_2$ and 2,6-C$_6$H$_4$—NMe$_2$) 7.55 (m, 3H) and 7.66 (m, 2H) (ArH), 8.41 (s, 1H, imidazo[4,5-b]pyridine 5-H);

LC-MS (ESI, m/z): 5.32 min—461, 463 [(M+H)$^+$, Cl isotopic pattern]; ESI-HRMS: Found: 461.2214, calculated for C$_{26}$H$_{29}$ClN$_6$ (M+H)$^+$: 461.2220.

Example 18

(4-(2-Amino-5-chloro-3-nitropyridin-4-yl)piperazin-1-yl)(4-methoxyphenyl)methanone

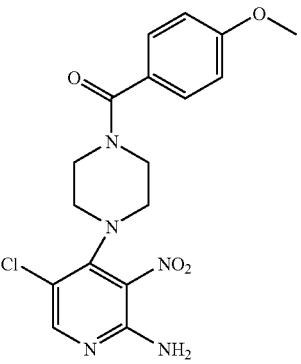

The method followed that used to prepare 2-[4-(2-amino-5-chloro-3-nitro-pyridin-4-yl)-piperazin-1-yl]-N-thiazol-2-yl-acetamide (Example 1, step 5), but using 2-amino-4,5-dichloro-3-nitropyridine (0.034 g, 0.16 mmol), isopropanol (3.0 ml), and (4-methoxyphenyl)(piperazin-1-yl)methanone (0.055 g, 0.25 mmol). Purification of the crude product on an isolute silica column using a gradient of ethyl acetate in dichloromethane as eluant (10 to 30%) afforded the title compound as a yellow solid (0.038 g, 61%). $^1$H-NMR (500 Mz, DMSO-$d_6$) 3.13 (br s, 4H, piperazine N(CH$_2$)$_2$), 3.65 (br s, 4H, piperazine N(CH$_2$)$_2$), 3.86 (s, 3H, OCH$_3$), 7.06 (d, J=8.27 Hz, 2H) and 7.47 (d, J=8.21 Hz, 2H) (2,6-C$_6$H$_4$—OMe and 3,5-C$_6$H$_4$—OMe), 7.14 (s, 2H, 2-NH$_2$), 8.19 (s, 1H, 6-H);

LC-MS (ESI, m/z): 6.97 min—392, 394 [(M+H)$^+$, Cl isotopic pattern].

(4-(6-Chloro-2-(4-(dimethylamino)phenyl)-3H-imidazo[4,5-b]pyridin-7-yl)piperazin-1-yl)(4-methoxyphenyl)methanone

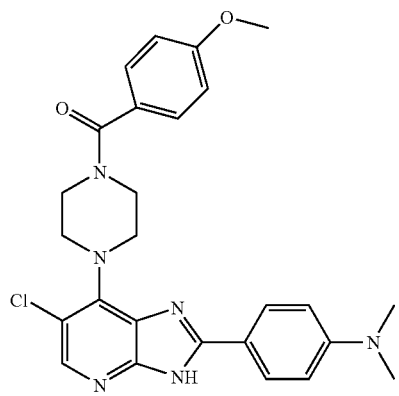

To a mixture of (4-(2-amino-5-chloro-3-nitropyridin-4-yl)piperazin-1-yl)(4-methoxyphenyl)methanone (0.034 g, 0.09 mmol), ethanol (3 ml), and 4-dimethylamino-benzaldehyde (0.018 g, 0.12 mmol) was added a freshly prepared aqueous solution of Na$_2$S$_2$O$_4$ (1M; 0.35 ml, 0.35 mmol). The reaction mixture was heated at 70° C. for 5 h, then allowed to cool to room temperature and the solvents were removed in vacuo. The residue was absorbed on silica gel and the free running powder was placed on a 10 g isolute silica column, which was eluted first with ethyl acetate/dichloromethane (v/v; 6:4) and then 2% methanol in ethyl acetate/dichloromethane (v/v; 1:1). The title compound was isolated as a pale yellow solid after trituration with diethyl ether (0.008 g, 20%); $^1$H-NMR (500 Mz, DMSO-d$_6$) 3.00 (s, 6H, N(CH$_3$)$_2$), 3.68 (br s), and 3.72 (br s) (8H, piperazine N(CH$_2$)$_2$), 3.81 (s, 3H, OCH$_3$), 6.82 (d, J=8.93 Hz, 2H), and 8.01 (d, J=8.85 Hz, 2H) (2,6-C$_6$H$_4$—NMe$_2$ and 3,5-C$_6$H$_4$—NMe$_2$), 7.02 (d, J=8.64 Hz, 2H) and 7.45 (d, J=8.62 Hz, 2H) (2,6-C$_6$H$_4$—OMe and 3,5-C$_6$H$_4$—OMe), 8.06 (s, 1H, imidazo[4,5-b]pyridine 5-H), 13.15 (s, 1H, imidazo[4,5-b]pyridine N—H);

LC-MS (ESI, m/z): 8.51 min—491, 493 [(M+H)$^+$, Cl isotopic pattern]; ESI-HRMS: Found: 491.1955, calculated for C$_{26}$H$_{28}$ClN$_6$O$_2$ (M+H)$^+$: 491.1962.

Example 19

2-(4-(6-Chloro-2-(4-methoxyphenyl)-3H-imidazo[4,5-b]pyridin-7-yl)piperazin-1-yl)-N-(thiazol-2-yl)acetamide

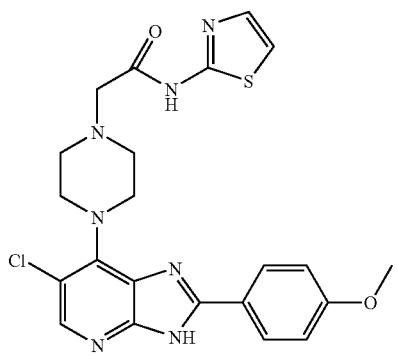

To a mixture of 2-[4-(2-amino-5-chloro-3-nitro-pyridin-4-yl)-piperazin-1-yl]-N-thiazol-2-yl-acetamide (0.040 g, 0.10 mmol), ethanol (3 ml), and p-methoxybenzaldehyde (0.019 g, 0.14 mmol) was added a freshly prepared aqueous solution of Na$_2$S$_2$O$_4$ (1M; 0.4 ml, 0.4 mmol). The reaction mixture was heated at 70° C. for 5 h, then allowed to cool to room temperature and the solvents were removed in vacuo. The residue was absorbed on silica gel and the free running powder was placed on a 10 g isolute silica column which was eluted with 50% dichloromethane in ethyl acetate and then 2.5% methanol in ethyl acetate/dichloromethane (v/v; 1:1). The title compound was obtained as a pale yellow solid after trituration with diethyl ether (0.012 g, 25%); $^1$H-NMR (500 MHz, DMSO-d$_6$) 2.76 (br s, 4H, piperazine N(CH$_2$)$_2$), 3.40 (s, 2H, NCH$_2$CO), 3.72 (br s, 4H, piperazine N(CH$_2$)$_2$), 3.83 (s, 3H, OCH$_3$), 7.10 (d, J=8.79 Hz, 2H, 3,5-ArH or 2,6-ArH), 7.24 (d, J=3.51 Hz, 1H) and 7.50 (d, J=3.55 Hz, 1H) (thiazole 4-H, 5-H), 8.09 (s, 1H, imidazo[4,5-b]pyridine 5-H), 8.13 (d, 2H, J=8.76 Hz, 3,5-ArH or 2,6-ArH); 11.95 (s, 1H, CONH), 13.72 (s, 1H, imidazo[4,5-b]pyridine N—H);

LC-MS (ESI, m/z): Rt=6.05 min—484, 486 [(M+H)$^+$, Cl isotopic pattern]. ESI-HRMS: Found: 484.1324, calculated for C$_{22}$H$_{23}$ClN$_7$O$_2$S (M+H)$^+$: 484.1322.

Example 20

2-(4-(2-Amino-5-bromo-3-nitropyridin-4-yl)piperazin-1-yl)-N-phenylacetamide

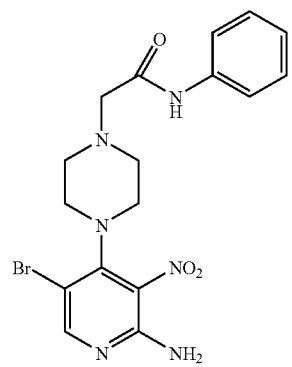

To a mixture of 5-bromo-4-chloro-3-nitro-pyridin-2-ylamine (0.126 g, 0.50 mmol) and isopropanol (10 ml) was added N-phenyl-2-piperazin-1-yl-acetamide×2HCl salt (0.160 g, 0.55 mmol) followed by diisopropylethylamine (0.32 ml, 1.76 mmol). The reaction mixture was heated at 45° C. for 18 h, then allowed to cool to room temperature and the solvents were removed in vacuo. The residue was absorbed on silica gel and the free running powder was placed on a 10 g isolute silica column which was eluted with 30% ethyl acetate in dichloromethane. The title compound was obtained as a pale yellow solid (0.134 g, 62%); $^1$H-NMR (500 MHz, DMSO-d$_6$) 2.67 (br s, 4H, piperazine N(CH$_2$)$_2$), 3.12 (br s, 4H, piperazine N(CH$_2$)$_2$), 3.19 (s, 2H, NCH$_2$CO), 7.06 (m, 3H, 2-NH$_2$, p-ArH), 7.31 (t, J=7.44 Hz, 2H, m-ArH), 7.62 (d, J=8.29 Hz, 2H, o-ArH), 8.16 (s, 1H, 6-H), 9.76 (s, 1H, CONH);

LC-MS (ESI, m/z): Rt=4.64 min—435, 437 [(M+H)$^+$, Br isotopic pattern].

2-(4-(6-Bromo-2-(4-(dimethylamino)phenyl)-3H-imidazo[4,5-b]pyridin-7-yl)piperazin-1-yl)-N-phenylacetamide

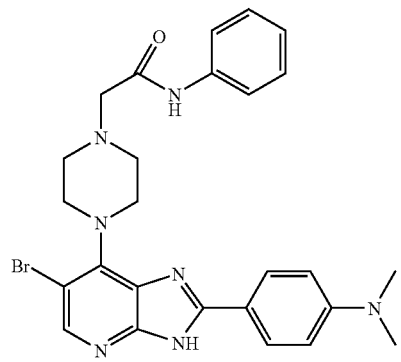

To a mixture of 2-(4-(2-amino-5-bromo-3-nitropyridin-4-yl)piperazin-1-yl)-N-phenylacetamide (0.052 g, 0.12 mmol), ethanol (3.5 ml), and 4-dimethylaminobenzaldehyde (0.025 g, 0.17 mmol) was added a freshly prepared aqueous solution of $Na_2S_2O_4$ (1M; 0.48 ml, 0.48 mmol). The reaction mixture was heated at 70° C. for 5 h, then allowed to cool to room temperature and the solvents were removed in vacuo. The residue was absorbed on silica gel and the free running powder was placed on a 10 g isolute silica column which was eluted with 50% dichloromethane in ethyl acetate and then 2% methanol in ethyl acetate/dichloromethane (v/v; 1:1). The title compound was obtained as a yellow solid after trituration with diethyl ether (0.011 g, 17%); $^1$H-NMR (500 MHz, DMSO-$d_6$) 2.76 (br s, 4H, piperazine N(CH$_2$)$_2$), 2.99 (s, 6H, N(CH$_3$)$_2$), 3.23 (s, 2H, NCH$_2$CO), 3.71 (br s, 4H, piperazine N(CH$_2$)$_2$), 6.81 (d, J=9.15 Hz, 2H, 3,5-C$_6$H$_4$NMe$_2$ or 2,6-C$_6$H$_4$—NMe$_2$), 7.06 (t, J=7.52 Hz, 1H, p-ArH), 7.32 (t, J=7.52 Hz, 2H, m-ArH), 7.68 (d, J=7.52 Hz, 2H, o-ArH), 8.02 (d, J=8.90 Hz, 2H, 3,5-C$_6$H$_4$NMe$_2$ or 2,6-C$_6$H$_4$—NMe$_2$), 8.16 (s, 1H, imidazo[4,5-b]pyridine 5-H), 9.82 (s, 1H, CONH), 13.20 (s, 1H, imidazo[4,5-b]pyridine N—H);

LC-MS (ESI, m/z): Rt=6.21 min—534, 536 [(M+H)$^+$, Br isotopic pattern]. ESI-HRMS: Found: 534.1623, calculated for $C_{26}H_{29}BrN_7O$ (M+H)$^+$: 534.1617.

Example 21

2-(4-(2-Amino-5-bromo-3-nitropyridin-4-yl)piperazin-1-yl)-N-(pyridin-3-yl)acetamide

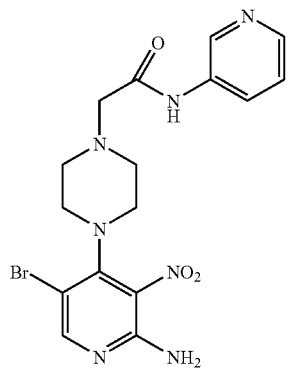

To a mixture of 5-bromo-4-chloro-3-nitro-pyridin-2-ylamine (0.126 g, 0.50 mmol) and isopropanol (10 ml) was added 2-(piperazin-1-yl)-N-(pyridin-3-yl)acetamide×3HCl salt (0.180 g, 0.55 mmol) followed by diisopropylethylamine (0.41 ml, 2.36 mmol). The reaction mixture was heated at 45° C. for 18 h, then allowed to cool to room temperature and the solvents were removed in vacuo. The residue was absorbed on silica gel and the free running powder was placed on a 10 g isolute silica column which was eluted with 2.5% methanol in ethyl acetate. The title compound was obtained as a yellow solid (0.180 g, 82%); $^1$H-NMR (500 MHz, DMSO-$d_6$) 2.68 (br s, 4H, piperazine N(CH$_2$)$_2$), 3.14 (br s, 4H, piperazine N(CH$_2$)$_2$), 3.24 (s, 2H, NCH$_2$CO), 6.98 (br s, 2H, NH$_2$), 7.34 (dd, J=8.10, 4.75 Hz, 1H, pyridyl 5-H), 8.06 (d, J=7.50 Hz, 1H, pyridyl 4-H), 8.16 (s, 1H, 6-H), 8.27 (dd, J=4.80, 1.96 Hz, 1H, pyridyl 6-H), 8.78 (d, J=2.30 Hz, 1H, pyridyl 2-H), 9.95 (s, 1H, CONH);

LC-MS (ESI, m/z): Rt=2.73 min—436, 438 [(M+H)$^+$, Br isotopic pattern].

2-(4-(6-Bromo-2-(4-(dimethylamino)phenyl)-3H-imidazo[4,5-b]pyridin-7-yl)piperazin-1-yl)-N-(pyridin-3-yl)acetamide

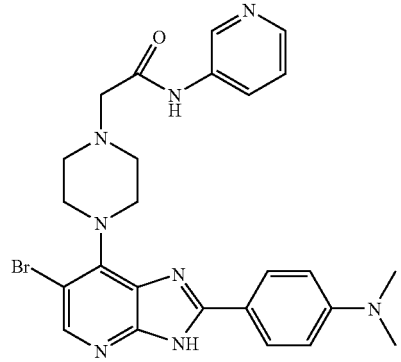

To a mixture of 2-(4-(2-amino-5-bromo-3-nitropyridin-4-yl)piperazin-1-yl)-N-(pyridin-3-yl)acetamide (0.052 g, 0.12 mmol), ethanol (3.5 ml), and 4-dimethylaminobenzaldehyde (0.025 g, 0.17 mmol) was added a freshly prepared aqueous solution of $Na_2S_2O_4$ (1M; 0.48 ml, 0.48 mmol). The reaction mixture was heated at 70° C. for 5.5 h, then allowed to cool to room temperature and the solvents were removed in vacuo. The residue was absorbed on silica gel and the free running powder was placed on a 10 g isolute silica column which was eluted with 50% dichloromethane in ethyl acetate and then 3% methanol in ethyl acetate/dichloromethane (v/v; 8:2). The title compound was obtained as a pale yellow solid after trituration with diethyl ether (0.022 g, 34%); $^1$H-NMR (500 MHz, DMSO-$d_6$) $^1$H-NMR (500 MHz, DMSO-$d_6$) 2.76 (br s, 4H, piperazine N(CH$_2$)$_2$), 3.00 (s, 6H, N(CH$_3$)$_2$), 3.72 (br s, 4H, piperazine N(CH$_2$)$_2$), 3.27 (s, 2H, NCH$_2$CO), 6.82 (d, J=9.07 Hz, 2H), and 8.01 (d, J=9.41 Hz, 2H) (3,5-C$_6$H$_4$—NMe$_2$ and 2,6-C$_6$H$_4$—NMe$_2$), 7.34 (dd, J=9.41, 4.70 Hz, 1H, pyridyl 5-H), 8.12 (d, J=8.46 Hz, 1H, pyrid-3-yl), 8.16 (s, 1H, imidazo[4,5-b]pyridine 5-H), 8.27 (d, J=4.70, 1H, pyrid-3-yl), 8.85 (s, 1H, pyridyl 2-H), 10.04 (s, 1H, CONH), 13.15 (s, 1H, imidazo[4,5-b]pyridine N—H); LC-MS (ESI, m/z): Rt=5.30 min—535, 537 [(M+H)$^+$, Br isotopic pattern]. ESI-HRMS: Found: 535.1596, calculated for $C_{25}H_{28}BrN_8O$ (M+H)$^+$: 535.1569.

Example 22

2-(4-(2-Amino-5-chloro-3-nitropyridin-4-yl)piperazin-1-yl)-N-phenylacetamide

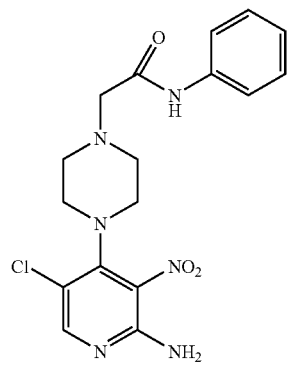

To a mixture of 2-amino-4,5-dichloro-3-nitropyridine (0.031 g, 0.15 mmol) and isopropanol (3.5 ml) was added N-phenyl-2-piperazin-1-yl-acetamide×2HCl salt (0.048 g, 0.16 mmol) followed by diisopropylethylamine (0.10 ml, 0.54 mmol). The reaction mixture was heated at 45° C. for 18 h, then allowed to cool to room temperature and the solvents were removed in vacuo. The residue was absorbed on silica gel and the free running powder was placed on a 10 g isolute silica column which was eluted with 10% to 30% ethyl acetate in dichloromethane. The title compound was obtained as a yellow solid (0.041 g, 71%); $^1$H-NMR (500 MHz, DMSO-$d_6$) 2.64 (br s, 4H, piperazine N(CH$_2$)$_2$), 3.13 (br s, 4H, piperazine N(CH$_2$)$_2$), 3.19 (s, 2H, NCH$_2$CO), 7.00 (br s, 2H, 2-NH$_2$), 7.06 (t, J=7.34 Hz, 1H, p-ArH), 7.31 (t, J=8.26 Hz, 2H, m-ArH), 7.63 (d, J=7.34 Hz, 2H, o-ArH), 8.07 (s, 1H, 6-H), 9.76 (s, 1H, CONH);

LC-MS (ESI, m/z): Rt=4.50 min—391, 393 [(M+H)$^+$, Cl isotopic pattern].

2-(4-(6-Chloro-2-(4-(dimethylamino)phenyl)-3H-imidazo[4,5-b]pyridin-7-yl)piperazin-1-yl)-N-phenylacetamide

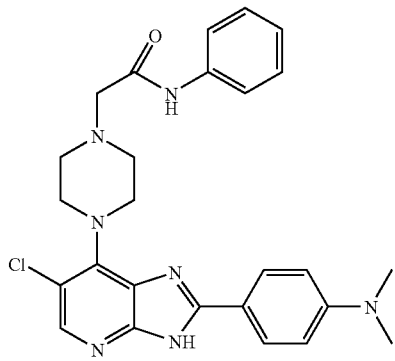

To a mixture of 2-(4-(2-amino-5-chloro-3-nitropyridin-4-yl)piperazin-1-yl)-N-phenylacetamide (0.040 g, 0.10 mmol), ethanol (3 ml), and 4-dimethylaminobenzaldehyde (0.019 g, 0.13 mmol) was added a freshly prepared aqueous solution of Na$_2$S$_2$O$_4$ (1M; 0.40 ml, 0.40 mmol). The reaction mixture was heated at 70° C. for 3 h, then allowed to cool to room temperature and the solvents were removed in vacuo. The residue was absorbed on silica gel and the free running powder was placed on a 10 g isolute silica column which was eluted with 20% ethyl acetate in dichloromethane and then 1% methanol in ethyl acetate/dichloromethane (v/v; 1:1). The title compound was obtained as a yellow solid after trituration with diethyl ether (0.006 g, 12%); $^1$H-NMR (500 MHz, DMSO-$d_6$) 2.76 (br s, 4H, piperazine N(CH$_2$)$_2$), 3.00 (s, 6H, N(CH$_3$)$_2$), 3.23 (s, 2H, NCH$_2$CO), 3.75 (br s, 4H, piperazine N(CH$_2$)$_2$), 6.81 (d, J=7.90 Hz, 2H) and 8.01 (d, J=8.49 Hz, 2H) (3,5-C$_6$H$_4$NMe$_2$ and 2,6-C$_6$H$_4$—NMe$_2$), 7.07 (t, J=7.27 Hz, 1H, p-ArH), 7.32 (t, J=8.48 Hz, 2H, m-ArH), 7.67 (d, J=8.48 Hz, 2H, o-ArH), 8.06 (s, 1H, imidazo[4,5-b]pyridine 5-H), 9.77 (s, 1H, CONH), 13.11 (s, 1H, imidazo[4,5-b]pyridine N—H);

LC (Method B)-MS (ESI, m/z): Rt=4.00 min—490, 492 [(M+H)$^+$, Cl isotopic pattern];

ESI-HRMS: Found: 490.2128, calculated for C$_{26}$H$_{29}$ClN$_7$O (M+H)$^+$: 490.2122.

Example 23 tert-Butyl 4-(2-(4-methylthiazol-2-ylamino)-2-oxoethyl)piperazine-1-carboxylate

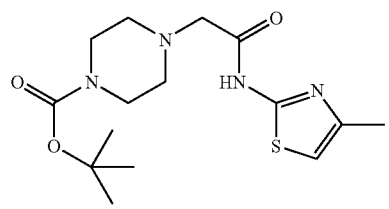

To a round-bottomed flask containing 2-(1-tert-butoxycarbonyl-piperazin-4-yl)-acetic acid×2HCl (0.100 g, 0.36 mmol) was added 2-amino-4-methylthiazole (0.045 g, 0.39 mmol) and anhydrous dichloromethane (4 ml). The reaction mixture was cooled into an ice-bath under argon, and then diisopropylethylamine (0.139 g, 1.08 mmol) was added followed by PyBOP (0.187 g, 0.36 mmol). The ice-bath was removed and the reaction mixture was allowed to stir for 20 h under argon. The solvent was removed in vacuo, the residue was absorbed on silica gel and the free running powder was placed on a 20 g isolute silica column which was eluted with 30% ethyl acetate in dichloromethane and then 60% ethyl acetate in dichloromethane. The title compound was obtained as a gummy material (0.076 g, 62%). $^1$H-NMR (500 MHz, DMSO-$d_6$) 1.39 (s, 9H, C(CH$_3$)$_3$), 2.25 (s, 3H, CH$_3$), 2.45 (br s, 4H, piperazine N(CH$_2$)$_2$), 3.27 (s, 2H, NCH$_2$CO), 6.76 (s, 1H, thiazole 5-H), 11.78 (s, 1H, CONH);

LC (Method B)-MS (ESI, m/z): Rt=3.40 min—341 [(M+H)$^+$, 100%].

2-(4-(2-Amino-5-chloro-3-nitropyridin-4-yl)piperazin-1-yl)-N-(4-methylthiazol-2-yl)acetamide

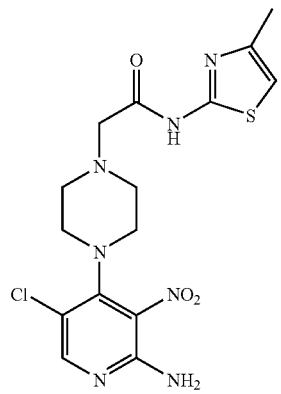

To a solution of tert-butyl 4-(2-(4-methylthiazol-2-ylamino)-2-oxoethyl)piperazine-1-carboxylate (0.072 g, 0.21 mmol) in dichloromethane (2 ml) was added trifluoroacetic acid (2.5 ml). The reaction mixture was stirred at room temperature for 1.5 h, then the solvents were removed under reduced pressure to afford N-(4-methylthiazol-2-yl)-2-(piperazin-1-yl)acetamide (a semi-solid material) that was dried in vacuo. To a mixture of this material (supposedly 0.20 mmol) and isopropanol (3.5 ml) was added 2-amino-4,5-dichloro-3-nitropyridine (0.031 g, 0.15 mmol) followed by diisopropylethylamine (0.14 ml, 0.80 mmol). The reaction mixture was stirred at 45° C. for 20 h, then allowed to cool to room temperature and the solvents were removed in vacuo. The residue was absorbed on silica gel and the free running powder was placed on a 10 g isolute silica column which was eluted with 20% ethyl acetate in dichloromethane. The title compound was obtained as an orange solid (0.044 g, 54%). $^1$H-NMR (500 MHz, DMSO-$d_6$) 2.26 (s, 3H, $CH_3$), 2.65 (br s, 4H, piperazine $N(CH_2)_2$), 3.10 (br s, 4H, piperazine $N(CH_2)_2$), 3.33 (s, 2H, $NCH_2CO$), 6.76 (s, 1H, thiazole 5-H), 6.96 (br s, 2H, $NH_2$), 8.07 (s, 1H, 6-H), 11.75 (s, 1H, CONH);

LC (Method B)-MS (ESI, m/z): Rt=3.29 min—412, 414 [(M+H)$^+$, Cl isotopic pattern].

2-(4-(6-Chloro-2-(4-(dimethylamino)phenyl)-3H-imidazo[4,5-b]pyridin-7-yl)piperazin-1-yl)-N-(4-methylthiazol-2-yl)acetamide

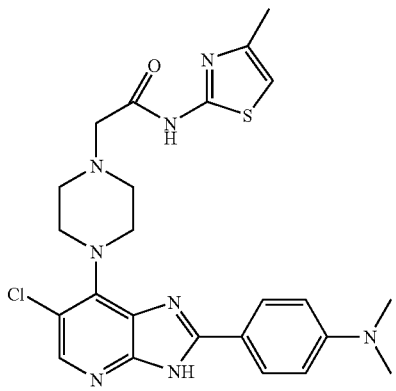

To a mixture of 2-(4-(2-amino-5-chloro-3-nitropyridin-4-yl)piperazin-1-yl)-N-(4-methylthiazol-2-yl)acetamide (0.034 g, 0.08 mmol), ethanol (3 ml), and 4-dimethylaminobenzaldehyde (0.015 g, 0.10 mmol) was added a freshly prepared aqueous solution of $Na_2S_2O_4$ (1M; 0.35 ml, 0.35 mmol). The reaction mixture was heated at 70° C. for 3.5 h, then allowed to cool to room temperature and the solvents were removed in vacuo. The residue was absorbed on silica gel and the free running powder was placed on a 10 g isolute silica column which was eluted with 40% ethyl acetate in dichloromethane and then 2.5% methanol in ethyl acetate/dichloromethane (v/v; 1:1). The title compound was obtained as a pale yellow solid after trituration with diethyl ether (0.010 g, 25%); $^1$H-NMR (500 MHz, DMSO-$d_6$) 2.27 (s, 3H, $CH_3$), 2.76 (br s, 4H, piperazine $N(CH_2)_2$), 3.00 (s, 6H, $N(CH_3)_2$), 3.71 (br s, 4H, piperazine $N(CH_2)_2$), 3.37 (s, 2H, $NCH_2CO$), 6.77 (s, 1H, thiazole 5-H), 6.81 (d, J=8.91 Hz, 2H) and 8.01 (d, J=8.88 Hz, 2H) (3,5-$C_6H_4NMe_2$ and 2,6-$C_6H_4$—$NMe_2$), 8.03 (s, 1H, imidazo[4,5-b]pyridine 5-H), 11.78 (s, 1H, CONH), 13.09 (s, 1H, imidazo[4,5-b]pyridine N—H); LC (Method B)-MS (ESI, m/z): Rt=4.30 min—511, 513 [(M+H)$^+$, Cl isotopic pattern]. ESI-HRMS: Found: 511.1794, calculated for $C_{24}H_{28}ClN_8OS$ (M+H)$^+$: 511.1795.

Example 24 tert-Butyl 4-(2-(3-chlorophenylamino)-2-oxoethyl)piperazine-1-carboxylate

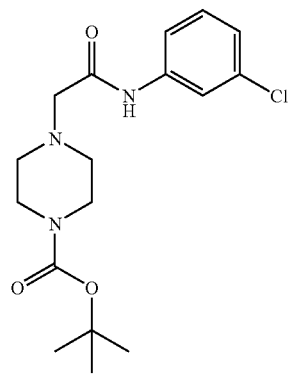

To a round-bottomed flask containing 2-(1-tert-butoxycarbonyl-piperazin-4-yl)-acetic acid×2HCl (0.100 g, 0.36 mmol) was added 3-chloroaniline (0.050 g, 0.40 mmol) with the aid of anhydrous dichloromethane (4.5 ml). The reaction mixture was cooled into an ice-bath under argon, and then diisopropylethylamine (0.139 g, 1.08 mmol) was added followed by PyBOP (0.187 g, 0.36 mmol). The ice-bath was removed and the reaction mixture was allowed to stir for 20 h under argon. The solvent was removed in vacuo, the residue was absorbed on silica gel and the free running powder was placed on a 10 g isolute silica column which was eluted with 25% ethyl acetate in dichloromethane. The title compound was obtained as a white solid (0.079 g, 62%). $^1$H-NMR (500 MHz, DMSO-$d_6$) 1.40 (s, 9H, $C(CH_3)_3$), 2.46 (br s, 4H, piperazine $N(CH_2)_2$), 3.39 (br s, 4H, piperazine $N(CH_2)_2$), 3.16 (s, 2H, $NCH_2CO$), 7.11 (d, J=8.59 Hz, 1H) and 7.55 (d, J=8.19 Hz, 1H) (4-ArH and 6-ArH), 7.34 (t, J=8.19 Hz, 1H, 5-ArH), 7.84 (t, J=1.9 Hz, 1H, 2-ArH), 9.89 (s, 1H, CONH);

LC (Method B)-MS (ESI, m/z): Rt=3.79 min—354, 356 [(M+H)$^+$, Cl isotopic pattern].

2-(4-(2-Amino-5-chloro-3-nitropyridin-4-yl)piperazin-1-yl)-N-(3-chlorophenyl)acetamide

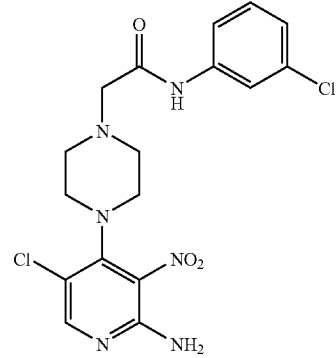

To a solution of tert-butyl 4-(2-(3-chlorophenylamino)-2-oxoethyl)piperazine-1-carboxylate (0.061 g, 0.17 mmol) in dichloromethane (2 ml) was added trifluoroacetic acid (2.5 ml). The reaction mixture was stirred at room temperature for 1.5 h, then the solvents were removed under reduced pressure to afford N-(3-chlorophenyl)-2-(piperazin-1-yl)acetamide trifluoroacetate salt (an oily material) that was dried in vacuo. To a mixture of this material (supposedly 0.17 mmol) and isopropanol (3.5 ml) was added 2-amino-4,5-dichloro-3-nitropyridine (0.031 g, 0.15 mmol) followed by diisopropylethylamine (0.14 ml, 0.80 mmol). The reaction mixture was stirred at 45° C. for 18 h, then allowed to cool to room temperature and the solvents were removed in vacuo. The residue was absorbed on silica gel and the free running powder was placed on a 10 g isolute silica column which was eluted with 15% ethyl acetate in dichloromethane. The title compound was obtained as an orange solid (0.040 g, 56%). $^1$H-NMR (500 MHz, DMSO-d$_6$) 2.65 (br s, 4H, piperazine N(CH$_2$)$_2$), 3.14 (br s, 4H, piperazine N(CH$_2$)$_2$), 3.21 (s, 2H, NCH$_2$CO), 6.95 (s, 2H, NH$_2$), 7.11 (dd, J=7.94, 1.23 Hz, 1H) and 7.54 (dd, J=8.29, 0.98 Hz, 1H) (4-ArH and 6-ArH), 7.34 (t, J=8.07 Hz, 1H, 5-ArH), 7.84 (t, J=1.80 Hz, 1H, 2-ArH), 8.07 (s, 1H, 6-H), 9.91 (s, 1H, CONH);

LC (Method B)-MS (ESI, m/z): Rt=3.89 min—425, 427, 429 [(M+H)$^+$, Cl$_2$ isotopic pattern].

2-(4-(6-Chloro-2-(4-(dimethylamino)phenyl)-3H-imidazo[4,5-b]pyridin-7-yl)piperazin-1-yl)-N-(3-chlorophenyl)acetamide

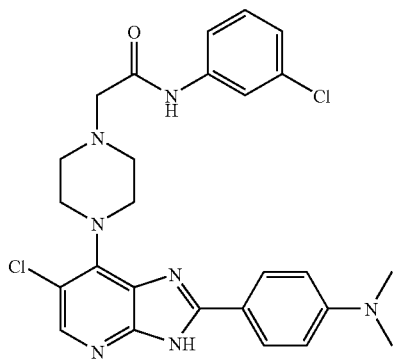

To a mixture of 2-(4-(2-amino-5-chloro-3-nitropyridin-4-yl)piperazin-1-yl)-N-(3-chlorophenyl)acetamide (0.036 g, 0.08 mmol), ethanol (3.5 ml), and 4-dimethylaminobenzaldehyde (0.017 g, 0.11 mmol) was added a freshly prepared aqueous solution of Na$_2$S$_2$O$_4$ (1M; 0.35 ml, 0.35 mmol). The reaction mixture was heated at 70° C. for 3 h, then allowed to cool to room temperature and the solvents were removed in vacuo. The residue was absorbed on silica gel and the free running powder was placed on a 10 g isolute silica column which was eluted with 30% ethyl acetate in dichloromethane and then 1.5% methanol in ethyl acetate/dichloromethane (v/v; 1:1). The title compound was obtained as a pale yellow solid after trituration with diethyl ether (0.004 g, 7%); $^1$H-NMR (500 MHz, DMSO-d$_6$) 2.78 (br s, 4H, piperazine N(CH$_2$)$_2$), 3.00 (s, 6H, N(CH$_3$)$_2$), 3.24 (s, 2H, NCH$_2$CO), 3.76 (br s, 4H, piperazine N(CH$_2$)$_2$), 6.82 (d, J=8.96 Hz, 2H) and 8.01 (d, J=8.91 Hz, 2H) (3,5-C$_6$H$_4$NMe$_2$ and 2,6-C$_6$H$_4$—NMe$_2$), 7.12 (d, J=7.62 Hz, 1H) and 7.60 (d, J=9.25 Hz, 1H) (4-ArH and 6-ArH), 7.34 (t, J=6.85 Hz, 1H, 5-ArH), 7.90 (s, 1H, 2-ArH), 8.03 (s, 1H, imidazo[4,5-b]pyridine 5-H), 9.96 (s, 1H, CONH), 13.09 (s, 1H, imidazo[4,5-b]pyridine N—H);

LC (Method B)-MS (ESI, m/z): Rt=4.53 min—524, 526, 528 [(M+H)$^+$, Cl$_2$ isotopic pattern]. ESI-HRMS: Found: 524.1729, calculated for C$_{26}$H$_{28}$Cl$_2$N$_7$O (M+H)$^+$: 524.1732.

Example 25

2-(4-(2-Amino-5-bromo-3-nitropyridin-4-yl)piperazin-1-yl)-1-(pyrrolidin-1-yl)ethanone

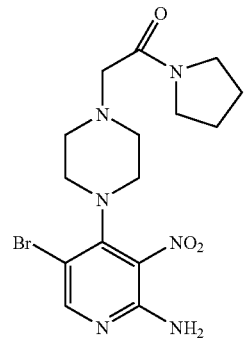

To a mixture of 5-bromo-4-chloro-3-nitro-pyridin-2-ylamine (0.126 g, 0.50 mmol) and isopropanol (9 ml) was added 2-(piperazin-1-yl)-1-(pyrrolidin-1-yl)ethanone (0.108 g, 0.55 mmol) followed by diisopropylethylamine (0.10 ml, 0.55 mmol). The reaction mixture was heated at 45° C. for 22 h, then allowed to cool to room temperature and the solvents were removed in vacuo. The residue was absorbed on silica gel and the free running powder was placed on a 10 g isolute silica column which was eluted with 70% ethyl acetate in dichloromethane and then 90% ethyl acetate in dichloromethane. The title compound was obtained as a yellow solid (0.162 g, 78%); $^1$H-NMR (500 MHz, DMSO-d$_6$) 1.74 (m, 2H) and 1.85 (m, 2H) (pyrrolidine 3-CH$_2$ and 4-CH$_2$), 2.60 (br s, 4H, piperazine N(CH$_2$)$_2$), 3.04 (br s, 4H, piperazine N(CH$_2$)$_2$), 3.16 (s, 2H, NCH$_2$CO), 3.27 (t, J=6.90 Hz, 2H) and 3.45 (t, J=6.70 Hz, 2H) (pyrrolidine 2-CH$_2$ and 5-CH$_2$), 7.02 (s, 2H, NH$_2$), 8.16 (s, 1H, 6-H);

LC (Method B)-MS (ESI, m/z) Rt=1.89 min—413, 415 [(M+H)$^+$, Br isotopic pattern].

2-(4-(6-Bromo-2-(4-(dimethylamino)phenyl)-3H-imidazo[4,5-b]pyridin-7-yl)piperazin-1-yl)-1-(pyrrolidin-1-yl)ethanone

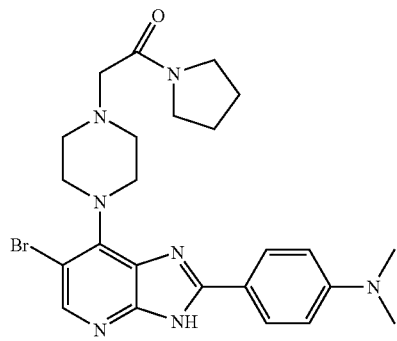

To a mixture of 2-(4-(2-amino-5-bromo-3-nitropyridin-4-yl)piperazin-1-yl)-1-(pyrrolidin-1-yl)ethanone (0.045 g, 0.11 mmol), ethanol (4 ml), and 4-dimethylaminobenzaldehyde (0.021 g, 0.14 mmol) was added a freshly prepared aqueous solution of $Na_2S_2O_4$ (1M; 0.44 ml, 0.44 mmol). The reaction mixture was heated at 70° C. for 3.5 h, then allowed to cool to room temperature and the solvents were removed in vacuo. The residue was absorbed on silica gel and the free running powder was placed on a 10 g isolute silica column which was eluted with 90% ethyl acetate in dichloromethane and then 2.5% to 7% methanol in ethyl acetate. The title compound was obtained as a yellow solid after trituration with diethyl ether (0.007 g, 12%); $^1$H-NMR (500 MHz, DMSO-$d_6$) 1.78 (m, 2H) and 1.90 (m, 2H) (pyrrolidine 3-$CH_2$ and 4-$CH_2$), 2.65 (br s, 4H, piperazine N($CH_2$)$_2$), 3.00 (s, 6H, N($CH_3$)$_2$), 3.18 (s, 2H, N$CH_2$CO), 3.32 (t, J=7.29 Hz, 2H) and 3.53 (t, J=6.48 Hz, 2H) (pyrrolidine 2-$CH_2$ and 5-$CH_2$), 3.63 (br s, 4H, piperazine N($CH_2$)$_2$), 6.82 (d, J=9.58 Hz, 2H) and 8.01 (d, J=9.58 Hz, 2H) (3,5-$C_6H_4$NMe$_2$ and 2,6-$C_6H_4$—NMe$_2$), 8.15 (s, 1H, imidazo[4,5-b]pyridine 5-H), 13.14 (s, 1H, imidazo[4,5-b]pyridine N—H);

LC (Method B)-MS (ESI, m/z): Rt=3.10 min—512, 514 [(M+H)$^+$, Br isotopic pattern]. ESI-HRMS: Found: 512.1763, calculated for $C_{24}H_{31}BrN_7O$ (M+H)$^+$: 512.1773.

Example 26

5-Bromo-4-(4-(4-chlorobenzyl)piperazin-1-yl)-3-nitropyridin-2-amine

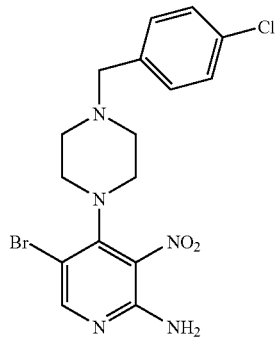

To a mixture of 5-bromo-4-chloro-3-nitro-pyridin-2-ylamine (0.126 g, 0.50 mmol) and isopropanol (15 ml) was added 1-(4-chlorobenzyl)-piperazine (0.115 g, 0.55 mmol) followed by diisopropylethylamine (0.10 ml, 0.55 mmol). The reaction mixture was heated at 45° C. for 18 h, then allowed to cool to room temperature. The precipitate was collected by filtration and washed with isopropanol and diethyl ether. The title compound was thus obtained as a yellow solid (0.148 g, 70%); $^1$H-NMR (500 MHz, DMSO-$d_6$) 3.05 (br s, 4H, piperazine N($CH_2$)$_2$), 3.52 (s, 2H, N$CH_2$), 7.02 (s, 2H, $NH_2$), 7.34 (d, J=8.52 Hz, 2H) and 7.38 (d, 2H) (3,5-ArH and 2,6-ArH), 8.16 (s, 1H, 6-H); LC (Method B)-MS (ESI, m/z): Rt=2.92 min—426, 428, 430 [(M+H)$^+$, BrCl isotopic pattern].

4-(6-Bromo-7-(4-(4-chlorobenzyl)piperazin-1-yl)-3H-imidazo[4,5-b]pyridin-2-yl)-N,N-dimethylaniline

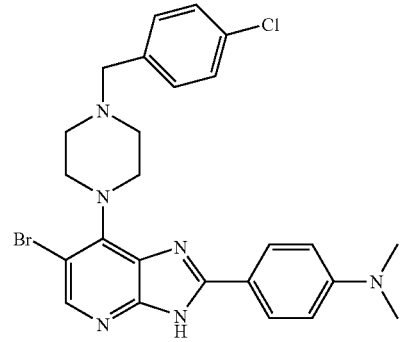

To a mixture of 5-bromo-4-(4-(4-chlorobenzyl)piperazin-1-yl)-3-nitropyridin-2-amine (0.047 g, 0.11 mmol), ethanol (8 ml), and 4-dimethylaminobenzaldehyde (0.021 g, 0.14 mmol) was added a freshly prepared aqueous solution of $Na_2S_2O_4$ (1M; 0.44 ml, 0.44 mmol). The reaction mixture was heated at 70° C. for 3.5 h, then allowed to cool to room temperature and the solvents were removed in vacuo. The residue was absorbed on silica gel and the free running powder was placed on a 10 g isolute silica column which was eluted with 20% ethyl acetate in dichloromethane and then 1% and 2.5% methanol in ethyl acetate/dichloromethane (v/v; 1:1). The title compound was obtained as a pale yellow solid after trituration with diethyl ether (0.004 g, 7%); $^1$H-NMR (500 MHz, DMSO-$d_6$) 2.60 (br s, 4H, piperazine N($CH_2$)$_2$), 3.00 (s, 6H, N($CH_3$)$_2$), 3.57 (s, 2H, N$CH_2$), 3.63 (br s, 4H, piperazine N($CH_2$)$_2$), 6.81 (d, J=9.00 Hz, 2H) and 8.01 (d, J=8.82 Hz, 2H) (3,5-$C_6H_4$NMe$_2$ and 2,6-$C_6H_4$—NMe$_2$), 7.41 (m, 4H) (3,5-ArH and 2,6-ArH), 8.14 (s, 1H, imidazo[4,5-b]pyridine 5-H), 13.12 (s, 1H, imidazo[4,5-b]pyridine N—H);

LC (Method B)-MS (ESI, m/z): Rt=3.90 min—525, 527, 529 [(M+H)$^+$, BrCl isotopic pattern]. ESI-HRMS: Found: 525.1167, calculated for $C_{25}H_{27}BrClN_6$ (M+H)$^+$: 525.1169.

Example 27

5-Bromo-3-nitro-4-(4-(pyridin-3-ylmethyl)piperazin-1-yl)pyridin-2-amine

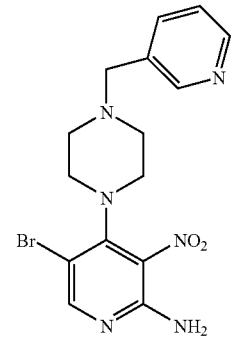

To a mixture of 5-bromo-4-chloro-3-nitro-pyridin-2-ylamine (0.126 g, 0.50 mmol) and isopropanol (9 ml) was added 1-[(3-pyridyl)-methyl]-piperazine (0.097 g, 0.55 mmol) followed by diisopropylethylamine (0.10 ml, 0.57 mmol). The reaction mixture was heated at 45° C. for 18 h, then allowed to cool to room temperature. The precipitate was collected by filtration and washed with isopropanol and diethyl ether. The title compound was thus obtained as a yellow solid (0.160 g, 82%); $^1$H-NMR (500 MHz, DMSO-$d_6$) 3.05 (br s, 4H, piperazine N(CH$_2$)$_2$), 3.56 (s, 2H, NCH$_2$), 7.02 (s, 2H, NH$_2$), 7.36 (dd, J=7.80, 4.75 Hz, 1H, pyridyl 5-H), 7.74 (dt, J=7.80, 1.70 Hz, 1H, pyridyl 4-H), 8.16 (s, 1H, 6-H), 8.47 (dd, J=4.75, 1.60 Hz, 1H, pyridyl 6-H), 8.50 (d, J=1.65 Hz, 1H, pyridyl 2-H);

LC (Method B)-MS (ESI, m/z): Rt=1.79 min—393, 395 [(M+H)$^+$, Br isotopic pattern].

4-(6-Bromo-7-(4-(pyridin-3-ylmethyl)piperazin-1-yl)-3H-imidazo[4,5-b]pyridin-2-yl)-N,N-dimethylaniline

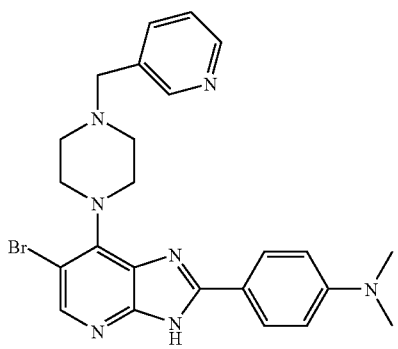

To a mixture of 5-bromo-3-nitro-4-(4-(pyridin-3-ylmethyl)piperazin-1-yl)pyridin-2-amine (0.043 g, 0.11 mmol), ethanol (4 ml), and 4-dimethylaminobenzaldehyde (0.021 g, 0.14 mmol) was added a freshly prepared aqueous solution of Na$_2$S$_2$O$_4$ (1M; 0.44 ml, 0.44 mmol). The reaction mixture was heated at 70° C. for 3.5 h, then allowed to cool to room temperature and the solvents were removed in vacuo. The residue was absorbed on silica gel and the free running powder was placed on a 10 g isolute silica column which was eluted with 90% ethyl acetate in dichloromethane and then 3% and 5% methanol in ethyl acetate. The title compound was obtained as a pale yellow solid after trituration with diethyl ether (0.012 g, 22%); $^1$H-NMR (500 MHz, DMSO-$d_6$) 2.61 (br s, 4H, piperazine N(CH$_2$)$_2$), 3.00 (s, 6H, N(CH$_3$)$_2$), 3.61 (s, 2H, NCH$_2$CO), 3.63 (br s, 4H, piperazine N(CH$_2$)$_2$), 6.81 (d, J=9.00 Hz, 2H) and 8.01 (d, J=8.80 Hz, 2H) (3,5-C$_6$H$_4$NMe$_2$ and 2,6-C$_6$H$_4$—NMe$_2$), 7.40 (dd, J=7.06, 3.92 Hz, 1H, pyridyl 5-H), 7.78 (d, J=8.64 Hz, 1H, pyridyl 4-H), 8.15 (s, 1H, imidazo[4,5-b]pyridine 5-H), 8.50 (dd, J=4.75, 1.50 Hz, 1H, pyridyl 6-H), 8.56 (d, J=1.50 Hz, 1H, pyridyl 2-H), 13.15 (s, 1H, imidazo[4,5-b]pyridine N—H);

LC (Method B)-MS (ESI, m/z) Rt=3.12 min—492, 494 [(M+H)$^+$, Br isotopic pattern]. ESI-HRMS: Found: 492.1513, calculated for C$_{24}$H$_{27}$BrN$_7$(M+H)$^+$: 492.1511.

Example 28

6-Bromo-2-(4-methoxyphenyl)-7-(4-(pyridin-3-ylmethyl)piperazin-1-yl)-3H-imidazo[4,5-b]pyridine

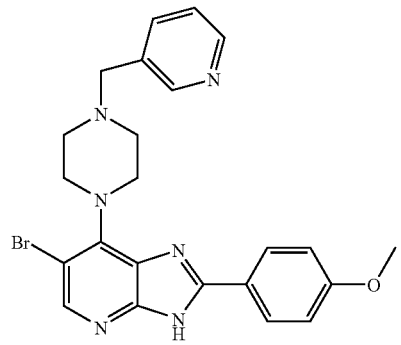

To a mixture of 5-bromo-3-nitro-4-(4-(pyridin-3-ylmethyl)piperazin-1-yl)pyridin-2-amine (0.043 g, 0.11 mmol) and ethanol (2.4 ml) was added 4-methoxybenzaldehyde (0.024 g, 0.18 mmol) with the aid of ethanol (1 ml) followed by a freshly prepared aqueous solution of Na$_2$S$_2$O$_4$ (1M; 0.44 ml, 0.44 mmol). The reaction mixture was heated at 70° C. for 4.5 h, then allowed to cool to room temperature and the solvents were removed in vacuo. The residue was absorbed on silica gel and the free running powder was placed on a 10 g isolute silica column which was eluted with 50% ethyl acetate in dichloromethane, and then 3% to 6% methanol in ethyl acetate/dichloromethane (v/v; 1:1). The title compound was obtained as a yellow solid after trituration with diethyl ether (0.015 g, 28%); $^1$H-NMR (500 MHz, DMSO-$d_6$) 2.62 (br s, 4H, piperazine N(CH$_2$)$_2$), 3.62 (s, 2H, NCH$_2$CO), 3.66 (br s, 4H, piperazine N(CH$_2$)$_2$), 3.84 (s, 3H, OCH$_3$), 7.10 (d, J=8.89 Hz, 2H) and 8.14 (d, J=8.57 Hz, 2H) (3,5-C$_6$H$_4$OMe and 2,6-C$_6$H$_4$—OMe), 7.39 (dd, J=7.91, 5.08 Hz, 1H, pyridyl 5-H), 7.76 (d, J=7.80 Hz, 1H, pyridyl 4-H), 8.20 (s, 1H, imidazo[4,5-b]pyridine 5-H), 8.50 (dd, J=4.76, 1.58 Hz, 1H, pyridyl 6-H), 8.56 (d, J=1.62 Hz, 1H, pyridyl 2-H), 13.37 (s, 1H, imidazo[4,5-b]pyridine N—H);

LC (Method B)-MS (ESI, m/z): Rt=3.04 min—479, 481 [(M+H)$^+$, Br isotopic pattern]. ESI-HRMS: Found: 479.1190, calculated for C$_{23}$H$_{24}$BrN$_6$O (M+H)$^+$: 479.1195.

Example 29

2-(4-(6-Bromo-2-(3-methoxyphenyl)-3H-imidazo[4,5-b]pyridin-7-yl)-N-(thiazol-2-yl)acetamide

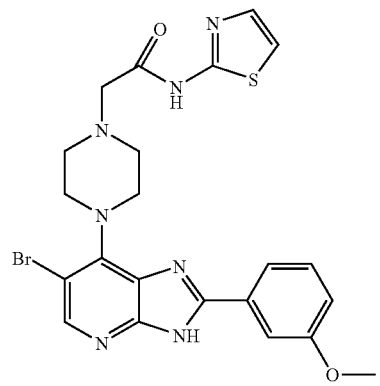

To a mixture of 2-(4-(2-amino-5-bromo-3-nitropyridin-4-yl)piperazin-1-yl)-N-(thiazol-2-yl)acetamide (0.050 g, 0.11 mmol) and ethanol (4 ml) was added 3-methoxybenzaldehyde (0.021 g, 0.15 mmol) followed by a freshly prepared aqueous solution of $Na_2S_2O_4$ (1M; 0.44 ml, 0.44 mmol). The reaction mixture was heated at 70° C. for 4.5 h, then allowed to cool to room temperature and the solvents were removed in vacuo. The residue was absorbed on silica gel and the free running powder was placed on a 10 g isolute silica column which was eluted with 25% ethyl acetate in dichloromethane, and then 2.5% methanol in ethyl acetate/dichloromethane (v/v; 1:1). The title compound was obtained as a yellow solid after trituration with diethyl ether (0.010 g, 17%); $^1$H-NMR (500 MHz, DMSO-$d_6$) 2.79 (br s, 4H, piperazine N(CH$_2$)$_2$), 3.41 (s, 2H, CH$_2$CO), 3.72 (br s, 4H, piperazine N(CH$_2$)$_2$), 3.85 (s, 3H, OCH$_3$), 7.08 (d, J=8.05 Hz, 1H) and 7.80 (d, J=7.60 Hz, 1H) (4-ArH and 6-ArH), 7.23 (d, J=3.50 Hz, 1H) and 7.49 (d, J=3.55 Hz, 1H) (thiazole 4-H, 5-H), 7.45 (t, J=7.90 Hz, 1H, 5-ArH), 7.76 (s, 1H, 2-ArH), 8.25 (s, 1H, imidazo[4,5-b]pyridine 5-H), 11.89 (s, 1H, CONH), 13.52 (s, 1H, imidazo[4,5-b]pyridine N—H);

LC (Method B)-MS (ESI, m/z): Rt=4.11 min—528, 530 [(M+H)$^+$, Br isotopic pattern]. ESI-HRMS: Found: 528.0816, calculated for $C_{22}H_{23}BrN_7O_2S$ (M+H)$^+$: 528.0817.

Example 30

5-Bromo-3-nitro-4-(4-(pyridin-2-ylmethyl)piperazin-1-yl)pyridin-2-amine

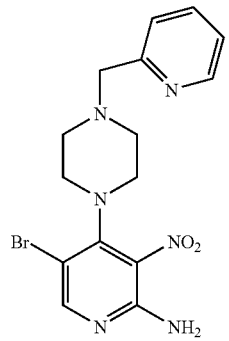

To a mixture of 5-bromo-4-chloro-3-nitro-pyridin-2-ylamine (0.126 g, 0.50 mmol) and isopropanol (9 ml) was added 1-[(2-pyridyl)-methyl]-piperazine (0.097 g, 0.55 mmol) followed by diisopropylethylamine (0.10 ml, 0.57 mmol). The reaction mixture was heated at 45° C. for 20 h, then allowed to cool to room temperature. The precipitate was collected by filtration and washed with isopropanol and diethyl ether. The title compound was thus obtained as a yellow solid (0.163 g, 83%); $^1$H-NMR (500 MHz, DMSO-$d_6$) 2.57 (br s, 4H, piperazine N(CH$_2$)$_2$), 3.08 (br s, 4H, piperazine N(CH$_2$)$_2$), 3.65 (s, 2H, NCH$_2$), 6.97 (s, 2H, NH$_2$), 7.26 (ddd, J=7.45, 4.80, 1.00 Hz, 1H), 7.46 (d, J=7.80 Hz, 1H), 7.77 (td, J=7.66, 1.80 Hz, 1H) and 8.48 (dm, J=4.09 Hz, 1H) (pyrid-2-yl protons), 8.16 (s, 1H, 6-H);

LC (Method B)-MS (ESI, m/z): Rt=2.00 min—393, 395 [(M+H)$^+$, Br isotopic pattern].

4-(6-Bromo-7-(4-(pyridin-2-ylmethyl)piperazin-1-yl)-3H-imidazo[4,5-b]pyridin-2-yl)-N,N-dimethylaniline

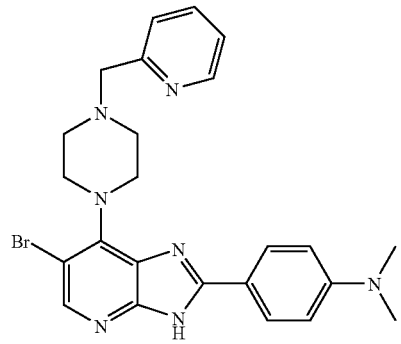

To a mixture of 5-bromo-3-nitro-4-(4-(pyridin-2-ylmethyl)piperazin-1-yl)pyridin-2-amine (0.043 g, 0.11 mmol), ethanol (4 ml), and 4-dimethylaminobenzaldehyde (0.021 g, 0.14 mmol) was added a freshly prepared aqueous solution of $Na_2S_2O_4$ (1M; 0.44 ml, 0.44 mmol). The reaction mixture was heated at 70° C. for 4 h, then allowed to cool to room temperature and the solvents were removed in vacuo. The residue was absorbed on silica gel and the free running powder was placed on a 10 g isolute silica column which was eluted with 1% to 5% methanol in ethyl acetate. The title compound was obtained as a yellow solid after trituration with diethyl ether (0.006 g, 11%); $^1$H-NMR (500 MHz, DMSO-$d_6$) $^1$H-NMR (500 MHz, DMSO-$d_6$) 2.66 (br s, 4H, piperazine N(CH$_2$)$_2$), 3.00 (s, 6H, N(CH$_3$)$_2$), 3.65 (br s, 4H, piperazine N(CH$_2$)$_2$), 3.70 (s, 2H, NCH$_2$), 6.82 (d, J=9.00 Hz, 2H) and 8.01 (d, J=8.76 Hz, 2H) (3,5-C$_6$H$_4$NMe$_2$ and 2,6-C$_6$H$_4$—NMe$_2$), 7.28 (dd, J=4.00, 5.86 Hz, 1H), 7.53 (d, J=9.00 Hz, 1H), 7.80 (td, J=1.70, 9.09 Hz, 1H), and 8.52 (d, J=4.96 Hz, 1H) (pyrid-2-yl protons), 8.14 (s, 1H, imidazo[4,5-b]pyridine 5-H), 13.13 (s, 1H, imidazo[4,5-b]pyridine N—H);

LC (Method B)-MS (ESI, m/z): Rt=3.27 min—492, 494 [(M+H)$^+$, Br isotopic pattern]. ESI-HRMS: Found: 492.1508, calculated for $C_{24}H_{27}BrN_7$ (M+H)$^+$: 492.1511.

Example 31

5-Bromo-3-nitro-4-(4-(pyridin-4-ylmethyl)piperazin-1-yl)pyridin-2-amine

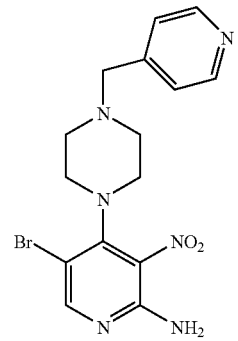

To a mixture of 5-bromo-4-chloro-3-nitro-pyridin-2-ylamine (0.126 g, 0.50 mmol) and isopropanol (9 ml) was added 1-[(4-pyridyl)-methyl]-piperazine (0.097 g, 0.55 mmol) followed by diisopropylethylamine (0.10 ml, 0.57 mmol). The reaction mixture was heated at 45° C. for 20 h, then allowed to cool to room temperature. The precipitate was collected by filtration and washed with isopropanol and diethyl ether. The title compound was thus obtained as an orange solid (0.080 g). The filtrate was concentrated in vacuo, and purification of the residue on a isolute silica column using 1 to 5% methanol in ethyl acetate as eluant gave an additional 0.055 g of the product (total yield: 68%); $^1$H-NMR (500 MHz, DMSO-$d_6$) 2.53 (br s, 4H, piperazine N(CH$_2$)$_2$), 3.08 (br s, 4H, piperazine N(CH$_2$)$_2$), 3.57 (s, 2H, NCH$_2$), 6.97 (s, 2H, NH$_2$), 7.34 (d, J=5.88 Hz, 2H), and 8.51 (d, J=4.48 Hz, 2H) (pyrid-4-yl protons), 8.16 (s, 1H, 6-H); LC (Method B)-MS (ESI, m/z): Rt=2.00 min—393, 395 [(M+H)$^+$, Br isotopic pattern].

4-(6-Bromo-7-(4-(pyridin-4-ylmethyl)piperazin-1-yl)-3H-imidazo[4,5-b]pyridin-2-yl)-N,N-dimethylaniline

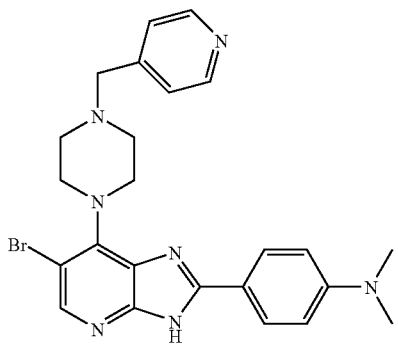

To a mixture of 5-bromo-3-nitro-4-(4-(pyridin-4-ylmethyl)piperazin-1-yl)pyridin-2-amine (0.043 g, 0.11 mmol), ethanol (4 ml), and 4-dimethylaminobenzaldehyde (0.021 g, 0.14 mmol) was added a freshly prepared aqueous solution of Na$_2$S$_2$O$_4$ (1M; 0.44 ml, 0.44 mmol). The reaction mixture was heated at 70° C. for 5 h, then allowed to cool to room temperature and the solvents were removed in vacuo. The residue was absorbed on silica gel and the free running powder was placed on a 10 g isolute silica column which was eluted with 1 to 4% methanol in ethyl acetate/dichloromethane (v/v; 1:1). The title compound was obtained as a yellow solid after trituration with diethyl ether (0.013 g, 24%); $^1$H-NMR (500 MHz, DMSO-$d_6$) 2.63 (br s, 4H, piperazine N(CH$_2$)$_2$), 3.00 (s, 6H, N(CH$_3$)$_2$), 3.66 (br s, 4H, piperazine N(CH$_2$)$_2$), 3.62 (s, 2H, NCH$_2$), 6.81 (d, J=9.04 Hz, 2H) and 8.01 (d, J=8.81 Hz, 2H) (3,5-C$_6$H$_4$NMe$_2$ and 2,6-C$_6$H$_4$—NMe$_2$), 7.40 (d, J=5.86 Hz, 2H), and 8.54 (d, J=4.42 Hz, 2H) (pyrid-4-yl protons), 8.15 (s, 1H, imidazo[4,5-b]pyridine 5-H), 13.14 (s, 1H, imidazo[4,5-b]pyridine N—H); LC (Method B)-MS (ESI, m/z) Rt=3.35 min—492, 494 [(M+H)$^+$, Br isotopic pattern]. ESI-HRMS: Found: 492.1508, calculated for C$_{24}$H$_{27}$BrN$_7$(M+H)$^+$: 492.1511.

Example 32

5-Bromo-4-(4-isobutylpiperazin-1-yl)-3-nitropyridin-2-amine

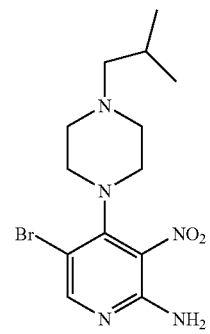

To a mixture of 5-bromo-4-chloro-3-nitro-pyridin-2-ylamine (0.126 g, 0.50 mmol) and isopropanol (9 ml) was added 1-isobutylpiperazine (0.078 g, 0.55 mmol) with the aid of isopropanol (5 ml) followed by diisopropylethylamine (0.10 ml, 0.57 mmol). The reaction mixture was heated at 45° C. for 20 h, then allowed to cool to room temperature. The precipitate was collected by filtration and washed with isopropanol and diethyl ether. The title compound was thus obtained as a yellow solid (0.112 g, 63%). $^1$H-NMR (500 MHz, DMSO-$d_6$) 0.87 (d, J=6.56 Hz, 6H, CH(CH$_3$)$_2$), 1.77 (m, 1H, CH(CH$_3$)$_2$), 2.08 (d, J=7.35 Hz, 2H, N—CH$_2$), 2.47 (br s, 4H, piperazine N(CH$_2$)$_2$), 3.04 (br s, 4H, piperazine N(CH$_2$)$_2$), 6.96 (s, 2H, NH$_2$), 8.15 (s, 1H, 6-H);

LC (Method B)-MS (ESI, m/z): Rt=1.80 min—358, 360 [(M+H)$^+$, Br isotopic pattern].

4-(6-Bromo-7-(4-isobutylpiperazin-1-yl)-3H-imidazo[4,5-b]pyridin-2-yl)-N,N-dimethylaniline

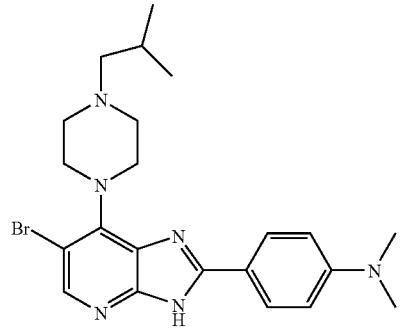

To a mixture of 5-bromo-4-(4-isobutylpiperazin-1-yl)-3-nitropyridin-2-amine (0.039 g, 0.11 mmol), ethanol (4 ml), and 4-dimethylaminobenzaldehyde (0.021 g, 0.14 mmol) was added a freshly prepared aqueous solution of Na$_2$S$_2$O$_4$ (1M; 0.44 ml, 0.44 mmol). The reaction mixture was heated at 70° C. for 5 h, then allowed to cool to room temperature and the solvents were removed in vacuo. The residue was absorbed on silica gel and the free running powder was placed on a 10 g isolute silica column which was eluted with 1 to 2.5% methanol in ethyl acetate/dichloromethane (v/v; 1:1). The title compound was obtained as a yellow solid after trituration with diethyl ether (0.013 g, 26%); $^1$H-NMR (500 MHz, DMSO-d$_6$) 0.91 (d, J=6.55 Hz, 6H, CH(CH$_3$)$_2$), 1.82 (m, 1H, CH(CH$_3$)$_2$), 2.12 (d, J=7.35 Hz, 2H, N—CH$_2$), 2.56 (br s, 4H, piperazine N(CH$_2$)$_2$), 3.00 (s, 6H, N(CH$_3$)$_2$), 3.63 (br s, 4H, piperazine N(CH$_2$)$_2$), 6.82 (d, J=9.01 Hz, 2H) and 8.02 (d, J=8.87 Hz, 2H) (3,5-C$_6$H$_4$NMe$_2$ and 2,6-C$_6$H$_4$—NMe$_2$), 8.14 (s, 1H, imidazo[4,5-b]pyridine 5-H), 13.17 (s, 1H, imidazo[4,5-b]pyridine N—H);

LC (Method B)-MS (ESI, m/z): Rt=3.19 min—457, 459 [(M+H)$^+$, Br isotopic pattern]. ESI-HRMS: Found: 457.1713, calculated for C$_{22}$H$_{30}$BrN$_6$ (M+H)$^+$: 457.1715.

Example 33

6-Bromo-2-(4-methoxyphenyl)-7-(4-(pyridin-2-ylmethyl)piperazin-1-yl)-3H-imidazo[4,5-b]pyridine

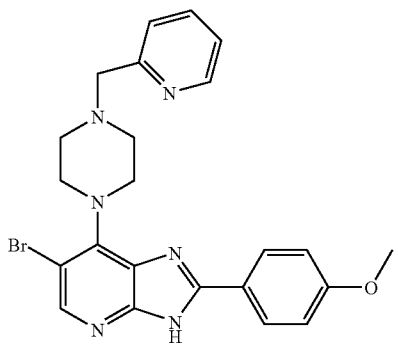

To a mixture of 5-bromo-3-nitro-4-(4-(pyridin-2-ylmethyl)piperazin-1-yl)pyridin-2-amine (0.043 g, 0.11 mmol), and ethanol (2.5 ml) was added 4-methoxybenzaldehyde (0.024 g, 0.18 mmol) with the aid of ethanol (1 ml) followed by a freshly prepared aqueous solution of Na$_2$S$_2$O$_4$ (1M; 0.44 ml, 0.44 mmol). The reaction mixture was heated at 70° C. for 4 h, then allowed to cool to room temperature and the solvents were removed in vacuo. The residue was absorbed on silica gel and the free running powder was placed on a 10 g isolute silica column which was eluted with ethyl acetate/dichloromethane (v/v; 1:1), and then 4% methanol in ethyl acetate/dichloromethane (v/v; 1:1). The title compound was obtained as a yellow solid after trituration with diethyl ether (0.010 g, 19%); $^1$H-NMR (500 MHz, DMSO-d$_6$) 2.67 (br s, 4H, piperazine N(CH$_2$)$_2$), 3.68 (br s, 4H, piperazine N(CH$_2$)$_2$), 3.70 (s, 2H, NCH$_2$), 3.84 (s, 3H, OMe), 7.10 (d, J=8.86 Hz, 2H) and 8.13 (d, J=8.75 Hz, 2H) (3,5-C$_6$H$_4$OMe and 2,6-C$_6$H$_4$—OMe), 7.28 (dd, J=5.00, 6.45 Hz, 1H), 7.52 (d, J=7.80 Hz, 1H), 7.79 (td, J=1.75, 7.65 Hz, 1H) and 8.52 (d, J=4.80 Hz, 1H) (pyrid-2-yl protons), 8.20 (s, 1H, imidazo[4,5-b]pyridine 5-H), 13.35 (s, 1H, imidazo[4,5-b]pyridine N—H);

LC (Method B)-MS (ESI, m/z); Rt=3.20 min—479, 481 [(M+H)$^+$, Br isotopic pattern]. ESI-HRMS: Found: 479.1191, calculated for C$_{23}$H$_{24}$BrN$_6$O (M+H)$^+$: 479.1195.

Example 34

5-Bromo-4-(4-(4-fluorobenzyl)-1,4-diazepan-1-yl)-3-nitropyridin-2-amine

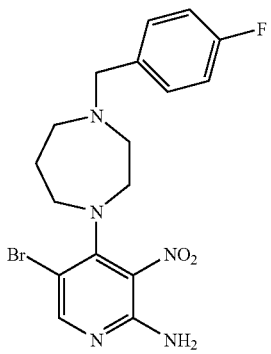

To a mixture of 5-bromo-4-chloro-3-nitro-pyridin-2-ylamine (0.126 g, 0.50 mmol) and isopropanol (9 ml) was added 1-(4-fluorobenzyl)-1,4-diazepane×2HCl (0.155 g, 0.55 mmol) followed by diisopropylethylamine (0.30 ml, 1.70 mmol). The reaction mixture was heated at 45° C. for 24 h, then allowed to cool to room temperature. The precipitate was collected by filtration and washed with isopropanol and diethyl ether. The title compound was thus obtained as a yellow solid (0.110 g, 52%); $^1$H-NMR (500 MHz, DMSO-d$_6$) 1.82 (m, 2H), 2.67 (m, 4H), 3.17 (m, 2H) and 3.24 (t, J=5.85 Hz, 2H) (homopiperazine protons), 3.61 (s, 2H, N—CH$_2$), 6.95 (s, 2H, NH$_2$), 7.15 (t, J=9.10 Hz, 2H) and 7.35 (dd, J=10.20, 3.60 Hz, 2H) (3,5-ArH and 2,6-ArH), 8.17 (s, 1H, 6-H);

LC (Method B)-MS (ESI, m/z): Rt=2.50 min—424, 426 [(M+H)$^+$, Br isotopic pattern].

4-(6-Bromo-7-(4-(4-fluorobenzyl)-1,4-diazepan-1-yl)-3H-imidazo[4,5-b]pyridin-2-yl)-N,N-dimethylaniline

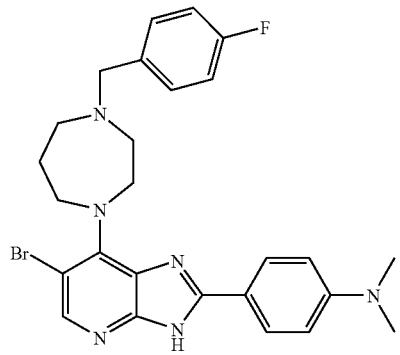

To a mixture of 5-bromo-4-(4-(4-fluorobenzyl)-1,4-diazepan-1-yl)-3-nitropyridin-2-amine (0.047 g, 0.11 mmol), ethanol (4 ml) and 4-dimethylaminobenzaldehyde (0.021 g, 0.14 mmol) was added a freshly prepared aqueous solution of Na$_2$S$_2$O$_4$ (1M; 0.44 ml, 0.44 mmol). The reaction mixture was heated at 70° C. for 4.5 h, then allowed to cool to room temperature and the solvents were removed in vacuo. The residue was absorbed on silica gel and the free running powder was placed on a 10 g isolute silica column which was eluted with 0 to 5% methanol in ethyl acetate/dichloromethane (v/v; 1:1). The title compound was obtained as a yellow solid (0.020 g, 35%); $^1$H-NMR (500 MHz, DMSO-d$_6$) 2.00 (m, 2H), 2.75-2.85 (m, 4H) and 3.86 (m, 4H) (homopiperazine protons), 2.99 (s, 6H, N(CH$_3$)$_2$), 3.66 (s, 2H, N—CH$_2$), 6.82 (d, J=9.00 Hz, 2H) and 8.00 (d, J=8.84 Hz, 2H) (3,5-C$_6$H$_4$NMe$_2$ and 2,6-C$_6$H$_4$—NMe$_2$), 7.14 (t, J=8.93 Hz, 2H) and 7.39 (dd, J=8.13, 5.42 Hz, 2H) (3,5-ArH and 2,6-ArH), 8.11 (s, 1H, imidazo[4,5-b]pyridine 5-H), 13.08 (s, 1H, imidazo[4,5-b]pyridine N—H);

LC (Method B)-MS (ESI, m/z): Rt=3.54 min—523, 525 [(M+H)$^+$, Br isotopic pattern]. ESI-HRMS: Found: 523.1621; calculated for C$_{26}$H$_{29}$BrFN$_6$(M+H)$^+$: 523.1621.

Example 35

5-Chloro-3-nitro-4-(4-(pyridin-4-ylmethyl)piperazin-1-yl)pyridin-2-amine

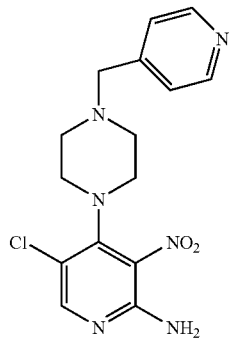

To a mixture of 2-amino-4,5-dichloro-3-nitropyridine (0.052 g, 0.25 mmol) and isopropanol (4.5 ml) was added 1-[(4-pyridyl)-methyl]-piperazine (0.049 g, 0.28 mmol) followed by diisopropylethylamine (0.05 ml, 0.28 mmol). The reaction mixture was heated at 45° C. for 24 h, then allowed to cool to room temperature, and diluted with isopropanol (3 ml). The precipitate was collected by filtration and washed with isopropanol and diethyl ether. The title compound was thus obtained as yellow solid (0.035 g). The filtrate was concentrated in vacuo, and purification of the residue on a isolute silica column using 0 to 5% methanol in ethyl acetate/dichloromethane (v/v; 1:1) as eluant gave an additional 0.036 g of the product (total yield: 81%); $^1$H-NMR (500 MHz, DMSO-d$_6$) 3.09 (br s, 4H, piperazine N(CH$_2$)$_2$), 3.57 (s, 2H, NCH$_2$), 6.96 (s, 2H, NH$_2$), 7.34 (d, J=5.81 Hz, 2H), and 8.51 (d, J=5.88 Hz, 2H) (pyrid-4-yl protons), 8.06 (s, 1H, 6-H);

LC (Method B)-MS (ESI, m/z): Rt=1.95 min—349, 351 [(M+H)$^+$, Cl isotopic pattern].

6-Chloro-2-(4-methoxyphenyl)-7-(4-(pyridin-4-ylmethyl)piperazin-1-yl)-3H-imidazo[4,5-b]pyridine

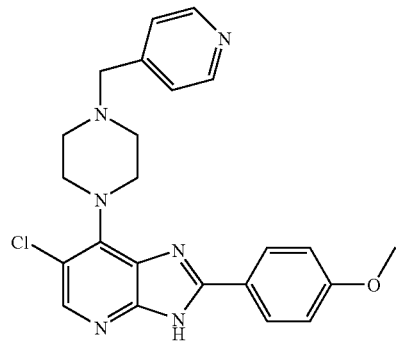

To a mixture of 5-chloro-3-nitro-4-(4-(pyridin-4-ylmethyl)piperazin-1-yl)pyridin-2-amine (0.031 g, 0.09 mmol), and ethanol (3.0 ml) was added 4-methoxybenzaldehyde (0.020 g, 0.14 mmol) with the aid of ethanol (1 ml) followed by a freshly prepared aqueous solution of Na$_2$S$_2$O$_4$ (1M; 0.36 ml, 0.36 mmol). The reaction mixture was heated at 70° C. for 5 h, then allowed to cool to room temperature and the solvents were removed in vacuo. The residue was triturated with water, and the precipitate was collected by filtration, washed with water, ethanol, and diethyl ether. This material was further purified on a 10 g isolute silica column using a gradient of methanol (0 to 5%) in ethyl acetate/dichloromethane (v/v; 1:1) as eluant. The title compound was obtained as a pale yellow solid (0.007 g, 18%); $^1$H-NMR (500 MHz, DMSO-d$_6$) 2.61 (br s, 4H, piperazine N(CH$_2$)$_2$), 3.71 (br s, 4H, piperazine N(CH$_2$)$_2$), 3.61 (s, 2H, NCH$_2$), 3.83 (s, 3H, OMe), 7.09 (d, J=8.85 Hz, 2H) and 8.12 (d, J=8.80 Hz, 2H) (3,5-C$_6$H$_4$OMe and 2,6-C$_6$H$_4$—OMe), 7.40 (d, J=5.86 Hz, 2H), and 8.54 (d, J=4.48 Hz, 2H) (pyrid-4-yl protons), 8.08 (s, 1H, imidazo[4,5-b]pyridine 5-H), 13.37 (s, 1H, imidazo[4,5-b]pyridine N—H);

LC (Method B)-MS (ESI, m/z): Rt=3.20 min—435, 437 [(M+H)$^+$, Cl isotopic pattern]. ESI-HRMS: Found: 435.1695, calculated for C$_{23}$H$_{24}$ClN$_6$O (M+H)$^+$: 435.1700.

Example 36

5-Chloro-4-(4-isobutylpiperazin-1-yl)-3-nitropyridin-2-amine

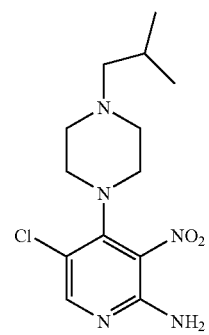

To a mixture of 2-amino-4,5-dichloro-3-nitropyridine (0.060 g, 0.29 mmol) and isopropanol (4.5 ml) was added 1-isobutyl-piperazine (0.045 g, 0.32 mmol) with the aid of isopropanol (0.5 ml) followed by diisopropylethylamine (0.06 ml, 0.32 mmol). The reaction mixture was heated at 45° C. for 18 h, then allowed to cool to room temperature, and concentrated in vacuo. The residue was absorbed on silica gel, the free running powder was placed on a 10 g isolute silica column which was eluted with ethyl acetate/dichloromethane (v/v; 1:1). The title compound was obtained as an orange solid (0.054 g, 60%); $^1$H-NMR (500 MHz, DMSO-$d_6$) 0.87 (d, J=6.57 Hz, 6H, CH(CH$_3$)$_2$), 1.77 (m, 1H, CH(CH$_3$)$_2$), 2.08 (d, J=7.39 Hz, 2H, N—CH$_2$), 2.45 (br s, 4H, piperazine N(CH$_2$)$_2$), 3.05 (br s, 4H, piperazine N(CH$_2$)$_2$), 6.94 (s, 2H, NH$_2$), 8.06 (s, 1H, 6-H);

LC (Method B)-MS (ESI, m/z): Rt=1.70 min—314, 316 [(M+H)$^+$, Cl isotopic pattern].

6-Chloro-7-(4-isobutylpiperazin-1-yl)-2-(4-methoxyphenyl)-3H-imidazo[4,5-b]pyridine

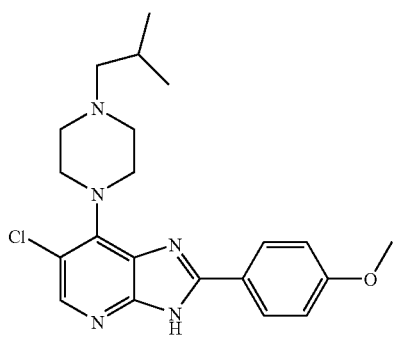

To a mixture of 5-chloro-4-(4-isobutylpiperazin-1-yl)-3-nitropyridin-2-amine (0.032 g, 0.10 mmol), and ethanol (3.0 ml) was added 4-methoxybenzaldehyde (0.023 g, 0.17 mmol) with the aid of ethanol (1 ml) followed by a freshly prepared aqueous solution of Na$_2$S$_2$O$_4$ (1M; 0.4 ml, 0.4 mmol). The reaction mixture was heated at 70° C. for 4.5 h, then allowed to cool to room temperature and the solvents were removed in vacuo. The residue was absorbed on silica gel and the free running powder was placed on a 10 g isolute silica column which was eluted with 40% ethyl acetate in dichloromethane, and then 2.5% methanol in ethyl acetate/dichloromethane (v/v; 1:1). The title compound was obtained as a white solid (0.013 g, 32%); $^1$H-NMR (500 MHz, DMSO-$d_6$) 0.90 (d, J=6.55 Hz, 6H, CH(CH$_3$)$_2$), 1.83 (m, 1H, CH(CH$_3$)$_2$), 2.12 (d, J=7.39 Hz, 2H, N—CH$_2$), 2.55 (br s, 4H, piperazine N(CH$_2$)$_2$), 3.68 (br s, 4H, piperazine N(CH$_2$)$_2$), 3.84 (s, 3H, OCH$_3$), 7.10 (d, J=8.83 Hz, 2H) and 8.13 (d, J=8.78 Hz, 2H) (3,5-C$_6$H$_4$OMe$_2$ and 2,6-C$_6$H$_4$—OMe), 8.07 (s, 1H, imidazo[4,5-b]pyridine 5-H), 13.30 (s, 1H, imidazo[4,5-b]pyridine N—H);

LC (Method B)-MS (ESI, m/z): Rt=3.02 min—400, 402 [(M+H)$^+$, Cl isotopic pattern]. ESI-HRMS: Found: 400.1900, calculated for C$_{21}$H$_{27}$ClN$_5$O (M+H)$^+$: 400.1904.

Example 37

5-Chloro-4-(4-(4-chlorobenzyl)piperazin-1-yl)-3-nitropyridin-2-amine

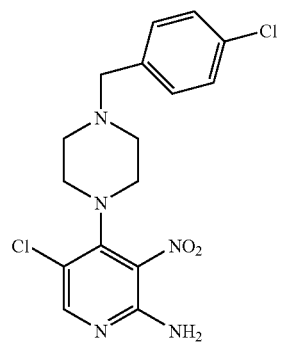

To a mixture of 2-amino-4,5-dichloro-3-nitropyridine (0.038 g, 0.18 mmol) and isopropanol (3 ml) was added 1-(4-chlorobenzyl)piperazine (0.042 g, 0.20 mmol) with the aid of isopropanol (0.5 ml) followed by diisopropylethylamine (0.035 ml, 0.20 mmol). The reaction mixture was heated at 45° C. for 18 h, then allowed to cool to room temperature, and diluted with isopropanol (4 ml). The precipitate was collected by filtration, washed with isopropanol and diethyl ether. The title compound was thus obtained as a yellow solid (0.034 g, 50%); $^1$H-NMR (500 MHz, DMSO-$d_6$) 2.48 (br s, obscured by DMSO peak, 4H, piperazine N(CH$_2$)$_2$), 3.06 (br s, 4H, piperazine N(CH$_2$)$_2$), 3.52 (s, 2H, NCH$_2$), 6.95 (s, 2H, NH$_2$), 7.35 (d, J=8.50 Hz, 2H) and 7.38 (d, J=8.55 Hz, 2H) (3,5-ArH and 2,6-ArH), 8.06 (s, 1H, 6-H);

LC (Method B)-MS (ESI, m/z): Rt=2.89 min—382, 384, 386 [(M+H)$^+$, Cl$_2$ isotopic pattern].

6-Chloro-7-(4-(4-chlorobenzyl)piperazin-1-yl)-2-(4-methoxyphenyl)-3H-imidazo[4,5-b]pyridine

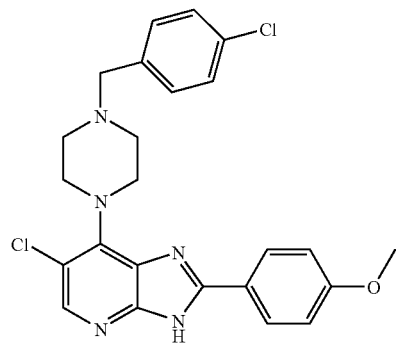

To a mixture of 5-chloro-4-(4-(4-chlorobenzyl)piperazin-1-yl)-3-nitropyridin-2-amine (0.027 g, 0.07 mmol), and ethanol (3.0 ml) was added 4-methoxybenzaldehyde (0.014 g, 0.10 mmol) with the aid of ethanol (1 ml) followed by a freshly prepared aqueous solution of Na$_2$S$_2$O$_4$ (1M; 0.3 ml, 0.3 mmol). The reaction mixture was heated at 70° C. for 4.5 h, then allowed to cool to room temperature and the solvents were removed in vacuo. The residue was absorbed on silica gel and the free running powder was placed on a 10 g isolute silica column which was eluted with 30% ethyl acetate in dichloromethane, and then 2% methanol in ethyl acetate/dichloromethane (v/v; 1:1). The title compound was obtained as a white solid (0.009 g, 28%); $^1$H-NMR (500 MHz, DMSO-$d_6$) 2.59 (br s, 4H, piperazine N(CH$_2$)$_2$), 3.56 (s, 2H, NCH$_2$), 3.69 (br s, 4H, piperazine N(CH$_2$)$_2$), 3.84 (s, 3H, OCH$_3$), 7.10 (d, J=8.86 Hz, 2H) and 8.12 (d, J=8.82 Hz, 2H) (3,5-C$_6$H$_4$OMe and 2,6-C$_6$H$_4$-Ome), 7.41 (s, 4H) (3,5-ArH and 2,6-ArH), 8.07 (s, 1H, imidazo[4,5-b]pyridine 5-H), 13.35 (s, 1H, imidazo[4,5-b]pyridine N—H);

LC (Method B)-MS (ESI, m/z): Rt=3.79 min—468, 470, 472 [(M+H)$^+$, Cl$_2$ isotopic pattern]. ESI-HRMS: Found: 468.1363, calculated for C$_{24}$H$_{24}$Cl$_2$N$_5$O (M+H)$^+$: 468.1358.

Example 38

1-(4-(2-amino-5-bromo-3-nitropyridin-4-yl)piperazin-1-yl)-2-phenoxyethanone

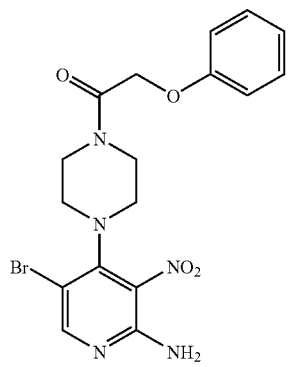

To a mixture of 5-bromo-4-chloro-3-nitro-pyridin-2-ylamine (0.126 g, 0.50 mmol) and isopropanol (9 ml) was added 2-phenoxy-1-(piperazin-1-yl)ethanone×HCl (0.141 g, 0.55 mmol) followed by diisopropylethylamine (0.20 ml, 1.10 mmol). The reaction mixture was heated at 45° C. for 22 h, then allowed to cool to room temperature and diluted with isopropanol (4 ml). The precipitate was collected by filtration and washed with isopropanol and diethyl ether. The title compound was thus obtained as a yellow solid (0.163 g, 75%). $^1$H-NMR (500 MHz, DMSO-$d_6$) 3.08 (br s) and 3.59 (br s) (8H, 2× piperazine N(CH$_2$)$_2$), 4.87 (s, 2H, COCH$_2$O), 6.93 (m, 3H) and 7.28 (m, 2H) (ArH), 7.08 (s, 2H, NH$_2$), 8.21 (s, 1H, 6-H);

LC (Method B)-MS (ESI, m/z): Rt=4.52 min—436, 438 [(M+H)$^+$, Br isotopic pattern].

1-(4-(6-Bromo-2-(4-(dimethylamino)phenyl)-3H-imidazo[4,5-b]pyridin-7-yl)piperazin-1-yl)-2-phenoxyethanone

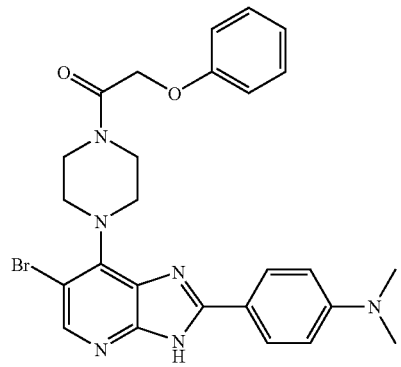

To a mixture of 1-(4-(2-amino-5-bromo-3-nitropyridin-4-yl)piperazin-1-yl)-2-phenoxyethanone (0.048 g, 0.11 mmol), and ethanol (4.0 ml) was added 4-dimethylaminobenzaldehyde (0.021 g, 0.14 mmol) followed by a freshly prepared aqueous solution of Na$_2$S$_2$O$_4$ (1M; 0.44 ml, 0.44 mmol). The reaction mixture was heated at 70° C. for 4 h, then allowed to cool to room temperature and concentrated in vacuo. The residue was triturated with water, the precipitate was collected by filtration, washed with water, ethanol, and diethyl ether to afford the title compound as a pale yellow solid (0.027 g, 46%); $^1$H-NMR (500 MHz, DMSO-$d_6$) 3.00 (s, 6H, N(CH$_3$)$_2$), 3.58 (br s) and 3.70 (br s) (8H, 2× piperazine N(CH$_2$)$_2$), 4.92 (s, 2H, COCH$_2$O), 6.95 (m, 3H) and 7.30 (m, 2H) (ArH), 6.82 (d, J=9.02 Hz, 2H) and 8.02 (d, J=8.92 Hz, 2H) (3,5-C$_6$H$_4$NMe$_2$ and 2,6-C$_6$H$_4$—NMe$_2$), 8.19 (s, 1H, imidazo[4,5-b]pyridine 5-H), 13.23 (s, 1H, imidazo[4,5-b]pyridine N—H);

LC (Method B)-MS (ESI, m/z): Rt=5.55 min—535, 537 [(M+H)$^+$, Br isotopic pattern]. ESI-HRMS: Found: 535.1465, calculated for C$_{26}$H$_{28}$BrN$_6$O$_2$ (M+H)$^+$: 535.1457.

Example 39

4-(2-Amino-5-bromo-3-nitropyridin-4-yl)-N-phenylpiperazine-1-carboxamide

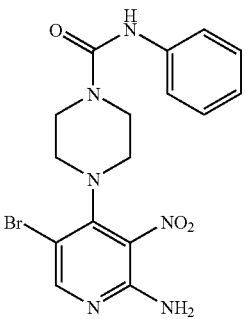

A solution of tert-butyl 4-(2-amino-5-bromo-3-nitropyridin-4-yl)piperazine-1-carboxylate (250 mg, 0.62 mmol) in CH$_2$Cl$_2$ (2.5 mL) at 0° C. was treated with TFA (2.5 mL) and stirred at 0° C. for 1.5 h. After this time, the solvents were evaporated in vacuo and the excess TFA removed by azeotroping with toluene (3×10 ml). The residue was suspended in CHCl$_3$ (2.5 mL) and treated with DIPEA (5 eq, 3.11 mmol, 0.54 mL) and phenyl isocyanate (1.05 eq, 0.65 mmol, 0.07 mL). The reaction was warmed to room temperature and stirred for 12 h. The formed precipitate was filtered off and dried to give the product as a yellow solid (221 mg, 84% for two steps); $^1$H-NMR (500 MHz, DMSO-d$_6$) 3.07 (br s, 4H, piperazine N(CH$_2$)$_2$), 3.58 (br s, 4H, piperazine N(CH$_2$)$_2$), 6.94 (tt, J=7.4, 1.1 Hz, 1H, phenyl H-4), 7.03 (br s, 2H, NH$_2$), 7.24 (dd, J=8.5, 7.5 Hz, 2H, phenyl H-3 & H-5), 7.45 (dd, J=8.5, 1.1 Hz, 2H, phenyl H-2 & H-6), 8.21 (s, 1H, pyridine H-6), 8.59 (br s, 1H, NH);

LC (Method B)-MS (ESI, m/z): Rt=4.47 min-(C$_{16}$H$_{17}$BrN$_6$O$_3$) (Found: [$^{79}$M+H]$^+$, 421.0624. C$_{16}$H$_{17}$BrN$_6$O$_3$ requires 421.0611).

4-(6-Bromo-2-(4-(dimethylamino)phenyl)-3H-imidazo[4,5-b]pyridin-7-yl)-N-phenylpiperazine-1-carboxamide

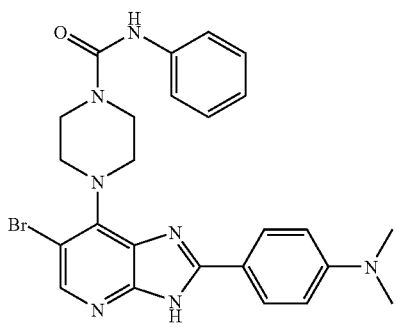

A solution of 4-(2-amino-5-bromo-3-nitropyridin-4-yl)-N-phenylpiperazine-1-carboxamide (100 mg, 0.25 mmol) and 4-(N,N-dimethylamino)benzaldehyde (1.05 eq, 0.26 mmol, 39 mg) in DMF (1.25 mL) was treated with a freshly prepared 1M aqueous solution of Na$_2$S$_2$O$_4$ (3 eq, 0.75 mmol, 0.75 mL) and stirred at 80° C. for 4 h. After this time, the precipitate which had formed was filtered off and washed with hexane to give the product (64 mg, 53%) as an off-white solid; $^1$H-NMR (500 MHz, DMSO-d$_6$) 3.00 (s, 6H, N(CH$_3$)$_2$), 3.64-3.68 (m, 8H, 2× piperazine N(CH$_2$)$_2$), 6.82 (d, J=8.4 Hz, 2H, N,N-dimethylaminophenyl), 6.94 (t, J=7.4 Hz, 1H, phenyl H-4), 7.25 (t, J=7.5 Hz, 2H, phenyl H-3 & H-5), 7.51 (d, J=8.2 Hz, 2H, phenyl H-2 & H-6), 8.02 (d, J=8.2 Hz, 2H, N,N-dimethylaminophenyl), 8.20 (s, 1H, imidazo[4,5-b]pyridine H-5), 8.61 (s, br, 1H, PhNH), 13.19 (s, br, 1H, imidazo[4,5-b]pyridine NH);

LC (Method A)-MS (ESI, m/z): Rt=8.34 min—520, 522 [(M+H)$^+$, bromine isotopic pattern). ESI-HRMS: Found: 520.1450, calculated for C$_{25}$H$_{26}$BrN$_7$O (M+H)$^+$: 520.1460.

Example 40

5-Bromo-3-nitro-4-(4-(phenylsulfonyl)piperazin-1-yl)pyridin-2-amine

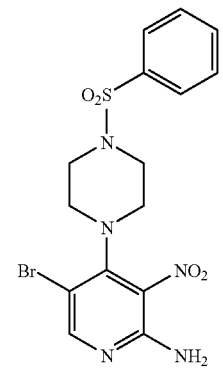

A solution of tert-butyl 4-(2-amino-5-bromo-3-nitropyridin-4-yl)piperazine-1-carboxylate (250 mg, 0.62 mmol) in CH$_2$Cl$_2$ (2.5 mL) at 0° C. was treated with TFA (2.5 mL) and stirred at 0° C. for 1.5 h. After this time, the solvents were evaporated in vacuo and the excess TFA removed by azeotroping with toluene (3×10 mL). The residue was suspended in CHCl$_3$ (3 mL) and pyridine (3 mL) and treated with benzenesulfonyl chloride (1.1 eq, 0.68 mmol, 0.09 mL), warmed to room temperature and stirred for 12 h. The solvents were removed in vacuo and the residue partition between water (5 mL) and EtOAc (5 mL). The aqueous layer was extracted with EtOAc (2×5 mL) and the combined organic extracts were dried (MgSO$_4$) and concentrated in vacuo. Column chromatography (hexane-EtOAc, 1:1) gave the product (107 mg, 39% for two steps) as a yellow solid; $^1$H-NMR (500 MHz, DMSO-d$_6$) 3.09 (br s, 8H, 2× piperazine N(CH$_2$)$_2$), 7.08 (br s, 2H, NH$_2$), 7.67-7.70 (m, 2H, phenyl H-3 & H-5), 7.74-7.78 (m, 3H, phenyl H-2, H-4 & H-6), 8.16 (s, 1H, pyridine H-6);

LC (Method A)-MS (ESI, m/z): Rt=7.04 min—442, 444 [(M+H)$^+$, Br isotopic pattern).

4-(6-Bromo-7-(4-(phenylsulfonyl)piperazin-1-yl)-3H-imidazo[4,5-b]pyridin-2-yl)-N,N-dimethylaniline

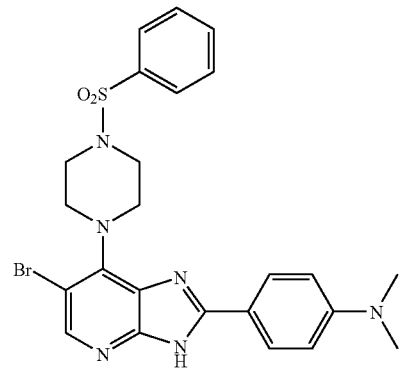

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(phenylsulfonyl)piperazin-1-yl)pyridin-2-amine (40 mg, 0.090 mmol), DMF (1 mL), 1M Na$_2$S$_2$O$_4$ (3 eq, 0.27 mmol, 0.27 mL) and 4-(N,N-dimethylamino)benzaldehyde (1.1 eq, 0.099 mmol, 15 mg). After 18 h, the reaction was quenched with NH$_4$OH and extracted with EtOAc (5×5 mL). The organic extracts were dried (MgSO$_4$), filtered and concentrated in vacuo to give the product (11 mg, 23%) as a pale yellow solid; $^1$H-NMR (500 MHz, DMSO-d$_6$) 3.01 (s, 6H, N(CH$_3$)$_2$), 3.17-3.27 (m, 4H, piperazine N(CH$_2$)$_2$), 3.65 (t, J=4.7 Hz, 4H, piperazine N(CH$_2$)$_2$), 6.82 (d, J=9.0 Hz, 2H, N,N-dimethylaminophenyl), 7.68-7.70 (m, 2H, phenyl H-3 & H-5), 7.73-7.76 (m, 1H, phenyl H-4), 7.81 (dd, J=7.1, 1.5 Hz, 2H, phenyl H-2 & H-6), 7.99 (d, J=9.0, 2H, N,N-dimethylaminophenyl), 8.14 (s, 1H, imidazo[4,5-b]pyridine H-5), 13.21 (s, br, 1H, imidazo[4,5-b]pyridine NH).

LC (Method A)-MS (ESI, m/z): Rt=8.62 min; 541, 543 [(M+H)$^+$, Br isotopic pattern); ESI-HRMS: Found: 541.1013, calculated for C$_{24}$H$_{25}$BrN$_6$O$_2$S (M+H)$^+$: 541.1021.

Example 41 tert-Butyl 4-(2-(3-phenylureido)ethyl)piperazine-1-carboxylate

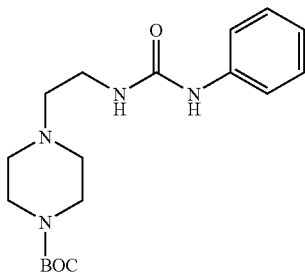

A solution of the amine tert-butyl 4-(2-aminoethyl)piperazine-1-carboxylate (*Org. Proc. Res. Dev.* 2005, 9, 102-104) (300 mg, 1.31 mmol) in CHCl$_3$ (5 mL) at 0° C. was treated with phenyl isocyanate (1.05 eq, 1.37 mmol, 0.15 mL), warmed to room temperature and stirred for 4 h. Concentration in vacuo gave a solid which was pure enough to be used in future reactions. Further purification by column chromatography (EtOAc-MeOH, 9:1) gave the pure product (381 mg, 84%) as a colourless solid; $^1$H-NMR (500 MHz, DMSO-d$_6$) 1.40 (s, 9H, C(CH$_3$)$_3$), 2.35 (t, br, J=4.9 Hz, 4H, piperazine N(CH$_2$)$_2$), 2.40 (t, J=6.3 Hz, 2H, NCH$_2$), 3.20 (q, J=6.2 Hz, 2H, NHCH$_2$), 3.32 (t, br, J=4.8 Hz, 4H, piperazine N(CH$_2$)$_2$), 6.04 (t, br, J=5.3 Hz, 1H, NHCH$_2$), 6.87 (tt, J=7.5, 1.1 Hz, 1H, phenyl H-4), 7.20 (dd, J=8.6, 7.4 Hz, 2H, phenyl H-3 & H-5), 7.37 (dd, J=8.7, 1.1 Hz, 2H, phenyl H-2 & H-6), 8.56 (s, br, 1H, PhNH).

1-(2-(4-(2-Amino-5-bromo-3-nitropyridin-4-yl)piperazin-1-yl)ethyl)-3-phenylurea

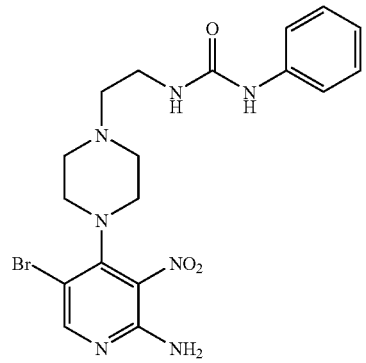

This was prepared using the same procedure as for 5-bromo-3-nitro-4-(4-(1-(pyridin-2-yl)ethyl)piperazin-1-yl)pyridin-2-amine, but here using tert-butyl 4-(2-(3-phenylureido)ethyl)piperazine-1-carboxylate (1.1 eq, 0.43 mmol, 150 mg), TFA (1 mL) and CH$_2$Cl$_2$ (2 mL), then 5-bromo-4-chloro-3-nitropyridin-2-amine (103 mg, 0.29 mmol) in $^i$PrOH (2 mL) and DIPEA (0.5 mL). Filtration and washing as previously described gave the product (190 mg, 95% for two steps) as a bright yellow solid; $^1$H-NMR (500 MHz, DMSO-d$_6$) 2.45-2.65 (2 m, 4H, piperazine N(CH$_2$)$_2$), 3.08-3.17 (2 m, 6H, piperazine N(CH$_2$)$_2$ & CH$_2$), 3.60-3.63 (m, 2H, CH$_2$), 6.10 (br s, 1H, NH), 6.89 (t, J=6.9 Hz, 1H, phenyl H-4), 7.02 (br s, 2H, NH$_2$), 7.21 (t, br, J=7.4 Hz, 2H, phenyl H-3 & H-5), 7.38 (d, J=7.5 Hz, 2H, phenyl H-2 & H-6), 8.17 (s, 1H, pyridine H-6), 8.66 (s, br, 1H, NH);

LC (Method A)-MS (ESI, m/z): Rt=3.54 min—464, 466 [(M+H)$^+$, Br isotopic pattern); ESI-HRMS: Found: 464.1039, calculated for C$_{18}$H$_{22}$BrN$_7$O$_3$ (M+H)$^+$: 464.1046.

1-(2-(4-(6-Bromo-2-(4-(dimethylamino)phenyl)-3H-imidazo[4,5-b]pyridin-7-yl)piperazin-1-yl)ethyl)-3-phenylurea

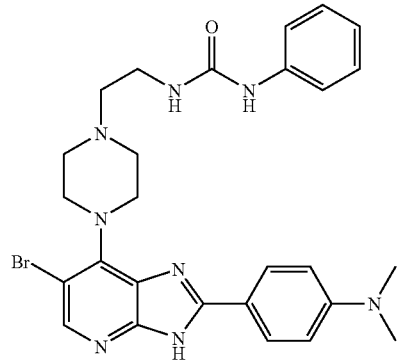

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 1-(2-(4-(2-amino-5-bromo-3-nitropyridin-4-yl)piperazin-1-yl)ethyl)-3-phenylurea (100 mg, 0.22 mmol), DMF (1.25 mL), 1M Na$_2$S$_2$O$_4$ (3 eq, 0.66 mmol, 0.66 mL) and 4-(N,N-dimethylamino)benzaldehyde (1.05 eq, 0.23 mmol, 34 mg). After filtration, a small sample of the solid product was further purified by semi-preparative hplc to give the pure product as an off-white solid; $^1$H-NMR (500 MHz, DMSO-d$_6$) 2.50 (2H, obscured by DMSO peak, NCH$_2$), 2.53-2.57 (m, 4H, piperazine N(CH$_2$)$_2$), 3.00 (s, 6H, N(CH$_3$)$_2$), 3.27 (q, J=5.7 Hz, 2H, NHCH$_2$), 3.67 (t, J=4.6 Hz, 4H, piperazine N(CH$_2$)$_2$), 6.13 (t, br, J=5.0 Hz, 1H, NHCH$_2$), 6.82 (d, J=9.0 Hz, 2H, N,N-dimethylaminophenyl), 6.88 (tt, J=7.4, 1.0 Hz, 1H, phenyl H-4), 7.22 (dd, J=8.4, 7.5 Hz, 2H, phenyl H-3 & H-5), 7.40 (dd, J=8.5, 1.0 Hz, 2H, phenyl H-3 & H-5), 8.01 (d, J=8.9 Hz, 2H, N,N-dimethylaminophenyl), 8.16 (s, 1H, imidazo[4,5-b]pyridine H-5), 8.64 (br s, 1H, PhNH), 13.13 (br s, 1H, imidazo[4,5-b]pyridine NH);

LC (Method A)-MS (ESI, m/z): Rt=5.39 min—563, 565 [(M+H)$^+$, Br isotopic pattern). ESI-HRMS: Found: 563.1874, calculated for C$_{27}$H$_{31}$BrN$_8$O (M+H)$^+$: 563.1882.

Example 42

4-(6-Bromo-2-(4-(dimethylamino)phenyl)-3H-imidazo[4,5-b]pyridin-7-yl)-N-(thiazol-2-yl)piperazine-1-carboxamide

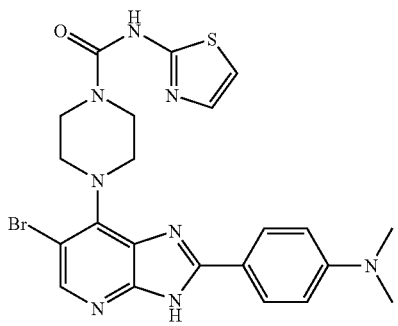

A solution of prop-1-en-2-yl thiazol-2-ylcarbamate (prepared according to the procedure described in *J. Org. Chem.* 2005, 70, 6960-6963) (40 mg, 0.054 mmol) and 4-(6-bromo-7-(piperazin-1-yl)-3H-imidazo[4,5-b]pyridin-2-yl)-N,N-dimethylaniline (1.0 eq, 0.054 mmol, 22 mg) in THF (0.5 mL) was heated to 55° C. Then N-methylpyrrolidine (0.1 eq, 0.005 mmol, 5 µL) was added and the mixture stirred at 55° C. for 2 h. Concentration in vacuo gave crude material as a solid. A small sample was purified by semi-preparative hplc to give the pure product as a colourless solid; $^1$H-NMR (500 MHz, DMSO-d$_6$) 2.99 (s, 6H, N(CH$_3$)$_2$), 3.58-3.62 (m, 4H, piperazine N(CH$_2$)$_2$), 3.74-3.78 (m, 4H, piperazine N(CH$_2$)$_2$), 6.81 (d, J=8.9 Hz, 2H, N,N-dimethylaminophenyl), 7.22 (d, J=3.6 Hz, 1H, thiazole H-4 or H-5), 7.35 (br s, 1H, NH), 7.48 (d, J=3.6 Hz, 1H, thiazole H-4 or H-5), 8.02 (d, J=8.9 Hz, 2H, N,N-dimethylaminophenyl), 8.19 (s, 1H, imidazo[4,5-b]pyridine H-5).

Example 43

4-(6-Bromo-2-(4-(dimethylamino)phenyl)-3H-imidazo[4,5-b]pyridin-7-yl)-N-ethylpiperazine-1-carboxamide

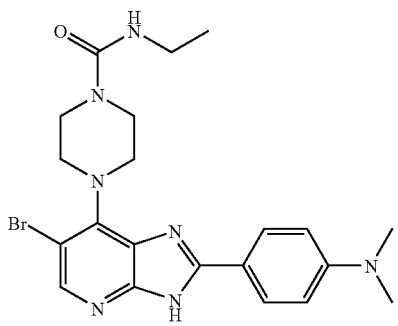

This was prepared from [4-(6-bromo-7-piperazin-1-yl-3H-imidazo[4,5-b]pyridin-2-yl)-phenyl]-dimethyl-amine (20 mg, 0.050 mmol), using CHCl$_3$ (1.5 mL) and ethyl isocyanate (1.1 eq, 0.055 mmol, 43 µL). Filtration of the precipitate after 16 h gave the product (13 mg, 56%) as a pale yellow solid; $^1$H-NMR (500 MHz, DMSO-d$_6$) 1.05 (t, J=7.1 Hz, 3H, CH$_2$CH$_3$), 3.00 (s, 6H, N(CH$_3$)$_2$), 3.09 (qd, J=7.1, 5.4 Hz, 2H, NHCH$_2$), 3.50-3.52 (m, 4H, piperazine N(CH$_2$)$_2$), 3.55-3.57 (4H, m, piperazine N(CH$_2$)$_2$), 6.55 (t, J=5.4 Hz, 1H, NHCH$_2$), 6.82 (d, J=9.0 Hz, 2H, N,N-dimethylaminophenyl), 8.01 (d, J=9.0 Hz, 2H, N,N-dimethylaminophenyl), 8.17 (s, 1H, imidazo[4,5-b]pyridine H-5), 13.18 (s, br, 1H, imidazo[4,5-b]pyridine NH);

LC (Method B)-MS (ESI, m/z): Rt=4.92 min—472, 474 [(M+H)$^+$, Br isotopic pattern]; ESI-HRMS: Found: 472.1464, calculated for C$_{21}$H$_{26}$BrN$_7$O (M+H)$^+$: 472.1460.

Example 44

2-(4-(6-Bromo-2-(pyridin-3-yl)-3H-imidazo[4,5-b]pyridin-7-yl)piperazin-1-yl)-N-(thiazol-2-yl)acetamide

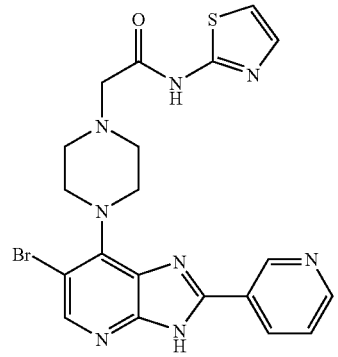

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 2-(4-(2-amino-5-bromo-3-nitropyridin-4-yl)piperazin-1-yl)-N-(thiazol-2-yl)acetamide (50 mg, 0.11 mmol), DMF (1 mL), 1M Na$_2$S$_2$O$_4$ (3 eq, 0.33 mmol, 0.33 mL) and 3-pyridinecarboxaldehyde (1.05 eq, 0.12 mmol, 0.011 mL). After 16 h, the DMF was removed in vacuo, the residue taken up in water (2 mL) and extracted with EtOAc (2×3 mL) and CH$_2$Cl$_2$ (2×3 mL). The combined extracts were dried (Na$_2$SO$_4$) and concentrated in vacuo to give the product (21 mg, 38%) as a pale brown solid; $^1$H-NMR (500 MHz, DMSO-d$_6$) 3.30 (hidden by water-in-DMSO peak, 6H, NCH$_2$CO and piperazine N(CH$_2$)$_2$), 3.89 (br s, 4H, piperazine N(CH$_2$)$_2$), 7.28 (br s, 1H, thiazole H-4 or H-5), 7.52 (d, J=3.5 Hz, 1H, thiazole H-4 or H-5), 7.60 (dd, J=7.9, 4.8 Hz, 1H, pyridine H-5), 8.32 (s, 1H, imidazo[4,5-b]pyridine H-5), 8.52 (d, br, J=8.0 Hz, 1H, pyridine H-4), 8.71 (d, br, J=4.7 Hz, 1H, pyridine H-6), 9.38 (s, 1H, pyridine H-2), 13.80 (s, br, 1H, imidazo[4,5-b]pyridine NH);

LC (Method B)-MS (ESI, m/z): Rt=3.45 min—499, 501 [(M+H)$^+$, Br isotopic pattern]. ESI-HRMS: Found: 499.0667, calculated for C$_{20}$H$_{19}$BrN$_8$OS (M+H)$^+$: 499.0664.

Example 45

Ethyl 2-(6-bromo-7-(4-(2-oxo-2-(thiazol-2-ylamino) ethyl)piperazin-1-yl)-3H-imidazo[4,5-b]pyridin-2-yl)cyclopropanecarboxylate

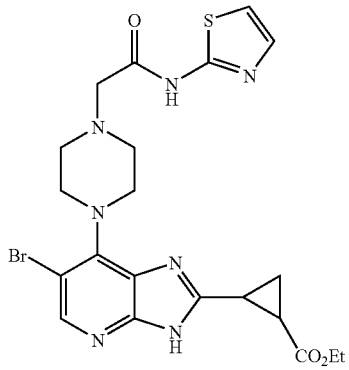

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 2-(4-(2-amino-5-bromo-3-nitropyridin-4-yl)piperazin-1-yl)-N-(thiazol-2-yl)acetamide (63 mg, 0.14 mmol), DMF (1.3 mL), ethanol (0.2 mL), 1M Na$_2$S$_2$O$_4$ (3 eq, 0.43 mmol, 0.43 mL) and ethyl 2-formyl-1-cyclopropanecarboxylate (1.1 eq, 0.16 mmol, 0.021 mL). After 16 h, concentration in vacuo and preparation by preparative tlc (EtOAc—CH$_2$Cl$_2$-MeOH, 50:50:2) gave the product (19 mg, 25%) as a colourless solid; $^1$H-NMR (500 MHz, DMSO-d$_6$) 1.21 (t, J=7.1 Hz, 3H, CH$_2$CH$_3$), 1.56 (app. quintet, J=4.6 Hz, 1H, cyclopropane CH$_A$H$_B$), 1.64-1.67 (m, 1H, cyclopropane CH$_A$H$_B$), 2.26 (app. quintet, J=5.0 Hz, cyclopropane CH), 2.73 (br s, 4H, piperazine N(CH$_2$)$_2$), 3.38 (s, 2H, NCH$_2$CO), 3.57 (br s, 4H, piperazine N(CH$_2$)$_2$), 4.13 (q, J=7.1 Hz, 2H, CH$_2$CH$_3$), 7.23 (d, J=3.5 Hz, 1H, thiazole H-4 or H-5), 7.48 (d, J=3.5 Hz, 1H, thiazole H-4 or H-5), 8.17 (s, 1H, imidazo[4,5-b]pyridine H-5), 11.86 (br s, 1H, CONH or imidazo[4,5-b]pyridine NH), 12.94 (br s, 1H, CONH or imidazo[4,5-b]pyridine NH);

LC (Method B)-MS (ESI, m/z): Rt=3.84 min—534, 536 [(M+H)$^+$, Br isotopic pattern]. ESI-HRMS: Found: 534.0933, calculated for C$_{21}$H$_{24}$BrN$_7$O$_3$S (M+H)$^+$: 534.0923.

Example 46

2-(6-Bromo-7-(4-(2-oxo-2-(thiazol-2-ylamino)ethyl) piperazin-1-yl)-3H-imidazo[4,5-b]pyridin-2-yl)cyclopropanecarboxamide

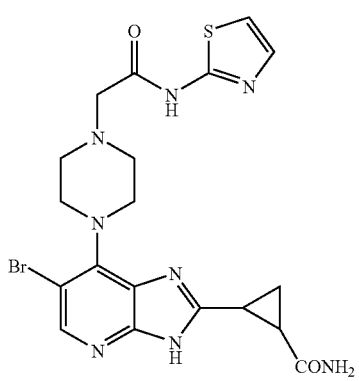

A solution of ethyl 2-(6-bromo-7-(4-(2-oxo-2-(thiazol-2-ylamino)ethyl)piperazin-1-yl)-3H-imidazo[4,5-b]pyridin-2-yl)cyclopropanecarboxylate (15 mg, 0.028 mmol) in ammonium hydroxide (2.5 mL) was heated in a sealed tube at 100° C. for 16 h. After this time, LC-MS analysis showed that only the desired product was present. Evaporation of the solvents in vacuo provided the product (9 mg, 64%) as a colourless solid; $^1$H-NMR (500 MHz, DMSO-d$_6$) 1.40 (app. quintet, J=4.4 Hz, 1H, cyclopropane CH$_A$H$_B$), 1.46-1.51 (m, 1H, cyclopropane CH$_A$H$_B$), 2.20-2.24 (m, 1H, cyclopropane CH), 2.40 (br s, 1H, cyclopropane CH), 2.74 (t, J=4.9 Hz, 4H, piperazine N(CH$_2$)$_2$), 3.38 (s, 2H, NCH$_2$CO), 3.54 (br s, 4H, piperazine N(CH$_2$)$_2$), 6.53 (d, J=3.7 Hz, 1H, thiazole H-4 or H-5), 6.83 (br s, 2H, NH$_2$), 6.92 (d, J=3.7 Hz, 1H, thiazole H-4 or H-5), 7.02 (br s, 1H, CONH), 7.74 (br s, 1H, imidazo[4,5-b]pyridine H-5);

LC (Method A)-MS (ESI, m/z): Rt=4.39 min—505, 507 [(M+H)$^+$, Br isotopic pattern]; ESI-HRMS: Found: 505.0778, calculated for C$_{19}$H$_{21}$BrN$_8$O$_2$S (M+H)$^+$: 505.0770.

Example 47

5-Bromo-4-(4-ethylpiperazin-1-yl)-3-nitropyridin-2-amine

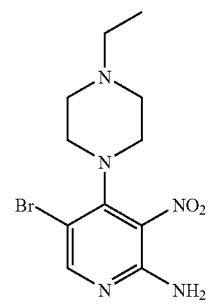

This was prepared using the same procedure as for 2-(4-(2-amino-5-bromo-3-nitropyridin-4-yl)piperazin-1-yl)-N-(thiazol-2-yl)acetamide, but here using 5-bromo-4-chloro-3-nitropyridin-2-amine (300 mg, 1.19 mmol), DIPEA (1.1 eq, 1.31 mmol, 0.23 mL), isopropanol (7 mL) and 1-ethylpiperazine (1.1 eq, 1.31 mmol, 0.17 mL). After 18 h the precipitate was filtered and washed with cold water (2×3 mL) to give the product (212 mg, 54%) as a yellow solid; $^1$H-NMR (500 MHz, DMSO-d$_6$) 1.04 (t, J=7.0 Hz, 3H, CH$_2$CH$_3$), 2.46-2.58 (2 m, 6H, CH$_2$CH$_3$ and piperazine N(CH$_2$)$_2$), 3.08 (br s, 4H, piperazine N(CH$_2$)$_2$), 6.98 (br s, 2H, NH$_2$), 8.16 (s, 1H, pyridine H-6);

LC (Method B)-MS (ESI, m/z): Rt=1.20 min—330, 332 [(M+H)$^+$, Br isotopic pattern]; ESI-HRMS: Found: 330.0565, calculated for C$_{11}$H$_{16}$BrN$_5$O$_2$ (M+H)$^+$: 330.0566.

4-(6-Bromo-7-(4-ethylpiperazin-1-yl)-3H-imidazo[4,5-b]pyridin-2-yl)-N,N-dimethylaniline

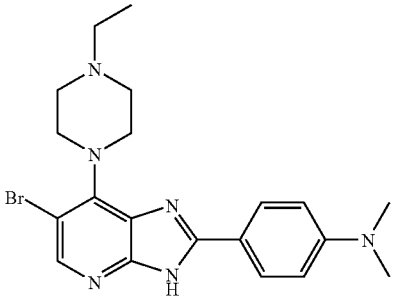

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-4-(4-ethylpiperazin-1-yl)-3-nitropyridin-2-amine (100 mg, 0.30 mmol), DMF (1.5 mL), 1M $Na_2S_2O_4$ (3 eq, 0.90 mmol, 0.90 mL) and 4-(N,N-dimethylamino)benzaldehyde (1.05 eq, 0.32 mmol, 47 mg). After 18 h, filtration of the precipitate gave pure product (47 mg, 49%) as an off-white solid; $^1$H-NMR (500 MHz, DMSO-$d_6$) 1.22 (br s, 3H, $CH_2CH_3$), 2.55 (s, 2H, $CH_2CH_3$), 2.73 (s, 2H, piperazine $NCH_2$), 2.89 (s, 2H, piperazine $NCH_2$), 3.01 (s, 6H, $N(CH_3)_2$), 3.80 (br s, 4H, piperazine $N(CH_2)_2$), 6.83 (d, J=8.9 Hz, 2H, N,N-dimethylaminophenyl), 8.02 (d, J=8.9 Hz, 2H, N,N-dimethylaminophenyl), 8.20 (s, 1H, imidazo[4,5-b]pyridine H-5), 13.23 (br s, 1H, imidazo[4,5-b]pyridine NH);

LC (Method A)-MS (ESI, m/z): Rt=4.20 min—429, 431 [(M+H)$^+$, Br isotopic pattern]; ESI-HRMS: Found: 429.1396, calculated for $C_{20}H_{25}BrN_6$ (M+H)$^+$: 429.1402.

Example 48

5-Bromo-3-nitro-4-(4-phenylpiperazin-1-yl)pyridin-2-amine

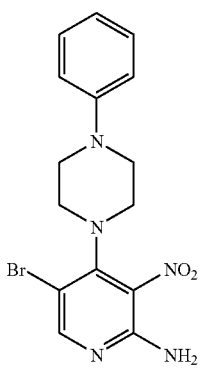

This was prepared using the same procedure as for 2-(4-(2-amino-5-bromo-3-nitropyridin-4-yl)piperazin-1-yl)-N-(thiazol-2-yl)acetamide, but here using 5-bromo-4-chloro-3-nitropyridin-2-amine (300 mg, 1.19 mmol), DIPEA (3.5 eq, 4.16 mmol, 0.72 mL), isopropanol (7 mL) and 1-phenylpiperazine hydrochloride (1.1 eq, 1.31 mmol, 260 mg). After 18 h the precipitate was filtered and washed with cold water (2×3 mL) to give the product (407 mg, 91%) as an orange solid;

$^1$H-NMR (500 MHz, DMSO-$d_6$) 3.20 (br s, 4H, piperazine $N(CH_2)_2$), 3.30 (hidden by DMSO peak, 4H, piperazine $N(CH_2)_2$), 6.83 (t, J=7.5 Hz, 1H, phenyl H-4), 6.98 (d, J=8.4 Hz, 2H, phenyl H-2 & H-6), 7.04 (br s, 2H, $NH_2$), 7.25 (t, J=7.9 Hz, 2H, phenyl H-3 & H-5), 8.21 (s, 1H, pyridine H-6);

LC (Method B)-MS (ESI, m/z): Rt=5.30 min—378, 380 [(M+H)$^+$, Br isotopic pattern]; ESI-HRMS: Found: 378.0551, calculated for $C_{15}H_{16}BrN_5O_2$ (M+H)$^+$: 378.0566.

4-(6-Bromo-7-(4-phenylpiperazin-1-yl)-3H-imidazo[4,5-b]pyridin-2-yl)-N,N-dimethylaniline

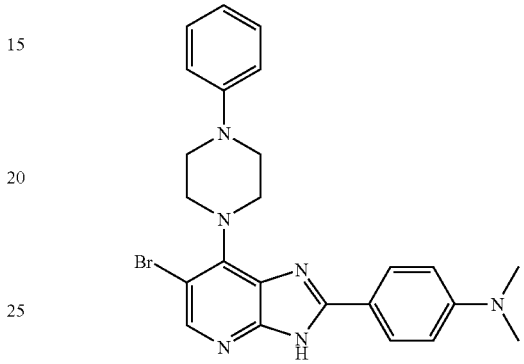

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-phenylpiperazin-1-yl)pyridin-2-amine (75 mg, 0.20 mmol), DMF (1.5 mL), 1M $Na_2S_2O_4$ (3 eq, 0.60 mmol, 0.60 mL) and 4-(N,N-dimethylamino)benzaldehyde (1.05 eq, 0.21 mmol, 31 mg). After 18 h, filtration of the precipitate and trituration with $Et_2O$ gave the product (34 mg, 36%) as a pale yellow solid; $^1$H-NMR (500 MHz, DMSO-$d_6$) 3.00 (s, 6H, $N(CH_3)_2$), 3.36-3.38 (m, 4H, piperazine $N(CH_2)_2$), 3.78-3.80 (m, 4H, piperazine $N(CH_2)_2$), 6.80-6.83 (m, 1H, phenyl H-4), 6.82 (d, J=8.7 Hz, 2H, N,N-dimethylaminophenyl), 7.03 (d, J=8.0 Hz, 2H, phenyl H-2 & H-6), 7.25 (t, br, J=8.0 Hz, 2H, phenyl H-3 & H-5), 8.02 (d, J=8.8 Hz, 2H, N,N-dimethylaminophenyl), 8.19 (s, 1H, imidazo[4,5-b]pyridine H-5), 13.14 (s, br, 1H, imidazo[4,5-b]pyridine NH);

LC-MS (Method B)-MS (ESI, m/z): Rt=6.01 min—477, 479 [(M+H)$^+$, Br isotopic pattern]; ESI-HRMS: Found: 477.1392, calculated for $C_{24}H_{25}BrN_6$ (M+H)$^+$: 477.1402.

Example 49

5-Bromo-4-(4-(methylsulfonyl)piperazin-1-yl)-3-nitropyridin-2-amine

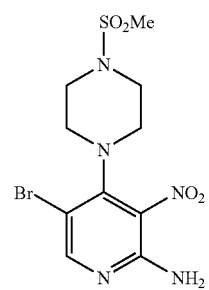

This was prepared using the same procedure as for 2-(4-(2-amino-5-bromo-3-nitropyridin-4-yl)piperazin-1-yl)-N-(thiazol-2-yl)acetamide, but here using 5-bromo-4-chloro-3-nitropyridin-2-amine (200 mg, 0.79 mmol), isopropanol (12 mL) and 1-methanesulfonylpiperazine (1.1 eq, 0.87 mmol, 143 mg). After 18 h the precipitate was filtered and washed with cold water (2×3 mL) to give the product (101 mg, 34%) as an orange solid; $\delta_H$ (500 MHz, DMSO-$d_6$) 2.94 (s, 3H, CH$_3$), 3.12 (s, br, 4H, piperazine N(CH$_2$)$_2$), 3.25 (s, br, 4H, piperazine N(CH$_2$)$_2$), 7.06 (s, br, 2H, NH$_2$), 8.22 (s, 1H, pyridine H-6);

LC (Method B)-MS (ESI, m/z): Rt=3.57 min—380, 382 [(M+H)$^+$, Br isotopic pattern]; ESI-MS: Found: 380.0024, calculated for $C_{10}H_{14}BrN_5O_4S$ (M+H)$^+$: 380.0028.

4-(6-Bromo-7-(4-(methylsulfonyl)piperazin-1-yl)-3H-imidazo[4,5-b]pyridin-2-yl)-N,N-dimethylaniline

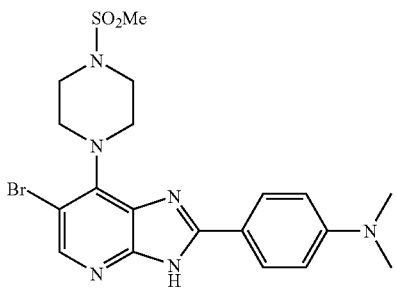

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-4-(4-(methylsulfonyl)piperazin-1-yl)-3-nitropyridin-2-amine (100 mg, 0.26 mmol), DMF (1.6 mL), ethanol (0.2 mL), 1M Na$_2$S$_2$O$_4$ (4 eq, 1.05 mmol, 1.05 mL) and 4-(N,N-dimethylamino)benzaldehyde (1.1 eq, 0.29 mmol, 43 mg). After 6 h, filtration of the precipitate and washing with cold ethanol (1 mL) and cold water (1 mL) gave the product (49 mg, 39%) as a pale yellow solid; $^1$H-NMR (500 MHz, DMSO-$d_6$) 2.97 (s, 3H, SO$_2$CH$_3$), 3.01 (s, 6H, N(CH$_3$)$_2$), 3.34-3.38 (m, 4H, piperazine N(CH$_2$)$_2$), 3.70-3.73 (m, 4H, piperazine N(CH$_2$)$_2$), 6.83 (d, J=9.0 Hz, 2H, N,N-dimethylaminophenyl) 8.05 (d, J=8.9 Hz, 2H, N,N-dimethylaminophenyl), 8.21 (s, 1H, imidazo[4,5-b]pyridine H-5), 13.21 (br s, 1H, imidazo[4,5-b]pyridine NH);

LC (Method B)-MS (ESI, m/z): Rt=4.89 min—479, 481 [(M+H)$^+$, Br isotopic pattern]; ESI-HRMS: Found: 479.0864, calculated for $C_{19}H_{23}BrN_6O_2S$ (M+H)$^+$: 479.0865.

Example 50 tert-Butyl 4-(1-(pyridin-2-yl)ethyl)piperazine-1-carboxylate

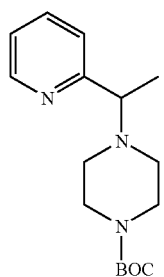

A solution of the alcohol 1-(pyridin-2-yl)ethanol (prepared following the procedure described in *J. Chem. Soc., Perkin Trans.* 1, 2000, 4439-4444) (100 mg, 0.81 mmol) in CH$_2$Cl$_2$ (4 mL) at 0° C. was treated with triethylamine (5.0 eq, 4.05 mmol, 0.56 mL) and MsCl (2.0 eq, 1.62 mmol, 0.13 mL) and stirred at 0° C. for 30 minutes. It was then washed with water, brine, dried (MgSO$_4$) and concentrated in vacuo to give the crude mesylate. This was immediately redissolved in DMSO (3 mL) at room temperature, treated with N—BOC piperazine (4.0 eq, 3.24 mmol, 605 mg) and stirred at 60° C. for 18 h. After this time, the mixture was poured into water and extracted with EtOAc (2×10 mL) and CHCl$_3$ (2×10 mL). The combined extracts were dried (MgSO$_4$), concentrated in vacuo and purified by column chromatography (EtOAc) to give the product (161 mg, 68% for two steps) as a colourless oil; $^1$H-NMR (500 MHz, CDCl$_3$) 1.46 (s, 9H, C(CH$_3$)$_3$), 1.65 (br s, 3H, CHCH$_3$), 2.34-2.58 (m, 4H, piperazine N(CH$_2$)$_2$), 3.48-3.62 (m, 5H, CHCH$_3$ & piperazine N(CH$_2$)$_2$), 7.18 (br s, 1H, pyridine H-3 or H-5), 7.40 (br s, 1H, pyridine H-3 or H-5), 7.68 (br s, 1H, pyridine H-4), 8.58 (br s, 1H, pyridine H-6);

LC (Method B)-MS (ESI, m/z): Rt=2.07 min—292 [(M+H)$^+$, 100%).

5-Bromo-3-nitro-4-(4-(1-(pyridin-2-yl)ethyl)piperazin-1-yl)pyridin-2-amine

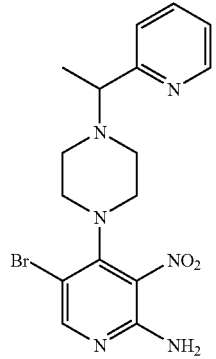

A solution of tert-butyl 4-(1-(pyridin-2-yl)ethyl)piperazine-1-carboxylate (1.1 eq, 1.10 mmol, 321 mg) in TFA (4 mL) and CH$_2$Cl$_2$ (4 mL) at 0° C. was stirred for 30 minutes and concentrated in vacuo. The remaining TFA was removed by azeotroping with toluene (3×10 mL) and drying at high vacuum for 2 h. Then the residue was reacted with 5-bromo-4-chloro-3-nitropyridin-2-amine (253 mg, 1.00 mmol) in $^i$PrOH (5 mL) and DIPEA (2 mL) using the same procedure described for 2-(4-(2-amino-5-bromo-3-nitropyridin-4-yl)piperazin-1-yl)-N-(thiazol-2-yl)acetamide. After 18 h, the precipitate was filtered and washed with cold water (2×3 mL) and hexane (3 mL) to give the product (313 mg, 70% for two steps) as a yellow solid; $^1$H-NMR (500 MHz, DMSO-$d_6$) 1.33 (d, J=6.7 Hz, 3H, CH$_3$), 2.48-2.62 (2 m, 4H, piperazine N(CH$_2$)$_2$), 3.04-3.13 (m, 4H, piperazine N(CH$_2$)$_2$), 3.63-3.69 (m, 1H, CH), 6.95 (br s, 2H, NH$_2$), 7.25 (dd, br, J=6.8, 5.2 Hz, 1H, pyridine H-5), 7.44 (d, J=7.8 Hz, 1H, pyridine H-3), 7.77 (td, J=7.7, 1.6 Hz, 1H, pyridine H-4), 8.13 (s, 1H, bromopyridine H-6), 8.50 (d, br, J=4.2 Hz, 1H, pyridine H-6);

LC (Method B)-MS (ESI, m/z): Rt=2.09 min; 407, 409 [(M+H)$^+$, Br isotopic pattern]; ESI-HRMS: Found: 407.0811, calculated for $C_{16}H_{19}BrN_6O_2$ (M+H)$^+$: 407.0831.

4-(6-Bromo-7-(4-(1-(pyridin-2-yl)ethyl)piperazin-1-yl)-3H-imidazo[4,5-b]pyridin-2-yl)-N,N-dimethylaniline

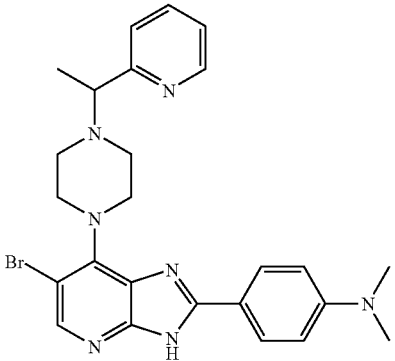

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(1-(pyridin-2-yl)ethyl)piperazin-1-yl)pyridin-2-amine (100 mg, 0.24 mmol), DMF (1.5 mL), 1M Na$_2$S$_2$O$_4$ (3 eq, 0.74 mmol, 0.74 mL) and 4-(N,N-dimethylamino)benzaldehyde (1.05 eq, 0.26 mmol, 38 mg). After 16 h, filtration of the precipitate, washing with cold water (1 mL) and trituration with Et$_2$O gave the product (61 mg, 49%) as a pale yellow solid; $^1$H-NMR (500 MHz, DMSO-d$_6$) 1.58 (br s, 3H, CHCH$_3$), 2.44-2.58 (2 m, 4H, piperazine N(CH$_2$)$_2$), 3.01 (s, 6H, N(CH$_3$)$_2$), 3.72-3.90 (br s, 5H, piperazine N(CH$_2$)$_2$ & CHCH$_3$), 6.83 (d, J=9.0 Hz, 2H, N,N-dimethylaminophenyl), 7.43 (br, 1H, pyridine H-5 or H-3), 7.52 (s, br, 1H, pyridine H-3 or H-5), 7.91-7.98 (m, 1H, pyridine H-4), 8.00 (d, J=8.9 Hz, 2H, N,N-dimethylaminophenyl), 8.17 (s, 1H, imidazo[4,5-b]pyridine H-5), 8.70 (br, 1H, pyridine H-6), 13.20 (br s, 1H, imidazo[4,5-b]pyridine NH);

LC (Method A)-MS (ESI, m/z): Rt=5.04 min—506, 508 [(M+H)$^+$, Br isotopic pattern]; ESI-HRMS: Found: 506.1674, calculated for C$_{25}$H$_{28}$BrN$_7$ (M+H)$^+$: 506.1668.

Example 51

6-Bromo-2-(4-methoxyphenyl)-7-(4-(1-(pyridin-2-yl)ethyl)piperazin-1-yl)-3H-imidazo[4,5-b]pyridine

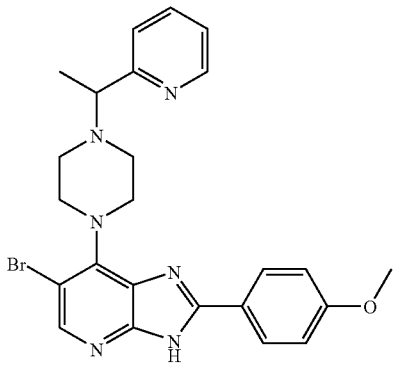

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(1-(pyridin-2-yl)ethyl)piperazin-1-yl)pyridin-2-amine (50 mg, 0.12 mmol), DMF (0.85 mL), ethanol (0.15 mL), 1M Na$_2$S$_2$O$_4$ (3 eq, 0.42 mmol, 0.42 mL) and 4-methoxybenzene carboxaldehyde (1.1 eq, 0.14 mmol, 18 mg). After 16 h, concentration in vacuo and preparation by preparative tlc (EtOAc—CH$_2$Cl$_2$-MeOH, 50:50:2) gave the product (29 mg, 48%) as a colourless solid; $\delta_H$ (500 MHz, DMSO-d$_6$) 1.38 (d, J=6.8 Hz, 3H, CHCH$_3$), 2.60 (s, br, 2H, piperazine NCH$_2$), 2.70 (br s, 2H, piperazine NCH$_2$), 3.64 (s, br, 4H, piperazine N(CH$_2$)$_2$), 3.84 (s, 3H, OCH$_3$), 7.10 (d, J=8.9 Hz, 2H, methoxyphenyl), 7.25-7.28 (m, 1H, pyridine H-5), 7.50 (d, J=7.9 Hz, 1H, pyridine H-3), 7.79 (td, J=7.7, 1.5 Hz, 1H, pyridine H-4), 8.12 (d, J=8.9 Hz, 2H, methoxyphenyl), 8.18 (s, 1H, imidazo[4,5-b]pyridine H-5), 8.53 (d, J=4.2 Hz, 1H, pyridine H-6), 13.37 (br s, 1H, imidazo[4,5-b]pyridine NH);

LC (Method B)-MS (ESI, m/z): Rt=3.29 min—493, 495 [(M+H)$^+$, Br isotopic pattern]; ESI-HRMS: Found: 493.1336, calculated for C$_{24}$H$_{25}$BrN$_6$O (M+H)$^+$: 493.1351.

Example 52 tert-Butyl 4-(1-(pyridin-3-yl)ethyl)piperazine-1-carboxylate

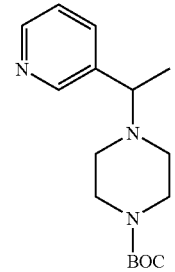

This was prepared using the same procedure as for tert-butyl 4-(1-(pyridin-2-yl)ethyl)piperazine-1-carboxylate, but here using 1-(pyridin-3-yl)ethanol (J. Chem. Soc., Perkin Trans. 1, 2000, 4439-4444) (200 mg, 1.62 mmol), triethylamine (5.0 eq, 8.12 mmol, 1.13 mL), MsCl (2.0 eq, 3.25 mmol, 0.26 mL), CH$_2$Cl$_2$ (8 mL) at 0° C. for 30 minutes. A solution of ether-pentane (1:1, 20 mL) was added, the solid removed by filtration and the solvents removed in vacuo. The residue was then treated with N—BOC piperazine (4.0 eq, 6.50 mmol, 1.21 g) in DMSO (6 mL) at 60° C. for 18 h. Work up as described for tert-butyl 4-(1-(pyridin-2-yl)ethyl)piperazine-1-carboxylate, followed by column chromatography (EtOAc-MeOH, 95:5) gave the product (186 mg, 39% for two steps) as a colourless oil; $^1$H-NMR (500 MHz, CDCl$_3$) 1.36 (d, J=6.8 Hz, 3H, CH$_3$), 1.42 (s, 9H, C(CH$_3$)$_3$), 2.29-2.45 (m, 4H, piperazine N(CH$_2$)$_2$), 3.38 (t, J=5.0 Hz, 4H, piperazine N(CH$_2$)$_2$), 3.45 (q, J=6.8 Hz, 1H, CH), 7.23 (dd, br, J=7.9, 4.7 Hz, 1H, pyridine H-5), 7.64 (dt, J=7.8, 1.9 Hz, 1H, pyridine H-4), 8.47 (dd, J=4.8, 1.8 Hz, 1H, pyridine H-6), 8.52 (d, br, J=1.9 Hz, 1H, pyridine H-2);

LC (Method B)-MS (ESI, m/z): Rt=1.89 min—292 [(M+H)+, 78%].

5-Bromo-3-nitro-4-(4-(1-(pyridin-3-yl)ethyl)piperazin-1-yl)pyridin-2-amine

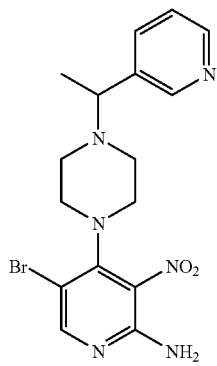

This was prepared using the same procedure as for 5-bromo-3-nitro-4-(4-(1-(pyridin-2-yl)ethyl)piperazin-1-yl)pyridin-2-amine, but here using tert-butyl 4-(1-(pyridin-3-yl)ethyl)piperazine-1-carboxylate (1.1 eq, 0.64 mmol, 186 mg), TFA (2 mL) and CH$_2$Cl$_2$ (2 mL), then 5-bromo-4-chloro-3-nitropyridin-2-amine (147 mg, 0.58 mmol) in $^i$PrOH (3 mL) and DIPEA (1.5 mL). Filtration and washing as previously described gave the product (106 mg, 41% for two steps) as a yellow solid; $^1$H-NMR (500 MHz, DMSO-d$_6$) 1.33 (d, J=6.7 Hz, 1H, CH$_3$), 3.04 (s, br, 4H, piperazine N(CH$_2$)$_2$), 3.20 (s, br, 4H, piperazine N(CH$_2$)$_2$), 3.59 (q, J=6.8 Hz, 1H, CH), 6.95 (s, br, 2H, NH$_2$), 7.36 (dd, J=7.8, 4.8 Hz, 1H, pyridine H-5), 7.73 (d, br, J=7.8 Hz, 1H, pyridine H-4), 8.14 (s, 1H, bromopyridine H-6), 8.46 (d, br, J=4.7 Hz, 1H, pyridine H-6), 8.52 (s, br, 1H, pyridine H-2);

LC (Method B)-MS (ESI, m/z): 1.94 min—407, 409 [(M+H)]+, Br isotopic pattern); ESI-HRMS: Found: 407.0823, calculated for C$_{16}$H$_{19}$BrN$_6$O$_2$ (M+H)+: 407.0831.

4-(6-Bromo-7-(4-(1-(pyridin-3-yl)ethyl)piperazin-1-yl)-3H-imidazo[4,5-b]pyridin-2-yl)-N,N-dimethylaniline

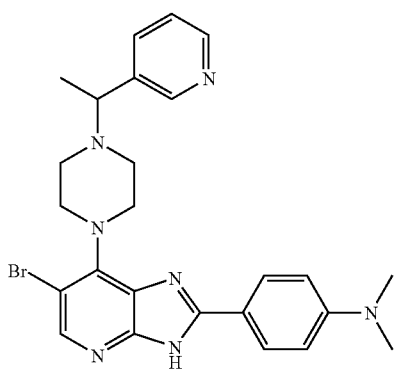

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(1-(pyridin-3-yl)piperazin-1-yl)pyridin-2-amine (300 mg, 0.73 mmol), DMF (4.4 mL), ethanol (0.6 mL), 1M Na$_2$S$_2$O$_4$ (3 eq, 2.19 mmol, 2.19 mL) and 4-(N,N-dimethylamino)benzaldehyde (1.1 eq, 0.81 mmol, 121 mg). After 16 h, concentration in vacuo and column chromatography (EtOAc-DCM-MeOH, 50:50:2) gave the product (49 mg, 13%) as a pale yellow solid; $^1$H-NMR (500 MHz, DMSO-d$_6$) 1.39 (d, J=6.6 Hz, 3H, CHCH$_3$), 2.51-2.67 (2 m, 4H, piperazine N(CH$_2$)$_2$), 3.00 (s, 6H, N(CH$_3$)$_2$), 3.58-3.66 (m, 5H, piperazine N(CH$_2$)$_2$ & CHCH$_3$), 6.81 (d, J=8.9 Hz, 2H, N,N-dimethylaminophenyl), 7.39 (dd, J=7.6, 4.8 Hz, 1H, pyridine H-5), 7.78 (d, br, J=7.7 Hz, 1H, pyridine H-4), 8.00 (d, J=8.9 Hz, 2H, N,N-dimethylaminophenyl), 8.13 (s, 1H, imidazo[4,5-b]pyridine H-5), 8.48 (d, br, J=4.4 Hz, 1H, pyridine H-6), 8.58 (br s, 1H, pyridine H-2), 13.11 (br s, 1H, imidazo[4,5-b]pyridine NH);

LC (Method B)-MS (ESI, m/z): Rt=4.20 min—506, 508 [(M+H)+, Br isotopic pattern]; ESI-HRMS: Found: 506.1667, calculated for C$_{25}$H$_{28}$BrN$_7$ (M+H)+: 506.1668.

Example 53 tert-Butyl 4-(1-(pyridin-4-yl)ethyl)piperazine-1-carboxylate

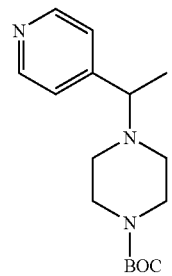

This was prepared using the same procedure as for tert-butyl 4-(1-(pyridin-2-yl)ethyl)piperazine-1-carboxylate, but here using 1-(pyridin-4-yl)ethanol (*J. Chem. Soc., Perkin Trans. 1*, 2000, 4439-4444) (100 mg, 0.81 mmol), triethylamine (5.0 eq, 4.05 mmol, 0.56 mL), MsCl (2.0 eq, 1.62 mmol, 0.13 mL), CH$_2$Cl$_2$ (4 mL) at 0° C. for 30 minutes, then N—BOC piperazine (4.0 eq, 3.24 mmol, 605 mg), DMSO (3 mL) at 60° C. for 18 h. Work up as described for tert-butyl 4-(1-(pyridin-2-yl)ethyl)piperazine-1-carboxylate, followed by column chromatography (EtOAc-MeOH, 95:5) gave the product (163 mg, 69% for two steps) as a colourless oil; $^1$H-NMR (500 MHz, CDCl$_3$) 1.50 (s, 9H, C(CH$_3$)$_3$), 1.72 (s, br, 3H, CH$_3$), 2.42-2.60 (m, 4H, piperazine N(CH$_2$)$_2$), 3.49 (s, br, 5H, CH & piperazine N(CH$_2$)$_2$), 7.32 (d, J=5.7 Hz, 2H, pyridine H-3 & H-5), 8.59 (d, J=5.7 Hz, 2H, pyridine H-2 & H-6);

LC (Method B)-MS (ESI, m/z): Rt=1.95 min—292 [(M+H)⁺, 52%)].

5-Bromo-3-nitro-4-(4-(1-(pyridin-4-yl)ethyl)piperazin-1-yl)pyridin-2-amine

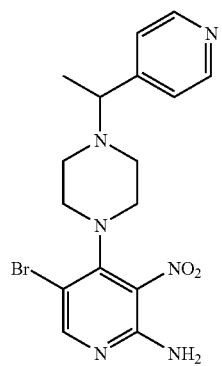

This was prepared using the same procedure as for 5-bromo-3-nitro-4-(4-(1-(pyridin-2-yl)ethyl)piperazin-1-yl)pyridin-2-amine, but here using tert-butyl 4-(1-(pyridin-4-yl)ethyl)piperazine-1-carboxylate (1.1 eq, 1.12 mmol, 327 mg), TFA (5 mL) and CH₂Cl₂ (5 mL), then 5-bromo-4-chloro-3-nitropyridin-2-amine (257 mg, 1.02 mmol) in ⁱPrOH (5 mL) and DIPEA (2 mL). Filtration and washing as previously described gave the product (265 mg, 58% for two steps) as a yellow solid; ¹H-NMR (500 MHz, DMSO-d₆) 1.29 (d, J=6.8 Hz, CH₃), 2.46-2.56 (2 m, 4H, piperazine N(CH₂)₂), 3.05 (s, br, 4H, piperazine N(CH₂)₂), 3.53 (q, J=6.7 Hz, 1H, CH), 6.96 (s, br, 2H, NH₂), 7.34 (dd, J=4.5, 1.5 Hz, 2H, pyridine H-3 & H-5), 8.14 (s, 1H, bromopyridine H-6), 8.52 (dd, J=4.4, 1.5 Hz, 2H, pyridine H-2 & H-6);

LC (Method B)-MS (ESI, m/z): Rt=2.09 min—407, 409 [(M+H)⁺, Br isotopic pattern]; ESI-HRMS: Found: 407.0825, calculated for C₁₆H₁₉BrN₆O₂ (M+H)⁺: 407.0831.

4-(6-Bromo-7-(4-(1-(pyridin-4-yl)ethyl)piperazin-1-yl)-3H-imidazo[4,5-b]pyridin-2-yl)-N,N-dimethylaniline

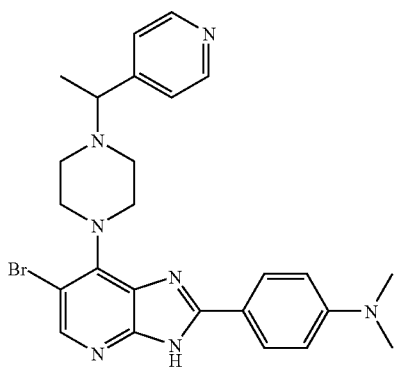

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(1-(pyridin-4-yl)ethyl)piperazin-1-yl)pyridin-2-amine (100 mg, 0.24 mmol), DMF (1.5 mL), 1M Na₂S₂O₄ (3 eq, 0.74 mmol, 0.74 mL) and 4-(N,N-dimethylamino)benzaldehyde (1.05 eq, 0.26 mmol, 38 mg). After 16 h, filtration of the precipitate and trituaration with Et₂O gave the product (50 mg, 40%) as a pale yellow solid; ¹H-NMR (500 MHz, DMSO-d₆) 1.43-1.51 (br s, 3H, CHCH₃), 2.49-2.57 (2 m, 4H, piperazine N(CH₂)₂), 3.01 (s, 6H, N(CH₃)₂), 3.69 (br, 5H, piperazine N(CH₂)₂ & CHCH₃), 6.82 (d, J=8.9 Hz, 2H, N,N-dimethylaminophenyl), 7.48 (s, br, 2H, pyridine H-3 & H-5), 8.00 (d, J=8.7 Hz, 2H, N,N-dimethylaminophenyl), 8.16 (s, 1H, imidazo[4,5-b]pyridine H-5), 8.61 (s, br, 2H, pyridine H-2 & H-6), 13.18 (br s, 1H, imidazo[4,5-b]pyridine NH);

LC (Method A)-MS (ESI, m/z): 5.19 min—506, 508 [(M+H)⁺, Br isotopic pattern]; ESI-HRMS: Found: 506.1673, calculated for C₂₅H₂₈BrN₇ (M+H)⁺: 506.1668.

Example 54

6-Bromo-2-(4-methoxyphenyl)-7-(4-(1-(pyridin-4-yl)ethyl)piperazin-1-yl)-3H-imidazo[4,5-b]pyridine

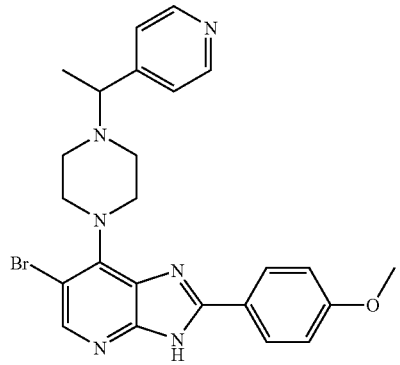

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(1-(pyridin-4-yl)ethyl)piperazin-1-yl)pyridin-2-amine (30 mg, 0.074 mmol), DMF (1 mL), 1M Na₂S₂O₄ (3 eq, 0.22 mmol, 0.22 mL) and 4-methoxybenzene carboxaldehyde (1.05 eq, 0.077 mmol, 0.0096 mL). After 16 h, filtration of the precipitate and washing with ethanol (1 mL) and cold water (1 mL) gave the product (15 mg, 42%) as a pale yellow solid; ¹H-NMR (500 MHz, DMSO-d₆) 1.37 (d, J=6.7 Hz, 3H, CHCH₃), 2.56-2.65 (2 m, 4H, piperazine N(CH₂)₂), 3.58 (q, J=6.9 Hz, 1H, CHCH₃), 3.66 (br s, 4H, piperazine N(CH₂)₂), 3.85 (s, 3H, OCH₃), 7.11 (d, J=8.8 Hz, 2H, methoxyphenyl), 7.40 (d, J=5.4 Hz, 2H, pyridine H-3 & H-5), 8.14 (d, J=8.5 Hz, 2H, methoxyphenyl), 8.20 (s, 1H, imidazo[4,5-b]pyridine H-5), 8.55 (d, J=5.4 Hz, 2H, pyridine H-2 & H-6), 13.40 (br s, 1H, imidazo[4,5-b]pyridine NH);

LC (Method B)-MS (ESI, m/z): 3.29 min—493, 495 [(M+H)$^+$, Br isotopic pattern); ESI-HRMS: Found: 493.1351, calculated for $C_{24}H_{25}BrN_6O$ (M+H)$^+$: 493.1351).

Example 55

6-Bromo-2-(2-methoxypyridin-3-yl)-7-(4-(pyridin-3-ylmethyl)piperazin-1-yl)-3H-imidazo[4,5-b]pyridine

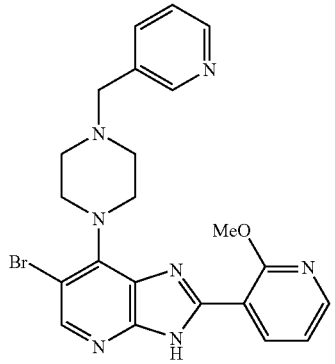

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (75 mg, 0.19 mmol), DMF (0.85 mL), ethanol (0.15 mL), 1M $Na_2S_2O_4$ (3 eq, 0.57 mmol, 0.57 mL) and 2-methoxy-3-pyridinecarboxaldehyde (1.1 eq, 0.21 mmol, 0.024 mL). After 16 h, concentration in vacuo and preparation by preparative tlc ($CH_2Cl_2$-MeOH, 95:5) gave the product (41 mg, 50%) as a pale yellow solid; $^1$H-NMR (500 MHz, DMSO-$d_6$) 2.61 (br s, 2H, piperazine $NCH_2$), 2.72 (s, br, 2H, piperazine $NCH_2$), 2.89 (s, 2H, $CH_2$), 3.59-3.69 (m, 4H, piperazine $N(CH_2)_2$), 4.05 (s, 3H, $OCH_3$), 7.19 (dd, J=7.5, 4.9 Hz, 1H, pyridine H-5), 7.38-7.41 (m, 1H, methoxypyridine H-5), 7.77 (dt, J=7.7, 1.8 Hz, 1H, pyridine H-4), 8.28 (s, 1H, imidazo[4,5-b]pyridine H-5), 8.33 (dd, J=4.8, 1.8 Hz, 1H, pyridine H-6), 8.48 (d, br, J=3.4 Hz, 1H, methoxypyridine H-6), 8.53 (d, J=6.8 Hz, 1H, methoxypyridine H-4), 8.56 (s, br, 1H, pyridine H-2);
LC (Method B)-MS (ESI, m/z): 2.90 min—480, 482 [(M+H)$^+$, Br isotopic pattern]; ESI-HRMS: Found: 480.1147, calculated for $C_{22}H_{22}BrN_7O$ (M+H)$^+$: 480.1147.

Example 56

6-Bromo-2-(1-methyl-1H-pyrazol-4-yl)-7-(4-(pyridin-3-ylmethyl)piperazin-1-yl)-3H-imidazo[4,5-b]pyridine

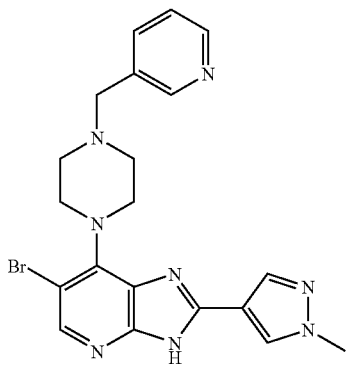

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (75 mg, 0.19 mmol), DMF (0.85 mL), ethanol (0.15 mL), 1M $Na_2S_2O_4$ (3 eq, 0.57 mmol, 0.57 mL) and 1-methyl-1H-pyrazole-4-carboxaldehyde (1.1 eq, 0.21 mmol, 23 mg). After 6 h, concentration in vacuo and preparation by preparative tlc ($CH_2Cl_2$-MeOH, 9:1) gave the product (23 mg, 24%) as a colourless solid; $^1$H-NMR (500 MHz, DMSO-$d_6$) 2.60 (br s, 4H, piperazine $N(CH_2)_2$), 3.60 (t, J=4.5 Hz, 4H, piperazine $N(CH_2)_2$), 3.61 (s, 2H, $CH_2$), 3.93 (s, 3H, $NCH_3$), 7.40 (dd, J=7.6, 4.8 Hz, 1H, pyridine H-5), 7.78 (d, br, J=7.7 Hz, 1H, pyridine H-4), 8.06 (s, 1H, pyrazole H-2 or H-4), 8.19 (s, 1H, imidazo[4,5-b]pyridine H-5), 8.35 (s, 1H, pyrazole H-2 or H-4), 8.50 (d, br, J=4.7 Hz, 1H, pyridine H-6), 8.57 (s, br, 1H, pyridine H-2), 13.21 (br s, 1H, imidazo[4,5-b]pyridine NH);
LC (Method B)-MS (ESI, m/z): 2.35 min—453, 455 [(M+H)$^+$, Br isotopic pattern); ESI-HRMS: Found: 453.1144, calculated for $C_{20}H_{21}BrN_8$ (M+H)$^+$: 453.1151.

Example 57

6-Bromo-7-(4-(pyridin-3-ylmethyl)piperazin-1-yl)-2-(1,3,5-trimethyl-1H-pyrazol-4-yl)-3H-imidazo[4,5-b]pyridine

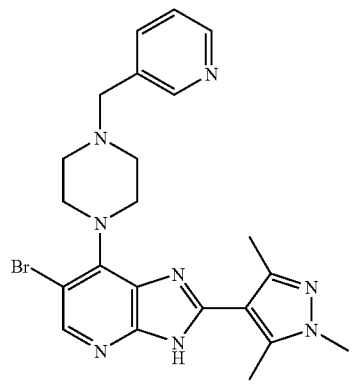

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (75 mg, 0.19 mmol), DMF (0.85 mL), ethanol (0.15 mL), 1M $Na_2S_2O_4$ (3 eq, 0.57 mmol, 0.57 mL) and 1,3,5-trimethyl-1H-pyrazole-4-carboxaldehyde (1.1 eq, 0.21 mmol, 29 mg). After 6 h, concentration in vacuo and preparation by preparative tlc ($CH_2Cl_2$-MeOH, 9:1) gave the product (31 mg, 34%) as a colourless solid; $^1$H-NMR (500 MHz, DMSO-$d_6$) 2.36 (s, 3H, $CH_3$), 2.49 (s, 3H, $CH_3$), 2.60 (s, br, 4H, piperazine $N(CH_2)_2$), 3.61 (s, 2H, $CH_2$), 3.64 (t, J=4.2 Hz, 4H, piperazine $N(CH_2)_2$), 3.74 (s, 3H, $NCH_3$), 7.38 (dd, J=7.7, 4.8 Hz, 1H, pyridine H-5), 7.77 (dt, J=7.8, 1.5 Hz, 1H, pyridine H-4), 8.19 (s, 1H, imidazo[4,5-b]pyridine H-5), 8.49 (dd, J=4.7, 1.4 Hz, 1H, pyridine H-6), 8.55 (d, J=1.5 Hz, 1H, pyridine H-2), 12.67 (s, br, 1H, imidazo[4,5-b]pyridine NH);
LC (Method B)-MS (ESI, m/z): 2.45 min—481, 483 [(M+H)$^+$, Br isotopic pattern]; ESI-HRMS: Found: 481.1461, calculated for $C_{22}H_{25}BrN_8$ (M+H)$^+$: 481.1464.

Example 58

6-Bromo-2-(3-((4-methylpiperazin-1-yl)methyl)phenyl)-7-(4-(pyridin-3-ylmethyl)piperazin-1-yl)-3H-imidazo[4,5-b]pyridine

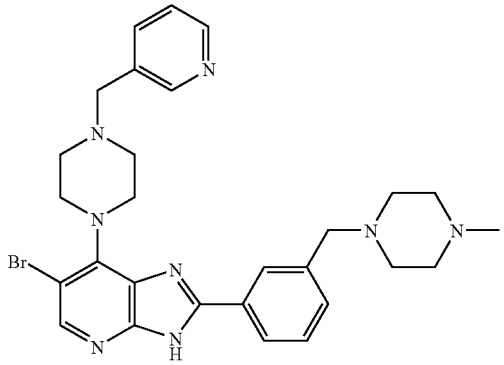

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (75 mg, 0.19 mmol), DMF (0.85 mL), ethanol (0.15 mL), 1M $Na_2S_2O_4$ (3 eq, 0.57 mmol, 0.57 mL) and 3-[(4-methylpiperazin-1-yl)methyl]benzaldehyde (1.1 eq, 0.21 mmol, 46 mg). After 6 h, concentration in vacuo and preparation by preparative tlc ($CH_2Cl_2$-MeOH, 9:1) gave the product (19 mg, 18%) as a colourless solid; $^1$H-NMR (500 MHz, DMSO-$d_6$) 2.15 (s, 3H, $NCH_3$), 2.50 (hidden by DMSO peak, 4H, piperazine $N(CH_2)_2$), 2.64 (br, 4H, piperazine $N(CH_2)_2$), 3.30 (hidden by watert-in-DMSO peak, 4H, piperazine $N(CH_2)_2$), 3.56 (s, 2H, $CH_2$), 3.63 (s, 2H, $CH_2$), 3.68 (t, J=4.8 Hz, 4H, piperazine $N(CH_2)_2$), 7.40 (dd, J=7.8, 4.8 Hz, 1H, pyridine H-5), 7.43 (d, J=7.8 Hz, 1H, phenyl H-4 or H-6), 7.50 (t, J=7.8 Hz, 1H, phenyl H-5), 7.79 (d, br, J=7.7 Hz, 1H, pyridine H-4), 8.07 (d, br, J=8.5 Hz, 1H, phenyl H-4 or H-6), 8.14 (s, br, 1H, phenyl H-2), 8.25 (s, 1H, imidazo[4,5-b]pyridine H-5), 8.50 (dd, J=4.8, 1.5 Hz, 1H, pyridine H-6), 8.57 (d, J=1.6 Hz, 1H, pyridine H-2), 13.52 (br s, 1H, imidazo[4,5-b]pyridine NH);

LC (Method B)-MS (ESI, m/z): 1.99 min—561, 563 [(M+H)$^+$, Br isotopic pattern];

ESI-HRMS: Found: 561.2100, calculated for $C_{28}H_{33}BrN_8$ (M+H)$^+$: 561.2090.

Example 59 tert-Butyl 4-(6-bromo-7-(4-(pyridin-3-ylmethyl)piperazin-1-yl)-3H-imidazo[4,5-b]pyridin-2-yl)benzylcarbamate

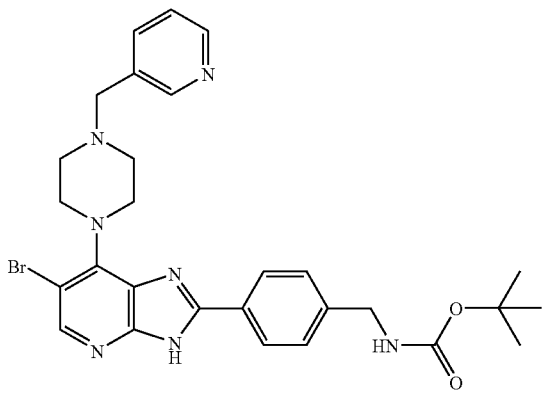

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (200 mg, 0.51 mmol), DMF (2.55 mL), ethanol (0.45 mL), 1M $Na_2S_2O_4$ (3 eq, 1.53 mmol, 1.53 mL) and tert-butyl N-(4-formylbenzyl)carbamate (1.1 eq, 0.21 mmol, 46 mg). After 18 h, filtration of the precipitate and washing with cold water (1 mL) gave the product (79 mg, 27%) as a colourless solid; $^1$H-NMR (500 MHz, DMSO-$d_6$) 1.41 (s, 9H, $C(CH_3)_3$), 2.63-2.76 (m, 2H, piperazine $NCH_2$), 2.89 (s, 2H, piperazine $NCH_2$), 3.71-3.77 (m, 6H, piperazine $N(CH_2)_2$ & $NCH_2Ar$), 4.19 (d, J=5.8 Hz, 2H, $CH_2NH$—BOC), 7.39 (d, J=8.1 Hz, 2H, phenyl H-2 & H-6), 7.40-7.44 (m, 1H, pyridine H-5), 7.82 (s, br, 1H, pyridine H-4), 7.95 (s, br, 1H, NH—BOC), 8.12 (d, J=8.1 Hz, 2H, phenyl H-3 & H-5), 8.25 (s, 1H, imidazo[4,5-b]pyridine H-5), 8.53 (br s, 1H, pyridine H-6), 8.60 (s, br, 1H, pyridine H-2), 13.49 (br s, 1H, imidazo[4,5-b]pyridine NH);

LC (Method A)-MS (ESI, m/z): 5.27 min; —578, 580 [(M+H)$^+$, Br isotopic pattern]; ESI-HRMS: Found: 578.1878, calculated for $C_{28}H_{32}BrN_7O_2$ (M+H)$^+$: 578.1879.

Example 60

(4-(6-Bromo-7-(4-(pyridin-3-ylmethyl)piperazin-1-yl)-3H-imidazo[4,5-b]pyridin-2-yl)phenyl)methanamine

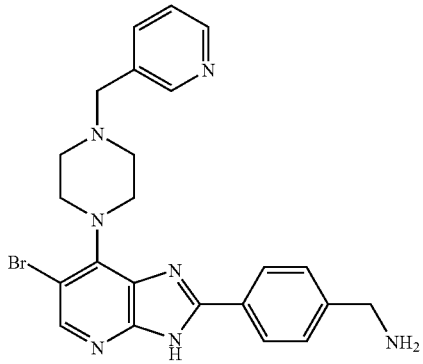

A solution of tert-butyl 4-(6-bromo-7-(4-(pyridin-3-ylmethyl)piperazin-1-yl)-3H-imidazo[4,5-b]pyridin-2-yl)benzylcarbamate (50 mg, 0.086 mmol) in $CH_2Cl_2$ (2 mL) at 0° C. was treated dropwise with TFA (0.6 mL), warmed to room temperature and stirred for 3 h. Concentration in vacuo and purified on a 2 g SCX cartridge (first eluting with MeOH, then 0.5M $NH_3$ in MeOH) to give the product (30 mg, 73%) as a colourless solid; $^1$H-NMR (500 MHz, DMSO-$d_6$) 2.55 (s, 2H, piperazine $NCH_2$), 2.64 (s, br, 2H, piperazine $NCH_2$), 3.63 (s, 2H, $NCH_2Ar$), 3.65-3.68 (m, 4H, piperazine $N(CH_2)_2$), 4.09 (s, 2H, $CH_2NH_2$), 7.39-7.46 (m, 1H, pyridine H-5), 7.61 (d, J=7.8 Hz, 2H, phenyl H-2 & H-6), 7.79 (d, J=7.9 Hz, 1H, pyridine H-4), 8.21 (d, J=7.8 Hz, 2H, phenyl H-3 & H-5), 8.27 (s, 1H, imidazo[4,5-b]pyridine H-5), 8.51 (d, J=4.4 Hz, 1H, pyridine H-6), 8.58 (s, br, 1H, pyridine H-2);

LC (Method A)-MS (ESI, m/z): 2.45 min—478, 480 [(M+H)$^+$, Br isotopic pattern]; ESI-HRMS: Found: 478.1364, calculated for $C_{23}H_{24}BrN_7$ (M+H)$^+$: 478.1355.

Example 61

1-(4-(6-Bromo-7-(4-(pyridin-3-ylmethyl)piperazin-1-yl)-3H-imidazo[4,5-b]pyridin-2-yl)phenyl)-N,N-dimethylmethanamine

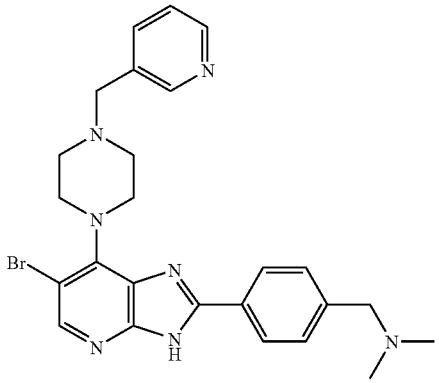

A solution of (4-(6-bromo-7-(4-(pyridin-3-ylmethyl)piperazin-1-yl)-3H-imidazo[4,5-b]pyridin-2-yl)phenyl)methanamine (10 mg, 0.021 mmol) in dry THF (1 mL) and dry MeOH (1 mL) was treated with 38% formaldehyde (2.5 eq, 0.052 mmol, 4 μL) and NaBH$_3$CN (2.5 eq, 0.052 mmol, 3.5 mg) and stirred at room temperature for 3 h. Concentration in vacuo and purification by preparative tlc (DCM-MeOH, 9:1) gave the product (10 mg, 94%) as a colourless solid; $^1$H-NMR (500 MHz, DMSO-d$_6$) 2.27 (s, 6H, N(CH$_3$)$_2$), 2.62-2.69 (m, 4H, piperazine N(CH$_2$)$_2$), 3.62 (s, 2H, NCH$_2$Ar), 3.66-3.69 (m, 6H, piperazine N(CH$_2$)$_2$ & CH$_2$NMe$_2$), 7.40 (dd, J=7.5, 4.6 Hz, 1H, pyridine H-5), 7.49 (d, J=7.8 Hz, 2H, phenyl H-2 & H-6), 7.79 (d, J=7.7 Hz, 1H, pyridine H-4), 8.16 (d, J=8.0 Hz, phenyl H-3 & H-5), 8.25 (s, 1H, imidazo[4,5-b]pyridine H-5), 8.50 (d, br, J=4.5 Hz, 1H, pyridine H-6), 8.58 (s, br, 1H, pyridine H-2), 13.51 (br s, 1H, imidazo[4,5-b]pyridine NH);

LC (Method B)-MS (ESI, m/z): 1.75 min—506, 508 [(M+H)$^+$, Br isotopic pattern]; ESI-HRMS: Found: 506.1660, calculated for $C_{25}H_{28}BrN_7$ (M+H)$^+$: 506.1668.

Example 62

2-(4-(6-Cyano-2-(4-(dimethylamino)phenyl)-3H-imidazo[4,5-b]pyridin-7-yl)piperazin-1-yl)-N-(thiazol-2-yl)acetamide

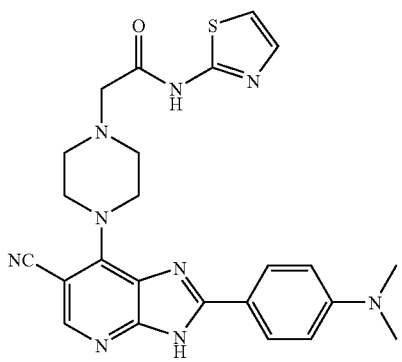

A solution of 2-(4-(6-bromo-2-(4-(dimethylamino)phenyl)-3H-imidazo[4,5-b]pyridin-7-yl)piperazin-1-yl)-N-(thiazol-2-yl)acetamide (75 mg, 0.14 mmol) in degassed DMF (1 mL) containing Pd$_2$dba$_3$ (0.05 eq, 0.0069 mmol, 6 mg), dppf (0.1 eq, 0.014 mmol, 8 mg) and Zn(CN)$_2$ (1.5 eq, 0.21 mmol, 24 mg) was stirred with microwave heating at 180° C. for 30 minutes. After this time, further Pd$_2$(dba)$_3$ (6 mg), dppf (8 mg) and Zn(CN)$_2$ (24 mg) were added and the mixture stirred under the same conditions for a further 30 minutes. hplc then showed partial conversion to the desired compound. Concentration in vacuo and purification of a small sample by semi-preparative hplc gave the pure product as a colourless solid; $^1$H-NMR (500 MHz, DMSO-d$_6$) 2.80 (t, br, J=4.7 Hz, 4H, piperazine N(CH$_2$)$_2$), 3.00 (s, 6H, N(CH$_3$)$_2$), 3.42 (s, 2H, NCH$_2$CO), 4.11 (s, br, 4H, piperazine N(CH$_2$)$_2$), 6.82 (d, J=9.0 Hz, 2H, N,N-dimethylaminophenyl), 7.24 (d, J=3.5 Hz, 1H, thiazole H-4 or H-5), 7.50 (d, J=3.5 Hz, 1H, thiazole H-4 or H-5), 7.99 (d, J=9.0 Hz, 2H, N,N-dimethylaminophenyl), 8.23 (s, 1H, imidazo[4,5-b]pyridine H-5), 11.91 (br s, 1H, CONH), 13.46 (br s, 1H, imidazo[4,5-b]pyridine NH);

LC (Method A)-MS (ESI, m/z): 6.87 min—488 [(M+H)$^+$, 100%]; ESI-HRMS: Found: 488.1993, calculated for $C_{24}H_{25}N_9OS$ (M+H)$^+$: 488.1981.

Example 63

2-Bromo-N-(3-methylisoxazol-5-yl)acetamide

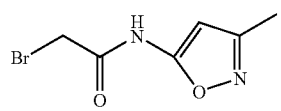

Prepared by following a methodology reported by M. Ohkubo et al. in *Chem Pharm Bull.* 1995, 43 (9), 1497-1504.

To a solution of 5-amino-3-methylisoxazole (0.165 g, 1.67 mmol) in anhydrous toluene (6.5 ml) and anhydrous pyridine (0.18 ml, 2.0 mmol) cooled in an ice/water bath (T=~10° C.) was slowly added bromoacetyl bromide (0.402 g, 2.0 mmol). The reaction mixture was stirred for 1.5 h under argon, then poured into water (20 ml), and extracted with ethyl acetate (2×40 ml). The combined organics were washed with water (30 ml), brine (30 ml), dried (Na$_2$SO$_4$), and concentrated in vacuo. The residue was triturated with diethyl ether, the precipitate was removed by filtration, and the filtrate was concentrated in vacuo to afford the title compound as a white solid (0.200 g, 55%); $^1$H-NMR (500 MHz, DMSO-d$_6$) 2.18 (s, 3H, CH$_3$), 4.08 (s, 2H, CH$_2$Br), 6.15 (s, 1H, isoxazole C—H), 11.94 (s, 1H, CONH);

LC (Method B)-MS (ESI, m/z): Rt=2.92 min—219, 221 [(M+H)$^+$, Br isotopic pattern].

tert-Butyl 4-(2-(3-methylisoxazol-5-ylamino)-2-oxoethyl)piperazine-1-carboxylate

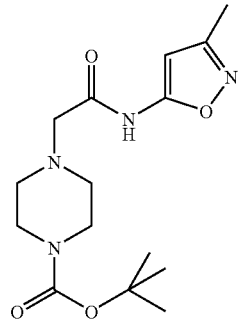

To a stirred solution of 2-bromo-N-(3-methylisoxazol-5-yl)acetamide (0.122 g, 0.58 mmol) in anhydrous dichoromethane (4.5 ml) under argon was added 1-BOC-piperazine (0.241 g, 1.30 mmol). The reaction mixture was stirred at room temperature for 2 h under argon, then partitioned between ethyl acetate (100 ml) and 6% aqueous $Na_2CO_3$ (50 ml). The organic layer was washed with more 6% aqueous $Na_2CO_3$ (50 ml), and concentrated in vacuo. The residue was absorbed on silica gel and the free-running powder was placed on a 10 g isolute column. Elution of the column with 30% ethyl acetate in dichloromethane afforded the title compound as a white solid (0.096 g, 51%). $^1$H-NMR (500 MHz, DMSO-$d_6$) 1.39 (s, 9H, C(CH$_3$)$_3$), 2.18 (s, 3H, CH$_3$), 2.45 (t, J=5.1 Hz, 4H, piperazine N(CH$_2$)$_2$), 3.23 (s, 2H, NCH$_2$CO), 3.34 (t, J=4.7 Hz, 4H, piperazine N(CH$_2$)$_2$), 6.13 (s, 1H, isoxazole C—H), 11.28 (s, 1H, CONH);

LC (Method B)-MS (ESI, m/z): Rt=3.09 min—325 (M+H)$^+$.

2-(4-(2-Amino-5-chloro-3-nitropyridin-4-yl)piperazin-1-yl)-N-(3-methylisoxazol-5-yl)acetamide

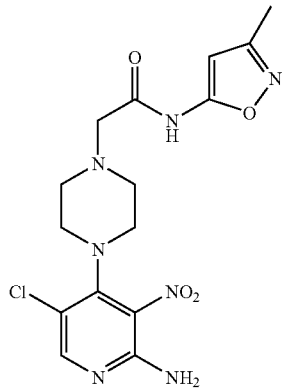

To a solution of tert-butyl 4-(2-(3-methylisoxazol-5-ylamino)-2-oxoethyl)piperazine-1-carboxylate (0.087 g, 0.27 mmol) in anhydrous dichloromethane (3 ml) was added TFA (3.7 ml). The reaction mixture was stirred at room temperature for 1 h and 45 min, then the solvent was removed in vacuo and the residue was dried in vacuo over $P_2O_5$. To a solution of this material (supposedly 0.27 mmol) in isopropanol (5 ml) was added 2-amino-4,5-dichloro-3-nitro-pyridine (0.050 g, 0.24 mmol) followed by diisopropylethylamine (0.22 ml, 1.25 mmol). The reaction mixture was stirred at 45° C. for 18 h, then allowed to cool to room temperature, and diluted with isopropanol (6 ml). The precipitate was collected by filtration, washed with isopropanol (2×6 ml), and diethyl ether (2×6 ml), and dried. The title compound was obtained as an orange solid (0.042 g). The filtrate was concentrated in vacuo, and purification of the residue by chromatography (10 g isolute column) on elution with dichloromethane/ethyl acetate (v/v; 1:1), and 2% methanol in dichloromethane/ethyl acetate (v/v; 1:1) afforded an additional 0.025 g of the product (overall yield: 63%). $^1$H-NMR (500 MHz, DMSO-$d_6$) 2.18 (s, 3H, CH$_3$), 2.63 (s, 4H, piperazine N(CH$_2$)$_2$), 3.28 (s, 2H, NCH$_2$CO), 3.10 (s, 4H, piperazine N(CH$_2$)$_2$), 6.15 (s, 1H, isoxazole C—H), 7.00 (s, 2H, NH$_2$), 8.07 (s, 1H, 6-H), 11.37 (s, 1H, CONH);

LC (Method B)-MS (ESI, m/z): Rt=2.99 min—396, 398 [(M+H)$^+$, Cl isotopic pattern].

2-(4-(6-Chloro-2-(4-(dimethylamino)phenyl)-3H-imidazo[4,5-b]pyridin-7-yl)piperazin-1-yl)-N-(3-methylisoxazol-5-yl)acetamide

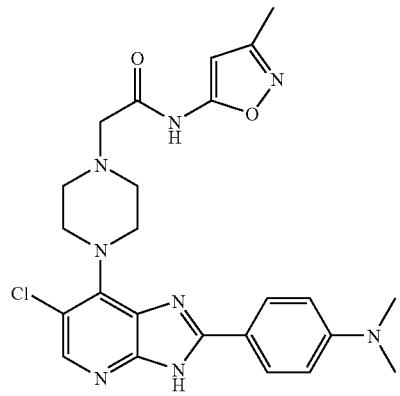

To a mixture of 2-(4-(2-amino-5-chloro-3-nitropyridin-4-yl)piperazin-1-yl)-N-(3-methylisoxazol-5-yl)acetamide (0.036 g, 0.09 mmol) and ethanol (4 ml) was added 4-dimethylaminobenzaldehyde (0.018 g, 0.11 mmol) followed by a freshly prepared 1M aqueous solution of $Na_2S_2O_4$ (0.36 ml, 0.36 mmol). The reaction mixture was stirred at 70° C. for 4.5 h, then allowed to cool to room temperature and concentrated in vacuo. The residue was triturated with water (4 ml); the brown precipitate was collected by filtration, washed with water (3×2 ml), ethanol (3×2 ml) and diethyl ether (2×5 ml). This solid was absorbed on silica gel, and the free-running powder was placed on a 10 g isolute silica column which was eluted with ethyl acetate/dichloromethane (v/v; 1:1), and 4% methanol in ethyl acetate/dichloromethane (v/v; 1:1). The title compound was obtained as a yellow solid after trituration with diethyl ether (0.007 g, 16%). $^1$H-NMR (500 MHz, DMSO-$d_6$) 2.19 (s, 3H, isoxazole CH$_3$), 2.73 (s, 4H, piperazine N(CH$_2$)$_2$), 3.00 (s, 6H, N(CH$_3$)$_2$), 3.31 (s, 2H, NCH$_2$CO), 3.71 (s, 4H, piperazine N(CH$_2$)$_2$), 6.18 (s, 1H, isoxazole C—H), 6.82 (d, J=8.9 Hz, 2H) and 8.01 (d, J=8.9 Hz, 2H) (3,5-C$_6$H$_4$NMe$_2$ and 2,6-C$_6$H$_4$NMe$_2$), 8.03 (s, 1H, imidazo[4,5-b]pyridine 5-H), 11.45 (br s, 1H, CONH), 13.15 (br s, 1H, imidazo[4,5-b]pyridine N—H);

Example 64

2-(4-(6-Chloro-2-(4-methoxyphenyl)-3H-imidazo[4,5-b]pyridin-7-yl)piperazin-1-yl)-N-(3-methylisoxazol-5-yl)acetamide

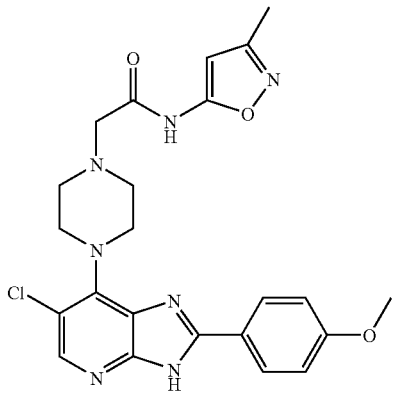

To a mixture of 2-(4-(2-amino-5-chloro-3-nitropyridin-4-yl)piperazin-1-yl)-N-(3-methylisoxazol-5-yl)acetamide (0.036 g, 0.09 mmol) and ethanol (3 ml) was added p-anisaldehyde (0.024 g, 0.18 mmol) with the aid of ethanol (1 ml) followed by a freshly prepared 1M aqueous solution of $Na_2S_2O_4$ (0.36 ml, 0.36 mmol). The reaction mixture was stirred at 70° C. for 6.5 h, then allowed to cool to room temperature and concentrated in vacuo. The residue was absorbed on silica gel, and the free-running powder was placed on a 10 g silica isolute column which was eluted with ethyl acetate/dichloromethane (v/v; 1:1), and 2% methanol in ethyl acetate/dichloromethane (v/v; 1:1). The title compound was obtained as a pale yellow solid after trituration with diethyl ether (0.008 g, 18%). $^1$H-NMR (500 MHz, DMSO-$d_6$) 2.19 (s, 3H, isoxazole $CH_3$), 2.73 (s, 4H, piperazine $N(CH_2)_2$), 3.32 (s, 2H, $NCH_2CO$), 3.73 (s, 4H, piperazine $N(CH_2)_2$), 3.83 (s, 3H, $OCH_3$), 6.18 (s, 1H, isoxazole C—H), 7.11 (d, J=8.9 Hz, 2H) and 8.13 (d, J=8.8 Hz, 2H) (3,5-$C_6H_4$OMe and 2,6-$C_6H_4$OMe), 8.09 (s, 1H, imidazo[4,5-b]pyridine 5-H), 11.43 (br s, 1H, CONH), 13.38 (br s, 1H, imidazo[4,5-b]pyridine N—H);

LC (Method B)-MS (ESI, m/z): Rt=4.00 min—482, 484 [(M+H)$^+$, Cl isotopic pattern]. ESI-HRMS: Found: 482.1703, calculated for $C_{23}H_{25}ClN_7O_3$ (M+H)$^+$: 482.1707.

Example 65

6-Bromo-2-(4-morpholin-4-ylmethyl-phenyl)-7-(4-pyridin-3-ylmethyl-piperazin-1-yl)-3H-imidazo[4,5-b]pyridine

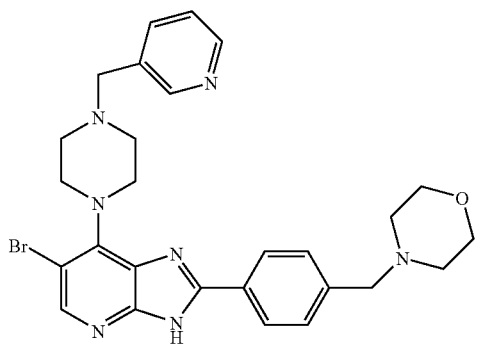

To a mixture of 5-bromo-3-nitro-4-(4-pyridin-3-ylmethyl-piperazin-1-yl)-pyridin-2-ylamine (0.047 g, 0.12 mmol) and EtOH (3.5 ml) was added 4-morpholin-4-ylmethyl-benzaldehyde (0.032 g, 0.16 mmol) followed by a freshly prepared aqueous solution of $Na_2S_2O_4$ (1M; 0.48 ml, 0.48 mmol). The reaction mixture was stirred at 80° C. for 20 h, then allowed to cool to room temperature and concentrated in vacuo. The residue was absorbed on silica gel, the free-running powder was placed on a 10 g isolute silica column, and elution of the column with a gradient of methanol (2 to 12%) in ethyl acetate/dichloromethane (v:v; 4:1) afforded a yellow solid which was triturated with diethyl ether. The precipitate was collected by filtration, and was successively washed with diethyl ether, water, and diethyl, then dried in vacuo (0.009 g, 14%). $^1$H-NMR (500 MHz, DMSO-$d_6$) 2.38 (br t, 4H) and 3.59 (t, J=4.6 Hz, 4H) (morpholine $N(CH_2)_2$ and morpholine $O(CH_2)_2$), 2.62 (br s, 4H, piperazine $N(CH_2)_2$), 3.67 (br s, 4H, piperazine $N(CH_2)_2$), 3.53 (s, 2H) and 3.62 (s, 2H) ($NCH_2$-pyridyl and $C_6H_4CH_2$), 7.39 (dd, J=5.3, 7.1 Hz, pyridine 5-H), 7.47 (d, J=7.7 Hz, 2H) and 8.14 (d, J=8.0 Hz, 2H) (3,5-$C_6H_4$ and 2,6-$C_6H_4$), 7.78 (d, J=7.5 Hz, 1H, pyridine 4-H), 8.23 (s, 1H, imidazo[4,5-b]pyridine 5-H), 8.50 (dd, J=1.6, 4.7 Hz, 1H, pyridine 6-H), 8.56 (d, J=1.6 Hz, 1H, pyridine 6-H), 13.48 (br s, 1H, imidazo[4,5-b]pyridine N—H);

LC (Method B)-MS (ESI, m/z): Rt=1.94 min—548, 550 [(M+H)$^+$, Br isotopic pattern]. ESI-HRMS: Found: 548.1776, calculated for $C_{27}H_{31}BrN_7O$ (M+H)$^+$: 548.1773.

Example 66

6-Bromo-2-(3-morpholin-4-ylmethyl-phenyl)-7-(4-pyridin-3-ylmethyl-piperazin-1-yl)-3H-imidazo[4,5-b]pyridine

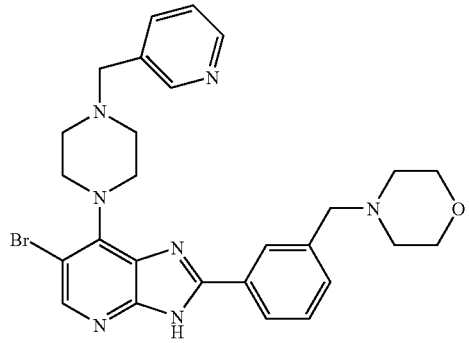

To a mixture of 5-bromo-3-nitro-4-(4-pyridin-3-ylmethyl-piperazin-1-yl)-pyridin-2-ylamine (0.060 g, 0.15 mmol) and EtOH (4.5 ml) was added 3-morpholin-4-ylmethyl-benzaldehyde (0.035 g, 0.17 mmol) followed by a freshly prepared 1M aqueous solution of $Na_2S_2O_4$ (0.55 ml, 0.55 mmol). The reaction mixture was stirred at 70° C. for 9 h, then allowed to cool to room temperature and concentrated in vacuo. The residue was absorbed on silica gel, and the free-running powder was placed on a 10 g isolute silica column. Elution of the column with a gradient of methanol (2 to 10%) in ethyl acetate/dichloromethane (v:v; 4:1) afforded a yellow solid which was triturated with diethyl ether. The pale yellow precipitate was collected by filtration, and was successively washed with diethyl ether, water, and diethyl, then dried in vacuo (0.003 g, 4%). $^1$H-NMR (500 MHz, DMSO-$d_6$) 2.40 (br s, 4H) and 3.59 (t, J=4.50 Hz, 4H) (morpholine $N(CH_2)_2$, and morpholine $O(CH_2)_2$), 2.63 (br s, 4H, piperazine $N(CH_2)_2$), 3.68 (br s, 4H, piperazine $N(CH_2)_2$), 3.56 (s, 2H) and 3.62 (s, 2H) ($NCH_2$-pyridyl and $C_6H_4CH_2$), 7.40 (dd, J=4.5, 7.7 Hz, 1H, pyridine 5-H), 7.45 (d, J=7.7 Hz, 1H, PhH), 7.49 (t, J=7.7 Hz, 1H, PhH), 7.78 (d, J=7.8 Hz, 1H, pyridine 4-H), 8.07 (d, J=7.6 Hz, 1H, PhH), 8.14 (s, 1H, PhH), 8.23 (s, 1H, imidazo[4,5-b]pyridine 5-H), 8.50 (dd, J=1.5, 4.8 Hz, 1H, pyridine 6-H), 8.56 (d, J=1.4 Hz, 1H, pyridine 2-H), 13.48 (br s, 1H, imidazo[4,5-b]pyridine N—H);

LC (Method B)-MS (ESI, m/z): Rt=1.87 min—548, 550 [(M+H)$^+$, Br isotopic pattern]. ESI-HRMS: Found: 548.1783, calculated for $C_{27}H_{31}BrN_7O$ (M+H)$^+$: 548.1773.

Example 67

6-Bromo-2-(4-methoxy-phenyl)-7-(4-pyridin-4-ylmethyl-piperazin-1-yl)-3H-imidazo[4,5-b]pyridine

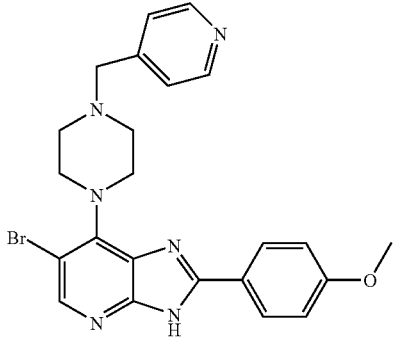

To a mixture of 5-bromo-3-nitro-4-(4-pyridin-4-ylmethyl-piperazin-1-yl)-pyridin-2-ylamine (0.047 g, 0.12 mmol) and ethanol (3.0 ml) was added 4-methoxybenzaldehyde (0.026 g, 0.18 mmol) with the aid of ethanol (1.0 ml), followed by a freshly prepared aqueous solution of $Na_2S_2O_4$ (1M; 0.50 ml, 0.50 mmol). The reaction mixture was stirred at 70° C. for 8.5 h, then allowed to cool to room temperature and concentrated in vacuo. The residue was absorbed on silica gel, and the free-running powder was placed on a 10 g isolute silica column which was eluted with a gradient of methanol (0 to 4%) in ethyl acetate/dichloromethane (v/v; 1:1). The title compound was obtained as a pale yellow solid after trituration with diethyl ether (0.018 g, 31%). $^1$H-NMR (500 MHz, DMSO-$d_6$) 2.63 (br s, 4H, piperazine N(CH$_2$)$_2$), 3.68 (br s, 4H, piperazine N(CH$_2$)$_2$), 3.62 (s, 2H, NCH$_2$-pyridyl), 3.84 (s, 3H, OCH$_3$), 7.10 (d, J=8.9 Hz, 2H) and 8.14 (d, J=8.8 Hz, 2H) (3,5-C$_6$H$_4$OMe and 2,6-C$_6$H$_4$OMe), 7.40 (d, J=5.9 Hz, 2H, pyridine 3-H and 5-H), 8.20 (s, 1H, imidazo[4,5-b]pyridine 5-H), 8.54 (d, J=5.9 Hz, 2H, pyridine 2-H and 6-H), 13.38 (br s, 1H, imidazo[4,5-b]pyridine N—H);

LC (Method B)-MS (ESI, m/z): Rt=3.29 min—479, 481 [(M+H)$^+$, Br isotopic pattern]. ESI-HRMS: Found: 479.1197, calculated for $C_{23}H_{24}BrN_6O$ (M+H)$^+$: 479.1195.

Example 68

6-Bromo-2-(4-morpholin-4-ylmethyl-phenyl)-7-(4-pyridin-4-ylmethyl-piperazin-1-yl)-3H-imidazo[4,5-b]pyridine

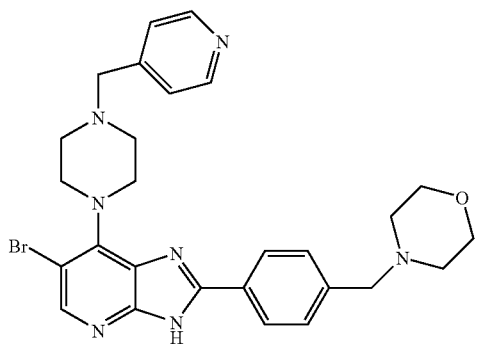

To a mixture of 5-bromo-3-nitro-4-(4-pyridin-4-ylmethyl-piperazin-1-yl)-pyridin-2-ylamine (0.050 g, 0.13 mmol) and EtOH (4.5 ml) was added 4-morpholin-4-ylmethyl-benzaldehyde (0.032 g, 0.16 mmol) followed by a freshly prepared aqueous solution of $Na_2S_2O_4$ (1M; 0.50 ml, 0.50 mmol). The reaction mixture was stirred at 70° C. for 9 h, then allowed to cool to room temperature and concentrated in vacuo. The residue was absorbed on silica gel, the free-running powder was placed on a 10 g isolute silica column and elution with a gradient of methanol (0 to 15%) in ethyl acetate/dichloromethane (v:v; 4:1). afforded a yellow solid. This material was triturated with diethyl ether, and the pale yellow precipitate was collected by filtration, successively washed with diethyl ether, water, and diethyl, then dried in vacuo (0.002 g, 3%). $^1$H-NMR (500 MHz, DMSO-$d_6$) 2.38 (br s, 4H) and 3.59 (t, J=5.0 Hz, 4H) (morpholine protons), 2.63 (br s, 4H, piperazine N(CH$_2$)$_2$), 3.69 (br s, 4H, piperazine N(CH$_2$)$_2$), 3.54 (s, 2H) and 3.62 (s, 2H) (NCH$_2$-pyridyl and C$_6$H$_4$CH$_2$), 7.40 (d, J=4.9 Hz, 2H pyridine 3-H and 5-H), 7.48 (d, J=8.2 Hz, 2H) and 8.14 (d, J=8.2 Hz, 2H) (3,5-C$_6$H$_4$— and 2,6-C$_6$H$_4$—), 8.24 (s, 1H, imidazo[4,5-b]pyridine 5-H), 8.54 (d, J=5.5 Hz, 2H, pyridine 2-H and 6-H), 13.48 (br s, 1H, imidazo[4,5-b]pyridine N—H);

LC (Method B)-MS (ESI, m/z): Rt=1.88 min—548, 550 [(M+H)$^+$, Br isotopic pattern]. ESI-HRMS: Found: 548.1785, calculated for $C_{27}H_{31}BrN_7O$ (M+H)$^+$: 548.1773.

Example 69

6-Bromo-7-[4-(4-chloro-benzyl)-piperazin-1-yl]-2-(4-morpholin-4-ylmethyl-phenyl)-3H-imidazo[4,5-b]pyridine

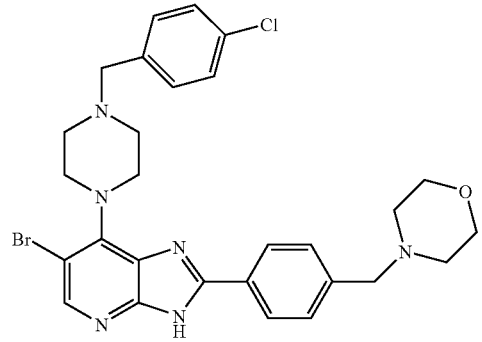

To a mixture of 5-bromo-4-[4-(4-chloro-benzyl)-piperazin-1-yl]-3-nitro-pyridin-2-ylamine (0.064 g, 0.15 mmol) and EtOH (6.5 ml) was added 4-morpholin-4-ylmethyl-benzaldehyde (0.038 g, 0.18 mmol) followed by a freshly prepared aqueous solution of $Na_2S_2O_4$ (1M; 0.60 ml, 0.60 mmol). The reaction mixture was stirred at 70° C. for 9 h, then allowed to cool to room temperature and concentrated in vacuo. The residue was absorbed on silica gel, the free-running powder was placed on a 10 g isolute silica column and elution with a gradient of methanol (0 to 9%) in ethyl acetate/dichloromethane (v:v; 1:1) afforded a yellow solid. The title compound was obtained as a pale yellow solid after trituration with diethyl ether (0.003 g, 3%). $^1$H-NMR (500 MHz, DMSO-$d_6$) 2.38 (br s, 4H) and 3.59 (t, J=4.5 Hz, 4H) (morpholine N(CH$_2$)$_2$ and morpholine O(CH$_2$)$_2$), 2.61 (br s, 4H, piperazine N(CH$_2$)$_2$), 3.66 (br s, 4H, piperazine N(CH$_2$)$_2$), 3.54 (s, 2H) and 3.57 (s, 2H) (NCH$_2$—C$_6$H$_4$Cl and C$_6$H$_4$CH$_2$), 7.41 (m, 4H, C$_6$H$_4$Cl), 7.47 (d, J=8.2 Hz, 2H) and 8.14 (d, J=8.2 Hz, 2H) (3,5-C$_6$H$_4$ and 2,6-C$_6$H$_4$), 8.23 (s, 1H, imidazo[4,5-b]pyridine 5-H), 13.48 (br s, 1H, imidazo[4,5-b]pyridine N—H);

LC (Method B)-MS (ESI, m/z): Rt=2.41 min—581, 583, 585 [(M+H)+, BrCl isotopic pattern]. ESI-HRMS: Found: 581.1442, calculated for $C_{28}H_{31}BrClN_6O$ (M+H)+: 581.1431.

Example 70

5-Bromo-3-nitro-4-(4-(1-phenylethyl)piperazin-1-yl) pyridin-2-amine

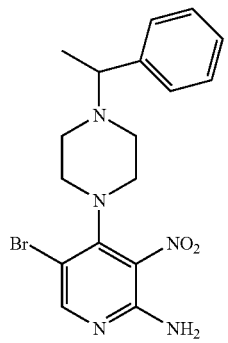

To a mixture of 2-amino-5-bromo-4-chloro-3-nitropyridine (0.252 g, 1.00 mmol) and isopropanol (18 ml) was added 1-(1-phenylethyl)piperazine (0.209 g, 1.10 mmol) followed by diisopropylethylamine (0.20 ml, 1.15 mmol). The reaction mixture was stirred at 45° C. for 20 h, then allowed to cool to room temperature and diluted with isopropanol (10 ml). The resulting precipitate was collected by filtration, washed with isopropanol (3×5 ml), diethyl ether (3×5 ml), and dried. The title compound was obtained as a yellow solid (0.300 g, 74%). $^1$H-NMR (500 MHz, DMSO-$d_6$) 1.30 (d, J=6.7 Hz, 3H, CHCH$_3$), 2.42 (m, 2H) and 2.54 (m, 2H) (piperazine N(CH$_2$)$_2$), 3.03 (br s, 4H, piperazine N(CH$_2$)$_2$), 3.45 (q, J=6.7 Hz, 1H, CHCH$_3$), 6.95 (s, 2H, NH$_2$), 7.23 (m, 1H) and 7.32 (m, 4H) (PhH), 8.13 (s, 1H, pyridine 6-H);
LC (Method B)-MS (ESI, m/z): Rt=2.51 min—406, 408 [(M+H)+, Br isotopic pattern].

6-Bromo-2-(4-morpholin-4-ylmethyl-phenyl)-7-[4-(1-phenyl-ethyl)-piperazin-1-yl]-3H-imidazo[4,5-b] pyridine

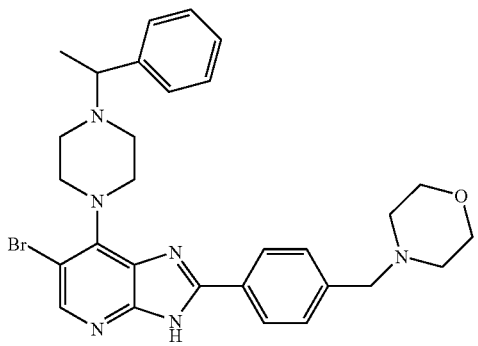

To a mixture of 5-bromo-3-nitro-4-[4-(1-phenyl-ethyl)-piperazin-1-yl]-pyridin-2-ylamine (0.060 g, 0.15 mmol) and EtOH (6.0 ml) was added 4-morpholin-4-ylmethyl-benzaldehyde (0.039 g, 0.19 mmol) followed by a freshly prepared aqueous solution of Na$_2$S$_2$O$_4$ (1M; 0.60 ml, 0.60 mmol). The reaction mixture was stirred at 70° C. for 5 h, then allowed to cool to room temperature, and concentrated in vacuo. The residue was absorbed on silica gel, the free-running powder was placed on a 10 g isolute silica column and elution with a gradient of methanol (0 to 9%) in ethyl acetate/dichloromethane (v:v; 1:1) afforded a yellow solid which was triturated with diethyl ether. The precipitate was collected by filtration, successively washed with diethyl ether, water, diethyl ether, and dried (0.002 g, 3%). $^1$H-NMR (500 MHz, DMSO-$d_6$) 1.37 (d, J=6.6 Hz, 3H, CHCH$_3$), 2.38 (br s, 4H) and 3.59 (t, J=4.6 Hz, 4H) (morpholine N(CH$_2$)$_2$ and morpholine O(CH$_2$)$_2$), 2.54 (br s, 2H), 2.63 (br s, 2H) and 3.65 (br s, 4H) piperazine N(CH$_2$)$_2$), 3.50 (q, 1H, CHCH$_3$), 3.57 (s, 2H, C$_6$H$_4$CH$_2$), 7.26 (m, 1H) and 7.37 (m, 4H) (PhH), 7.47 (d, J=8.9 Hz, 2H) and 8.13 (d, J=8.2 Hz, 2H) (3,5-C$_6$H$_4$— and 2,6-C$_6$H$_4$—), 8.22 (s, 1H, imidazo[4,5-b]pyridine 5-H), 13.45 (br s, 1H, imidazo[4,5-b]pyridine N—H);
LC (Method B)-MS (ESI, m/z): Rt=2.14 min—561, 563 [(M+H)+, Br isotopic pattern]. ESI-HRMS: Found: 561.1971, calculated for $C_{29}H_{34}BrN_6O$ (M+H)+: 561.1977.

Example 71

6-Bromo-2-[4-(4-methyl-piperazin-1-yl)-phenyl]-7-[4-(1-phenyl-ethyl)-piperazin-1-yl]-3H-imidazo[4,5-b]pyridine

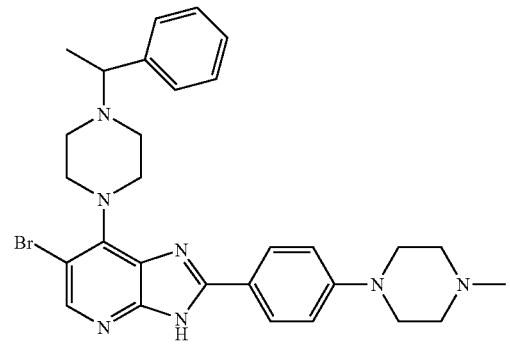

To a mixture of 5-bromo-3-nitro-4-[4-(1-phenyl-ethyl)-piperazin-1-yl]-pyridin-2-ylamine (0.065 g, 0.16 mmol) and EtOH (7.5 ml) was added 4-(4-methyl-piperazin-1-yl)-benzaldehyde (0.042 g, 0.20 mmol) followed by a freshly prepared aqueous solution of Na$_2$S$_2$O$_4$ (1M; 0.65 ml, 0.65 mmol). The reaction mixture was stirred at 80° C. for 20 h, then allowed to cool to room temperature, and concentrated in vacuo. The residue was absorbed on silica gel, the free-running powder was placed on a 10 g isolute silica column which was eluted first with 2% methanol in ethyl acetate/dichloromethane (v:v; 1:1) and then a gradient of methanol (2 to 8%) in chloroform. The titled compound was obtained as a brown solid after trituration with diethyl ether a (0.007 g, 8%). $^1$H-NMR (500 MHz, CD$_3$OD) 1.55 (d, J=6.4 Hz, 3H, CHCH$_3$), 2.50 (s, 3H, N—CH$_3$), 2.80 (br s, 6H), 2.90 (br s, 2H), 3.42 (br s, 4H) and 3.80 (br s, 4H) (8× piperazine N(CH$_2$)$_2$), 3.70 (m, 1H, CHCH$_3$), 7.10 (d, J=8.9 Hz, 2H) and 8.02 (d, J=8.7 Hz, 2H) (3,5-C$_6$H$_4$—N and 2,6-C$_6$H$_4$—N), 7.31 (t, J=7.2 Hz, 1H, PhH), 7.39 (t, J=7.6 Hz, 2H, PhH), 7.37 (d, J=7.2 Hz, 2H) (PhH), 8.20 (s, 1H, imidazo[4,5-b]pyridine 5-H);

LC (Method B)-MS (ESI, m/z): Rt=2.62 min—560, 562 [(M+H)⁺, Br isotopic pattern]. ESI-HRMS: Found: 560.2141, calculated for $C_{29}H_{35}BrN_7$ (M+H)⁺: 560.2137.

Example 72

6-Bromo-7-[4-(4-chloro-benzyl)-piperazin-1-yl]-2-(4-methoxy-phenyl)-3H-imidazo[4,5-b]pyridine

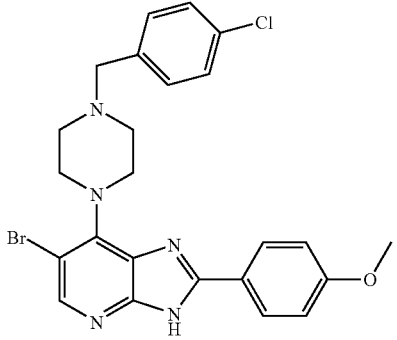

To a mixture of 5-bromo-4-[4-(4-chloro-benzyl)-piperazin-1-yl]-3-nitro-pyridin-2-ylamine (0.051 g, 0.12 mmol) and EtOH (3 ml) was added 4-methoxybenzaldehyde (0.026 g, 0.18 mmol) with the aid of EtOH (1 ml), followed by a freshly prepared aqueous solution of $Na_2S_2O_4$ (1M; 0.50 ml, 0.50 mmol). The reaction mixture was stirred at 70° C. for 18 h, then allowed to cool to room temperature and concentrated in vacuo. The residue was absorbed on silica gel, the free-running powder was placed on a 10 g isolute silica column and elution with a gradient of methanol (0 to 3%) in ethyl acetate/dichloromethane (v:v; 2:3) afforded a pale yellow solid. The title compound was obtained as a white solid after trituration with diethyl ether (0.026 g, 42%). ¹H-NMR (500 MHz, DMSO-d₆) 2.60 (br s, 4H, piperazine N(CH₂)₂), 3.57 (s, 2H, NCH₂—C₆H₄Cl), 3.66 (br s, 4H, piperazine N(CH₂)₂), 3.84 (s, 3H, OCH₃), 7.10 (d, J=8.1 Hz, 2H) and 8.13 (d, J=8.1 Hz, 2H) (3,5-C₆H₄OMe and 2,6-C₆H₄OMe), 7.41 (m, 4H, C₆H₄Cl), 8.20 (s, 1H, imidazo[4,5-b]pyridine 5-H), 13.37 (br s, 1H, imidazo[4,5-b]pyridine N—H);

LC (Method B)-MS (ESI, m/z): Rt=3.79 min—512, 514, 516 [(M+H)⁺, BrCl isotopic pattern]. ESI-HRMS: Found: 512.0853, calculated for $C_{24}H_{24}BrClN_5O$ (M+H)⁺: 512.0853.

Example 73

5-Bromo-4-(4-cyclopropylmethyl-piperazin-1-yl)-3-nitro-pyridin-2-ylamine

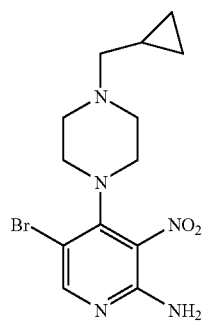

To a mixture of 2-amino-5-bromo-4-chloro-3-nitropyridine (0.126 g, 0.50 mmol) and isopropanol (6 ml) was added 1-cyclopropylmethylpiperazine (0.078 g, 0.55 mmol) with the aid of isopropanol (3 ml), followed by diisopropylethylamine (0.10 ml, 0.57 mmol). The reaction mixture was stirred at 45° C. for 20 h, then allowed to cool to room temperature and diluted with isopropanol (4 ml). The resulting yellow precipitate was collected by filtration, washed with isopropanol (2×4 ml), diethyl ether (3×4 ml), and dried. The title compound was obtained as a yellow solid (0.096 g). The filtrate was concentrated in vacuo, and purification of the resulting residue by chromatography (10 g isolute column) eluting with a gradient of methanol (2 to 4%) in dichloromethane/ethyl acetate (v/v; 1:1) afforded an additional 0.038 g of the product (overall yield: 76%). ¹H-NMR (500 MHz, DMSO-d₆) 0.08 (m, 2H) and 0.46 (m, 2H), (cyclopropyl CH₂), 0.86 (m, 1H, cyclopropyl CH), 2.22 (d, J=6.6 Hz, 2H, N—CH₂cyclopropyl), 2.57 (br s, 4H, piperazine N(CH₂)₂), 3.06 (br s, 4H, piperazine N(CH₂)₂), 6.96 (s, 2H, NH₂), 8.15 (s, 1H, pyridine 6-H);

LC (Method B)-MS (ESI, m/z): Rt=1.62 min—356, 358 [(M+H)⁺, Br isotopic pattern].

6-Bromo-7-(4-cyclopropylmethyl-piperazin-1-yl)-2-(4-methoxy-phenyl)-3H-imidazo[4,5-b]pyridine

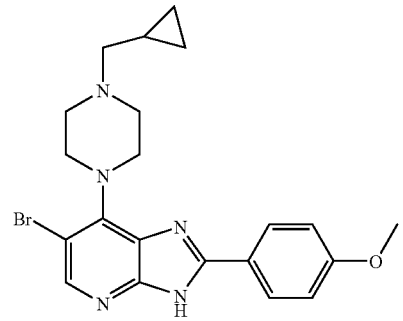

To a mixture of 5-bromo-4-(4-cyclopropylmethyl-piperazin-1-yl)-3-nitro-pyridin-2-ylamine (0.043 g, 0.12 mmol) and EtOH (3 ml) was added 4-methoxybenzaldehyde (0.027 g, 0.18 mmol) with the aid of EtOH (1 ml), followed by a freshly prepared aqueous solution of $Na_2S_2O_4$ (1M; 0.48 ml, 0.48 mmol). The reaction mixture was stirred at 70° C. for 20 h, then allowed to cool to room temperature and concentrated in vacuo. The residue was absorbed on silica gel, the free-running powder was placed on a 10 g isolute silica column and elution with a gradient of methanol (0 to 4%) in ethyl acetate/dichloromethane (v:v; 1:1) afforded a yellow solid. The title compound was obtained as a white solid after trituration with diethyl ether (0.012 g, 23%). ¹H-NMR (500 MHz, DMSO-d₆) 0.12 (m, 2H) and 0.50 (m, 2H) (cyclopropyl CH₂), 0.90 (m, 1H, cyclopropyl CH), 2.27 (d, J=6.4 Hz, 2H, N—CH₂cyclopropyl), 2.67 (br s, 4H, piperazine N(CH₂)₂), 3.66 (br s, 4H, piperazine N(CH₂)₂), 3.84 (s, 3H, OCH₃), 7.10 (d, J=8.8 Hz, 2H) and 8.14 (d, J=8.8 Hz, 2H) (3,5-C₆H₄OMe and 2,6-C₆H₄OMe), 8.20 (s, 1H, imidazo[4,5-b]pyridine 5-H), 13.34 (br s, 1H, imidazo[4,5-b]pyridine N—H);

LC (Method B)-MS (ESI, m/z): Rt=3.20 min—442, 444 [(M+H)⁺, Br isotopic pattern]. ESI-HRMS: Found: 442.1240, calculated for $C_{21}H_{25}BrN_5O$ (M+H)⁺: 442.1242.

Example 74

4-(5-Methyl-isoxazol-3-ylmethyl)-piperazine-1-carboxylic acid tert-butyl ester

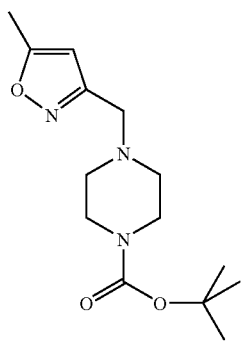

To a solution of 3-bromomethyl-5-methylisoxazole (0.102 g, 0.58 mmol) in dichloromethane (6 ml) was added 1-BOC-piperazine (0.240 g, 1.30 mmol). The reaction mixture was stirred at room temperature for 18 h under argon, then concentrated in vacuo. The resulting residue was absorbed on silica and the free-running powder was placed on a 10 g isolute silica column. Elution with a gradient of ethyl acetate (30 to 70%) in petroleum ether (60-80° C.) afforded the title compound as a white solid (0.124 g, 76%). ¹H-NMR (500 MHz, DMSO-d₆) 1.39 (s, 9H, C(CH₃)₃), 2.32 (t, J=5.1 Hz, 4H, piperazine N(CH₂)₂), 2.38 (s, 3H, isoxazole 5-CH₃), 3.35 (br t, 4H, piperazine N(CH₂)₂), 3.50 (s, 2H, NCH₂ isoxazole), 6.17 (s, 1H, isoxazole 4-H); LC (Method B)-MS (ESI, m/z): Rt=2.60 min—282 [(M+H)⁺, 5%], 226 [(M-ᵗBu)⁺, 100%].

5-Bromo-4-[4-(5-methyl-isoxazol-3-ylmethyl)-piperazin-1-yl]-3-nitro-pyridin-2-ylamine

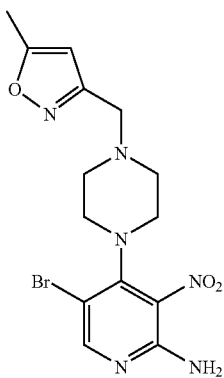

A solution of 4-(5-methyl-isoxazol-3-ylmethyl)-piperazine-1-carboxylic acid tert-butyl ester (0.200 g, 0.71 mmol) in dichloromethane (6 ml) and TFA (8 ml) was stirred at room temperature for 2 h then concentrated in vacuo, and the resulting residue was dried in vacuo. This material (supposedly 0.70 mmol) was dissolved in isopropanol (13 ml) and to this solution 2-amino-5-bromo-4-chloro-3-nitropyridine (0.157 g, 0.63 mmol) was added followed by diisopropylethylamine (0.65 ml, 3.70 mmol). The reaction mixture was stirred at 45° C. for 20 h, then allowed to cool to room temperature and diluted with isopropanol (5 ml). The resulting orange solid was collected by filtration, washed with isopropanol (2×5 ml), diethyl ether (3×5 ml), and dried (0.170 g, 60%); ¹H-NMR (500 MHz, DMSO-d₆) 2.38 (s, 3H, isoxazole 5-CH₃), 2.53 (br s, 4H, piperazine N(CH₂)₂), 3.05 (br s, 4H, piperazine N(CH₂)₂), 3.55 (s, 2H, NCH₂ isoxazole), 6.21 (s, 1H, isoxazole 4-H), 6.97 (s, 2H, NH₂), 8.16 (s, 1H, pyridine 6-H);

LC (Method B)-MS (ESI, m/z): Rt=2.67 min—397, 399 [(M+H)⁺, Br isotopic pattern].

6-Bromo-2-(4-methoxy-phenyl)-7-[4-(5-methyl-isoxazol-3-ylmethyl)-piperazin-1-yl]-3H-imidazo[4,5-b]pyridine

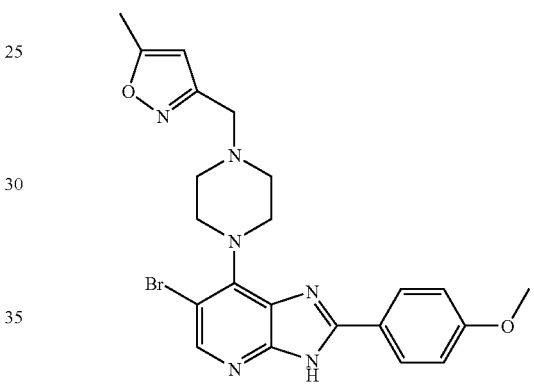

To a mixture of 5-bromo-4-[4-(5-methyl-isoxazol-3-ylmethyl)-piperazin-1-yl]-3-nitro-pyridin-2-ylamine (0.044 g, 0.11 mmol) and EtOH (3 ml) was added 4-methoxybenzaldehyde (0.023 g, 0.17 mmol) with the aid of EtOH (1 ml), followed by a freshly prepared aqueous solution of $Na_2S_2O_4$ (1M; 0.44 ml, 0.44 mmol). The reaction mixture was stirred at 70° C. for 18 h, then allowed to cool to room temperature and concentrated in vacuo. The resulting residue was absorbed on silica, and the free-running powder was placed on a 10 g isolute silica column. Elution with ethyl acetate/dichloromethane (v:v; 3:7) and then 2.5% methanol in ethyl acetate/dichloromethane (v:v; 1:1) afforded a yellow solid. The title compound was obtained as a pale yellow solid after trituration with diethyl ether (0.023 g, 43%); 1H-NMR (500 MHz, DMSO-d₆) 2.40 (s, 3H, isoxazole 5-CH₃), 2.64 (br s, 4H, piperazine N(CH₂)₂), 3.60 (s, 2H, NCH₂), 3.65 (br s, 4H, piperazine N(CH₂)₂), 3.84 (s, 3H, OCH₃), 6.25 (s, 1H, isoxazole 4-H), 7.10 (d, J=8.9 Hz, 2H) and 8.13 (d, J=8.8 Hz, 2H) (3,5-C₆H₄ OMe and 2,6-C₆H₄OMe), 8.20 (s, 1H, imidazo[4,5-b]pyridine 5-H), 13.35 (br s, 1H, imidazo[4,5-b]pyridine N—H);

Example 75

6-Bromo-7-[4-(5-methyl-isoxazol-3-ylmethyl)-piperazin-1-yl]-2-(4-morpholin-4-ylmethyl-phenyl)-3H-imidazo[4,5-b]pyridine

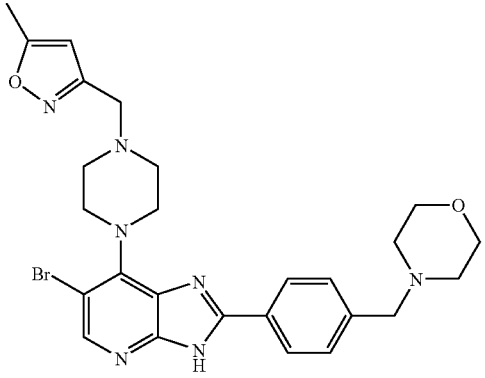

To a mixture of 5-bromo-4-[4-(5-methyl-isoxazol-3-ylmethyl)-piperazin-1-yl]-3-nitro-pyridin-2-ylamine (0.044 g, 0.11 mmol) and EtOH (3.5 ml) was added 4-morpholin-4-ylmethyl-benzaldehyde (0.029 g, 0.14 mmol) followed by a freshly prepared aqueous solution of $Na_2S_2O_4$ (1M; 0.44 ml, 0.44 mmol). The reaction mixture was stirred at 80° C. for 19 h, then allowed to cool to room temperature and concentrated in vacuo. The resulting residue was absorbed on silica, and the free-running powder was placed on a 10 g isolute silica column. Elution with ethyl acetate/dichloromethane (v:v; 2:3) and then a gradient of methanol (2 to 8%) in ethyl acetate/dichloromethane (v:v; 1:1) afforded a yellow solid. The title compound was obtained as a pale yellow solid after trituration with diethyl ether (0.012 g, 20%); $^1$H-NMR (500 MHz, DMSO-$d_6$) 2.38 (br s, 4H) and 3.59 (t, J=4.6 Hz, 4H) (morpholine $N(CH_2)_2$ and morpholine $O(CH_2)_2$), 2.40 (s, 3H, isoxazole 5-$CH_3$), 2.64 (br s, 4H, piperazine $N(CH_2)_2$), 3.54 (s, 2H) and 3.60 (s, 2H) ($C_6H_4CH_2N$ and $NCH_2$ isoxazole), 3.67 (br s, 4H, piperazine $N(CH_2)_2$), 6.25 (s, 1H, isoxazole 4-H), 7.48 (d, J=8.2 Hz, 2H) and 8.14 (d, J=8.2 Hz, 2H) (3,5-$C_6H_4$— and 2,6-$C_6H_4$—), 8.23 (s, 1H, imidazo[4,5-b]pyridine 5-H), 13.48 (br s, 1H, imidazo[4,5-b]pyridine N—H);

LC (Method B)-MS (ESI, m/z): Rt=2.32 min—552, 554 [(M+H)$^+$, Br isotopic pattern]. ESI-HRMS: Found: 552.1713, calculated for $C_{26}H_{31}BrN_7O_2$ (M+H)$^+$: 552.1722.

Example 76

2-{4-[6-Chloro-2-(4-morpholin-4-ylmethyl-phenyl)-3H-imidazo[4,5-b]pyridin-7-yl]-piperazin-1-yl}-N-thiazol-2-yl-acetamide

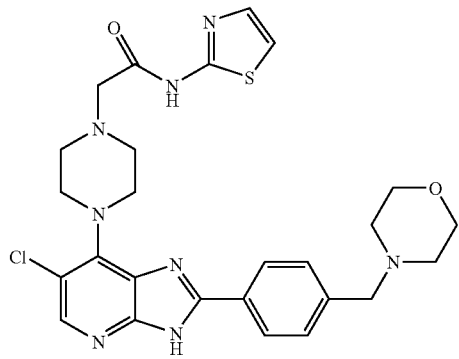

To a mixture of 2-[4-(2-amino-5-chloro-3-nitro-pyridin-4-yl)-piperazin-1-yl]-N-thiazol-2-yl-acetamide (0.044 g, 0.11 mmol) and EtOH (4.0 ml) was added 4-morpholin-4-ylmethyl-benzaldehyde (0.029 g, 0.14 mmol) followed by a freshly prepared aqueous solution of $Na_2S_2O_4$ (1M; 0.44 ml, 0.44 mmol). The reaction mixture was stirred at 80° C. for 20 h, then allowed to cool to room temperature and concentrated in vacuo. The resulting residue was absorbed on silica, and the free-running powder was placed on a 10 g isolute silica column. Elution with a gradient of methanol (0 to 6%) in ethyl acetate/dichloromethane (v:v; 1:1) afforded a yellow solid. The title compound was obtained as a pale yellow solid after trituration with diethyl ether (0.020 g, 33%); $^1$H-NMR (500 MHz, DMSO-$d_6$) 2.38 (br s, 4H) and 3.59 (t, J=4.5 Hz, 4H) (morpholine $N(CH_2)_2$ and morpholine $O(CH_2)_2$), 2.78 (br s, 4H, piperazine $N(CH_2)_2$), 3.40 (s, 2H) and 3.53 (s, 2H) ($C_6H_4CH_2N$ and $NCH_2CO$), 3.75 (br s, 4H, piperazine $N(CH_2)_2$), 7.24 (d, J=3.5 Hz, 1H, thiazole-H), 7.48 (m, 3H, 3,5-$C_6H_4$— and thiazole-H), 8.12 (d, J=9.7 Hz, 2H, 2,6-$C_6H_4$—), 8.15 (s, 1H, imidazo[4,5-b]pyridine 5-H), 11.89 (s, 1H, CONH), 13.46 (br s, 1H, imidazo[4,5-b]pyridine N—H);

LC (Method B)-MS (ESI, m/z): Rt=2.50 min—553, 555 [(M+H)$^+$, Cl isotopic pattern]. ESI-HRMS: Found: 553.1903, calculated for $C_{26}H_{30}ClN_8O_2S$ (M+H)$^+$: 553.1901.

Example 77

6-Bromo-7-[4-(5-methyl-isoxazol-3-ylmethyl)-piperazin-1-yl]-2-(4-pyrazol-1-ylmethyl-phenyl)-3H-imidazo[4,5-b]pyridine

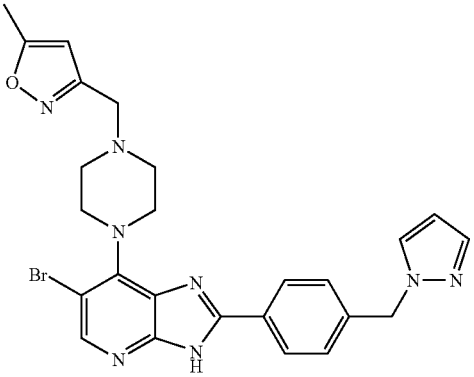

To a mixture of 5-bromo-4-[4-(5-methyl-isoxazol-3-ylmethyl)-piperazin-1-yl]-3-nitro-pyridin-2-ylamine (0.040 g, 0.10 mmol) and EtOH (3.5 ml) was added 4-pyrazol-1-ylmethyl-benzaldehyde (0.024 g, 0.13 mmol) followed by a freshly prepared aqueous solution of $Na_2S_2O_4$ (1M; 0.40 ml, 0.40 mmol). The reaction mixture was stirred at 80° C. for 20 h, then allowed to cool to room temperature and concentrated in vacuo. The resulting residue was absorbed on silica, and the free-running powder was placed on a 10 g isolute silica column. Elution with a gradient of methanol (0 to 3%) in ethyl acetate/dichloromethane (v:v; 1:1) afforded a solid. The title compound was obtained as a white solid after trituration with diethyl ether (0.020 g, 38%). $^1$H-NMR (500 MHz, DMSO-$d_6$) 2.40 (s, 3H, isoxazole 5-$CH_3$), 2.63 (br s, 4H, piperazine $N(CH_2)_2$), 3.60 (s, 2H, $NCH_2$ isoxazole), 3.66 (br s, 4H, piperazine $N(CH_2)_2$), 5.42 (s, 2H, $C_6H_4CH_2N$), 6.24 (s, 1H, isoxazole 4-H), 6.30 (t, J=2.0 Hz, 1H, pyrazole 4-H), 7.35 (d, J=8.3 Hz, 2H) and 8.14 (d, J=8.2 Hz, 2H) (3,5-$C_6H_4$ and 2,6-$C_6H_4$), 7.49 (d, J=1.4 Hz, pyrazole-H), 7.86 (d, J=2.0 Hz, 1H, pyrazole-H), 8.24 (s, 1H, imidazo[4,5-b]pyridine 5-H), 13.50 (br s, 1H, imidazo[4,5-b]pyridine N—H);

LC (Method B)-MS (ESI, m/z): Rt=3.64 min—533, 535 [(M+H)⁺, Br isotopic pattern]. ESI-HRMS: Found: 533.1418, calculated for $C_{25}H_{26}BrN_8O$ (M+H)⁺: 533.1413.

Example 78

2-(4-((1H-Pyrazol-1-yl)methyl)phenyl)-6-bromo-7-(4-(pyridin-4-ylmethyl)piperazin-1-yl)-3H-imidazo[4,5-b]pyridine

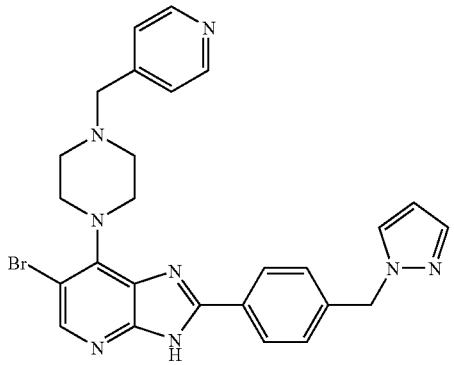

To a mixture of 5-bromo-3-nitro-4-(4-pyridin-4-ylmethyl-piperazin-1-yl)-pyridin-2-ylamine (0.039 g, 0.10 mmol) and EtOH (3.5 ml) was added 4-pyrazol-1-ylmethyl-benzaldehyde (0.024 g, 0.13 mmol) followed by a freshly prepared aqueous solution of $Na_2S_2O_4$ (1M; 0.40 ml, 0.40 mmol). The reaction mixture was stirred at 80° C. for 20 h, then allowed to cool to room temperature and concentrated in vacuo. The resulting residue was absorbed on silica, and the free-running powder was placed on a 10 g isolute silica column. Elution with a gradient of methanol (2 to 5%) in ethyl acetate/dichloromethane (v:v; 1:1) afforded a solid. The title compound was obtained as a white solid after trituration with diethyl ether (0.025 g, 48%); ¹H-NMR (500 MHz, DMSO-d₆) 2.63 (br s, 4H, piperazine N(CH₂)₂), 3.61 (s, 2H, NCH₂pyridyl), 3.69 (br s, 4H, piperazine N(CH₂)₂), 5.42 (s, 2H, $C_6H_4CH_2N$), 6.30 (t, J=2.0 Hz, 1H, pyrazole 4-H), 7.35 (d, J=8.3 Hz, 2H) and 8.14 (d, J=8.2 Hz, 2H) (3,5-$C_6H_4$— and 2,6-$C_6H_4$—), 7.39 (d, J=5.9 Hz, 2H, pyridine 3-H, 5-H), 7.49 (d, J=1.7 Hz, 1H, pyrazole-H), 7.86 (d, J=2.2 Hz, 1H, pyrazole-H), 8.24 (s, 1H, imidazo[4,5-b]pyridine 5-H), 8.54 (d, J=5.9 Hz, 2H, pyridine 2-H, 6-H), 13.50 (br s, 1H, imidazo[4,5-b]pyridine N—H);

LC (Method B)-MS (ESI, m/z): Rt=3.35 min—529, 531 [(M+H)⁺, Br isotopic pattern]. ESI-HRMS: Found: 529.1458, calculated for $C_{26}H_{26}BrN_8$ (M+H)⁺: 529.1464.

Example 79

5-Chloro-3-nitro-4-(4-(pyridin-3-ylmethyl)piperazin-1-yl)pyridin-2-amine

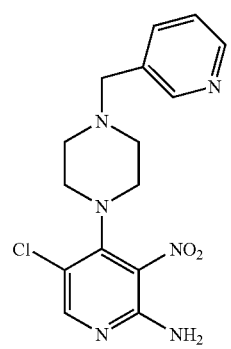

To a mixture of 2-amino-4,5-dichloro-3-nitropyridine (0.030 g, 0.14 mmol) and isopropanol (3.0 ml) was added 1-[(3-pyridyl)-methyl]-piperazine (0.028 g, 0.16 mmol) followed by diisopropylethylamine (0.03 ml, 0.18 mmol). The reaction mixture was heated at 45° C. for 20 h, then allowed to cool to room temperature, and diluted with isopropanol (2.5 ml). The precipitate was collected by filtration and washed with isopropanol and diethyl ether. The title compound was thus obtained as a yellow solid (0.036 g, 75%); ¹H-NMR (500 MHz, DMSO-d₆) 3.06 (br t, 4H, piperazine N(CH₂)₂), 3.57 (s, 2H, NCH₂pyridyl), 6.95 (s, 2H, NH₂), 7.36 (dd, J=7.8, 5.4 Hz, 1H, pyridine 5-H), 7.73 (dt, J=7.8, 1.8 Hz, 1H, pyridine 4-H), 8.07 (s, 1H, 6-H), 8.47 (dd, J=4.8, 1.6 Hz, 1H, pyridine 6-H), 8.51 (d, J=1.7 Hz, 1H, pyridine 2-H);

LC (Method B)-MS (ESI, m/z) Rt=1.77 min—349, 351 [(M+H)⁺, Cl isotopic pattern].

6-Chloro-2-(4-morpholin-4-ylmethyl-phenyl)-7-(4-pyridin-3-ylmethyl-piperazin-1-yl)-3H-imidazo[4,5-b]pyridine

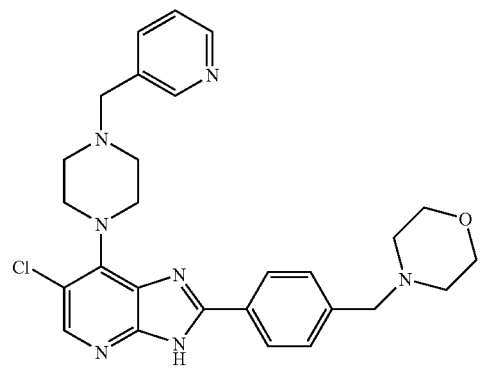

To a mixture of 5-chloro-3-nitro-4-(4-pyridin-3-ylmethyl-piperazin-1-yl)-pyridin-2-ylamine (0.031 g, 0.09 mmol) and EtOH (3.0 ml) was added 4-morpholin-4-ylmethyl-benzaldehyde (0.025 g, 0.12 mmol) followed by a freshly prepared aqueous solution of $Na_2S_2O_4$ (1M; 0.36 ml, 0.36 mmol). The reaction mixture was stirred at 80° C. for 20 h, then allowed to cool to room temperature and concentrated in vacuo. The resulting residue was absorbed on silica, and the free-running powder was placed on a 10 g isolute silica column. Elution with a gradient of methanol (2 to 13%) in ethyl acetate/dichloromethane (v:v; 4:1) afforded a yellow solid. The title compound was obtained as a pale yellow solid after trituration with diethyl ether (0.014 g, 30%); ¹H-NMR (500 MHz, DMSO-d₆) 2.38 (br s, 4H) and 3.59 (t, J=4.5 Hz, 4H) (morpholine N(CH₂)₂ and morpholine O(CH₂)₂), 2.62 (br s, 4H, piperazine N(CH₂)₂), 3.53 (s, 2H) and 3.61 (s, 2H) (NCH₂-pyridyl and $C_6H_4CH_2N$), 3.71 (br s, 4H, piperazine N(CH₂)₂), 7.39 (dd, J=5.30, 8.2 Hz, pyridine 5-H), 7.47 (d, J=8.2 Hz, 2H) and 8.12 (d, J=8.7 Hz, 2H) (3,5-$C_6H_4$— and 2,6-$C_6H_4$—), 7.78 (d, J=6.9 Hz, 1H, pyridine 4-H), 8.14 (s, 1H, imidazo[4,5-b]pyridine 5-H), 8.50 (dd, J=1.50, 4.6 Hz, 1H, pyridine 6-H), 8.56 (d, J=1.5 Hz, 1H, pyridine 2-H), 13.42 (br s, 1H, imidazo[4,5-b]pyridine N—H);

LC (Method B)-MS (ESI, m/z): Rt=1.87 min—504, 506 [(M+H)⁺, Cl isotopic pattern]. ESI-HRMS: Found: 504.2272, calculated for $C_{27}H_{31}ClN_7O$ (M+H)⁺: 504.2278.

Example 80

5-Chloro-4-[4-(5-methyl-isoxazol-3-ylmethyl)-piperazin-1-yl]-3-nitro-pyridin-2-ylamine

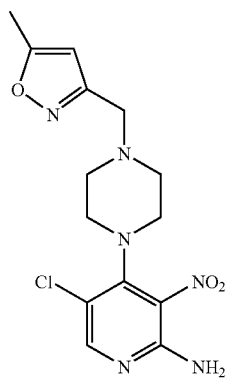

A solution of 4-(5-methyl-isoxazol-3-ylmethyl)-piperazine-1-carboxylic acid tert-butyl ester (0.126 g, 0.45 mmol) in dichloromethane (3.7 ml) and TFA (5 ml) was stirred at room temperature for 1.5 h then concentrated in vacuo, and the resulting residue was dried in vacuo. Part of this material (estimated 0.15 mmol) was dissolved in isopropanol (3 ml) and to this solution 2-amino-4,5-dichloro-3-nitropyridine (0.031 g, 0.15 mmol) was added followed by diisopropylethylamine (0.15 ml, 0.80 mmol). The reaction mixture was stirred at 45° C. for 20 h, then allowed to cool to room temperature and diluted with isopropanol (3 ml). The resulting yellow precipitate was collected by filtration, washed with isopropanol (2×3 ml), diethyl ether (2×3 ml), and dried (0.038 g, 73%); $^1$H-NMR (500 MHz, DMSO-d$_6$) 2.38 (s, 3H, isoxazole 5-CH$_3$), 2.52 (br s 4H, piperazine N(CH$_2$)$_2$), 3.06 (br t, J=4.1 Hz, 4H, piperazine N(CH$_2$)$_2$), 3.56 (s, 2H, NCH$_2$ isoxale), 6.21 (s, 1H, isoxazole 4-H), 6.96 (s, 2H, NH$_2$), 8.06 (s, 1H, pyridine 6-H);

LC (Method B)-MS (ESI, m/z): Rt=2.49 min—353, 355 [(M+H)$^+$, Cl isotopic pattern].

6-Chloro-7-[4-(5-methyl-isoxazol-3-ylmethyl)-piperazin-1-yl]-2-(4-morpholin-4-ylmethyl-phenyl)-3H-imidazo[4,5-b]pyridine

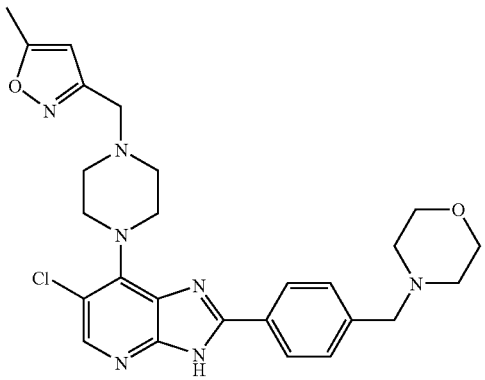

To a mixture of 5-chloro-4-[4-(5-methyl-isoxazol-3-ylmethyl)-piperazin-1-yl]-3-nitro-pyridin-2-ylamine (0.031 g, 0.09 mmol) and EtOH (3.0 ml) was added 4-morpholin-4-ylmethyl-benzaldehyde (0.025 g, 0.12 mmol) followed by a freshly prepared aqueous solution of Na$_2$S$_2$O$_4$ (1M; 0.36 ml, 0.36 mmol). The reaction mixture was stirred at 80° C. for 20 h, then allowed to cool to room temperature and concentrated in vacuo. The resulting residue was absorbed on silica, and the free-running powder was placed on a 10 g isolute silica column. Elution with a gradient of methanol (0 to 7%) in ethyl acetate/dichloromethane (v:v; 1:1) afforded a yellow solid. The title compound was obtained as a yellow solid after trituration with diethyl ether (0.018 g, 39%); $^1$H-NMR (500 MHz, DMSO-d$_6$) 2.38 (br s, 4H) and 3.58 (t, J=4.8 Hz, 4H) (morpholine N(CH$_2$)$_2$ and morpholine O(CH$_2$)$_2$), 2.40 (s, 3H, isoxazole 5-CH$_3$), 2.63 (br s, 4H, piperazine N(CH$_2$)$_2$), 3.53 (s, 2H) and 3.60 (s, 2H) (C$_6$H$_4$CH$_2$N and NCH$_2$ isoxazole), 3.70 (br s, 4H, piperazine N(CH$_2$)$_2$), 6.25 (s, 1H, isoxazole 4-H), 7.47 (d, J=8.2 Hz, 2H) and 8.13 (d, J=8.2 Hz, 2H) (3,5-C$_6$H$_4$— and 2,6-C$_6$H$_4$—), 8.11 (s, 1H, imidazo[4,5-b]pyridine 5-H), 13.48 (br s, 1H, imidazo[4,5-b]pyridine N—H);

LC (Method B)-MS (ESI, m/z): Rt=2.38 min—508, 510 [(M+H)$^+$, Cl isotopic pattern]. ESI-HRMS: Found: 508.2229, calculated for C$_{26}$H$_{31}$ClN$_7$O$_2$ (M+H)$^+$: 508.2228.

Example 81

6-Bromo-2-(3-methoxy-phenyl)-7-[4-(5-methyl-isoxazol-3-ylmethyl)-piperazin-1-yl]-3H-imidazo[4,5-b]pyridine

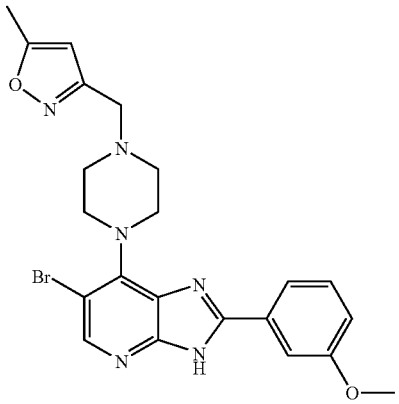

To a mixture of 5-bromo-4-[4-(5-methyl-isoxazol-3-ylmethyl)-piperazin-1-yl]-3-nitro-pyridin-2-ylamine (0.040 g, 0.10 mmol) and EtOH (3 ml) was added 3-methoxybenzaldehyde (0.022 g, 0.16 mmol) with the aid of EtOH (1 ml), followed by a freshly prepared aqueous solution of Na$_2$S$_2$O$_4$ (1M; 0.40 ml, 0.40 mmol). The reaction mixture was stirred at 80° C. for 20 h, then allowed to cool to room temperature and concentrated in vacuo. The resulting residue was absorbed on silica, and the free-running powder was placed on a 10 g isolute silica column. Elution with ethyl acetate/dichloromethane (v:v; 3:7) and then a gradient of methanol (0 to 2%) in ethyl acetate/dichloromethane (v:v; 1:1) afforded a yellowish solid. The title compound was obtained as a white solid after trituration with diethyl ether (0.010 g, 21%); $^1$H-NMR (500 MHz, DMSO-d$_6$) 2.40 (s, 3H, isoxazole 5-CH$_3$), 2.64 (br s, 4H, piperazine N(CH$_2$)$_2$), 3.60 (s, 2H, NCH$_2$ isoxazole), 3.67 (br s, 4H, piperazine N(CH$_2$)$_2$), 3.85 (s, 3H, OCH$_3$), 6.25 (s, 1H, isoxazole 4-H), 7.09 (dd, J=1.9, 8.3 Hz, 1H, PhH), 7.45 (t, J=8.3 Hz, 1H, Ph 5-H), 7.76 (s, 1H, Ph 2-H), 7.79 (d, J=8.3 Hz, PhH), 8.24 (s, 1H, imidazo[4,5-b]pyridine 5-H), 13.50 (br s, 1H, imidazo[4,5-b]pyridine N—H);

LC (Method B)-MS (ESI, m/z): Rt=3.81 min—483, 485 [(M+H)$^+$, Br isotopic pattern]. ESI-HRMS: Found: 483.1146, calculated for C$_{22}$H$_{24}$BrN$_6$O$_2$ (M+H)$^+$: 483.1144.

Example 82

6-Bromo-2-[4-(2-morpholin-4-yl-ethoxy)-phenyl]-7-(4-pyridin-4-ylmethyl-piperazin-1-yl)-3H-imidazo[4,5-b]pyridine

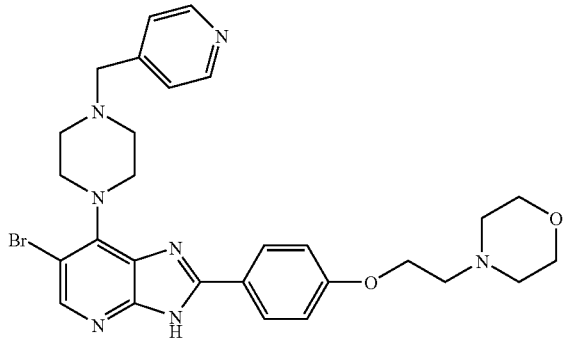

To a mixture of 5-bromo-3-nitro-4-(4-pyridin-4-ylmethyl-piperazin-1-yl)-pyridin-2-ylamine (0.040 g, 0.10 mmol) and EtOH (3.0 ml) was added 4-(2-morpholin-4-yl-ethoxy)-benzaldehyde (0.031 g, 0.13 mmol) with the aid of ethanol (1 ml) followed by a freshly prepared aqueous solution of $Na_2S_2O_4$ (1M; 0.40 ml, 0.40 mmol). The reaction mixture was stirred at 80° C. for 20 h, then allowed to cool to room temperature and concentrated in vacuo. The resulting residue was absorbed on silica, and the free-running powder was placed on a 10 g isolute silica column. Elution with a gradient of methanol (0 to 10%) in ethyl acetate/dichloromethane (v:v; 1:1). afforded a pale yellow solid. This material was triturated with diethyl ether, and the resulting white precipitate was collected by filtration, and successively washed with diethyl ether, water, and diethyl ether, then dried in vacuo (0.014 g, 24%); $^1$H-NMR (500 MHz, DMSO-$d_6$) 2.63 (br s, 4H, piperazine $N(CH_2)_2$), 2.72 (t, J=5.7 Hz, 2H, $OCH_2CH_2N$), 3.59 (t, J=4.7 Hz, 4H, morpholine $O(CH_2)_2$), 3.62, (s, 2H, $NCH_2$-pyridyl), 3.68 (br t, 4H, piperazine $N(CH_2)_2$), 4.18 (t, J=5.8 Hz, 2H, $OCH_2CH_2N$), 7.11 (d, J=8.9 Hz, 2H) and 8.12 (d, J=8.9 Hz, 2H) (3,5-$C_6H_4$— and 2,6-$C_6H_4$—), 7.39 (d, J=5.9 Hz, 2H, pyridine 3-H, 5-H), 8.20 (s, 1H, imidazo[4,5-b]pyridine 5-H), 8.54 (d, J=5.9 Hz, 2H, pyridine 2-H, 6-H), 13.34 (br s, 1H, imidazo[4,5-b]pyridine N—H);

LC (Method B)-MS (ESI, m/z): Rt=2.12 min—578, 580 [(M+H)$^+$, Br isotopic pattern]. ESI-HRMS: Found: 578.1885, calculated for $C_{28}H_{33}BrN_7O_2$ (M+H)$^+$: 578.1879.

Example 83

2-(4-((1H-Pyrazol-1-yl)methyl)phenyl)-6-chloro-7-(4-(pyridin-4-ylmethyl)piperazin-1-yl)-3H-imidazo[4,5-b]pyridine

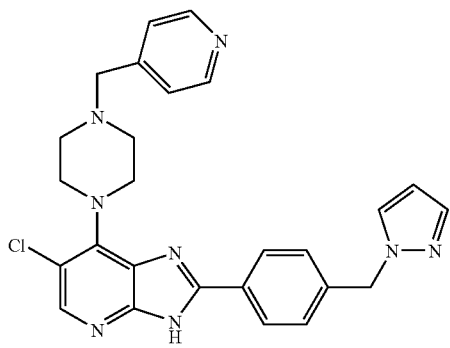

To a mixture of 5-chloro-3-nitro-4-(4-pyridin-4-ylmethyl-piperazin-1-yl)-pyridin-2-ylamine (0.022 g, 0.06 mmol) and EtOH (2.5 ml) was added 4-pyrazol-1-ylmethyl-benzaldehyde (0.015 g, 0.08 mmol) followed by a freshly prepared aqueous solution of $Na_2S_2O_4$ (1M; 0.24 ml, 0.24 mmol). The reaction mixture was stirred at 80° C. for 20 h, then allowed to cool to room temperature and concentrated in vacuo. The resulting residue was absorbed on silica, and the free-running powder was placed on a 10 g isolute silica column. Elution with a gradient of methanol (0 to 8%) in ethyl acetate/dichloromethane (v:v; 1:1) afforded a yellow solid. The title compound was obtained as a pale yellow solid after trituration with diethyl ether (0.008 g, 27%); $^1$H-NMR (500 MHz, DMSO-$d_6$) 2.62 (br s, 4H, piperazine $N(CH_2)_2$), 3.61 (s, 2H, $NCH_2$pyridyl), 3.72 (br s, 4H, piperazine $N(CH_2)_2$), 5.42 (s, 2H, $C_6H_4CH_2N$), 6.30 (t, J=2.0 Hz, 1H, pyrazole 4-H), 7.35 (d, J=8.3 Hz, 2H) and 8.13 (d, J=8.3 Hz, 2H) (3,5-$C_6H_4$— and 2,6-$C_6H_4$—), 7.40 (d, J=5.8 Hz, 2H, pyridine 3-H, 5-H), 7.49 (d, J=1.5 Hz, 1H, pyrazole-H), 7.86 (d, J=1.8 Hz, 1H, pyrazole-H), 8.11 (s, 1H, imidazo[4,5-b]pyridine 5-H), 8.54 (d, J=5.9 Hz, 2H, pyridine 2-H, 6-H), 13.45 (br s, 1H, imidazo[4,5-b]pyridine N—H);

LC (Method B)-MS (ESI, m/z): Rt=3.22 min—485, 487 [(M+H)$^+$, Cl isotopic pattern]. ESI-HRMS: Found: 485.1966, calculated for $C_{26}H_{26}ClN_8$ (M+H)$^+$: 485.1969.

Example 84

2-(4-(2-(4-((1H-Pyrazol-1-yl)methyl)phenyl)-6-chloro-3H-imidazo[4,5-b]pyridin-7-yl)piperazin-1-yl)-N-(thiazol-2-yl)acetamide

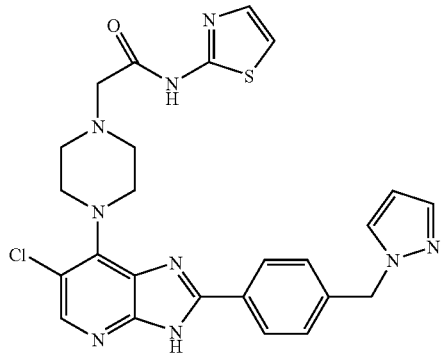

To a mixture of 2-[4-(2-amino-5-chloro-3-nitro-pyridin-4-yl)-piperazin-1-yl]-N-thiazol-2-yl-acetamide (0.028 g, 0.07 mmol) and EtOH (3.0 ml) was added 4-pyrazol-1-ylmethyl-benzaldehyde (0.017 g, 0.09 mmol) followed by a freshly prepared aqueous solution of $Na_2S_2O_4$ (1M; 0.30 ml, 0.30 mmol). The reaction mixture was stirred at 80° C. for 20 h, then allowed to cool to room temperature and concentrated in vacuo. The resulting residue was absorbed on silica, and the free-running powder was placed on a 10 g isolute silica column. Elution with a gradient of methanol (0 to 5%) in ethyl acetate/dichloromethane (v:v; 1:1) afforded a pale yellow solid. The title compound was obtained as a white solid after trituration with diethyl ether (0.006 g, 16%); $^1$H-NMR (500 MHz, DMSO-$d_6$) 2.77 (br s, 4H, piperazine $N(CH_2)_2$), 3.40 (s, 2H, $NCH_2CON$), 3.73 (br s, 4H, piperazine $N(CH_2)_2$), 5.41 (s, 2H, $C_6H_4CH_2N$), 6.30 (t, J=1.9 Hz, 1H, pyrazole 4-H), 7.23 (d, J=3.5 Hz, 1H, thiazole H), 7.35 (d, J=7.6 Hz, 2H) and 8.14 (d, J=8.3 Hz, 2H) (3,5-$C_6H_4$— and 2,6-$C_6H_4$—), 7.49 (d, 2H, thiazole-H, and pyrazole-H), 7.86 (d, J=1.84 Hz, 1H, pyrazole-H), 8.11 (s, 1H, imidazo[4,5-b]pyridine 5-H), 11.89 (s, 1H, CONH), 13.48 (br s, 1H, imidazo[4,5-b]pyridine N—H); LC (Method B)-MS (ESI, m/z):

Rt=3.89 min—534, 536 [(M+H)⁺, Cl isotopic pattern]. ESI-HRMS: Found: 534.1595, calculated for $C_{25}H_{25}ClN_9OS$ (M+H)⁺: 534.1591.

Example 85

2-(4-((1H-Pyrazol-1-yl)methyl)phenyl)-6-bromo-7-(4-(4-chlorobenzyl)piperazin-1-yl)-3H-imidazo[4,5-b]pyridine

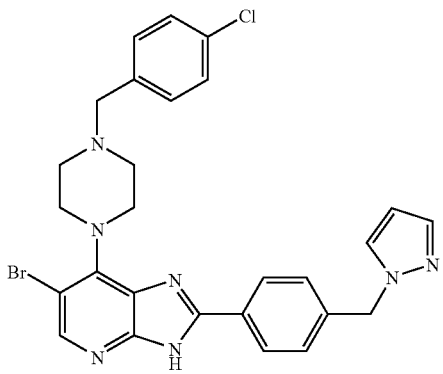

To a mixture of 5-bromo-4-[4-(4-chloro-benzyl)-piperazin-1-yl]-3-nitro-pyridin-2-ylamine (0.043 g, 0.10 mmol) and EtOH (4.0 ml) was added 4-pyrazol-1-ylmethyl-benzaldehyde (0.024 g, 0.13 mmol) followed by a freshly prepared aqueous solution of $Na_2S_2O_4$ (1M; 0.40 ml, 0.40 mmol). The reaction mixture was stirred at 80° C. for 22 h, then allowed to cool to room temperature and concentrated in vacuo. The resulting residue was absorbed on silica, and the free-running powder was placed on a 10 g isolute silica column. Elution with a gradient of methanol (0 to 2%) in ethyl acetate/dichloromethane (v:v; 1:1) afforded a yellow solid. The title compound was obtained as a white solid after trituration with diethyl ether (0.023 g, 40%); ¹H-NMR (500 MHz, DMSO-d₆) 2.66 (br s, 4H, piperazine $N(CH_2)_2$), 3.56 (s, 2H, $NCH_2C_6H_4Cl$), 3.66 (br s, 4H, piperazine $N(CH_2)_2$), 5.42 (s, 2H, $C_6H_4CH_2N$), 6.30 (t, J=1.9 Hz, 1H, pyrazole 4-H), 7.35 (d, J=7.6 Hz, 2H) and 8.14 (d, J=8.3 Hz, 2H) (3,5-$C_6H_4CH_2N$ and 2,6-$C_6H_4CH_2N$), 7.40 (m, 4H, $C_6H_4Cl$), 7.49 (d, J=1.5 Hz, 1H, pyrazole-H), 7.86 (d, J=1.8 Hz, 1H, pyrazole-H), 8.23 (s, 1H, imidazo[4,5-b]pyridine 5-H), 13.54 (br s, imidazo[4,5-b]pyridine N—H);

LC (Method B)-MS (ESI, m/z): Rt=3.72 min—562, 564, 566 [(M+H)⁺, BrCl isotopic pattern]. ESI-HRMS: Found: 562.1116, calculated for $C_{27}H_{26}BrClN_7$(M+H)⁺: 562.1122.

Example 86

6-Bromo-7-[4-(4-chloro-benzyl)-piperazin-1-yl]-2-[4-(4-methyl-piperazin-1-yl)-phenyl]-3H-imidazo[4,5-b]pyridine

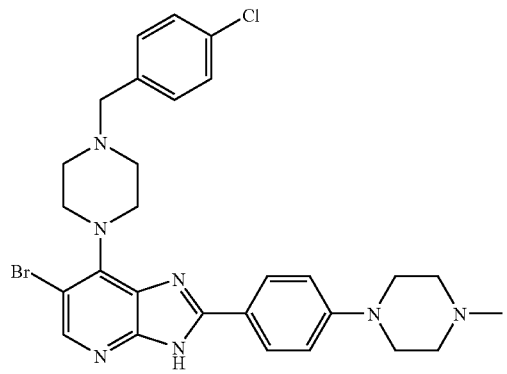

To a mixture of 5-bromo-4-[4-(4-chloro-benzyl)-piperazin-1-yl]-3-nitro-pyridin-2-ylamine (0.043 g, 0.10 mmol) and EtOH (6.0 ml) was added 4-(4-methyl-piperazin-1-yl)-benzaldehyde (0.027 g, 0.13 mmol) followed by a freshly prepared aqueous solution of $Na_2S_2O_4$ (1M; 0.40 ml, 0.40 mmol). The reaction mixture was stirred at 80° C. for 20 h, then allowed to cool to room temperature and concentrated in vacuo. The resulting residue was absorbed on silica, and the free-running powder was placed on a 10 g isolute silica column. Elution with a gradient of methanol (0 to 8%) in ethyl acetate/dichloromethane (v:v; 1:1) afforded a yellow solid which was triturated with diethyl ether. The title compound was collected by filtration, and successively washed with diethyl ether, water, and diethyl ether (0.014 g, 24%); ¹H-NMR (500 MHz, $CD_3OD$) 2.40 (s, 3H, N-Me), 2.67 (br t, 4H, piperazine $N(CH_2)_2$), 3.74 (br s, 4H, piperazine $N(CH_2)_2$), 3.37 (br s, 4H, piperazine $N(CH_2)_2$), 3.64 (s, 2H, $NCH_2C_6H_4Cl$), 3.79 (br s, 4H, piperazine $N(CH_2)_2$), 7.09 (d, J=8.8 Hz, 2H) and 8.02 (d, J=8.9 Hz, 2H) (3,5-$C_6H_4$—N and 2,6-$C_6H_4$—N), 7.37 (d, J=8.5 Hz, 2H) and 7.41 (d, J=8.5 Hz, 2H) ($C_6H_4Cl$), 8.17 (s, 1H, imidazo[4,5-b]pyridine 5-H);

LC (Method B)-MS (ESI, m/z): Rt=2.54 min—580, 582, 584 [(M+H)⁺, BrCl isotopic pattern]. ESI-HRMS: Found: 580.1587; calculated for $C_{28}H_{31}BrClN_7$(M+H)⁺: 580.1586.

Example 87

2-{4-[6-Chloro-2-(2,3-dihydro-benzo[1,4]dioxin-6-yl)-3H-imidazo[4,5-b]pyridin-7-yl]-piperazin-1-yl}-N-thiazol-2-yl-acetamide

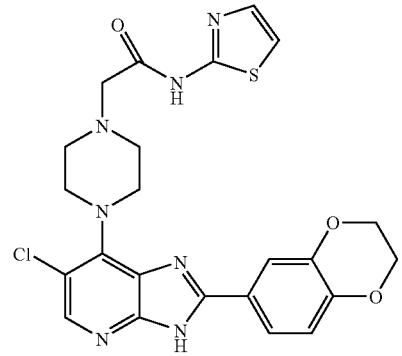

To a mixture of 2-[4-(2-amino-5-chloro-3-nitro-pyridin-4-yl)-piperazin-1-yl]-N-thiazol-2-yl-acetamide (0.024 g, 0.06 mmol) and EtOH (3.0 ml) was added 2,3-dihydro-benzo[1,4]dioxine-6-carbaldehyde (0.017 g, 0.10 mmol) followed by a freshly prepared aqueous solution of $Na_2S_2O_4$ (1M; 0.35 ml, 0.35 mmol). The reaction mixture was stirred at 80° C. for 22 h, then allowed to cool to room temperature and concentrated in vacuo. The resulting residue was absorbed on silica, and the free-running powder was placed on a 10 g isolute silica column. Elution with 2% methanol in ethyl acetate/dichloromethane (v:v; 1:1) afforded a pale yellow solid. The title compound was obtained as a white solid after trituration with diethyl ether (0.007 g, 23%); ¹H-NMR (500 MHz, DMSO-d₆) 2.77 (br s, 4H, piperazine $N(CH_2)_2$), 3.40 (s, 2H, $NCH_2CON$), 3.73 (br s, 4H, piperazine $N(CH_2)_2$), 4.31 (s, 4H, $OCH_2CH_2O$), 7.01 (d, J=8.2 Hz, 2H, PhH), 7.24 (d, J=3.5 Hz, 1H, thiazole H), 7.48 (d, J=3.5 Hz, 1H, thiazole H), 7.69 (m, 3H, PhH), 8.08 (s, 1H, imidazo[4,5-b]pyridine 5-H), 11.87 (s, 1H, CONH), 13.30 (br s, 1H, imidazo[4,5-b]pyridine N—H);

LC (Method B)-MS (ESI, m/z): Rt=4.04 min—512, 514 [(M+H)+, Cl isotopic pattern]. ESI-HRMS: Found: 512.1271, calculated for $C_{23}H_{23}ClN_7O_3S$ (M+H)+: 512.1272.

Example 88

1-(4-{6-Bromo-7-[4-(1-phenyl-ethyl)-piperazin-1-yl]-3H-imidazo[4,5-b]pyridin-2-yl}-phenyl)-piperidin-4-ol

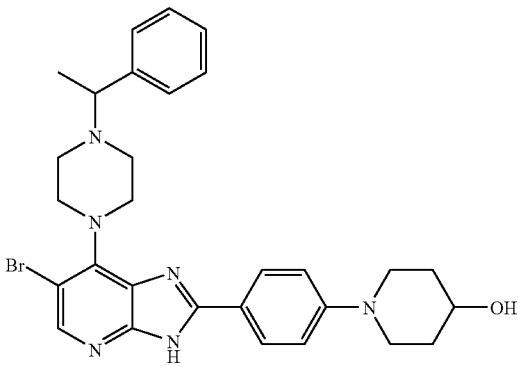

To a mixture of 5-bromo-3-nitro-4-[4-(1-phenyl-ethyl)-piperazin-1-yl]-pyridin-2-ylamine (0.036 g, 0.09 mmol) and EtOH (4.5 ml) was added 4-(4-hydroxy-piperidin-1-yl)-benzaldehyde (0.025 g, 0.12 mmol) followed by a freshly prepared aqueous solution of $Na_2S_2O_4$ (1M; 0.38 ml, 0.38 mmol). The reaction mixture was stirred at 80° C. for 22 h, then allowed to cool to room temperature, and concentrated in vacuo. The residue was absorbed on silica gel, the free-running powder was placed on a 10 g isolute silica column and elution with a gradient of methanol (0 to 5%) in ethyl acetate/dichloromethane (v:v; 1:1) afforded a yellow solid. The title compound was obtained as a white solid after trituration with diethyl ether (0.016 g, 32%); $^1$H-NMR (500 MHz, DMSO-d$_6$) 1.35 (d, J=6.7 Hz, 3H, CHCH$_3$), 1.45 (m, 2H) and 1.82 (m, 2H) (piperidine CH$_2$), 2.54 (m, 2H), 2.62 (br s, 2H), 2.98 (t, 2H) and 3.70 (m, 3H) (piperazine N—(CH$_2$)$_2$, piperidine CH$_2$ and piperidine CHOH), 3.50 (q, J=6.7 Hz, 1H, CHCH$_3$), 3.67 (br s, 4H, piperazine N(CH$_2$)$_2$), 4.67 (d, J=4.1 Hz, CHOH, exchangeable with D$_2$O), 7.03 (d, J=8.9 Hz, 2H) and 8.00 (d, J=8.8 Hz, 2H) (3,5-C$_6$H$_4$—N and 2,6-C$_6$H$_4$—N), 8.14 (s, 1H, imidazo[4,5-b]pyridine 5-H), 13.16 (br s, 1H, imidazo[4,5-b]pyridine N—H); LC (Method B)-MS (ESI, m/z): Rt=3.39 min—561, 563 [(M+H)+, Br isotopic pattern]. ESI-HRMS: Found: 561.1975, calculated for $C_{29}H_{34}BrN_6O$ (M+H)+: 561.1977.

Example 89 tert-Butyl 4-(2-oxo-2-(thiazol-2-ylamino)ethyl)piperazine-1-carboxylate

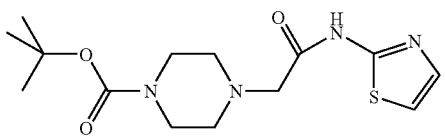

To a round-bottomed flask containing 2-(1-tert-butoxycarbonyl-piperazin-4-yl)-acetic acid×2HCl (0.150 g, 0.54 mmol) was added 2-aminothiazole (0.059 g, 0.59 mmol) and anhydrous dichloromethane (7 ml). The reaction mixture was cooled into an ice-bath under argon, and then diisopropylethylamine (0.29 ml, 1.66 mmol) was added followed by PyBOP (0.280 g, 0.54 mmol). The ice-bath was removed, and the reaction mixture was allowed to stir for 20 h under argon. The solvent was removed in vacuo, the residue was absorbed on silica gel and the free running powder was placed on a 20 g isolute silica column which was eluted with 30 to 50% ethyl acetate in dichloromethane. The title compound was obtained as a colourless oil that solidified on standing at room temperature (0.123 g, 70%); $^1$H-NMR (500 MHz, DMSO-d$_6$) 1.40 (s, 9H, C(CH$_3$)$_3$), 2.47 (br t obscured by solvent peak, piperazine NCH$_2$), 3.31 (s, 2H, NCH$_2$CO), 3.34 (br t, 4H, piperazine N(CH$_2$)$_2$), 7.22 (d, J=3.5 Hz, 1H, thiazole H), 7.47 (d, J=3.5 Hz, 1H, thiazole H), 11.84 (s, 1H, CONH);

LC (Method B)-MS (ESI, m/z) Rt=3.00 min—327 [(M+H)+, 100%].

Tert-butyl 4-(2-(methyl(thiazol-2-yl)amino)-2-oxoethyl)piperazine-1-carboxylate

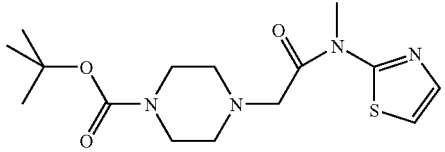

To a solution of tert-butyl 4-(2-oxo-2-(thiazol-2-ylamino)ethyl)piperazine-1-carboxylate (0.056 g, 0.17 mmol) in anhydrous DMF (1.0 mL) cooled into an ice-bath under argon was added sodium hydride (60% dispersion; 7.8 mg, 0.19 mmol). Stirring was continued at 0° C. for ~2 min and then methyl iodide (0.048 g, 0.34 mmol) was added with the aid of DMF (0.4 mL), the reaction mixture was stirred for 1.5 h under argon, and then partitioned between ethyl acetate (30 mL) and brine (30 mL). The aqueous layer was extracted with ethyl acetate (30 mL), and the combined organics were washed with brine (2×30 mL), dried (Na$_2$SO$_4$), and concentrated in vacuo. Purification by chromatography (10 g isolute column, 80% ethyl acetate in petroleum ether 60-80° C.) afforded the title compound as an oil (0.036 g, 62%); $^1$H-NMR (500 MHz, DMSO-d$_6$) 1.40 (s, 9H, C(CH$_3$)$_3$), 3.33 (s, 4H, piperazine N(CH$_2$)$_2$), 3.58 (s, 2H, NCH$_2$CO), 3.68 (s, 3H, CH$_3$), 7.27 (d, J=3.5 Hz, 1H, thiazole H), 7.53 (d, J=3.5 Hz, 1H, thiazole H);

LC (Method B)-MS (ESI, m/z) Rt=2.63 min—341 [(M+H)+, 100%].

2-(4-(2-Amino-5-bromo-3-nitropyridin-4-yl)piperazin-1-yl)-N-methyl-N-(thiazol-2-yl)acetamide

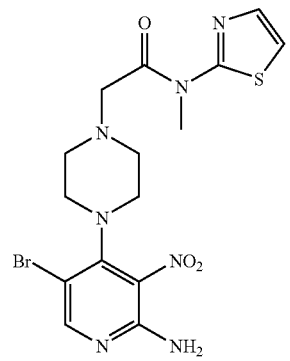

To a solution of tert-butyl 4-(2-(methyl(thiazol-2-yl)amino)-2-oxoethyl)piperazine-1-carboxylate (0.20 mmol) in dichloromethane (2 ml) was added trifluoroacetic acid (2.0 ml). The reaction mixture was stirred at room temperature for 1.5 h, then the solvents were removed under reduced pressure to afford N-methyl-2-(piperazin-1-yl)-N-(thiazol-2-yl)acetamide as the TFA salt that was dried in vacuo. To a mixture of this material (supposedly 0.20 mmol) and isopropanol (3.8 ml) was added 2-amino-5-bromo-4-chloro-3-nitropyridine (0.050 g, 0.20 mmol) followed by diisopropylethylamine (0.126 g, 0.97 mmol). The reaction mixture was stirred at 45° C. for 20 h, then allowed to cool to room temperature and the solvents were removed in vacuo. The residue was absorbed on silica gel and the free running powder was placed on a 10 g isolute silica column which was eluted with 20% to 40% ethyl acetate in dichloromethane. The title compound was obtained as a yellow solid (0.042 g, 46%); $^1$H-NMR (500 MHz, DMSO-d$_6$) 2.69 (br s, 4H, piperazine N(CH$_2$)$_2$), 3.08 (br s, 4H, piperazine N(CH$_2$)$_2$), 3.63 (s, 2H, NCH$_2$CO), 3.70 (s, 3H, N—CH$_3$), 6.98 (s, 2H, NH$_2$), 7.27 (d, J=3.6 Hz, 1H, thiazole H), 7.53 (d, J=3.6 Hz, 1H, thiazole H), 8.17 (s, 1H, 6-H);

LC (Method B)-MS (ESI, m/z) Rt=2.75 min—456, 458 [(M+H)$^+$, Br isotopic pattern].

2-(4-(6-Bromo-2-(4-(dimethylamino)phenyl)-3H-imidazo[4,5-b]pyridin-7-yl)piperazin-1-yl)-N-methyl-N-(thiazol-2-yl)acetamide

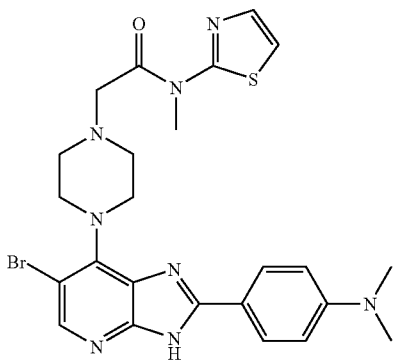

To a mixture of 2-(4-(2-amino-5-bromo-3-nitropyridin-4-yl)piperazin-1-yl)-N-methyl-N-(thiazol-2-yl)acetamide (0.035 g, 0.08 mmol), ethanol (3.5 ml), and 4-dimethylaminobenzaldehyde (0.016 g, 0.11 mmol) was added a freshly prepared aqueous solution of Na$_2$S$_2$O$_4$ (1M; 0.32 ml, 0.32 mmol). The reaction mixture was heated at 70° C. for 3 h, then allowed to cool to room temperature and the solvents were removed in vacuo. The residue was absorbed on silica gel and the free running powder was placed on a 10 g isolute silica column which was eluted with 30% to 60% ethyl acetate in dichloromethane. The title compound was obtained as a pale yellow solid after trituration with diethyl ether (0.006 g, 14%); $^1$H-NMR (500 MHz, DMSO-d$_6$) 2.76 (br s, 4H, piperazine N(CH$_2$)$_2$), 2.99 (s, 6H, N(CH$_3$)$_2$), 3.66 (br s, 6H, piperazine N(CH$_2$)$_2$ and NCH$_2$CO), 3.75 (s, 3H, N—CH$_3$), 6.81 (d, J=9.2 Hz, 2H) and 8.01 (d, J=9.7 Hz, 2H) (3,5-C$_6$H$_4$NMe$_2$ and 2,6-C$_6$H$_4$—NMe$_2$), 7.31 (d, J=3.5 Hz, 1H, thiazole 5-H), 7.55 (d, J=3.9 Hz, 1H, thiazole-H), 8.15 (s, 1H, imidazo[4,5-b]pyridine 5-H), 13.19 (s, 1H, imidazo[4,5-b]pyridine N—H);

LC (Method B)-MS (ESI, m/z) Rt=3.77 min—555, 557 [(M+H)$^+$, Br isotopic pattern]. ESI-HRMS: Found: 555.1294, calculated for C$_{24}$H$_{28}$BrN$_8$OS (M+H)$^+$: 555.1290.

Example 90 tert-Butyl 4-(2-oxo-2-(thiazol-2-ylamino)ethyl)piperidine-1-carboxylate

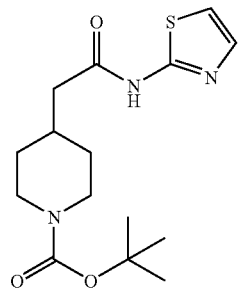

To a mixture of 2-(1-tert-butoxycarbonyl)piperidin-4-yl)acetic acid (0.200 g, 0.8 mmol), 2-aminothiazole (0.099 g, 0.98 mmol), and anhydrous chloroform (10 ml) was added diisopropylethylamine (0.28 ml, 1.64 mmol) followed by HBTU (0.371 g, 0.98 mmol). The reaction mixture was stirred at room temperature overnight, then concentrated in vacuo. The residue was absorbed on silica gel, and placed on a 20 g isolute column. Elution of the column with ethyl acetate/dichloromethane (v/v; 1:1) afforded the title compound as a white solid; LC (Method B)-MS (ESI, m/z) Rt=7.11 min—348 [(M+Na)$^+$, 70%].

2-(1-(2-Amino-5-bromo-3-nitropyridin-4-yl)piperidin-4-yl)-N-(thiazol-2-yl)acetamide

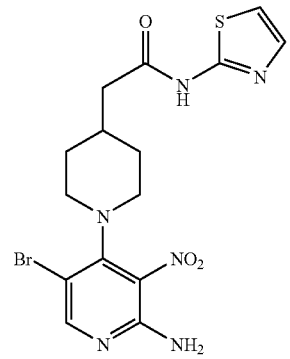

To a solution of tert-butyl 4-(2-oxo-2-(thiazol-2-ylamino)ethyl)piperidine-1-carboxylate (0.82 mmol) in dichloromethane (10 ml) was slowly added trifluoroacetic acid (2 ml). The reaction mixture was stirred at room temperature for 1 h, and then concentrated in vacuo. The crude product was placed on a 5 g SCX column which was eluted with 0.1M ammonia in methanol to afford the desired product as a white solid. Part of this material (0.098 g, 0.43 mmol) was added to a mixture of 5-bromo-4-chloro-3-nitro-pyridin-2-ylamine (0.100 g, 0.39 mmol), isopropanol (10 ml), and diisopropylethylamine (0.10 ml, 0.59 mmol). The reaction mixture was stirred at 50° C. overnight, then allowed to cool to room temperature, concentrated in vacuo, and the residue was placed on a 10 g isolute silica column. Elution of the column with dichloromethane, 30% ethyl acetate in dichloromethane, and finally 3% methanol in chloroform afforded the title compound as a dark orange solid (0.164 g, 94%); $^1$H NMR (500 MHz, DMSO-$d_6$) 1.42 (m, 2H) and 1.69 (d, J=10.5 Hz, 2H) (piperidine C(CH$_2$)$_2$), 1.99 (m, 1H, piperidine CH), 2.43 (d, J=7.1 Hz, 2H), 2.81 (t, J=11.0 Hz, 2H) and 3.23 (br d, 2H), (piperidine N(CH$_2$) and CH$_2$CON), 6.95 (s, 2H, NH$_2$), 7.18 (d, J=3.6 Hz, 1H) and 7.45 (d, J=3.5 Hz, 1H) (thiazole 4-H and 5-H), 8.14 (s, 1H, 6-H), 12.08 (s, 1H, CONH); LC (Method B)-MS (ESI, m/z) Rt=7.17 min—441, 443 [(M+H$^+$), Br isotopic pattern, 100%];

2-{1-[6-Bromo-2-(4-dimethylamino-phenyl)-3H-imidazo[4,5-b]pyridin-7-yl]-piperidin-4-yl}-N-thiazol-2-yl-acetamide

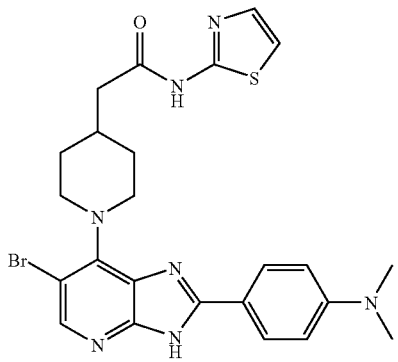

To a mixture of 2-(1-(2-amino-5-bromo-3-nitropyridin-4-yl)piperidin-4-yl)-N-(thiazol-2-yl)acetamide (0.110 g, 0.25 mmol) and ethanol (6 ml) was added 4-dimethylaminobenzaldehyde (0.049 g, 0.32 mmol) followed by a freshly prepared 1M aqueous solution of Na$_2$S$_2$O$_4$ (1.0 ml, 1.0 mmol). The reaction mixture was stirred at 80° C. for 18 h, then allowed to cool to room temperature and concentrated in vacuo. The residue was absorbed on silica gel, and the free-running powder was placed on a 10 g silica isolute column which was eluted with ethyl acetate/dichloromethane (v/v; 1:1), 3% methanol in ethyl acetate/dichloromethane (v/v; 1:1), 3% methanol in ethyl acetate, and 3% MeOH in chloroform. The title compound was obtained as a solid after trituration with diethyl ether/methanol (0.027 g, 20%);

$^1$H-NMR (500 MHz, DMSO-$d_6$) 1.46 (m, 2H) and 1.80 (br d, 2H), (piperidine CCH$_2$), 2.08 (m, 1H, piperidine CH), 2.99 (s, 6H, N(CH$_3$)$_2$), 2.47 (d, 2H, J=7.1 Hz), 3.38 (m, obscured by water signal), and 3.81 (d, J=11.5 Hz, 2H), (piperidine N(CH$_2$)$_2$, and CH$_2$CON), 6.80 (d, 2H, J=8.9 Hz, 3,5-ArH), 7.20 (d, 1H, J=3.6 Hz) and 7.47 (d, 1H, J=3.6 Hz) (thiazole 4-H and 5-H), 8.00 (d, 2H, J=8.9 Hz, 2,6-ArH), 8.13 (s, 1H, imidazo[4,5-b]pyridine 5-H), 12.14 (s, 1H, CONH), 13.13 (s, 1H, imidazo[4,5-b]pyridine NH);

LC (Method B)-MS (ESI, m/z) Rt=8.25 min—540/542 [(M+H$^+$), Br isotopic pattern, 100%];

ESI-HRMS Found: 540.1182, calculated for $C_{24}H_{27}BrN_7OS$ (M+H)$^+$: 540.1181.

Example 91 tert-Butyl 3-(6-bromo-7-(4-(pyridin-3-ylmethyl)piperazin-1-yl)-3H-imidazo[4,5-b]pyridin-2-yl)benzylcarbamate

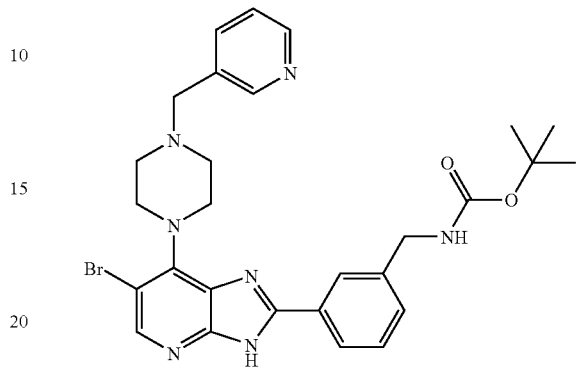

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (200 mg, 0.51 mmol), DMF (0.45 mL), ethanol (2.55 mL), 1M Na$_2$S$_2$O$_4$ (3 eq, 1.53 mmol, 1.53 mL) and tert-butyl N-(3-formylbenzyl)carbamate (1.1 eq, 0.21 mmol, 132 mg). After 18 h, concentration in vacuo and column chromatography (CH$_2$Cl$_2$-MeOH, 95:5) gave the product (89 mg, 30%) as a colourless solid; $\delta_H$ (500 MHz, DMSO-$d_6$) 1.38 (s, 9H, C(CH$_3$)$_3$), 2.62 (s, br, 4H, piperazine N(CH$_2$)$_2$), 3.61 (s, 2H, NCH$_2$Ar), 3.66 (s, br, 4H, piperazine N(CH$_2$)$_2$), 4.22 (d, J=6.0 Hz, 2H, CH$_2$NH—BOC), 7.36 (d, J=7.7 Hz, 1H, phenyl H-4 or H-6), 7.39 (dd, J=7.7, 2.7 Hz, 1H, pyridine H-5), 7.45 (t, br, J=5.7 Hz, 1H, NH—BOC), 7.48 (t, J=7.7 Hz, 1H, phenyl H-5), 7.78 (d, J=7.6 Hz, 1H, pyridine H-4), 8.01 (d, J=7.7 Hz, 1H, phenyl H-4 or H-6), 8.10 (s, br, 1H, phenyl H-2), 8.25 (s, 1H, imidazo[4,5-b]pyridine H-5), 8.50 (d, br, J=3.5 Hz, 1H, pyridine H-6), 8.57 (s, br, 1H, pyridine H-2), 13.52 (s, br, 1H, imidazo[4,5-b]pyridine NH);

LC (Method A)-MS (ESI, m/z): Rt=5.45 min—578, 580 [(M+H)$^+$, Br isotopic pattern]. ESI-HRMS: Found: 578.1884, calculated for $C_{28}H_{32}BrN_7O_2$ (M+H)$^+$: 578.1879.

Example 92

(3-(6-Bromo-7-(4-(pyridin-3-ylmethyl)piperazin-1-yl)-3H-imidazo[4,5-b]pyridin-2-yl)phenyl)methanamine

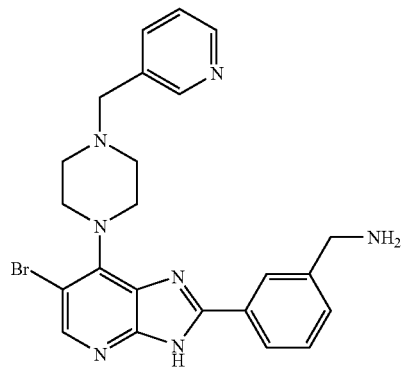

This was prepared using the same procedure as for (4-(6-bromo-7-(4-(pyridin-3-ylmethyl)piperazin-1-yl)-3H-imidazo[4,5-b]pyridin-2-yl)phenyl)methanamine, but here using tert-butyl 3-(6-bromo-7-(4-(pyridin-3-ylmethyl)piperazin-1-yl)-3H-imidazo[4,5-b]pyridin-2-yl)benzylcarbamate (70 mg, 0.12 mmol), TFA (0.6 mL) and CH$_2$Cl$_2$ (2 mL). The same purification procedure gave the desired product (49 mg, 84%) as a colourless solid; δ$_H$ (500 MHz, DMSO-d$_6$) 2.63 (s, br, 4H, piperazine N(CH$_2$)$_2$), 3.63 (s, 2H, NCH$_2$Ar), 3.68 (t, J=4.3 Hz, 4H, piperazine N(CH$_2$)$_2$), 3.84 (s, 2H, CH$_2$NH$_2$), 7.40 (dd, J=7.7, 4.8 Hz, 1H, pyridine H-5), 7.48-7.50 (m, 2H, phenyl H-4 & H-6), 7.80 (dt, J=7.7, 1.7 Hz, 1H, pyridine H-4), 8.02-8.05 (m, 1H, phenyl H-5), 8.18 (s, br, 1H, phenyl H-2), 8.25 (s, 1H, imidazo[4,5-b]pyridine H-5), 8.50 (dd, J=4.8, 1.5 Hz, 1H, pyridine H-6), 8.58 (d, J=1.6 Hz, 1H, pyridine H-2);

LC (Method A)-MS (ESI, m/z): Rt=2.44 min—478, 480 [(M+H)$^+$, Br isotopic pattern]. ESI-HRMS: Found: 478.1354, calculated for C$_{23}$H$_{24}$BrN$_7$ (M+H)$^+$: 478.1355.

Example 93

1-(3-(6-Bromo-7-(4-(pyridin-3-ylmethyl)piperazin-1-yl)-3H-imidazo[4,5-b]pyridin-2-yl)phenyl)-N,N-dimethylmethanamine

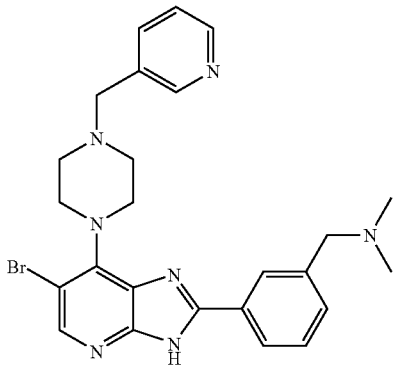

This was prepared using the same procedure as for 1-(4-(6-bromo-7-(4-(pyridin-3-ylmethyl)piperazin-1-yl)-3H-imidazo[4,5-b]pyridin-2-yl)phenyl)-N,N-dimethylmethanamine, but here using (3-(6-bromo-7-(4-(pyridin-3-ylmethyl)piperazin-1-yl)-3H-imidazo[4,5-b]pyridin-2-yl)phenyl)methanamine (30 mg, 0.063 mmol), THF (1 mL), MeOH (1 mL), formaldehyde (3.0 eq, 0.19 mmol, 15.0 μL) and NaBH$_3$CN (3.0 eq, 0.19 mmol, 12 mg). The same purification procedure gave the product (15 mg, 49%) as a colourless solid; δ$_H$ (500 MHz, DMSO-d$_6$) 2.17 (s, 6H, N(CH$_3$)$_2$), 2.64 (s, br, 4H, piperazine N(CH$_2$)$_2$), 3.63 (s, 2H, NCH$_2$Ar), 3.68 (s, br, 6H, CH$_2$NMe$_2$ & piperazine N(CH$_2$)$_2$), 7.39 (dd, J=7.7, 4.8 Hz, 1H, pyridine H-5), 7.43-7.52 (2 m, 2H, phenyl H-4 & H-6), 7.79 (dt, J=7.7, 1.6 Hz, 1H, pyridine H-4), 8.07-8.10 (m, 1H, phenyl H-5), 8.15 (s, br, 1H, phenyl H-2), 8.25 (s, 1H, imidazo[4,5-b]pyridine H-5), 8.50 (dd, J=4.7, 1.3 Hz, 1H, pyridine H-6), 8.57 (s, br, 1H, pyridine H-2), 13.53 (s, br, 1H, imidazo[4,5-b]pyridine NH);

LC (Method A)-MS (ESI, m/z): Rt=2.60 min—506, 508 [(M+H)$^+$, Br isotopic pattern]. ESI-HRMS: Found: 506.1671, calculated for C$_{25}$H$_{28}$BrN$_7$ (M+H)$^+$: 506.1668.

Example 94

6-Bromo-2-(6-methoxypyridin-3-yl)-7-(4-(pyridin-3-ylmethyl)piperazin-1-yl)-3H-imidazo[4,5-b]pyridine

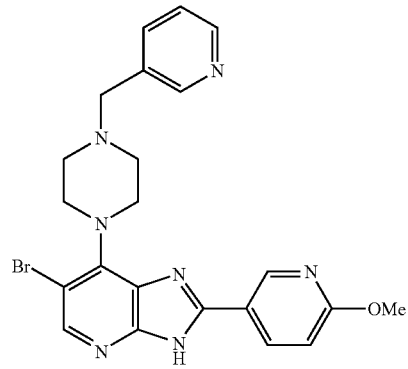

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (75 mg, 0.19 mmol), DMF (0.15 mL), ethanol (0.85 mL), 1M Na$_2$S$_2$O$_4$ (3 eq, 0.57 mmol, 0.57 mL) and 6-methoxy-3-pyridinecarboxaldehyde (1.1 eq, 0.21 mmol, 29 mg). After 6 h, concentration in vacuo and purification by preparative tlc (CH$_2$Cl$_2$-MeOH, 9:1) gave the product (31 mg, 34%) as a colourless solid; δ$_H$ (500 MHz, DMSO-d$_6$) 2.63 (br s, 4H, piperazine N(CH$_2$)$_2$), 3.62 (s, 2H, NCH$_2$Ar), 3.68 (br s, 4H, piperazine N(CH$_2$)$_2$), 3.95 (s, 3H, OCH$_3$), 7.00 (d, J=8.7 Hz, 1H, methoxypyridine H-5), 7.40 (dd, J=7.8, 4.8 Hz, 1H, pyridine H-5), 7.79 (d, br, J=7.8 Hz, 1H, pyridine H-4), 8.24 (s, 1H, imidazo[4,5-b]pyridine H-5), 8.43 (dd, J=8.7, 2.3 Hz, 1H, methoxypyridine H-4), 8.50 (d, br, J=3.5 Hz, 1H, pyridine H-6), 8.57 (s, 1H, pyridine H-2), 8.96 (d, J=2.3 Hz, 1H, methoxypyridine H-2), 13.53 (s, br, 1H, imidazo[4,5-b]pyridine NH);

LC (Method A)-MS (ESI, m/z): Rt=4.35 min—480, 482 [(M+H)$^+$, Br isotopic pattern]. ESI-HRMS: Found: 480.1140, calculated for C$_{22}$H$_{22}$BrN$_7$O (M+H)$^+$: 480.1147.

Example 95

6-Bromo-2-(3-((4-methylpiperazin-1-yl)methyl)phenyl)-7-(4-(1-(pyridin-4-yl)ethyl)piperazin-1-yl)-3H-imidazo[4,5-b]pyridine

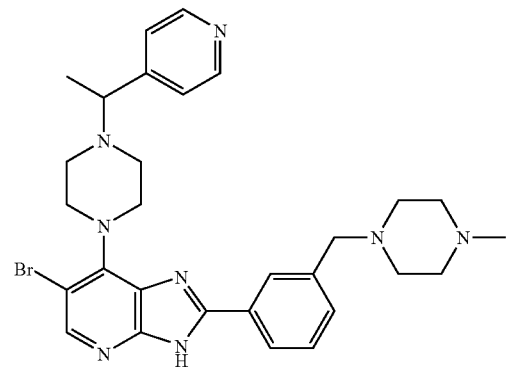

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(1-(pyridin-4-yl)ethyl)piperazin-1-yl)pyridin-2-amine (50 mg, 0.12 mmol), DMF (0.15 mL), ethanol (0.85 mL), 1M Na$_2$S$_2$O$_4$ (3 eq, 0.37 mmol, 0.37 mL) and 3-[(4-methylpiperazin-1-yl)methyl]benzaldehyde (1.1 eq, 0.14 mmol, 29 mg). After 6 h, concentration in vacuo and purification by preparative tlc (CH$_2$Cl$_2$-MeOH, 9:1) gave the product (19 mg, 27%) as a colourless solid; δ$_H$ (500 MHz, DMSO-d$_6$) 1.37 (d, J=6.7 Hz, 3H, CHCH$_3$), 2.17 (s, br, 4H, piperazine N(CH$_2$)$_2$), 2.37-2.48 (m, br, 4H, piperazine N(CH$_2$)$_2$), 2.55-2.58 (m, br, 4H, piperazine N(CH$_2$)$_2$), 2.64-2.67 (m, br, 4H, piperazine N(CH$_2$)$_2$), 3.56 (s, 2H, NCH$_2$Ar), 3.60 (q, J=6.5 Hz, 1H, CHCH$_3$), 3.68 (s, br, 4H, piperazine N(CH$_2$)$_2$), 7.41 (d, J=5.9 Hz, 2H, pyridine H-3 & H-5), 7.43 (d, J=7.7 Hz, 1H, phenyl H-6), 7.50 (t, J=7.7 Hz, 1H, phenyl H-5), 8.06 (d, J=7.7 Hz, 1H, phenyl H-4), 8.14 (s, br, 1H, phenyl H-2), 8.24 (s, 1H, imidazo[4,5-b]pyridine H-5), 8.56 (d, J=5.9 Hz, 1H, pyridine H-2 & H-6), 13.52 (s, br, 1H, imidazo[4,5-b]pyridine NH);

LC (Method A)-MS (ESI, m/z): Rt=3.07 min—575, 577 [(M+H)$^+$, Br isotopic pattern]. ESI-HRMS: Found: 575.2274, calculated for C$_{29}$H$_{35}$BrN$_8$ (M+H)$^+$: 575.2246.

Example 96

6-Bromo-2-(4-((4-methylpiperazin-1-yl)methyl)phenyl)-7-(4-(pyridin-3-ylmethyl)piperazin-1-yl)-3H-imidazo[4,5-b]pyridine

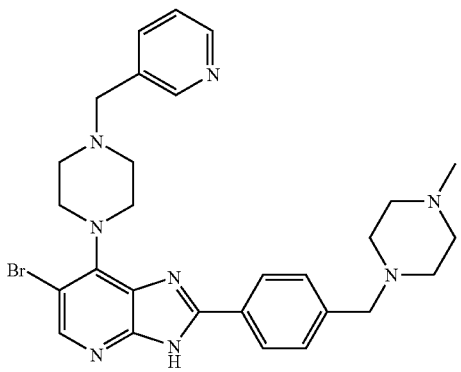

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (50 mg, 0.13 mmol), DMF (0.15 mL), ethanol (0.85 mL), 1M Na$_2$S$_2$O$_4$ (3 eq, 0.38 mmol, 0.38 mL) and 4-[(4-methylpiperazin-1-yl)methyl]benzaldehyde (1.1 eq, 0.14 mmol, 31 mg). After 6 h, concentration in vacuo and purification by preparative tlc (CH$_2$Cl$_2$-MeOH, 9:1) gave the product (15 mg, 21%) as a pale yellow solid; δ$_H$ (500 MHz, DMSO-d$_6$) 2.16 (s, 3H, CH$_3$), 2.34-2.38 (m, 8H, 2× piperazine N(CH$_2$)$_2$), 2.62 (t, J=4.7 Hz, 4H, piperazine N(CH$_2$)$_2$), 3.52 (s, 2H, NCH$_2$), 3.62 (s, 2H, NCH$_2$), 3.70 (t, J=4.6 Hz, 4H, piperazine N(CH$_2$)$_2$), 7.39 (dd, J=7.6, 4.6 Hz, 1H, pyridine H-5), 7.45 (d, J=8.4 Hz, 2H, phenyl H-3 & H-5), 7.79 (dt, J=7.7, 1.8 Hz, 1H, pyridine H-4), 8.13 (d, J=8.3 Hz, 2H, phenyl H-2 & H-6), 8.23 (s, 1H, imidazo[4,5-b]pyridine H-5), 8.49 (dd, J=4.8, 1.7 Hz, 1H, pyridine H-6), 8.56 (d, J=1.6 Hz, 1H, pyridine H-2), 13.47 (s, br, 1H, imidazo[4,5-b]pyridine NH);

LC (Method B)-MS (ESI, m/z): Rt=1.91 min—561, 563 [(M+H)$^+$, Br isotopic pattern]. ESI-HRMS: Found: 561.2086, calculated for C$_{28}$H$_{33}$BrN$_8$ (M+H)$^+$: 561.2090.

Example 97 tert-Butyl 2-(6-bromo-7-(4-(pyridin-3-ylmethyl)piperazin-1-yl)-3H-imidazo[4,5-b]pyridin-2-yl)ethylcarbamate

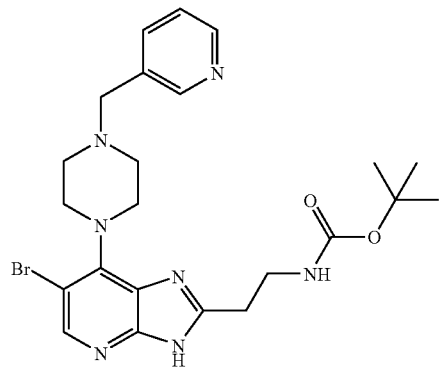

This was prepared using the same procedure as for 4-(6-bromo-2-(4-(dimethylamino)phenyl-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (64 mg, 0.16 mmol), DMF (0.15 mL), ethanol (0.85 mL), 1M Na$_2$S$_2$O$_4$ (3 eq, 0.49 mmol, 0.49 mL) and tert-butyl 3-oxopropylcarbamate (prepared according to the procedure described in *Tetrahedron* 2003, 59, 1719) (1.1 eq, 0.18 mmol, 31 mg). After 6 h, concentration in vacuo and purification by preparative tlc (CH$_2$Cl$_2$-MeOH, 9:1) gave the product (31 mg, 37%) as a colourless solid; δ$_H$ (500 MHz, DMSO-d$_6$) 1.35 (s, 9H, C(CH$_3$)$_3$), 2.58 (s, br, 4H, piperazine N(CH$_2$)$_2$), 2.89 (t, J=5.5 Hz, 2H, CH$_2$CH$_2$NH), 3.30 (hidden by DMSO peak, 2H, CH$_2$CH$_2$NH), 3.57 (t, J=4.4 Hz, 4H, piperazine N(CH$_2$)$_2$), 3.59 (s, 2H, NCH$_2$Ar), 6.92 (s, br, 1H, NH), 7.38 (dd, J=7.7, 4.8 Hz, 1H, pyridine H-5), 7.76 (dt, J=7.7, 1.5 Hz, 1H, pyridine H-4), 8.16 (s, 1H, imidazo[4,5-b]pyridine H-5), 8.48 (dd, J=4.8, 1.5 Hz, 1H, pyridine H-6), 8.54 (d, J=1.5 Hz, 1H, pyridine H-2), 12.79 (s, br, 1H, imidazo[4,5-b]pyridine NH);

LC (Method B)-MS (ESI, m/z): Rt=4.10 min—516, 518 [(M+H)$^+$, Br isotopic pattern]. ESI-HRMS: Found: 516.1735, calculated for C$_{23}$H$_{30}$BrN$_7$O$_2$ (M+H)$^+$: 516.1723.

Example 98

2-(6-Bromo-7-(4-(pyridin-3-ylmethyl)piperazin-1-yl)-3H-imidazo[4,5-b]pyridin-2-yl)ethanamine

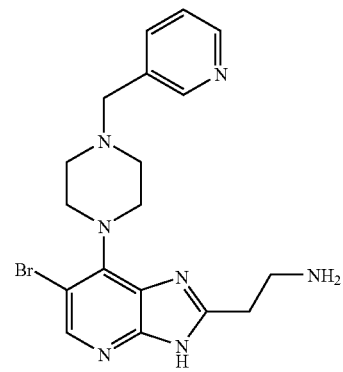

This was prepared using the same procedure as for (4-(6-bromo-7-(4-(pyridin-3-ylmethyl)piperazin-1-yl)-3H-imidazo[4,5-b]pyridin-2-yl)phenyl)methanamine, but here using tert-butyl 2-(6-bromo-7-(4-(pyridin-3-ylmethyl)piperazin-1-yl)-3H-imidazo[4,5-b]pyridin-2-yl)ethylcarbamate (20 mg, 0.058 mmol), TFA (0.2 mL) and CH$_2$Cl$_2$ (1 mL). The same purification procedure gave the desired product (15 mg, 93%) as a colourless solid; δ$_H$ (500 MHz, DMSO-d$_6$) 2.58 (s, br, 4H, piperazine N(CH$_2$)$_2$), 2.87 (t, J=6.7 Hz, 2H, CH$_2$CH$_2$NH$_2$), 3.00 (t, J=6.8 Hz, 2H, CH$_2$CH$_2$NH$_2$), 3.55 (t, J=4.5 Hz, 4H, piperazine N(CH$_2$)$_2$), 3.61 (s, 2H, NCH$_2$Ar), 7.39 (dd, J=7.8, 4.8 Hz, 1H, pyridine H-5), 7.77 (d, br, J=7.8 Hz, 1H, pyridine H-4), 8.18 (s, 1H, imidazo[4,5-b]pyridine H-5), 4.49 (dd, J=4.7, 1.0 Hz, 1H, pyridine H-6), 8.55 (d, J=1.1 Hz, 1H, pyridine H-2);

LC (Method B)-MS (ESI, m/z): Rt=0.73 min—416, 418 [(M+H)$^+$, Br isotopic pattern]. ESI-HRMS: Found: 416.1201, calculated for C$_{18}$H$_{22}$BrN$_7$ (M+H)$^+$: 416.1205.

Example 99 tert-Butyl (6-bromo-7-(4-(pyridin-3-ylmethyl)piperazin-1-yl)-3H-imidazo[4,5-b]pyridin-2-yl)methylcarbamate

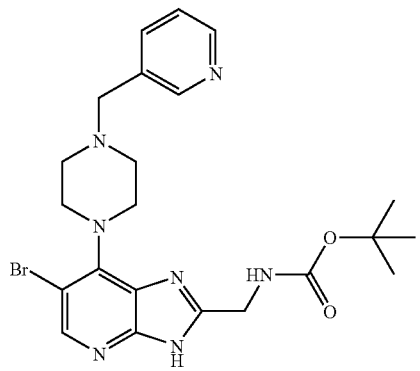

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (40 mg, 0.10 mmol), DMF (0.15 mL), ethanol (0.85 mL), 1M Na$_2$S$_2$O$_4$ (3 eq, 0.31 mmol, 0.31 mL) and tert-butyl 3-oxoethylcarbamate (prepared according to the procedure described in *Tetrahedron* 2003, 59, 1719) (1.1 eq, 0.11 mmol, 18 mg). After 6 h, concentration in vacuo and purification by preparative tlc (CH$_2$Cl$_2$-MeOH, 9:1) gave the product (10 mg, 19%) as a colourless solid; δ$_H$ (500 MHz, DMSO-d$_6$) 1.39 (s, 9H, C(CH$_3$)$_3$), 2.57 (s, br, 4H, piperazine N(CH$_2$)$_2$), 3.56 (t, J=4.7 Hz, 4H, piperazine N(CH$_2$)$_2$), 3.60 (s, 2H, NCH$_2$Ar), 4.30 (d, J=5.6 Hz, 2H, CH$_2$NH), 7.28 (s, br, 1H, NH), 7.37 (dd, J=7.5, 4.7 Hz, 1H, pyridine H-5), 7.75 (dt, J=7.8, 1.8 Hz, 1H, pyridine H-4), 8.19 (s, 1H, imidazo[4,5-b]pyridine H-5), 8.48 (dd, J=4.8, 1.7 Hz, 1H, pyridine H-6), 8.53 (d, J=1.7 Hz, 1H, pyridine H-2), 12.86 (s, br, 1H, imidazo[4,5-b]pyridine NH);

LC (Method B)-MS (ESI, m/z): Rt=4.01 min—502, 504 [(M+H)$^+$, Br isotopic pattern]. ESI-HRMS: Found: 502.1577, calculated for C$_{22}$H$_{28}$BrN$_7$O$_2$ (M+H)$^+$: 502.1566.

Example 100

(6-Bromo-7-(4-(pyridin-3-ylmethyl)piperazin-1-yl)-3H-imidazo[4,5-b]pyridin-2-yl)methanamine

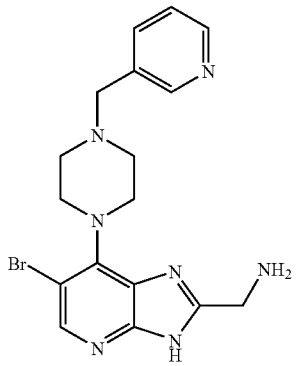

This was prepared using the same procedure as for (4-(6-bromo-7-(4-(pyridin-3-ylmethyl)piperazin-1-yl)-3H-imidazo[4,5-b]pyridin-2-yl)phenyl)methanamine, but here using tert-butyl (6-bromo-7-(4-(pyridin-3-ylmethyl)piperazin-1-yl)-3H-imidazo[4,5-b]pyridin-2-yl)methylcarbamate (10 mg, 0.020 mmol), TFA (0.2 mL) and CH$_2$Cl$_2$ (1 mL). The same purification procedure gave the desired product (7 mg, 88%) as a colourless solid; δ$_H$ (500 MHz, DMSO-d$_6$) 2.60 (s, br, 4H, piperazine N(CH$_2$)$_2$), 3.57 (s, br, 4H, piperazine N(CH$_2$)$_2$), 3.62 (s, 2H, NCH$_2$Ar), 4.04 (s, br, 2H, CH$_2$NH$_2$), 7.38 (dd, J=7.7, 4.7 Hz, 1H, pyridine H-5), 7.77 (dt, J=7.8, 1.7 Hz, 1H, pyridine H-4), 8.24 (s, 1H, imidazo[4,5-b]pyridine H-5), 8.50 (dd, J=4.7, 1.5 Hz, 1H, pyridine H-6), 8.56 (d, J=1.6 Hz, 1H, pyridine H-2);

LC (Method B)-MS (ESI, m/z): Rt=0.70 min—402, 404 [(M+H)$^+$, Br isotopic pattern]. ESI-HRMS: Found: 402.1045, calculated for C$_{17}$H$_{20}$BrN$_7$ (M+H)$^+$: 402.1042.

Example 101

6-Bromo-2-(4-(4-methylpiperazin-1-yl)phenyl)-7-(4-(pyridin-3-ylmethyl)piperazin-1-yl)-3H-imidazo[4,5-b]pyridine

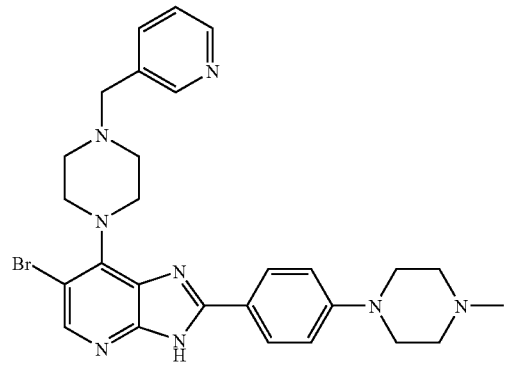

This was prepared using the same procedure as for 4-(6-bromo-2-(4-(dimethylamino)phenyl)-3H-imidazo[4,5-b]pyridin-7-yl)-N-phenyl piperazine-1-carboxamide, but here using 5-bromo-3-nitro-4-(4-(pyridin-3-ylmethyl)piperazin-1-yl)pyridin-2-amine (20 mg, 0.051 mmol), DMF (0.15 mL), ethanol (0.85 mL), 1M $Na_2S_2O_4$ (3 eq, 0.15 mmol, 0.15 mL) and 4-(4-methylpiperazino)benzaldehyde (1.1 eq, 0.056 mmol, 11 mg). After 6 h, concentration in vacuo and purification by preparative tlc ($CH_2Cl_2$-MeOH, 9:1) gave the product (11 mg, 39%) as a colourless solid; $\delta_H$ (500 MHz, DMSO-$d_6$) 2.26 (s, 3H, $CH_3$), 2.49 (s, br, 4H, piperazine $N(CH_2)_2$), 2.63 (s, br, 4H, piperazine $N(CH_2)_2$), 3.30 (hidden by DMSO peak, 4H, piperazine $N(CH_2)_2$), 3.62 (s, 2H, $NCH_2$), 3.65 (t, J=4.2 Hz, 4H, piperazine $N(CH_2)_2$), 7.06 (d, J=8.7 Hz, 2H, phenyl H-3 & H-5), 7.40 (dd, J=7.7, 4.8 Hz, 1H, pyridine H-5), 7.79 (d, br, J=7.7 Hz, 1H, pyridine H-4), 8.03 (d, J=8.7 Hz, 2H, phenyl H-2 & H-6), 8.18 (s, 1H, imidazo[4,5-b]pyridine H-5), 8.50 (d, J=4.5 Hz, 1H, pyridine H-6), 8.57 (s, br, 1H, pyridine H-2), 13.22 (s, br, 1H, imidazo[4,5-b]pyridine NH);

LC (Method B)-MS (ESI, m/z): Rt=1.98 min—547, 549 [(M+H)$^+$, Br isotopic pattern]. ESI-HRMS: Found: 547.1951, calculated for $C_{27}H_{31}BrN_8$ (M+H)$^+$: 547.1933.

Example 102

4-(4-(6-Bromo-7-(4-(pyridin-3-ylmethyl)piperazin-1-yl)-3H-imidazo[4,5-b]pyridin-2-yl)phenyl)morpholine

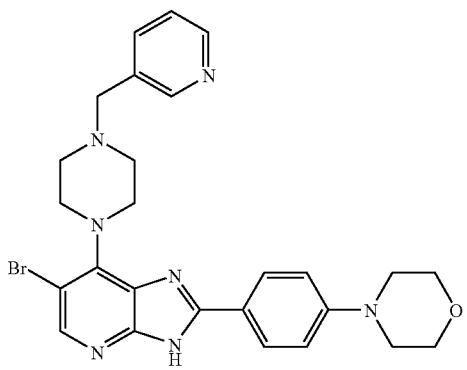

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (20 mg, 0.051 mmol), DMF (0.15 mL), ethanol (0.85 mL), 1M $Na_2S_2O_4$ (3 eq, 0.15 mmol, 0.15 mL) and 4-morpholin-4-yl-benzaldehyde (1.1 eq, 0.056 mmol, 11 mg). After 6 h, concentration in vacuo and purification by preparative tlc ($CH_2Cl_2$-MeOH, 95:5) gave the product (10 mg, 37%) as an off-white solid; $\delta_H$ (500 MHz, DMSO-$d_6$) 2.61 (s, br, 4H, piperazine $N(CH_2)_2$), 3.24 (t, J=4.9 Hz, 4H, morpholine $N(CH_2)_2$), 3.62 (s, 2H, $CH_2$), 3.64 (t, J=4.7 Hz, 4H, piperazine $N(CH_2)_2$), 3.76 (t, J=4.7 Hz, 4H, morpholine $O(CH_2)_2$), 7.06 (d, J=9.0 Hz, 2H, phenyl H-3 & H-5), 7.39 (dd, J=7.7, 4.8 Hz, 1H, pyridine H-5), 7.79 (dt, J=7.7, 1.7 Hz, 1H, pyridine H-4), 8.04 (d, J=9.0 Hz, 2H, phenyl H-2 & H-6), 8.17 (s, 1H, imidazo[4,5-b]pyridine H-5), 8.49 (dd, J=4.8, 1.6 Hz, 1H, pyridine H-6), 8.56 (d, J=1.5 Hz, 1H, pyridine H-2), 13.22 (s, br, 1H, imidazo[4,5-b]pyridine NH);

LC (Method B)-MS (ESI, m/z): Rt=3.12 min—534, 536 [(M+H)$^+$, Br isotopic pattern]. ESI-HRMS: Found: 534.1606, calculated for $C_{26}H_{28}BrN_7O$ (M+H)$^+$: 534.1617.

Example 103 tert-Butyl 4-(4-(6-bromo-7-(4-(pyridin-3-ylmethyl)piperazin-1-yl)-3H-imidazo[4,5-b]pyridin-2-yl)phenyl)piperazine-1-carboxylate

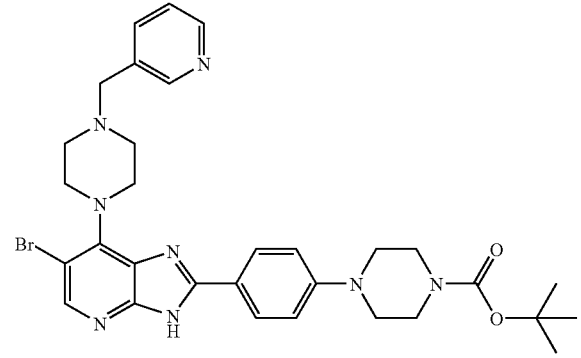

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (50 mg, 0.13 mmol), DMF (0.3 mL), ethanol (1.2 mL), 1M $Na_2S_2O_4$ (3 eq, 0.38 mmol, 0.38 mL) and 4-(4-formylphenyl)piperazine-1-carboxylic acid tert-butyl ester (1.1 eq, 0.14 mmol, 43 mg). After 6 h, concentration in vacuo and purification by preparative tlc ($CH_2Cl_2$-MeOH, 95:5) gave the product (25 mg, 31%) as an off-white solid; $\delta_H$ (500 MHz, DMSO-$d_6$) 1.43 (s, 9H, $C(CH_3)_3$), 2.61 (s, br, 4H, piperazine $N(CH_2)_2$), 3.26 (s, br, 4H, piperazine $N(CH_2)_2$), 3.48 (t, J=4.6 Hz, 4H, piperazine $N(CH_2)_2$), 3.61 (s, 2H, $CH_2$), 3.64 (t, J=4.6 Hz, 4H, piperazine $N(CH_2)_2$), 7.06 (d, J=9.0 Hz, 2H, phenyl H-3 & H-5), 7.39 (dd, J=7.6, 4.7 Hz, 1H, pyridine H-5), 7.78 (d, br, J=7.7 Hz, 1H, pyridine H-4), 8.03 (d, J=8.9 Hz, 2H, phenyl H-2 & H-6), 8.17 (s, 1H, imidazo[4,5-b]pyridine H-5), 8.50 (dd, J=4.6, 1.5 Hz, 1H, pyridine H-6), 8.56 (d, J=1.4 Hz, 1H, pyridine H-2), 13.22 (s, br, 1H, imidazo[4,5-b]pyridine NH);

LC (Method B)-MS (ESI, m/z): Rt=4.03 min—633, 635 [(M+H)$^+$, Br isotopic pattern]. ESI-HRMS: Found: 633.2293, calculated for $C_{31}H_{37}BrN_8O_2$ (M+H)$^+$: 633.2301.

Example 104

6-Bromo-2-(4-(piperazin-1-yl)phenyl)-7-(4-(pyridin-3-ylmethyl)piperazin-1-yl)-3H-imidazo[4,5-b]pyridine

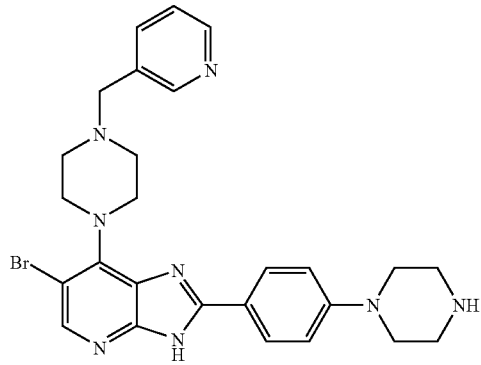

This was prepared using the same procedure as for (4-(6-bromo-7-(4-(pyridin-3-ylmethyl)piperazin-1-yl)-3H-imidazo[4,5-b]pyridin-2-yl)phenyl)methanamine, but here using tert-butyl 4-(4-(6-bromo-7-(4-(pyridin-3-ylmethyl)piperazin-1-yl)-3H-imidazo[4,5-b]pyridin-2-yl)phenyl)piperazine-1-carboxylate (16 mg, 0.025 mmol), TFA (0.25 mL) and $CH_2Cl_2$ (1 mL). The same purification procedure gave the desired product (10 mg, 75%) as a pale yellow solid; $\delta_H$ (500 MHz, DMSO-$d_6$) 2.50 (hidden by DMSO peak, 2H, piperazine $NCH_2$), 2.62 (s, br, 4H, piperazine $N(CH_2)_2$), 3.00 (s, br, 2H, piperazine $NCH_2$), 3.30 (hidden by DMSO peak, 4H, piperazine $N(CH_2)_2$), 3.61 (s, 2H, $NCH_2$), 3.64 (s, br, 4H, piperazine $N(CH_2)_2$), 7.06 (d, J=8.9 Hz, 2H, phenyl H-3 & H-5), 7.39 (dd, J=7.7, 4.8 Hz, 1H, pyridine H-5), 7.78 (d, br, J=7.7 Hz, 1H, pyridine H-4), 8.03 (d, J=8.9 Hz, 2H, phenyl H-2 & H-6), 8.17 (s, 1H, imidazo[4,5-b]pyridine H-5), 8.49 (dd, J=4.7, 1.4 Hz, 1H, pyridine H-6), 8.56 (s, br, 1H, pyridine H-2), 13.23 (s, br, 1H, imidazo[4,5-b]pyridine NH);

LC (Method B)-MS (ESI, m/z): Rt=2.72 min—533, 535 [(M+H)$^+$, Br isotopic pattern]. ESI-HRMS: Found: 533.1786, calculated for $C_{26}H_{29}BrN_8$ (M+H)$^+$: 533.1777.

Example 105 tert-Butyl 4-(4-(6-bromo-7-(4-(pyridin-3-ylmethyl)piperazin-1-yl)-3H-imidazo[4,5-b]pyridin-2-yl)benzyl)piperazine-1-carboxylate

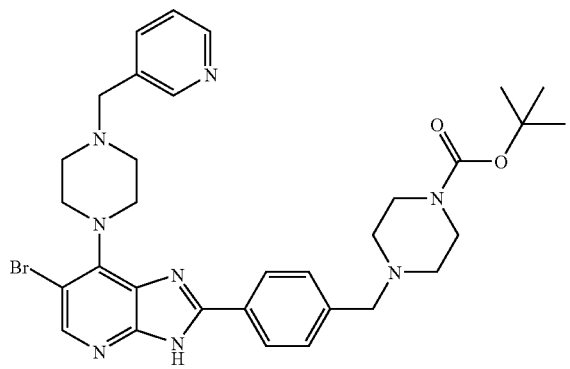

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (50 mg, 0.13 mmol), DMF (0.3 mL), ethanol (1.2 mL), 1M $Na_2S_2O_4$ (3 eq, 0.38 mmol, 0.38 mL) and tert-butyl 4-(4-formylbenzyl)piperazine-1-carboxylate (1.1 eq, 0.14 mmol, 45 mg). After 6 h, concentration in vacuo and purification by preparative tlc ($CH_2Cl_2$-MeOH, 95:5) gave the product (22 mg, 27%) as a pale yellow solid; $\delta_H$ (500 MHz, DMSO-$d_6$) 1.39 (s, 9H, $C(CH_3)_3$), 2.34 (t, J=5.0 Hz, 4H, piperazine $N(CH_2)_2$), 2.62 (s, br, 4H, piperazine $N(CH_2)_2$), 3.32 (s, br, 4H, piperazine $N(CH_2)_2$), 3.55 (s, 2H, $CH_2$), 3.62 (s, 2H, $CH_2$), 3.67 (t, J=4.8 Hz, 4H, piperazine $N(CH_2)_2$), 7.39 (dd, J=7.8, 4.8 Hz, 1H, pyridine H-5), 7.46 (d, J=8.1 Hz, 2H, phenyl H-3 & H-5), 7.78 (d, br, J=8.0 Hz, 1H, pyridine H-4), 8.14 (d, J=8.1 Hz, 2H, phenyl H-2 & H-6), 8.23 (s, 1H, imidazo[4,5-b]pyridine H-5), 8.50 (dd, J=4.8, 1.6 Hz, 1H, pyridine H-6), 8.56 (d, J=1.7 Hz, 1H, pyridine H-2), 13.46 (s, br, 1H, imidazo[4,5-b]pyridine NH);

LC (Method B)-MS (ESI, m/z): Rt=2.59 min—647, 649 [(M+H)$^+$, Br isotopic pattern]. ESI-HRMS: Found: 647.2461, calculated for $C_{32}H_{39}BrN_8O_2$ (M+H)$^+$: 647.2458.

Example 106

6-Bromo-2-(4-(piperazin-1-ylmethyl)phenyl)-7-(4-(pyridin-3-ylmethyl)piperazin-1-yl)-3H-imidazo[4,5-b]pyridine

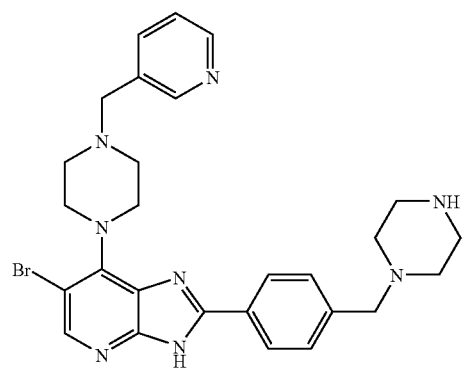

This was prepared using the same procedure as for (4-(6-bromo-7-(4-(pyridin-3-ylmethyl)piperazin-1-yl)-3H-imidazo[4,5-b]pyridin-2-yl)phenyl)methanamine, but here using tert-butyl 4-(4-(6-bromo-7-(4-(pyridin-3-ylmethyl)piperazin-1-yl)-3H-imidazo[4,5-b]pyridin-2-yl)benzyl)piperazine-1-carboxylate (10 mg, 0.015 mmol), TFA (0.25 mL) and $CH_2Cl_2$ (1 mL). The same purification procedure gave the desired product (6 mg, 71%) as a yellow solid; $\delta_H$ (500 MHz, DMSO-$d_6$ 2.46-2.49 (m, 1H, piperazine $NCH_2$), 2.62 (s, br, 4H, piperazine $N(CH_2)_2$), 2.93 (s, br, 2H, piperazine $NCH_2$), 3.30 (hidden by DMSO peak, 2H, piperazine $NCH_2$), 3.34-3.38 (m, 2H, piperazine $NCH_2$), 3.56 (s, 2H, $NCH_2$), 3.61 (s, 2H, $NCH_2$), 3.67 (s, br, 4H, piperazine $N(CH_2)_2$), 7.39 (dd, J=7.5, 4.5 Hz, 1H, pyridine H-5), 7.68 (d, J=7.8 Hz, 2H, phenyl H-3 & H-5), 7.78 (d, br, J=7.6 Hz, 1H, pyridine H-4), 8.13 (d, J=7.4 Hz, 2H, phenyl H-2 & H-6), 8.23 (s, 1H, imidazo[4,5-b]pyridine H-5), 8.49 (d, br, J=4.6 Hz, 1H, pyridine H-6), 8.56 (s, br, 1H, pyridine H-2);

LC (Method A)-MS (ESI, m/z): Rt=2.64 min—547, 549 [(M+H)$^+$, Br isotopic pattern]. ESI-HRMS: Found: 547.1919, calculated for $C_{27}H_{31}BrN_8$ (M+H)$^+$: 547.1933.

Example 107

2-(4-((1H-Pyrazol-1-yl)methyl)phenyl)-6-bromo-7-(4-(pyridin-3-ylmethyl)piperazin-1-yl)-3H-imidazo[4,5-b]pyridine

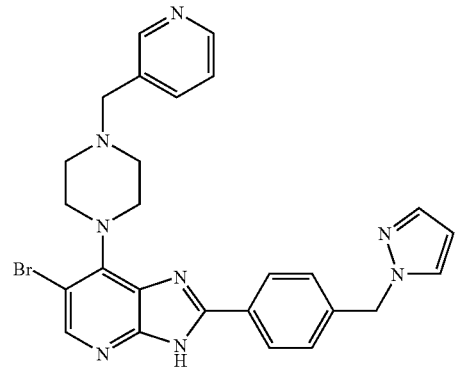

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (20 mg, 0.051 mmol), DMF (0.15 mL), ethanol (0.85 mL), 1M Na₂S₂O₄ (3 eq, 0.15 mmol, 0.15 mL) and 4-(1H-pyrazol-1-ylmethyl)benzaldehyde (1.1 eq, 0.056 mmol, 11 mg). After 6 h, concentration in vacuo and purification by preparative tlc (CH₂Cl₂-MeOH, 95:5) gave the product (11 mg, 41%) as a colourless solid; $\delta_H$ (500 MHz, DMSO-d₆) 2.62 (s, br, 4H, piperazine N(CH₂)₂), 3.61 (s, 2H, CH₂), 3.66 (s, br, 4H, piperazine N(CH₂)₂), 5.41 (s, 2H, PhCH₂), 6.30 (t, J=2.0 Hz, pyrazole H-4), 7.34 (d, J=8.2 Hz, 2H, phenyl H-3 & H-5), 7.39 (dd, J=7.8, 4.8 Hz, 1H, pyridine H-5), 7.49 (d, J=1.8 Hz, 1H, pyrazole H-3 or H-5), 7.78 (dt, J=7.8, 1.7 Hz, 1H, pyridine H-4), 7.86 (d, J=2.2 Hz, 1H, pyrazole H-3 or H-5), 8.14 (d, J=8.2 Hz, 2H, phenyl H-2 & H-6), 8.23 (s, 1H, imidazo[4,5-b]pyridine H-5), 8.49 (dd, J=4.7, 1.7 Hz, 1H, pyridine H-6), 8.56 (d, J=1.6 Hz, 1H, pyridine H-2), 13.49 (s, br, 1H, imidazo[4,5-b]pyridine NH); LC (Method B)-MS (ESI, m/z): Rt=3.03 min—529, 531 [(M+H)⁺, Br isotopic pattern]. ESI-HRMS: Found: 529.1450, calculated for C₂₆H₂₅BrN₈ (M+H)⁺: 529.1464.

Example 108

2-(4-(1H-pyrazol-1-yl)phenyl)-6-bromo-7-(4-(pyridin-3-ylmethyl)piperazin-1-yl)-3H-imidazo[4,5-b]pyridine

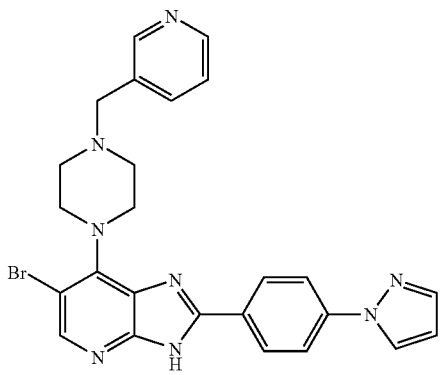

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (20 mg, 0.051 mmol), DMF (0.15 mL), ethanol (0.85 mL), 1M Na₂S₂O₄ (3 eq, 0.15 mmol, 0.15 mL) and 4-(1H-pyrazol-1-yl)benzaldehyde (1.1 eq, 0.056 mmol, 10 mg). After 6 h, concentration in vacuo and purification by preparative tlc (CH₂Cl₂-MeOH, 95:5) gave the product (10 mg, 38%) as a colourless solid; $\delta_H$ (500 MHz, DMSO-d₆) 2.63 (s, br, 4H, piperazine N(CH₂)₂), 3.63 (s, 2H, CH₂), 3.70 (s, br, 4H, piperazine N(CH₂)₂), 6.61 (t, br, J=2.0 Hz, 1H, pyrazole H-4), 7.41 (s, br, 1H, pyridine H-5), 7.80 (s, br, 1H, pyridine H-4), 7.81 (d, J=1.9 Hz, 1H, pyrazole H-3 or H-5), 8.03 (d, J=8.4 Hz, 2H, phenyl H-2 & H-6), 8.26 (s, br, 1H, imidazo[4,5-b]pyridine H-5), 8.30 (d, J=8.5 Hz, 2H, phenyl H-3 & H-5), 8.50 (s, br, 1H, pyridine H-6), 8.58 (s, br, 1H, pyridine H-2), 8.61 (d, J=2.4 Hz, 1H, pyrazole H-3 or H-5), 13.56 (s, br, 1H, imidazo[4,5-b]pyridine NH);

LC (Method B)-MS (ESI, m/z): Rt=3.23 min—515, 517 [(M+H)⁺, Br isotopic pattern]. ESI-HRMS: Found: 515.1316, calculated for C₂₅H₂₃BrN₈ (M+H)⁺: 515.1307.

Example 109

2-(4-(1H-Imidazol-1-yl)phenyl)-6-bromo-7-(4-(pyridin-3-ylmethyl)piperazin-1-yl)-3H-imidazo[4,5-b]pyridine

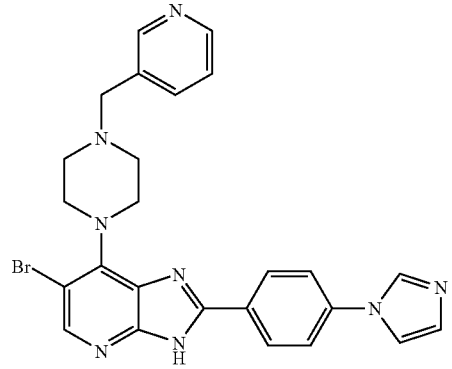

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (20 mg, 0.051 mmol), DMF (0.15 mL), ethanol (0.85 mL), 1M Na₂S₂O₄ (3 eq, 0.15 mmol, 0.15 mL) and 4-(1H-imidazol-1-yl)benzaldehyde (1.1 eq, 0.056 mmol, 10 mg). After 6 h, concentration in vacuo and purification by preparative tlc (CH₂Cl₂-MeOH, 9:1) gave the product (7 mg, 27%) as a colourless solid; $\delta_H$ (500 MHz, DMSO-d₆) 2.64 (s, br, 4H, piperazine N(CH₂)₂), 3.63 (s, br, 2H, CH₂), 3.70 (t, J=4.4 Hz, 4H, piperazine N(CH₂)₂), 7.16 (s, 1H, imidazole H-2), 7.39 (dd, J=7.8, 4.8 Hz, 1H, pyridine H-5), 7.79 (td, J=7.8, 1.5 Hz, 1H, pyridine H-4), 7.85 (s, br, 1H, imidazole H-4 or H-5), 7.86 (d, J=8.7 Hz, 2H, phenyl H-2 & H-6), 8.26 (s, 1H, imidazo[4,5-b]pyridine H-5), 8.30 (d, J=8.7 Hz, 2H, phenyl H-3 & H-5), 8.39 (s, br, 1H, imidazole H-4 or H-5), 8.50 (dd, J=4.7, 1.5 Hz, 1H, pyridine H-6), 8.57 (d, J=1.5 Hz, 1H, pyridine H-2), 13.59 (s, br, 1H, imidazo[4,5-b]pyridine NH);

LC (Method B)-MS (ESI, m/z): Rt=2.17 min—515, 517 [(M+H)⁺, Br isotopic pattern]. ESI-HRMS: Found: 515.1297, calculated for C₂₅H₂₃BrN₈ (M+H)⁺: 515.1307.

Example 110

2-(4-((1H-Imidazol-1-yl)methyl)phenyl)-6-bromo-7-(4-(pyridin-3-ylmethyl)piperazin-1-yl)-3H-imidazo[4,5-b]pyridine

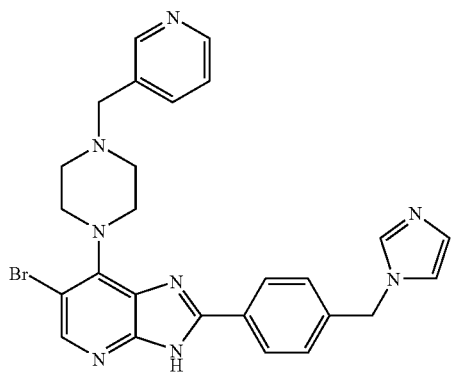

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (20 mg, 0.051 mmol), DMF (0.15 mL), ethanol (0.85 mL), 1M $Na_2S_2O_4$ (3 eq, 0.15 mmol, 0.15 mL) and 4-(1H-imidazol-1-ylmethyl)benzaldehyde (1.1 eq, 0.056 mmol, 11 mg). After 6 h, concentration in vacuo and purification by preparative tlc ($CH_2Cl_2$-MeOH, 9:1) gave the product (6 mg, 22%) as a colourless solid; $\delta_H$ (500 MHz, DMSO-$d_6$) 2.62 (s, br, 4H, piperazine $N(CH_2)_2$), 3.61 (s, 2H, $CH_2$), 5.28 (s, 2H, $PhCH_2$), 6.93 (s, br, 1H, imidazole H-2), 7.21 (s, br, 1H, imidazole H-4 or H-5), 7.39 (dd, J=7.8, 4.8 Hz, 1H, pyridine H-5), 7.40 (d, J=8.1 Hz, 2H, phenyl H-2 & H-6), 7.78 (td, J=7.7, 1.5 Hz, 1H, pyridine H-4), 7.79 (s, br, 1H, imidazole H-4 or H-5), 8.15 (d, J=8.2 Hz, 2H, phenyl H-3 & H-5), 8.24 (s, 1H, imidazo[4,5-b]pyridine H-5), 8.49 (dd, J=4.7, 1.4 Hz, 1H, pyridine H-6), 8.56 (d, J=1.5 Hz, 1H, pyridine H-2), 13.51 (s, br, 1H, imidazo[4,5-b]pyridine NH);

LC (Method B)-MS (ESI, m/z): Rt=2.03 min—529, 531 [(M+H)$^+$, Br isotopic pattern]. ESI-HRMS: Found: 529.1462, calculated for $C_{26}H_{25}BrN_8$ (M+H)$^+$: 529.1464.

Example 111

2-(4-(6-Bromo-7-(4-(pyridin-3-ylmethyl)piperazin-1-yl)-3H-imidazo[4,5-b]pyridin-2-yl)phenoxy)-N,N-dimethylethanamine

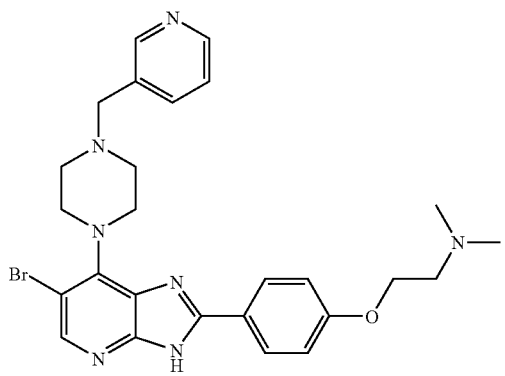

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (30 mg, 0.076 mmol), DMF (0.15 mL), ethanol (0.85 mL), 1M $Na_2S_2O_4$ (3 eq, 0.23 mmol, 0.23 mL) and 4-(2-(dimethylamino)ethoxy)benzaldehyde (1.2 eq, 0.091 mmol, 18 mg). After 6 h, concentration in vacuo and purification by preparative tlc ($CH_2Cl_2$-MeOH, 85:15) gave the product (10 mg, 23%) as a colourless solid; $\delta_H$ (500 MHz, DMSO-$d_6$) 2.23 (s, 6H, $N(CH_3)_2$), 2.62 (s, br, 4H, piperazine $N(CH_2)_2$), 2.65 (t, J=5.8 Hz, 2H, $Me_2NCH_2$), 3.61 (s, 2H, $NCH_2$), 3.65 (t, J=4.4 Hz, 4H, piperazine $N(CH_2)_2$), 4.13 (t, J=5.8 Hz, 2H, $OCH_2$), 7.09 (d, J=8.8 Hz, 2H, phenyl H-3 & H-5), 7.39 (dd, J=7.7, 4.8 Hz, 1H, pyridine H-5), 7.78 (dt, J=7.8, 1.7 Hz, 1H, pyridine H-4), 8.11 (d, J=8.8 Hz, 2H, phenyl H-2 & H-6), 8.20 (s, 1H, imidazo[4,5-b]pyridine H-5), 8.49 (dd, J=4.8, 1.4 Hz, 1H, pyridine H-6), 8.56 (d, J=1.4 Hz, 1H, pyridine H-2), 13.34 (s, br, 1H, imidazo[4,5-b]pyridine NH);

LC (Method B)-MS (ESI, m/z): Rt=1.89 min—536, 538 [(M+H)$^+$, Br isotopic pattern]. ESI-HRMS: Found: 536.1769, calculated for $C_{26}H_{30}BrN_7O$ (M+H)$^+$: 536.1773.

Example 112

4-(2-(4-(6-Bromo-7-(4-(pyridin-3-ylmethyl)piperazin-1-yl)-3H-imidazo[4,5-b]pyridin-2-yl)phenoxy)ethyl)morpholine

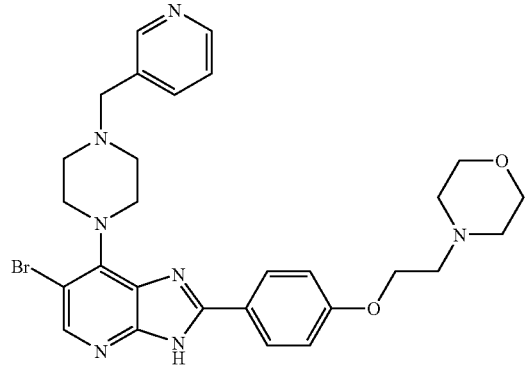

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (30 mg, 0.076 mmol), DMF (0.15 mL), ethanol (0.85 mL), 1M $Na_2S_2O_4$ (3 eq, 0.23 mmol, 0.23 mL) and 4-(2-morpholinoethoxy)benzaldehyde (1.2 eq, 0.091 mmol, 22 mg). After 6 h, concentration in vacuo and purification by preparative tlc ($CH_2Cl_2$-MeOH, 85:15) gave the product (8 mg, 19%) as a colourless solid; $\delta_H$ (500 MHz, DMSO-$d_6$) 2.62 (t, J=4.0 Hz, 4H, piperazine $N(CH_2)_2$), 2.72 (t, J=5.7 Hz, 2H, $PhOCH_2CH_2$), 3.30 (hidden by DMSO water peak, 4H, morpholine $N(CH_2)_2$), 3.59 (t, J=4.6 Hz, 4H, morpholine $O(CH_2)_2$), 3.61 (s, 2H, $NCH_2$), 3.65 (s, br, 4H, piperazine $N(CH_2)_2$), 4.17 (q, J=5.8 Hz, $PhOCH_2CH_2$), 7.10 (d, J=8.9 Hz, 2H, phenyl H-3 & H-5), 7.39 (ddd, J=7.6, 4.8, 0.4 Hz, 1H, pyridine H-5), 7.78 (dt, J=7.8, 1.8 Hz, pyridine H-4), 8.11 (d, J=8.8 Hz, 2H, phenyl H-2 & H-6), 8.20 (s, 1H, imidazo[4,5-b]pyridine H-5), 8.49 (dd, J=4.8, 1.7 Hz, 1H, pyridine H-6), 8.56 (d, J=1.7 Hz, 1H, pyridine H-2), 13.39 (s, br, 1H, imidazo[4,5-b]pyridine NH);

LC (Method B)-MS (ESI, m/z): Rt=1.92 min—578, 580 [(M+H)$^+$, Br isotopic pattern]. ESI-HRMS: Found: 578.1876, calculated for $C_{28}H_{32}BrN_7O_2$ (M+H)$^+$: 578.1879.

Example 113

6-Bromo-2-(4-(piperidin-4-yloxy)phenyl)-7-(4-(pyridin-3-ylmethyl)piperazin-1-yl)-3H-imidazo[4,5-b]pyridine

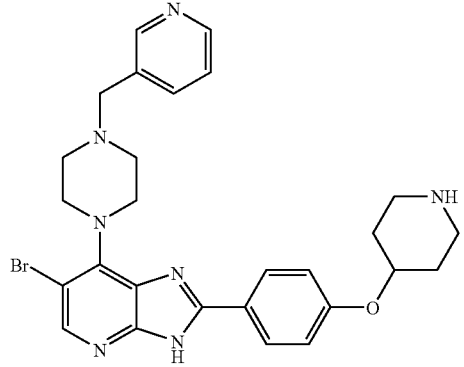

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (30 mg, 0.076 mmol), DMF (0.15 mL), ethanol (0.85 mL), 1M $Na_2S_2O_4$ (3 eq, 0.23 mmol, 0.23 mL) and 4-(piperidin-4-yloxy)benzaldehyde (1.2 eq, 0.091 mmol, 22 mg). After 6 h, concentration in vacuo and purification by preparative tlc ($CH_2Cl_2$-MeOH, 85:15) gave the product (10 mg, 24%) as a colourless solid; $\delta_H$ (500 MHz, DMSO-$d_6$) 1.77-1.81 (m, 2H, 2× piperidine $CH_AH_B$), 2.09-2.11 (m, 2H, 2× piperidine $CH_AH_B$), 2.62 (s, br, 4H, piperazine $N(CH_2)_2$), 3.00-3.07 (m, 2H, 2× piperidine $CH_AH_B$), 3.20-3.24 (m, 2H, 2× piperidine $CH_AH_B$), 3.62 (s, 2H, $NCH_2$), 3.66 (s, br, 4H, piperazine $N(CH_2)_2$), 4.70-4.76 (m, 1H, piperidine CH), 7.15 (d, J=8.9 Hz, 2H, phenyl H-3 & H-5), 7.39 (dd, J=7.6, 4.7 Hz, 1H, pyridine H-5), 7.78 (d, br, J=7.8 Hz, pyridine H-4), 8.13 (d, J=8.7 Hz, 2H, phenyl H-2 & H-6), 8.21 (s, 1H, imidazo[4,5-b]pyridine H-5), 8.49 (dd, J=4.7, 1.4 Hz, 1H, pyridine H-6), 8.56 (s, br, 1H, pyridine H-2), 13.42 (s, br, 1H, imidazo[4,5-b]pyridine NH);

LC (Method B)-MS (ESI, m/z): Rt=2.17 min—548, 550 [(M+H)$^+$, Br isotopic pattern]. ESI-HRMS: Found: 548.1774, calculated for $C_{27}H_{30}BrN_7O$ (M+H)$^+$: 548.1773.

Example 114

1-(4-(6-Bromo-7-(4-(pyridin-3-ylmethyl)piperazin-1-yl)-3H-imidazo[4,5-b]pyridin-2-yl)phenyl)piperidin-4-ol

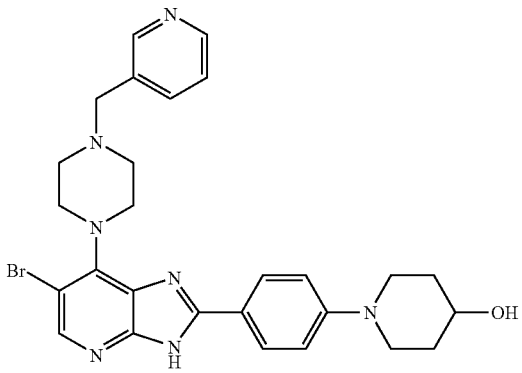

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (30 mg, 0.076 mmol), DMF (0.15 mL), ethanol (0.85 mL), 1M $Na_2S_2O_4$ (3 eq, 0.23 mmol, 0.23 mL) and 4-(4-hydroxypiperidin-1-yl)benzaldehyde (1.2 eq, 0.091 mmol, 19 mg). After 6 h, concentration in vacuo and purification by preparative tlc ($CH_2Cl_2$-MeOH, 85:15) gave the product (11 mg, 26%) as a colourless solid; $\delta_H$ (500 MHz, DMSO-$d_6$) 1.41-1.49 (m, 2H, 2× piperidine $CH_AH_B$), 1.81-1.84 (m, 2H, 2× piperidine $CH_AH_B$), 2.62 (s, br, 4H, piperazine $N(CH_2)_2$), 2.97-3.02 (m, 2H, 2× piperidine $CH_AH_B$), 3.62 (s, 2H, $NCH_2$), 3.64 (t, J=4.7 Hz, 4H, piperazine $N(CH_2)_2$), 3.66-3.70 (m, 2H, 2× piperidine $CH_AH_B$), 4.68 (d, J=4.2 Hz, 1H, CHOH), 7.04 (d, J=9.0 Hz, 2H, phenyl H-2 & H-6), 7.39 (dd, J=7.6, 4.7 Hz, 1H, pyridine H-5), 7.78 (d, br, J=7.8 Hz, 1H, pyridine H-4), 7.99 (d, J=9.0 Hz, 2H, phenyl H-3 & H-5), 8.16 (s, 1H, imidazo[4,5-b]pyridine H-5), 8.49 (d, br, J=4.5 Hz, 1H, pyridine H-6), 8.56 (s, br, 1H, pyridine H-2), 13.17 (s, br, 1H, imidazo[4,5-b]pyridine NH);

LC (Method B)-MS (ESI, m/z): Rt=2.87 min—548, 550 [(M+H)$^+$, Br isotopic pattern]. ESI-HRMS: Found: 548.1777, calculated for $C_{27}H_{30}BrN_7O$ (M+H)$^+$: 548.1773.

Example 115

4-(4-(6-Bromo-7-(4-(pyridin-3-ylmethyl)piperazin-1-yl)-3H-imidazo[4,5-b]pyridin-2-yl)phenyl)-1,1-dioxothiomorpholine

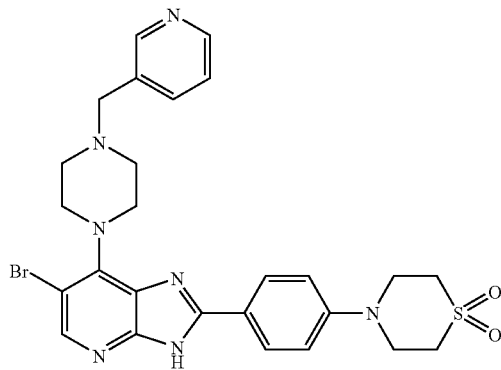

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyridin-3-ylmethyl)piperazin-1-yl)pyridin-2-amine (30 mg, 0.076 mmol), DMF (0.15 mL), ethanol (0.85 mL), 1M $Na_2S_2O_4$ (3 eq, 0.23 mmol, 0.23 mL) and 4-(1,1-dioxothiomorpholino)benzaldehyde (1.1 eq, 0.084 mmol, 20 mg). After 6 h, concentration in vacuo and purification by preparative tlc ($CH_2Cl_2$-MeOH, 95:5) gave the product (14 mg, 32%) as a colourless solid; $\delta_H$ (500 MHz, DMSO-$d_6$) 2.61 (s, br, 4H, piperazine $N(CH_2)_2$), 3.14 (t, J=4.7 Hz, 4H, 1,1-dioxothiomorpholine $N(CH_2)_2$), 3.61 (s, 2H, $NCH_2$), 3.65 (t, J=4.6 Hz, 4H, piperazine $N(CH_2)_2$), 3.91 (t, J=5.0 Hz, 4H, 1,1-dioxothiomorpholine $S(CH_2)_2$), 7.16 (d, J=9.0 Hz, 2H, phenyl H-2 & H-6), 7.39 (dd, J=7.5, 4.8 Hz, 1H, pyridine H-5), 7.78 (dt, J=7.8, 1.9 Hz, 1H, pyridine H-4), 8.06 (d, J=9.0 Hz, 2H, phenyl H-3 & H-5), 8.18 (s, 1H, imidazo[4,5-b]pyridine H-5), 8.49 (dd, J=4.7, 1.8 Hz, 1H, pyridine H-6), 8.56 (d, J=1.6 Hz, 1H, pyridine H-2), 13.26 (s, br, 1H, imidazo[4,5-b]pyridine NH);

LC (Method B)-MS (ESI, m/z): Rt=2.79 min—582, 584 [(M+H)$^+$, Br isotopic pattern].

Example 116 tert-Butyl 4-((6-methoxypyridin-3-yl)methyl)piperazine-1-carboxylate

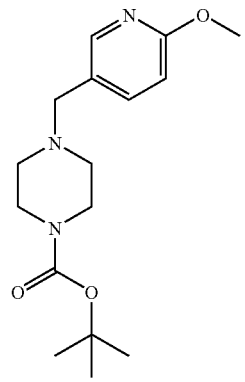

A solution of 6-methoxy-3-pyridine carboxaldehyde (100 mg, 0.73 mmol) in ethanol (2 mL) and acetic acid (0.2 mL) at room temperature was treated with tert-butyl-1-piperazine carboxylate (2.5 eq, 1.82 mmol, 339 mg) and stirred for 5 minutes. Sodium cyanoborohydride (0.95 eq, 0.69 mmol, 44 mg) was added portionwise and the reaction then stirred for 16 h. Concentration in vacuo and preparative tlc purification (EtOAc) gave the product (168 mg, 75%) as a colourless oil; $\delta_H$ (500 MHz, CDCl$_3$) 1.47 (s, 9H, C(CH$_3$)$_3$), 2.00 (s, br, 2H, piperazine NCH$_2$), 2.39 (t, J=4.7 Hz, 2H, piperazine NCH$_2$), 3.43 (t, J=4.9 Hz, 4H, piperazine N(CH$_2$)$_2$), 3.45 (s, 2H, CH$_2$), 3.94 (s, 3H, OCH$_3$), 6.73 (d, J=8.4 Hz, 1H, methoxypyridine H-5), 7.57 (dd, J=8.5, 2.4 Hz, 1H, methoxypyridine H-4), 8.05 (d, br, J=2.3 Hz, 1H, methoxypyridine H-2);

LC (Method B)-MS (ESI, m/z): Rt=2.08 min—308 [(M+H)$^+$]. ESI-HRMS: Found: 308.1964, calculated for C$_{16}$H$_{25}$N$_3$O$_3$ (M+H)$^+$: 208.1974.

5-Bromo-4-(4-((6-methoxypyridin-3-yl)methyl)piperazin-1-yl)-3-nitropyridin-2-amine

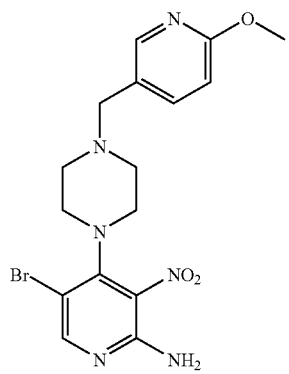

This was prepared using the same procedure as for 5-bromo-3-nitro-4-(4-(1-(pyridin-2-yl)ethyl)piperazin-1-yl)pyridin-2-amine, but here using tert-butyl 4-((6-methoxypyridin-3-yl)methyl)piperazine-1-carboxylate (1.1 eq, 0.54 mmol, 165 mg), TFA (1 mL) and CH$_2$Cl$_2$ (3 mL), then 5-bromo-4-chloro-3-nitropyridin-2-amine (123 mg, 0.49 mmol) in $^i$PrOH (3.5 mL) and DIPEA (1 mL). Filtration and washing as previously described gave the product (89 mg, 40% for two steps) as a yellow solid; $\delta_H$ (500 MHz, DMSO-d$_6$) 2.50 (hidden by DMSO peak, s, br, 4H, piperazine N(CH$_2$)$_2$), 3.05 (s, br, 4H, piperazine N(CH$_2$)$_2$), 3.48 (s, 2H, NCH$_2$), 3.84 (s, 3H, OCH$_3$), 6.80 (d, J=8.5 Hz, 1H, pyridine H-5), 6.98 (s, br, 2H, NH$_2$), 7.66 (dd, J=8.5, 2.3 Hz, 1H, pyridine H-4), 8.07 (d, J=1.1 Hz, 1H, pyridine H-2), 8.16 (s, 1H, bromopyridine H-6); LC (Method B)-MS (ESI, m/z): Rt=2.33 min—423, 425 [(M+H)$^+$, Br isotopic pattern]. ESI-HRMS: Found: 423.0777, calculated for C$_{16}$H$_{19}$BrN$_6$O$_3$ (M+H)$^+$: 423.0780.

6-Bromo-2-(4-methoxyphenyl)-7-(4-((6-methoxypyridin-3-yl)methyl)piperazin-1-yl)-3H-imidazo[4,5-b]pyridine

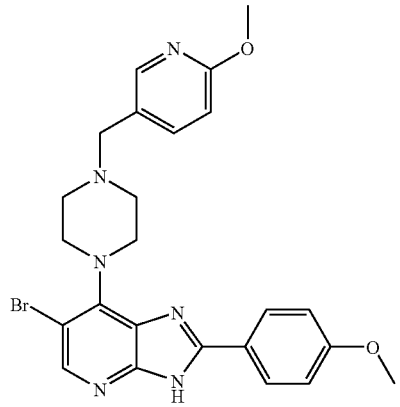

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-4-(4-((6-methoxypyridin-3-yl)methyl)piperazin-1-yl)-3-nitropyridin-2-amine (30 mg, 0.071 mmol), DMF (0.15 mL), ethanol (0.85 mL), 1M Na$_2$S$_2$O$_4$ (3 eq, 0.21 mmol, 0.21 mL) and 4-methoxybenzene carboxaldehyde (1.1 eq, 0.078 mmol, 10 mg). After 6 h, concentration in vacuo and purification by preparative tlc (CH$_2$Cl$_2$-MeOH, 95:5) gave the product (20 mg, 56%) as a colourless solid; $\delta_H$ (500 MHz, DMSO-d$_6$) 2.60 (s, br, 4H, piperazine N(CH$_2$)$_2$), 3.52 (s, 2H, NCH$_2$), 3.64 (t, J=4.5 Hz, 4H, piperazine N(CH$_2$)$_2$), 3.84 (s, 3H, OCH$_3$), 3.85 (s, 3H, OCH$_3$), 6.81 (d, J=8.5 Hz, 1H, methoxypyridine H-5), 7.09 (d, J=8.9 Hz, 2H, methoxyphenyl H-2 & H-6), 7.70 (dd, J=8.5, 2.6 Hz, 1H, methoxypyridine H-4), 8.11 (d, J=2.3 Hz, 1H, methoxypyridine H-2), 8.20 (s, 1H, imidazo[4,5-b]pyridine H-5), 13.34 (s, br, 1H, imidazo[4,5-b]pyridine NH);

LC (Method B)-MS (ESI, m/z): Rt=3.40 min—509, 511 [(M+H)$^+$, Br isotopic pattern]. ESI-HRMS: Found: 509.1298, calculated for C$_{24}$H$_{25}$BrN$_6$O$_2$ (M+H)$^+$: 509.1301.

Example 117

4-(4-(6-Bromo-7-(4-((6-methoxypyridin-3-yl)methyl)piperazin-1-yl)-3H-imidazo[4,5-b]pyridin-2-yl)benzyl)morpholine

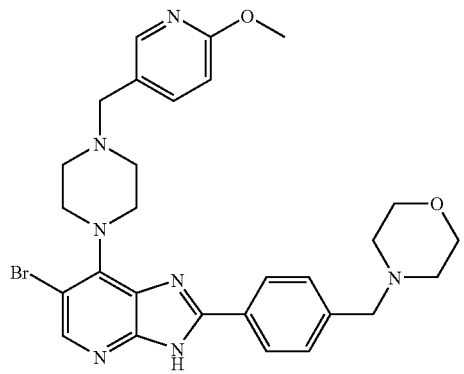

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-4-(4-((6-methoxypyridin-3-yl)methyl)piperazin-1-yl)-3-nitropyridin-2-amine (20 mg, 0.047 mmol), DMF (0.15 mL), ethanol (0.85 mL), 1M $Na_2S_2O_4$ (3 eq, 0.14 mmol, 0.14 mL) and 4-(morpholinomethyl)benzaldehyde (1.1 eq, 0.052 mmol, 11 mg). After 6 h, concentration in vacuo and purification by preparative tlc ($CH_2Cl_2$-MeOH, 95:5) gave the product (12 mg, 44%) as a colourless solid; $\delta_H$ (500 MHz, DMSO-$d_6$) 2.39 (s, br, 4H, morpholine $N(CH_2)_2$), 2.61 (s, br, 4H, piperazine $N(CH_2)_2$), 3.53 (s, 2H, $NCH_2$), 3.54 (s, 2H, $NCH_2$), 3.60 (t, J=4.4 Hz, 4H) and 3.67 (t, J=4.8 Hz, 4H) (piperazine $N(CH_2)_2$) and morpholine $O(CH_2)_2$), 3.86 (s, 3H, $OCH_3$), 6.83 (d, J=8.5 Hz, 2H, methoxypyridine H-5), 7.48 (d, J=8.1 Hz, 2H, phenyl H-3 & H-5), 7.71 (dd, J=8.5, 2.2 Hz, 1H, methoxypyridine H-4), 8.12 (d, J=2.0 Hz, 1H, methoxypyridine H-2), 8.14 (d, J=8.1 Hz, 2H, phenyl H-2 & H-6), 8.24 (s, 1H, imidazo[4,5-b]pyridine H-5), 13.49 (s, br 1H, imidazo[4,5-b]pyridine NH);

LC (Method B)-MS (ESI, m/z): Rt=2.17 min—578, 580 [(M+H)$^+$, Br isotopic pattern]. ESI-HRMS: Found: 578.1879, calculated for $C_{28}H_{32}BrN_7O_2$ (M+H)$^+$: 578.1879.

Example 118

4-(4-(6-Bromo-7-(4-(((6-methoxypyridin-3-yl)methyl)piperazin-1-yl)-3H-imidazo[4,5-b]pyridin-2-yl)phenyl)morpholine

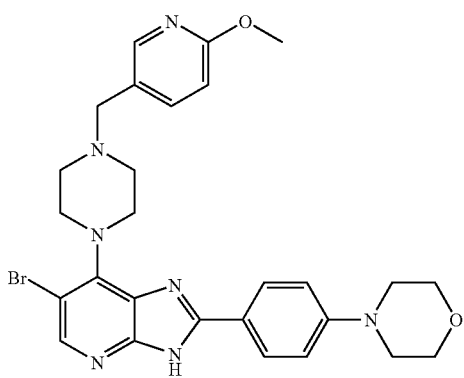

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-4-(4-((6-methoxypyridin-3-yl)methyl)piperazin-1-yl)-3-nitropyridin-2-amine (20 mg, 0.047 mmol), DMF (0.15 mL), ethanol (0.85 mL), 1M $Na_2S_2O_4$ (3 eq, 0.14 mmol, 0.14 mL) and 4-morpholin-4-yl-benzaldehyde (1.1 eq, 0.052 mmol, 10 mg). After 6 h, concentration in vacuo and purification by preparative tlc ($CH_2Cl_2$-MeOH, 95:5) gave the product (10 mg, 37%) as a colourless solid; $\delta_H$ (500 MHz, DMSO-$d_6$) 2.59 (s, br, 4H, piperazine $N(CH_2)_2$), 3.24 (t, J=4.8 Hz, 4H, morpholine $N(CH_2)_2$), 3.52 (s, 2H, $CH_2$), 3.63 (s, br, 4H, piperazine $N(CH_2)_2$), 3.76 (t, J=4.9 Hz, 4H, morpholine $O(CH_2)_2$), 3.85 (s, 3H, $OCH_3$), 6.81 (d, J=8.4 Hz, 1H, methoxypyridine H-5), 7.06 (d, J=9.0 Hz, 2H, phenyl H-3 & H-5), 7.70 (dd, J=8.6, 1.2 Hz, 1H, methoxypyridine H-4), 8.04 (d, J=8.9 Hz, 2H, phenyl H-2 & H-6), 8.11 (s, br, 1H, methoxypyridine H-2), 8.17 (s, 1H, imidazo[4,5-b]pyridine H-5), 13.22 (8.17 (s, br, 1H, imidazo[4,5-b]pyridine NH);

LC (Method B)-MS (ESI, m/z): Rt=3.38 min—564, 566 [(M+H)$^+$, Br isotopic pattern]. ESI-HRMS: Found: 564.1733, calculated for $C_{27}H_{30}BrN_7O_2$ (M+H)$^+$: 564.1723.

Example 119 tert-Butyl 4-(benzo[d][1,3]dioxol-4-ylmethyl)piperazine-1-carboxylate

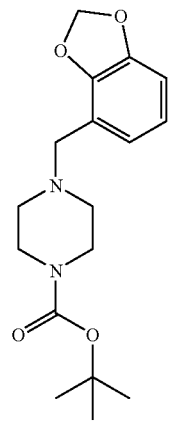

A solution of 1,3-benzodioxole-4-carbaldehyde (96 mg, 0.64 mmol) in ethanol (2 mL) and acetic acid (0.2 mL) at room temperature was treated with tert-butyl-1-piperazine carboxylate (2.5 eq, 1.60 mmol, 297 mg) and stirred for 5 minutes. Sodium cyanoborohydride (0.95 eq, 0.60 mmol, 38 mg) was added portionwise and the reaction then stirred for 16 h. Concentration in vacuo and preparative tlc purification ($CH_2Cl_2$-MeOH, 95:5) gave the product (131 mg, 62%) as a colourless oil; $\delta_H$ (500 MHz, $CDCl_3$) 1.47 and 1.48 (2 s, 9H, $C(CH_3)_3$), 1.99 (s, br, 1H, piperazine $NCH_AH_A$), 2.44 (t, J=4.7 Hz, 2H, piperazine $NCH_2$), 2.54-2.63 (m, 1H, piperazine $NCH_AH_A$), 3.45 (t, J=4.9 Hz, 4H, piperazine $N(CH_2)_2$), 3.55 (s, 1H, $NCH_AH_A$), 4.70 (s, 1H, $NCH_AH_A$), 5.97 (s, 1H, $OCH_AH_B$), 5.99 (s, 1H, $OCH_AH_B$), 6.75-6.96 (m, 3H, phenyl H-4, H-5, H-6);

LC (Method B)-MS (ESI, m/z): Rt=2.47 min—321 [(M+H)$^+$]. ESI-HRMS: Found: 321.1814, calculated for $C_{17}H_{24}N_2O_4$ (M+H)$^+$: 321.1814.

4-(4-(Benzo[d][1,3]dioxol-4-ylmethyl)piperazin-1-yl)-5-bromo-3-nitropyridin-2-amine

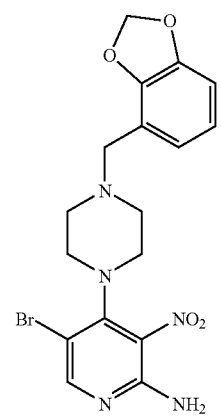

This was prepared using the same procedure as for 5-bromo-3-nitro-4-(4-(1-(pyridin-2-yl)ethyl)piperazin-1-yl)pyridin-2-amine, but here using tert-butyl 4-(benzo[d][1,3]dioxol-4-ylmethyl)piperazine-1-carboxylate (1.1 eq, 0.37 mmol, 120 mg), TFA (1.5 mL) and CH$_2$Cl$_2$ (3 mL), then 5-bromo-4-chloro-3-nitropyridin-2-amine (86 mg, 0.34 mmol) in $^i$PrOH (3.5 mL) and DIPEA (1 mL). Filtration and washing as previously described gave the product (131 mg, 80% for two steps) as a yellow solid; δ$_H$ (500 MHz, DMSO-d$_6$) 2.54 (s, br, 4H, piperazine N(CH$_2$)$_2$), 3.06 (s, br, 4H, piperazine N(CH$_2$)$_2$), 3.51 (s, 2H, NCH$_2$), 6.00 (s, 2H, OCH$_2$), 6.83-6.85 (m, 3H, phenyl H-4, H-5, H-6), 6.98 (s, br, 2H, NH$_2$), 8.16 (s, 1H, bromopyridine H-6);

LC (Method B)-MS (ESI, m/z): Rt=3.64 min—436, 438 [(M+H)$^+$, Br isotopic pattern]. ESI-HRMS: Found: 436.0615, calculated for C$_{17}$H$_{18}$BrN$_5$O$_4$ (M+H)$^+$: 436.0620.

7-(4-(Benzo[d][1,3]dioxol-4-ylmethyl)piperazin-1-yl)-6-bromo-2-(4-methoxyphenyl)-3H-imidazo[4,5-b]pyridine

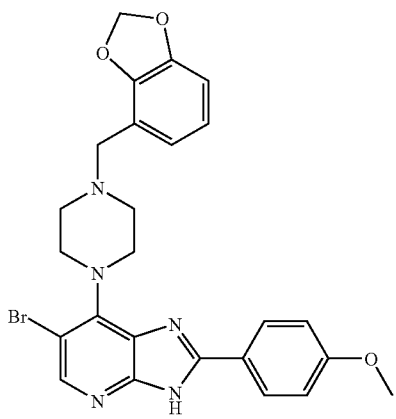

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 4-(4-(benzo[d][1,3]dioxol-4-ylmethyl)piperazin-1-yl)-5-bromo-3-nitropyridin-2-amine (30 mg, 0.068 mmol), DMF (0.15 mL), ethanol (0.85 mL), 1M Na$_2$S$_2$O$_4$ (3 eq, 0.21 mmol, 0.21 mL) and 4-methoxybenzene carboxaldehyde (1.1 eq, 0.075 mmol, 10 mg). After 6 h, concentration in vacuo and purification by preparative tlc (CH$_2$Cl$_2$-MeOH, 95:5) gave the product (22 mg, 63%) as a colourless solid; δ$_H$ (500 MHz, DMSO-d$_6$) 2.63 (s, br, 4H, piperazine N(CH$_2$)$_2$), 3.55 (s, 2H, NCH$_2$), 3.65 (t, J=4.3 Hz, 4H, piperazine N(CH$_2$)$_2$), 3.84 (s, 3H, OCH$_3$), 6.02 (s, 2H, OCH$_2$), 6.83 (d, J=4.2 Hz, 2H, benzo[d][1,3]dioxyl H-4 & H-6), 6.90 (app. q, J=4.4 Hz, 1H, benzo[d][1,3]dioxyl H-5), 7.09 (d, J=8.9 Hz, 2H, methoxyphenyl H-2 & H-6), 8.14 (d, J=8.9 Hz, 2H, methoxyphenyl H-3 & H-5), 8.20 (s, 1H, imidazo[4,5-b]pyridine H-5), 13.34 (s, br, 1H, imidazo[4,5-b]pyridine NH);

LC (Method B)-MS (ESI, m/z): Rt=3.60 min—522, 524 [(M+H)$^+$, Br isotopic pattern]. ESI-HRMS: Found: 522.1137, calculated for C$_{25}$H$_{24}$BrN$_5$O$_3$ (M+H)$^+$: 522.1141.

Example 120

4-(4-(7-(4-(Benzo[d][1,3]dioxol-4-ylmethyl)piperazin-1-yl)-6-bromo-3H-imidazo[4,5-b]pyridin-2-yl)benzyl)morpholine

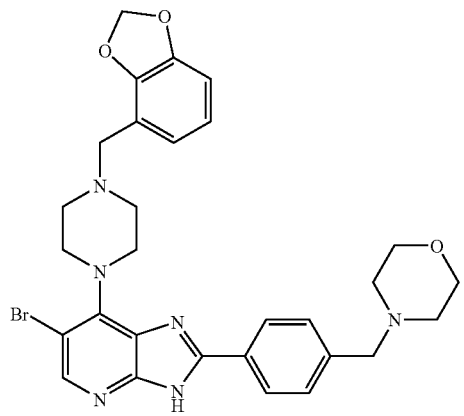

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 4-(4-(benzo[d][1,3]dioxol-4-ylmethyl)piperazin-1-yl)-5-bromo-3-nitropyridin-2-amine (20 mg, 0.046 mmol), DMF (0.15 mL), ethanol (0.85 mL), 1M Na$_2$S$_2$O$_4$ (3 eq, 0.14 mmol, 0.14 mL) and 4-(morpholinomethyl)benzaldehyde (1.1 eq, 0.050 mmol, 10 mg). After 6 h, concentration in vacuo and purification by preparative tlc (CH$_2$Cl$_2$-MeOH, 95:5) gave the product (11 mg, 41%) as a colourless solid; δ$_H$ (500 MHz, DMSO-d$_6$) 2.38 (t, J=4.1 Hz, 4H, morpholine N(CH$_2$)$_2$), 2.63 (s, br, 4H, piperazine N(CH$_2$)$_2$), 3.54 (s, 2H, NCH$_2$), 3.55 (s, 2H, NCH$_2$), 3.59 (t, J=4.6 Hz, 4H) and 3.66 (s, br, 4H) (piperazine N(CH$_2$)$_2$) and morpholine O(CH$_2$)$_2$), 6.02 (s, 2H, OCH$_2$), 6.83-6.85 (m, 2H, benzo[d][1,3]dioxyl H-4 & H-6), 6.88-6.91 (m, 1H, benzo[d][1,3]dioxyl H-5), 7.47 (d, J=8.1 Hz, 2H, phenyl H-3 & H-5), 8.14 (d, J=8.2 Hz, 2H, phenyl H-2 & H-6), 8.22 (s, 1H, imidazo[4,5-b]pyridine H-5), 13.46 (s, br, 1H, imidazo[4,5-b]pyridine NH);

LC (Method B)-MS (ESI, m/z): Rt=2.34 min—591, 593 [(M+H)$^+$, Br isotopic pattern]. ESI-HRMS: Found: 591.1718, calculated for C$_{29}$H$_{31}$BrN$_6$O$_3$ (M+H)$^+$: 591.1719.

Example 121 tert-Butyl 4-(pyrimidin-5-ylmethyl)piperazine-1-carboxylate

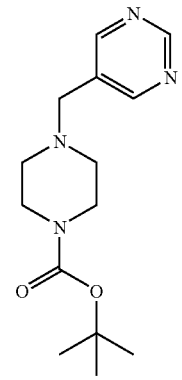

A solution of pyrimidine 5-carboxaldehyde (100 mg, 0.92 mmol) in ethanol (2 mL) and acetic acid (0.2 mL) at room temperature was treated with tert-butyl-1-piperazine carboxylate (2.5 eq, 2.31 mmol, 430 mg) and stirred for 5 minutes. Sodium cyanoborohydride (0.95 eq, 0.88 mmol, 55 mg) was added portionwise and the reaction then stirred for 16 h. Concentration in vacuo and preparative tlc purification (EtOAc) gave the product (141 mg, 55%) as a pale yellow oil; $\delta_H$ (500 MHz, CDCl$_3$) 1.47 (s, 9H, C(CH$_3$)$_3$), 1.95 (br, 2H, piperazine NCH$_2$), 2.42 (t, J=4.7 Hz, 2H, piperazine NCH$_2$), 3.45 (t, J=4.9 Hz, 4H, piperazine N(CH$_2$)$_2$), 3.54 (s, 2H, CH$_2$), 8.78 (s, 2H, pyrimidine H-4 & H-6), 9.15 (s, 1H, pyrimidine H-2);

LC (Method B)-MS (ESI, m/z): Rt=1.84 min—279 [(M+H)$^+$]. ESI-HRMS: Found: 279.1812, calculated for C$_{14}$H$_{22}$N$_4$O$_2$ (M+H)$^+$: 279.1821.

5-Bromo-3-nitro-4-(4-(pyrimidin-5-ylmethyl)piperazin-1-yl)pyridin-2-amine

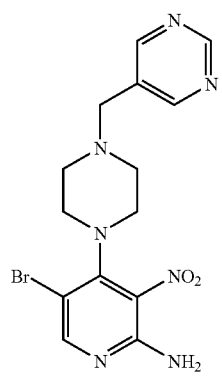

This was prepared using the same procedure as for 5-bromo-3-nitro-4-(4-(1-(pyridin-2-yl)ethyl)piperazin-1-yl)pyridin-2-amine, but here using tert-butyl 4-(pyrimidin-5-ylmethyl)piperazine-1-carboxylate (1.1 eq, 0.37 mmol, 104 mg), TFA (1.5 mL) and CH$_2$Cl$_2$ (4 mL), then 5-bromo-4-chloro-3-nitropyridin-2-amine (86 mg, 0.34 mmol) in $^i$PrOH (3 mL) and DIPEA (0.75 mL). Filtration and washing as previously described gave the product (99 mg, 67% for two steps) as a yellow solid; $\delta_H$ (500 MHz, DMSO-d$_6$) 2.54 (s, br, 4H, piperazine N(CH$_2$)$_2$), 3.06 (s, br, 4H, piperazine N(CH$_2$)$_2$), 3.60 (s, 2H, NCH$_2$), 6.97 (s, br, 2H, NH$_2$), 8.16 (s, 1H, bromopyridine H-6), 8.75 (s, 2H, pyrimidine H-4 & H-6), 9.10 (s, 1H, pyrimidine H-2);

LC (Method B)-MS (ESI, m/z): Rt=2.07 min—394, 396 [(M+H)$^+$, Br isotopic pattern]. ESI-HRMS: Found: 304.0628, calculated for C$_{14}$H$_{16}$BrN$_7$O$_2$ (M+H)$^+$: 394.0627.

6-Bromo-2-(4-methoxyphenyl)-7-(4-(pyrimidin-5-ylmethyl)piperazin-1-yl)-3H-imidazo[4,5-b]pyridine

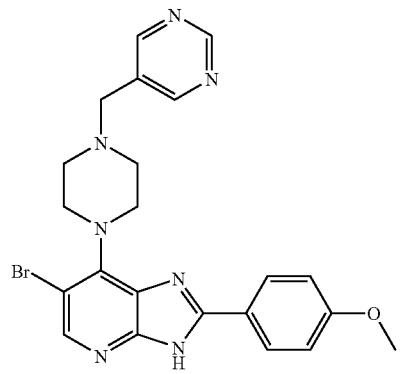

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyrimidin-5-ylmethyl)piperazin-1-yl)pyridin-2-amine (30 mg, 0.076 mmol), DMF (0.15 mL), ethanol (0.85 mL), 1M Na$_2$S$_2$O$_4$ (3 eq, 0.23 mmol, 0.23 mL) and 4-methoxybenzene carboxaldehyde (1.1 eq, 0.083 mmol, 12 mg). After 6 h, concentration in vacuo and purification by preparative tlc (CH$_2$Cl$_2$-MeOH, 95:5) gave the product (19 mg, 52%) as a colourless solid; $\delta_H$ (500 MHz, DMSO-d$_6$) 2.64 (s, br, 4H, piperazine N(CH$_2$)$_2$), 3.64 (s, 2H, NCH$_2$), 3.66 (t, J=4.6 Hz, 4H, piperazine N(CH$_2$)$_2$), 3.84 (s, 3H, OCH$_3$), 7.09 (d, J=8.9 Hz, 2H, methoxyphenyl H-2 & H-6), 8.13 (d, J=8.9 Hz, 2H, methoxyphenyl H-3 & H-5), 8.20 (s, 1H, imidazo[4,5-b]pyridine H-5), 8.80 (s, 2H, pyrimidine H-4 & H-6), 9.12 (s, 1H, pyrimidine H-2), 13.35 (s, br, 1H, imidazo[4,5-b]pyridine NH);

LC (Method B)-MS (ESI, m/z): Rt=3.37 min—480, 482 [(M+H)$^+$, Br isotopic pattern]. ESI-HRMS: Found: 480.1150, calculated for C$_{22}$H$_{22}$BrN$_7$O (M+H)$^+$: 480.1147.

Example 122

4-(4-(6-Bromo-7-(4-(pyrimidin-5-ylmethyl)piperazin-1-yl)-3H-imidazo[4,5-b]pyridin-2-yl)benzyl)morpholine

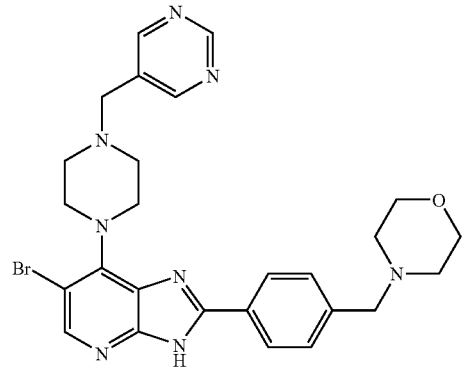

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyrimidin-5-ylmethyl)piperazin-1-yl)pyridin-2-amine (20 mg, 0.057 mmol), DMF (0.15 mL), ethanol (0.85 mL), 1M $Na_2S_2O_4$ (3 eq, 0.15 mmol, 0.15 mL) and 4-(morpholinomethyl)benzaldehyde (1.1 eq, 0.056 mmol, 11.5 mg). After 6 h, concentration in vacuo and preparation by preparative tlc ($CH_2Cl_2$-MeOH, 95:5) gave the product (10 mg, 36%) as a colourless solid; $\delta_H$ (500 MHz, DMSO-$d_6$) 2.39 (s, br, 4H, morpholine $N(CH_2)_2$), 2.65 (s, br, 4H, piperazine $N(CH_2)_2$), 3.54 (s, 2H, $NCH_2$), 3.60 (t, J=4.1 Hz, 4H) and 3.69 (t, J=4.6 Hz, 4H) (piperazine $N(CH_2)_2$) and morpholine $O(CH_2)_2$), 3.66 (s, 2H, $NCH_2$), 7.48 (d, J=7.8 Hz, 2H, phenyl H-3 & H-5), 8.15 (d, J=7.9 Hz, 2H, phenyl H-2 & H-6), 8.25 (s, 1H, imidazo[4,5-b]pyridine H-5), 8.82 (s, 2H, pyrimidine H-4 & H-6), 9.13 (s, 1H, pyrimidine H-2), 13.50 (s, br, 1H, imidazo[4,5-b]pyridine NH);

LC (Method B)-MS (ESI, m/z): Rt=2.00 min—549, 551 [(M+H)$^+$, Br isotopic pattern]. ESI-HRMS: Found: 549.1730, calculated for $C_{26}H_{29}BrN_8O$ (M+H)$^+$: 549.1726.

Example 123

4-(4-(6-Bromo-7-(4-(pyrimidin-5-ylmethyl)piperazin-1-yl)-3H-imidazo[4,5-b]pyridin-2-yl)phenyl)morpholine

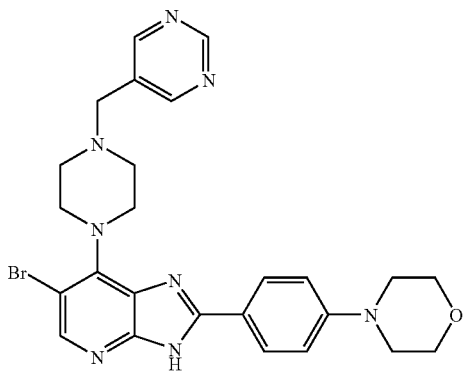

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(pyrimidin-5-ylmethyl)piperazin-1-yl)pyridin-2-amine (20 mg, 0.051 mmol), DMF (0.15 mL), ethanol (0.85 mL), 1M $Na_2S_2O_4$ (3 eq, 0.15 mmol, 0.15 mL) and 4-morpholin-4-yl-benzaldehyde (1.1 eq, 0.052 mmol, 11 mg). After 6 h, concentration in vacuo and purification by preparative tlc ($CH_2Cl_2$-MeOH, 95:5) gave the product (8 mg, 30%) as a pale yellow solid; $\delta_H$ (500 MHz, DMSO-$d_6$) 2.63 (s, br, 4H, piperazine $N(CH_2)_2$), 3.24 (t, J=4.7 Hz, 4H, morpholine $N(CH_2)_2$), 3.62-3.65 (m, 6H, piperazine $N(CH_2)_2$ & $CH_2$), 3.76 (t, J=4.8 Hz, 4H, morpholine $O(CH_2)_2$), 7.06 (d, J=9.0 Hz, 2H, phenyl H-3 & H-5), 8.04 (d, J=8.9 Hz, 2H, phenyl H-2 & H-6), 8.18 (s, 1H, imidazo[4,5-b]pyridine H-5), 8.80 (s, 2H, pyrimidine H-4 & H-6), 9.12 (s, 1H, pyrimidine H-2), 13.23 (s, br, 1H, imidazo[4,5-b]pyridine NH);

LC (Method B)-MS (ESI, m/z): Rt=3.35 min—535, 537 [(M+H)$^+$, Br isotopic pattern]. ESI-HRMS: Found: 535.1576, calculated for $C_{25}H_{27}BrN_8O$ (M+H)$^+$: 535.1569.

Example 124 tert-Butyl 4-((6-(trifluoromethyl)pyridin-3-yl)methyl)piperazine-1-carboxylate

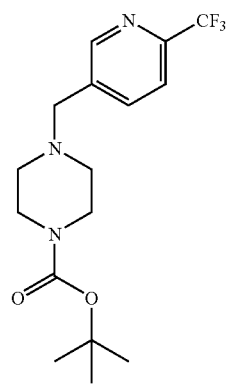

A solution of 6-trifluoromethylpyrimidine-3-carboxaldehyde (100 mg, 0.57 mmol) in ethanol (2 mL) and acetic acid (0.2 mL) at room temperature was treated with tert-butyl-1-piperazine carboxylate (2.5 eq, 1.43 mmol, 266 mg) and stirred for 5 minutes. Sodium cyanoborohydride (0.95 eq, 0.54 mmol, 34 mg) was added portionwise and the reaction then stirred for 16 h. Concentration in vacuo and preparative tlc purification (EtOAc) gave the product (151 mg, 76%) as a colourless solid; $\delta_H$ (500 MHz, CDCl$_3$) 1.47 (s, 9H, $C(CH_3)_3$), 2.42 (t, J=4.7 Hz, 4H, piperazine $N(CH_2)_2$), 3.45 (t, J=5.0 Hz, 4H, piperazine $N(CH_2)_2$), 3.61 (s, 2H, $CH_2$), 7.66 (d, J=8.0 Hz, 1H, pyridine H-5), 7.87 (dd, J=8.0, 1.0 Hz, 1H, pyridine H-4), 8.68 (d, J=1.0 Hz, 1H, pyridine H-2);

LC (Method A)-MS (ESI, m/z): Rt=4.89 min—346[(M+H)$^+$]. ESI-HRMS: Found: 346.1751, calculated for $C_{16}H_{22}F_3N_3O_3$ (M+H)$^+$: 346.1742.

5-Bromo-3-nitro-4-(4-((6-(trifluoromethyl)pyridin-3-yl)methyl)piperazin-1-yl)pyridin-2-amine

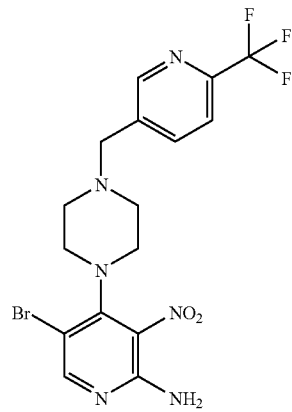

This was prepared using the same procedure as for 5-bromo-3-nitro-4-(4-(1-(pyridin-2-yl)ethyl)piperazin-1-yl)

pyridin-2-amine, but here using tert-butyl 4-((6-(trifluoromethyl)pyridin-3-yl)methyl)piperazine-1-carboxylate (1.1 eq, 0.27 mmol, 93 mg), TFA (1 mL) and CH₂Cl₂ (3 mL), then 5-bromo-4-chloro-3-nitropyridin-2-amine (62 mg, 0.24 mmol) in ⁱPrOH (3 mL) and DIPEA (1 mL). Filtration and washing as previously described gave the product (78 mg, 63% for two steps) as a yellow solid; $\delta_H$ (500 MHz, DMSO-d₆) 2.55 (s, br, 4H, piperazine N(CH₂)₂), 3.07 (s, br, 4H, piperazine N(CH₂)₂), 3.69 (s, 2H, NCH₂), 6.97 (s, br, 2H, NH₂), 7.87 (d, J=8.0 Hz, 1H, pyridine H-5), 8.03 (dd, J=8.0, 0.6 Hz, 1H, pyridine H-4), 8.16 (s, 1H, bromopyridine H-6), 8.71 (d, J=0.6 Hz, 1H, pyridine H-2);

LC (Method B)-MS (ESI, m/z): Rt=3.47 min—461, 463 [(M+H)⁺, Br isotopic pattern]. ESI-HRMS: Found: 461.0555, calculated for C₁₆H₁₆BrF₃N₆O₂ (M+H)⁺: 461.0548.

6-Bromo-2-(4-methoxyphenyl)-7-(4-((6-(trifluoromethyl)pyridin-3-yl)methyl)piperazin-1-yl)-3H-imidazo[4,5-b]pyridine

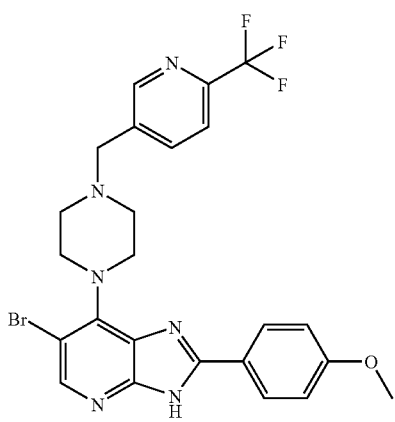

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-((6-(trifluoromethyl)pyridin-3-yl)methyl)piperazin-1-yl)pyridin-2-amine (20 mg, 0.043 mmol), DMF (0.15 mL), ethanol (0.85 mL), 1M Na₂S₂O₄ (3 eq, 0.13 mmol, 0.13 mL) and 4-methoxybenzene carboxaldehyde (1.1 eq, 0.048 mmol, 6.5 mg). After 6 h, concentration in vacuo and purification by preparative tlc (CH₂Cl₂-MeOH, 95:5) gave the product (10 mg, 52%) as a colourless solid; $\delta_H$ (500 MHz, DMSO-d₆) 2.64 (s, br, 4H, piperazine N(CH₂)₂), 3.67 (s, br, 4H, piperazine N(CH₂)₂), 3.73 (s, 2H, NCH₂), 3.84 (s, 3H, OCH₃), 7.10 (d, J=8.8 Hz, 2H, methoxyphenyl H-2 & H-6), 7.91 (d, br, J=7.6 Hz, 1H, pyridine H-5), 8.09 (d, br, J=7.7 Hz, 1H, pyridine H-4), 8.13 (d, J=8.7 Hz, 2H, methoxyphenyl H-3 & H-5), 8.21 (s, 1H, imidazo[4,5-b]pyridine H-5), 8.77 (s, br, 1H, pyridine H-2), 13.58 (s, br, 1H, imidazo[4,5-b]pyridine NH);

LC (Method B)-MS (ESI, m/z): Rt=4.34 min—547, 549 [(M+H)⁺, Br isotopic pattern]. ESI-HRMS: Found: 547.1062, calculated for C₂₄H₂₂BrF₃N₆O (M+H)⁺: 547.1069.

Example 125

4-(4-(6-Bromo-7-(4-((6-(trifluoromethyl)pyridin-3-yl)methyl)piperazin-1-yl)-3H-imidazo[4,5-b]pyridin-2-yl)benzyl)morpholine

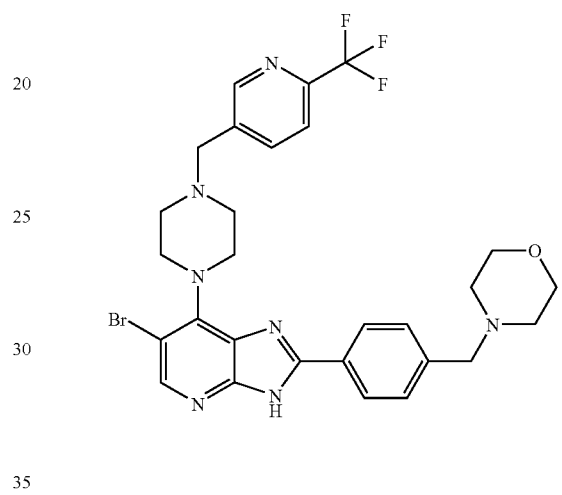

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-((6-(trifluoromethyl)pyridin-3-yl)methyl)piperazin-1-yl)pyridin-2-amine (20 mg, 0.043 mmol), DMF (0.15 mL), ethanol (0.85 mL), 1M Na₂S₂O₄ (3 eq, 0.13 mmol, 0.13 mL) and 4-(morpholinomethyl)benzaldehyde (1.1 eq, 0.048 mmol, 10 mg). After 6 h, concentration in vacuo and purification by preparative tlc (CH₂Cl₂-MeOH, 95:5) gave the product (9 mg, 33%) as a colourless solid; $\delta_H$ (500 MHz, DMSO-d₆) 2.39 (s, br, 4H, morpholine N(CH₂)₂), 2.66 (s, br, 4H, piperazine N(CH₂)₂), 3.55 (s, 2H, NCH₂), 3.60 (t, J=4.4 Hz, 4H) and 3.70 (t, J=4.8 Hz, 4H) (piperazine N(CH₂)₂) and morpholine O(CH₂)₂), 3.75 (s, 2H, NCH₂), 7.48 (d, J=8.0 Hz, 2H, phenyl H-3 & H-5), 7.92 (d, br, J=8.0 Hz, 1H, pyridine H-5), 8.10 (d, br, J=8.1 Hz, 1H, pyridine H-4), 8.15 (d, J=8.1 Hz, 2H, phenyl H-2 & H-6), 8.25 (s, 1H, imidazo[4,5-b]pyridine H-5), 8.78 (s, br, 1H, pyridine H-2), 13.50 (s, br 1H, imidazo[4,5-b]pyridine NH);

LC (Method B)-MS (ESI, m/z): Rt=2.66 min—616, 618 [(M+H)⁺, Br isotopic pattern]. ESI-HRMS: Found: 616.1656, calculated for C₂₈H₂₉BrF₃N₇O (M+H)⁺: 616.1647.

Example 126

4-(4-(6-Bromo-7-(4-((6-(trifluoromethyl)pyridin-3-yl)methyl)piperazin-1-yl)-3H-imidazo[4,5-b]pyridin-2-yl)phenyl)morpholine

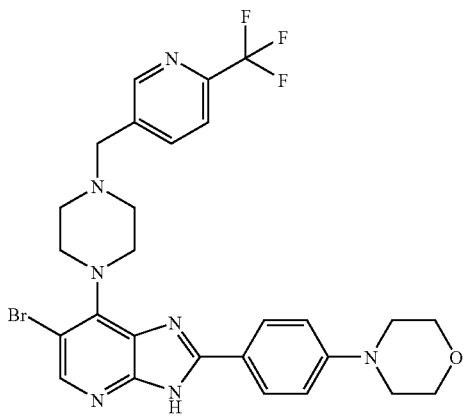

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-((6-(trifluoromethyl)pyridin-3-yl)methyl)piperazin-1-yl)pyridin-2-amine (20 mg, 0.043 mmol), DMF (0.15 mL), ethanol (0.85 mL), 1M Na$_2$S$_2$O$_4$ (3 eq, 0.13 mmol, 0.13 mL) and 4-morpholin-4-yl-benzaldehyde (1.1 eq, 0.048 mmol, 9 mg). After 6 h, concentration in vacuo and purification by preparative tlc (CH$_2$Cl$_2$-MeOH, 95:5) gave the product (6 mg, 23%) as a pale yellow solid; δ$_H$ (500 MHz, DMSO-d$_6$) 2.65 (t, J=4.4 Hz, 4H, piperazine N(CH$_2$)$_2$), 3.24 (t, J=4.9 Hz, 4H, morpholine N(CH$_2$)$_2$), 3.66 (t, J=4.5 Hz, 4H, piperazine N(CH$_2$)$_2$), 3.73 (s, 2H, CH$_2$), 3.76 (t, J=4.9 Hz, 4H, morpholine O(CH$_2$)$_2$), 7.06 (d, J=9.0 Hz, 2H, phenyl H-3 & H-5), 7.90 (d, br, J=8.0 Hz, 1H, pyridine H-5), 8.04 (d, J=9.0 Hz, 2H, phenyl H-2 & H-6), 8.08 (dd, J=8.1, 1.0 Hz, 1H, pyridine H-4), 8.18 (s, 1H, imidazo[4,5-b]pyridine H-5), 8.77 (s, br, 1H, pyridine H-2), 13.23 (s, br, 1H, imidazo[4,5-b]pyridine NH);

LC (Method B)-MS (ESI, m/z): Rt=4.20 min—602, 604 [(M+H)$^+$, Br isotopic pattern]. ESI-HRMS: Found: 602.1487, calculated for C$_{27}$H$_{27}$BrF$_3$N$_7$O (M+H)$^+$: 602.1491.

Example 127 tert-Butyl 4-((3,5-dimethylisoxazol-4-yl)methyl)piperazine-1-carboxylate

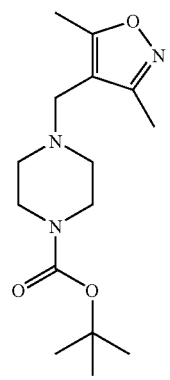

A solution of 4-chloromethyl-3,5-dimethylisoxazole (100 mg, 0.69 mmol) in CH$_2$Cl$_2$ (4 mL) was treated with tert-butyl-1-piperazine carboxylate (2.5 eq, 1.71 mmol, 320 mg) and $^i$Pr$_2$NEt (3.0 eq, 2.06 mmol, 0.36 mL) and stirred at 35° C. for 8 h. Concentration in vacuo and preparative tlc purification (EtOAc) gave the desired product (111 mg, 55%) as a colourless solid; δ$_H$ (500 MHz, DMSO-d$_6$) 1.39 (s, 9H, C(CH$_3$)$_3$), 2.17 (s, 3H, CH$_3$), 2.28 (t, J=4.5 Hz, 4H, piperazine N(CH$_2$)$_2$), 2.31 (s, 3H, CH$_3$), 3.23 (s, 2H, NCH$_2$), 3.30 (hidden by DMSO peak, 4H, piperazine N(CH$_2$)$_2$);

LC (Method B)-MS (ESI, m/z): Rt=2.80 min—296 [(M+H)$^+$]. ESI-HRMS: Found: 296.1968, calculated for C$_{15}$H$_{25}$N$_3$O$_3$ (M+H)$^+$: 296.1974.

5-Bromo-4-(4-((3,5-dimethylisoxazol-4-yl)methyl)piperazin-1-yl)-3-nitropyridin-2-amine

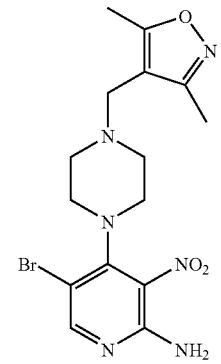

This was prepared using the same procedure as for 5-bromo-3-nitro-4-(4-(1-(pyridin-2-yl)ethyl)piperazin-1-yl)pyridin-2-amine, but here using tert-butyl 4-((3,5-dimethylisoxazol-4-yl)methyl)piperazine-1-carboxylate (1.1 eq, 0.35 mmol, 104 mg), TFA (1.25 mL) and CH$_2$Cl$_2$ (4 mL), then 5-bromo-4-chloro-3-nitropyridin-2-amine (81 mg, 0.32 mmol) in $^i$PrOH (3 mL) and DIPEA (1 mL). Filtration and washing as previously described gave the product (105 mg, 72% for two steps) as a yellow solid; δ$_H$ (500 MHz, DMSO-d$_6$) 2.19 (s, 3H, CH$_3$), 2.32 (s, 3H, CH$_3$), 2.47 (s, br, 4H, piperazine N(CH$_2$)$_2$), 3.03 (s, br, 4H, piperazine N(CH$_2$)$_2$), 3.30 (s, hidden by DMSO peak, 2H, NCH$_2$), 6.96 (s, br, 2H, NH$_2$), 8.16 (s, 1H, bromopyridine H-6);

LC (Method B)-MS (ESI, m/z): Rt=2.15 min—411, 413 [(M+H)$^+$, Br isotopic pattern]. ESI-HRMS: Found: 411.0776, calculated for C$_{15}$H$_{19}$BrN$_6$O$_3$ (M+H)$^+$: 411.0780.

4-((4-(6-Bromo-2-(4-methoxyphenyl)-3H-imidazo[4,5-b]pyridin-7-yl)piperazin-1-yl)methyl)-3,5-dimethylisoxazole

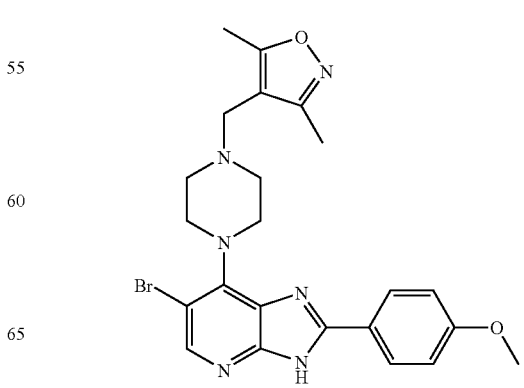

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-4-((3,5-dimethylisoxazol-4-yl)methyl)piperazin-1-yl)-3-nitropyridin-2-amine (20 mg, 0.049 mmol), DMF (0.15 mL), ethanol (0.85 mL), 1M Na$_2$S$_2$O$_4$ (3 eq, 0.14 mmol, 0.14 mL) and 4-methoxybenzene carboxaldehyde (1.1 eq, 0.053 mmol, 7 mg). After 6 h, concentration in vacuo and purification by preparative tlc (CH$_2$Cl$_2$-MeOH, 95:5) gave the product (10 mg, 42%) as a colourless solid; δ$_H$ (500 MHz, DMSO-d$_6$) 2.26 (s, 3H, CH$_3$), 2.39 (s, 3H, CH$_3$), 2.63 (t, J=4.6 Hz, 4H, piperazine N(CH$_2$)$_2$), 3.40 (s, 2H, CH$_2$), 3.72 (s, br, 4H, piperazine N(CH$_2$)$_2$), 3.88 (s, 3H, OCH$_3$), 7.08 (d, J=8.8 Hz, 2H, methoxyphenyl H-2 & H-6), 8.12 (d, J=8.7 Hz, 2H, methoxyphenyl H-3 & H-5), 8.21 (s, 1H, imidazo[4,5-b]pyridine H-5), 13.03 (s, br, 1H, imidazo[4,5-b]pyridine NH); LC (Method B)-MS (ESI, m/z): Rt=3.29 min—497, 499 [(M+H)$^+$, Br isotopic pattern]. ESI-HRMS: Found: 497.1301, calculated for C$_{23}$H$_{25}$BrN$_6$O$_2$ (M+H)$^+$: 497.1301.

Example 128

4-(4-(6-Bromo-7-(4-((3,5-dimethylisoxazol-4-yl)methyl)piperazin-1-yl)-3H-imidazo[4,5-b]pyridin-2-yl)benzyl)morpholine

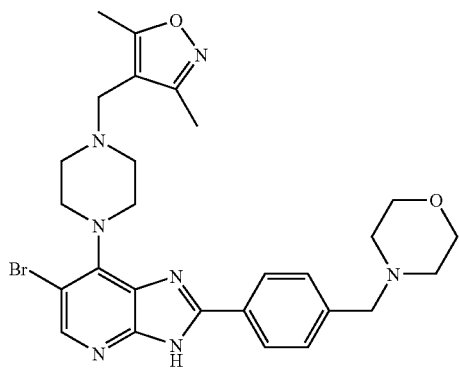

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using tert-butyl 4-((3,5-dimethylisoxazol-4-yl)methyl)piperazine-1-carboxylate (20 mg, 0.048 mmol), DMF (0.15 mL), ethanol (0.85 mL), 1M Na$_2$S$_2$O$_4$ (3 eq, 0.14 mmol, 0.14 mL) and 4-(morpholinomethyl)benzaldehyde (1.1 eq, 0.053 mmol, 11 mg). After 6 h, concentration in vacuo and purification by preparative tlc (CH$_2$Cl$_2$-MeOH, 95:5) gave the product (11 mg, 40%) as a colourless solid; δ$_H$ (500 MHz, DMSO-d$_6$) 2.24 (s, 3H, CH$_3$), 2.37 (s, 3H, CH$_3$), 2.37-2.40 (m, 4H, morpholine N(CH$_2$)$_2$), 2.58 (s, br, 4H, piperazine N(CH$_2$)$_2$), 3.26 (s, 2H, CH$_2$), 3.54 (s, 2H, CH$_2$), 3.59 (t, J=4.5 Hz, 4H) and 3.64 (t, J=4.8 Hz, 4H) (piperazine N(CH$_2$)$_2$ and morpholine O(CH$_2$)$_2$), 7.47 (d, J=8.2 Hz, 2H, phenyl H-3 & H-5), 8.14 (d, J=8.2 Hz, 2H, phenyl H-2 & H-6), 8.23 (s, 1H, imidazo[4,5-b]pyridine H-5), 13.48 (s, br, 1H, imidazo[4,5-b]pyridine NH);

LC (Method B)-MS (ESI, m/z): Rt=2.05 min—566, 568 [(M+H)$^+$, Br isotopic pattern]. ESI-HRMS: Found: 566.1879, calculated for C$_{27}$H$_{32}$BrN$_7$O$_2$ (M+H)$^+$: 566.1879.

Example 129

4-(4-(6-Bromo-7-(4-(1-(pyridin-4-yl)ethyl)piperazin-1-yl)-3H-imidazo[4,5-b]pyridin-2-yl)benzyl)morpholine

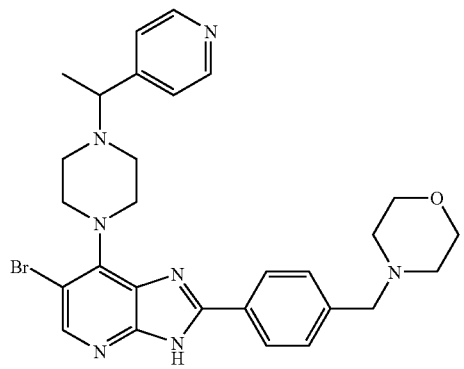

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(1-(pyridin-4-yl)ethyl)piperazin-1-yl)pyridin-2-amine (30 mg, 0.073 mmol), DMF (0.15 mL), ethanol (0.85 mL), 1M Na$_2$S$_2$O$_4$ (3 eq, 0.22 mmol, 0.22 mL) and 4-(morpholinomethyl)benzaldehyde (1.1 eq, 0.081 mmol, 17 mg). After 6 h, concentration in vacuo and purification by preparative tlc (CH$_2$Cl$_2$-MeOH, 95:5) gave the product (9 mg, 22%) as a colourless solid; δ$_H$ (500 MHz, DMSO-d$_6$) 1.40 (d, J=6.7 Hz, 3H, CH$_3$), 2.45 (t, J=4.7 Hz, 4H, morpholine N(CH$_2$)$_2$), 2.62-2.66 (m, 2H, piperazine NCH$_2$), 2.71-2.75 (m, 2H, piperazine NCH$_2$), 3.59 (2H, s, CH$_2$), 3.60-2.62 (m, 1H, CHCH$_3$), 3.63 (t, J=4.7 Hz, 4H) and 3.73 (s, br, 4H) (morpholine O(CH$_2$)$_2$) and piperazine N(CH$_2$)$_2$), 7.39 (d, J=6.0 Hz, 2H, pyridine H-3 & H-5), 7.48 (d, J=8.1 Hz, 2H, phenyl H-3 & H-5), 8.14 (d, J=8.1 Hz, 2H, phenyl H-2 & H-6), 8.21 (s, 1H, imidazo[4,5-b]pyridine H-5), 8.54 (d, J=6.0 Hz, 2H, pyridine H-2 & H-6), 13.04 (s, br, 1H, imidazo[4,5-b]pyridine NH);

LC (Method B)-MS (ESI, m/z): Rt=2.10 min—562, 564 [(M+H)$^+$, Br isotopic pattern]. ESI-HRMS: Found: 562.1935, calculated for C$_{28}$H$_{32}$BrN$_7$O (M+H)$^+$: 562.1930.

Example 130

4-(4-(6-Bromo-7-(4-(1-(pyridin-4-yl)ethyl)piperazin-1-yl)-3H-imidazo[4,5-b]pyridin-2-yl)phenyl)morpholine

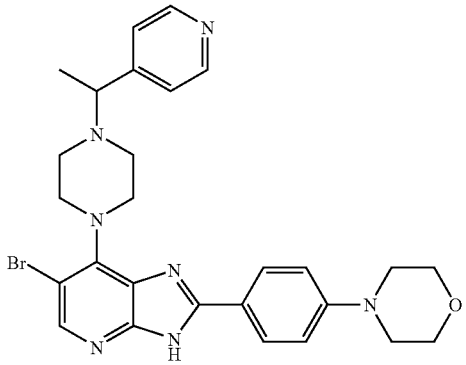

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(1-(pyridin-4-yl)ethyl)piperazin-1-yl)pyridin-2-amine (20 mg, 0.049 mmol), DMF (0.15 mL), ethanol (0.85 mL), 1M Na$_2$S$_2$O$_4$ (3 eq, 0.15 mmol, 0.15 mL) and 4-morpholin-4-yl-benzaldehyde (1.1 eq, 0.054 mmol, 10 mg). After 6 h, concentration in vacuo and purification by preparative tlc (CH$_2$Cl$_2$-MeOH, 95:5) gave the product (7 mg, 27%) as an off-white solid; $\delta_H$ (500 MHz, DMSO-d$_6$) 1.36 (d, J=6.4 Hz, 3H, CH$_3$), 2.36 (s, br, 2H, piperazine NCH$_2$), 2.63 (s, br, 2H, piperazine NCH$_2$), 3.30 (hidden by DMSO peak, 4H, morpholine N(CH$_2$)$_2$), 3.58-3.60 (m, 1H, CHCH$_3$), 3.64 (s, br, 4H, piperazine N(CH$_2$)$_2$), 3.76 (t, J=4.6 Hz, 4H, morpholine O(CH$_2$)$_2$), 7.07 (d, J=8.9 Hz, 2H, phenyl H-3 & H-5), 7.39 (d, br, J=6.2 Hz, 2H, pyridine H-3 & H-5), 8.04 (d, J=8.9 Hz, 2H, phenyl H-2 & H-6), 8.16 (s, 1H, imidazo[4,5-b]pyridine H-5), 8.55 (d, br, J=6.0 Hz, 2H, pyridine H-2 & H-6), 13.22 (s, br, 1H, imidazo[4,5-b]pyridine NH);

LC (Method B)-MS (ESI, m/z): Rt=3.35 min—548, 550 [(M+H)$^+$, Br isotopic pattern]. ESI-HRMS: Found: 548.1774, calculated for C$_{27}$H$_{30}$BrN$_7$O (M+H)$^+$: 548.1773.

Example 131

2-(4-(6-Bromo-7-(4-(1-(pyridin-4-yl)ethyl)piperazin-1-yl)-3H-imidazo[4,5-b]pyridin-2-yl)phenoxy)-N,N-dimethylethanamine

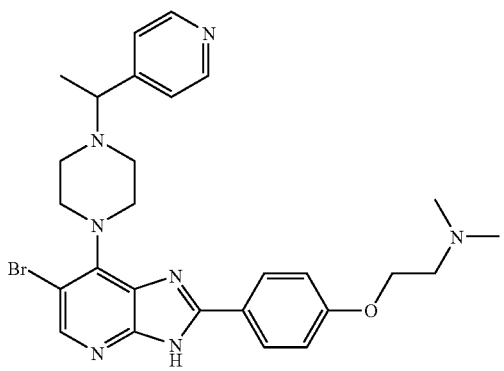

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-(1-(pyridin-4-yl)ethyl)piperazin-1-yl)pyridin-2-amine (30 mg, 0.074 mmol), DMF (0.15 mL), ethanol (0.85 mL), 1M Na$_2$S$_2$O$_4$ (3 eq, 0.22 mmol, 0.22 mL) and 4-(2-(dimethylamino)ethoxy)benzaldehyde (1.1 eq, 0.088 mmol, 17 mg). After 6 h, concentration in vacuo and purification by preparative tlc (CH$_2$Cl$_2$-MeOH, 85:15) gave the product (9 mg, 21%) as a colourless solid; $\delta_H$ (500 MHz, DMSO-d$_6$) 1.35 (d, J=6.7 Hz, 3H, CHCH$_3$), 2.25 (s, 6H, N(CH$_3$)$_2$), 2.51-2.55 (m, 2H, piperazine NCH$_2$), 2.63-2.65 (m, 2H, piperazine NCH$_2$), 2.67 (t, J=5.6 Hz, 2H, Me$_2$NCH$_2$), 3.57 (q, J=6.7 Hz, 1H, CHCH$_3$), 3.63-3.66 (m, 4H, piperazine N(CH$_2$)$_2$), 4.14 (q, J=5.8 Hz, 2H, OCH$_2$), 7.10 (d, J=8.9 Hz, 2H, phenyl H-3 & H-5), 7.39 (d, J=6.0 Hz, 2H, pyridine H-3 & H-5), 8.11 (d, J=8.8 Hz, 2H, phenyl H-2 & H-6), 8.19 (s, 1H, imidazo[4,5-b]pyridine H-5), 8.54 (d, J=5.9 Hz, 2H, pyridine H-2 & H-6), 13.33 (s, br, 1H, imidazo[4,5-b]pyridine NH);

LC (Method B)-MS (ESI, m/z): Rt=2.00 min—550, 552 [(M+H)$^+$, Br isotopic pattern]. ESI-HRMS: Found: 550.1922, calculated for C$_{27}$H$_{32}$BrN$_7$O (M+H)$^+$: 550.1930.

Example 132

4-(4-Benzylpiperidin-1-yl)-5-bromo-3-nitropyridin-2-amine

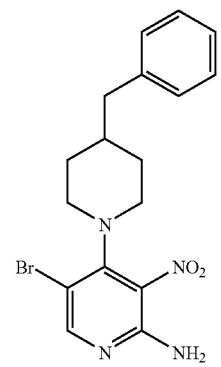

This was prepared using the same procedure as for 2-(4-(2-amino-5-bromo-3-nitropyridin-4-yl)piperazin-1-yl)-N-(thiazol-2-yl)acetamide, but here using 5-bromo-4-chloro-3-nitropyridin-2-amine (1.00 g, 3.96 mmol), DIPEA (3.5 eq, 13.86 mmol, 2.41 mL), isopropanol (20 mL) and 4-benzylpiperidine (1.1 eq, 4.36 mmol, 0.77 mL). Concentration in vacuo to half volume after 18 h gave a bright yellow solid, which was filtered and washed with cold water (2×5 mL) to give the product (1.12 g, 72%) as a yellow solid; $\delta_H$ (500 MHz, DMSO-d$_6$) 1.38 (qd, br, J=12.2, 3.5 Hz, 2H, 2× piperidine CH$_A$H$_B$), 1.60 (d, br, J=10.9 Hz, 2H, 2× piperidine CH$_A$H$_B$), 1.69-1.76 (m, 1H, piperidine CH), 2.55 (d, J=7.1 Hz, 2H, 2× piperidine NCH$_A$H$_A$), 2.74 (t, br, J=11.9 Hz, 2H, 2× piperidine NCH$_A$H$_A$), 3.22 (d, br, J=12.5 Hz, 2H, PhCH$_2$), 6.93 (s, br, 2H, NH$_2$), 7.16-7.18 (1H, m, phenyl H-4), 7.19 (d, J=7.4 Hz, 2H, phenyl H-2 & H-6), 7.28 (t, J=7.1 Hz, 2H, phenyl H-3 & H-5), 8.13 (s, 1H, pyridine H-6);

LC (Method B)-MS (ESI, m/z): Rt=5.92 min—391, 393 [(M+H)$^+$, Br isotopic pattern]. ESI-HRMS: Found: 391.0768, calculated for C$_{17}$H$_{19}$BrN$_4$O$_2$ (M+H)$^+$: 391.0770.

tert-Butyl 4-(7-(4-benzylpiperidin-1-yl)-6-bromo-3H-imidazo[4,5-b]pyridin-2-yl)benzylcarbamate

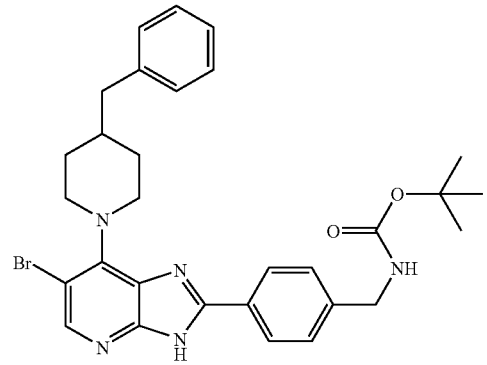

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 4-(4-benzylpiperidin-1-yl)-5-bromo-3-nitropyridin-2-amine (100 mg, 0.25 mmol), DMF (0.20 mL), ethanol (1.25 mL), 1M $Na_2S_2O_4$ (3 eq, 0.75 mmol, 0.75 mL) and tert-butyl N-(4-formylbenzyl)carbamate (1.1 eq, 0.28 mmol, 66 mg). After 6 h, concentration in vacuo and purification by preparative tlc ($CH_2Cl_2$-MeOH, 95:5) gave the product (32 mg, 22%) as a colourless solid; $\delta_H$ (500 MHz, DMSO-$d_6$) 1.41 (s, 9H, $C(CH_3)_3$), 1.44-1.49 (m, 2H, 2× piperidine $CH_AH_B$), 1.73 (app d, J=11.0 Hz, 2H, 2× piperidine $CH_AH_B$), 1.78-1.85 (m, 1H, piperidine CH), 2.61 (app d, J=7.1 Hz, 2H, $PhCH_2$), 3.31-3.34 (m, 2H, 2× piperidine $NCH_AH_A$), 3.85 (app d, J=11.9 Hz, 2H, 2× piperidine $NCH_AH_A$), 4.19 (d, J=7.9 Hz, 2H, $CH_2$—NHBOC), 7.20 (t, J=7.3 Hz, 1H, phenyl H-4), 7.23 (d, J=7.0 Hz, 2H, phenyl H-2 & H-6), 7.31 (t, br, J=7.4 Hz, 2H, phenyl H-3 & H-5), 7.38 (d, J=8.2 Hz, 2H, phenyl H-3' & H-5'), 7.43 (t, br, J=5.9 Hz, 1H, $CH_2$—NHBOC), 8.11 (d, J=8.9 Hz, 2H, phenyl H-2' & H-6'), 8.21 (s, 1H, imidazo[4,5-b]pyridine H-5), 13.03 (s, br, 1H, imidazo[4,5-b]pyridine NH);

LC (Method A)-MS (ESI, m/z): Rt=8.44 min—576, 578 [(M+H)$^+$, Br isotopic pattern].

Example 133

(4-(7-(4-Benzylpiperidin-1-yl)-6-bromo-3H-imidazo[4,5-b]pyridin-2-yl)phenyl)methanamine

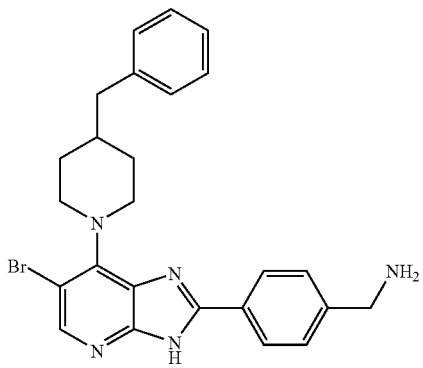

This was prepared using the same procedure as for (4-(6-bromo-7-(4-(pyridin-3-ylmethyl)piperazin-1-yl)-3H-imidazo[4,5-b]pyridin-2-yl)phenyl)methanamine, but here using tert-butyl 4-(7-(4-benzylpiperidin-1-yl)-6-bromo-3H-imidazo[4,5-b]pyridin-2-yl)benzylcarbamate (15 mg, 0.026 mmol), TFA (0.2 mL) and $CH_2Cl_2$ (1 mL). The same purification procedure gave the desired product (12 mg, 97%) as a colourless solid; $\delta_H$ (500 MHz, DMSO-$d_6$) 1.40-1.48 (m, 2H, 2× piperidine $CH_AH_B$), 1.73 (d, br, J=11.7 Hz, 2H, 2× piperidine $CH_AH_B$), 1.79-1.85 (m, 1H, piperidine CH), 2.61 (app d, J=7.1 Hz, 2H, $PhCH_2$), 3.31-3.36 (m, 2H, 2× piperidine $NCH_AH_A$), 3.79 (s, 2H, $CH_2NH_2$), 3.85 (app d, J=12.0 Hz, 2H, 2× piperidine $NCH_AH_A$), 7.20 (t, J=7.2 Hz, 1H, phenyl H-4), 7.23 (d, J=7.0 Hz, 2H, phenyl H-2 & H-6), 7.31 (t, J=7.5 Hz, 2H, phenyl H-3 & H-5), 7.48 (d, J=8.2 Hz, 2H, phenyl H-3' & H-5'), 8.10 (d, J=8.2 Hz, 2H, phenyl H-2' & H-6'), 8.21 (s, 1H, (s, 1H, imidazo[4,5-b]pyridine H-5).

Example 134

5-Bromo-3-nitro-4-(4-phenoxypiperidin-1-yl)pyridin-2-amine

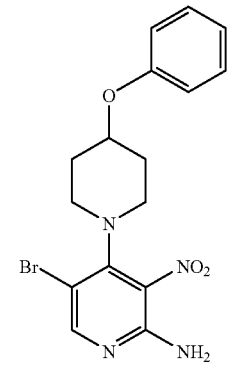

This was prepared using the same procedure as for 2-(4-(2-amino-5-bromo-3-nitropyridin-4-yl)piperazin-1-yl)-N-(thiazol-2-yl)acetamide, but here using 5-bromo-4-chloro-3-nitropyridin-2-amine (162 mg, 0.64 mmol), DIPEA (3.5 eq, 2.24 mmol, 0.39 mL), isopropanol (3 mL) and 4-phenoxypiperidine (1.1 eq, 0.70 mmol, 125 mg). Concentration in vacuo to half volume after 18 h gave a bright yellow solid, which was filtered and washed with cold water (2×2 mL) to give the product (212 mg, 84%) as a yellow solid; $\delta_H$ (500 MHz, DMSO-$d_6$) 1.74-1.81 (m, 2H, 2× piperidine $CH_AH_B$), 2.04-2.08 (m, br, 2H, 2× piperidine $CH_AH_B$), 2.98-3.03 (m, 2H, 2× piperidine $NCH_AH_A$), 3.24-3.27 (m, 2H, 2× piperidine $NCH_AH_A$), 4.63 (quintet, J=3.9 Hz, 1H, piperidine CH), 6.92 (t, J=7.4 Hz, 1H, phenyl H-6), 6.98 (s, br, 2H, $NH_2$), 6.99 (d, J=7.8 Hz, 2H, phenyl H-2 & H-4), 7.28 (dd, J=8.6, 7.8 Hz, 2H, phenyl H-3 & H-5), 8.17 (s, 1H, pyridine H-6);

LC (Method B)-MS (ESI, m/z): Rt=5.54 min—393, 395 [(M+H)$^+$, Br isotopic pattern]. ESI-HRMS: Found: 393.0562, calculated for $C_{16}H_{17}BrN_4O_3$ (M+H)$^+$: 393.0562.

tert-Butyl 4-(6-bromo-7-(4-phenoxypiperidin-1-yl)-3H-imidazo[4,5-b]pyridin-2-yl)benzylcarbamate

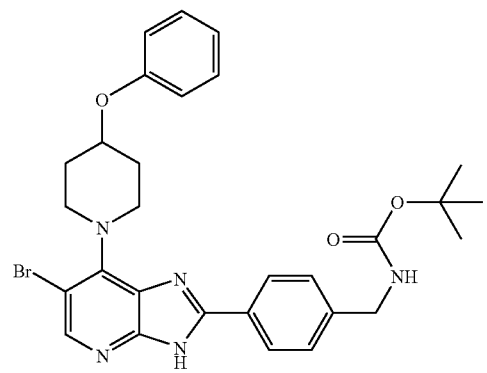

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-bromo-3-nitro-4-(4-phenoxypiperidin-1-yl)pyridin-2-amine (75 mg, 0.19 mmol), DMF (0.20 mL), ethanol (1.00 mL), 1M Na$_2$S$_2$O$_4$ (3 eq, 0.58 mmol, 0.58 mL) and tert-butyl N-(4-formylbenzyl)carbamate (1.1 eq, 0.21 mmol, 49 mg). After 6 h, concentration in vacuo and purification by preparative tlc (CH$_2$Cl$_2$-MeOH, 95:5) gave the product (29 mg, 20%) as a colourless solid; δ$_H$ (500 MHz, DMSO-d$_6$) 1.41 (s, 9H, C(CH$_3$)$_3$), 1.84-1.90 (m, 2H, 2× piperidine CH$_A$H$_B$), 2.16-2.19 (m, 2H, 2× piperidine CH$_A$H$_B$), 3.59-3.64 (m, 2H, 2× piperidine NCH$_A$H$_A$), 3.87-3.91 (m, 2H, 2× piperidine NCH$_A$H$_A$), 4.19 (d, J=5.9 Hz, 2H, CH$_2$NH), 4.70 (septet, J=3.9 Hz, 1H, piperidine CH), 6.94 (t, J=7.3 Hz, 1H, phenyl H-4), 7.04 (d, J=7.8 Hz, 2H, phenyl H-3' & H-5'), 7.31 (dd, J=8.6, 7.4 Hz, 2H, phenyl H-3 & H-5), 7.40 (d, J=8.3 Hz, 2H, phenyl H-2 & H-6), 8.13 (d, J=8.1 Hz, 2H, phenyl H-2' & H-6'), 8.24 (s, 1H, imidazo[4,5-b]pyridine H-5), 13.45 (s, br, 1H, imidazo[4,5-b]pyridine NH);

LC (Method A)-MS (ESI, m/z): Rt=7.59 min—578, 580 [(M+H)$^+$, Br isotopic pattern].

Example 135

(4-(6-Bromo-7-(4-phenoxypiperidin-1-yl)-3H-imidazo[4,5-b]pyridin-2-yl)phenyl)methanamine

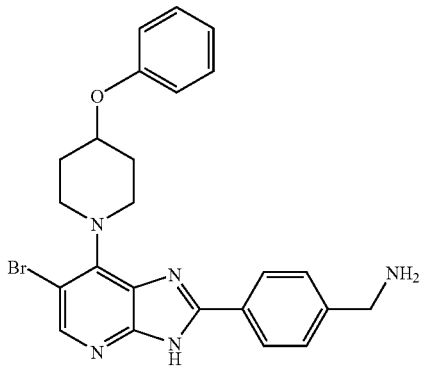

This was prepared using the same procedure as for (4-(6-bromo-7-(4-(pyridin-3-ylmethyl)piperazin-1-yl)-3H-imidazo[4,5-b]pyridin-2-yl)phenyl)methanamine, but here using tert-butyl 4-(6-bromo-7-(4-phenoxypiperidin-1-yl)-3H-imidazo[4,5-b]pyridin-2-yl)benzylcarbamate (17 mg, 0.029 mmol), TFA (0.25 mL) and CH$_2$Cl$_2$ (1 mL). The same purification procedure gave the desired product (13 mg, 93%) as a colourless solid; δ$_H$ (500 MHz, DMSO-d$_6$) 1.84-1.90 (m, 2H, 2× piperidine CH$_A$H$_B$), 2.17-2.19 (m, 2H, 2× piperidine CH$_A$H$_B$), 3.61 (ddd, J=12.4, 9.7, 1.8 Hz, 2× piperidine NCH$_A$H$_A$), 3.80 (s, 3H, OCH$_3$), 3.86-3.91 (m, 2H, 2× piperidine NCH$_A$H$_A$), 4.70 (septet, J=4.0 Hz, 1H, piperidine CH), 6.94 (t, J=7.3 Hz, 1H, phenyl H-4), 7.04 (d, J=7.8 Hz, 2H, phenyl H-2 & H-6), 7.30 (dd, J=8.6, 7.4 Hz, 2H, phenyl H-3 & H-5), 7.50 (d, J=8.6 Hz, 2H, phenyl H-3' & H-5'), 8.11 (d, J=8.4 Hz, 2H, phenyl H-2' & H-6'), 8.23 (s, 1H, imidazo[4,5-b]pyridine H-5);

LC (Method B)-MS (ESI, m/z): Rt=4.09 min—577, 479 [(M+H)$^+$, Br isotopic pattern].

Example 136 tert-Butyl 4-(4-(6-chloro-7-(4-(pyridin-3-ylmethyl)piperazin-1-yl)-3H-imidazo[4,5-b]pyridin-2-yl)phenyl)piperazine-1-carboxylate

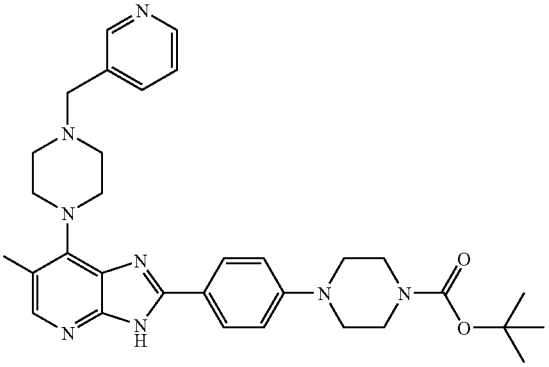

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-chloro-3-nitro-4-(4-(pyridin-3-ylmethyl)piperazin-1-yl)pyridin-2-amine (20 mg, 0.057 mmol), DMF (0.15 mL), ethanol (0.85 mL), 1M Na$_2$S$_2$O$_4$ (3 eq, 0.17 mmol, 0.17 mL) and 4-(4-formylphenyl)piperazine-1-carboxylic acid tert-butyl ester (1.1 eq, 0.063 mmol, 20 mg). After 6 h, concentration in vacuo and purification by preparative tlc (CH$_2$Cl$_2$-MeOH, 9:1) gave the product (11 mg, 41%) as a colourless solid; δ$_H$ (500 MHz, DMSO-d$_6$) 1.43 (s, 9H, C(CH$_3$)$_3$), 7.08 (d, J=9.0 Hz, 2H, phenyl H-3 & H-5), 7.55 (dd, J=8.5, 4.4 Hz, 1H, pyridine H-5), 7.99 (d, br, J=8.4 Hz, 1H, pyridine H-4), 8.03 (d, J=9.0 Hz, 2H, phenyl H-2 & H-6), 8.14 (s, 1H, imidazo[4,5-b]pyridine H-5), 8.69 (d, J=4.4 Hz, 1H, pyridine H-6), 8.75 (s, br, 1H, pyridine H-2), 13.36 (s, br, 1H, imidazo[4,5-b]pyridine NH);

LC (Method B)-MS (ESI, m/z): Rt=4.00 min—589, 591 [(M+H)$^+$, Cl isotopic pattern]. ESI-HRMS: Found: 589.2813, calculated for C$_{31}$H$_{37}$ClN$_8$O$_2$ (M+H)$^+$: 589.2806.

Example 137

6-Chloro-2-(4-(piperazin-1-yl)phenyl)-7-(4-(pyridin-3-ylmethyl)piperazin-1-yl)-3H-imidazo[4,5-b]pyridine

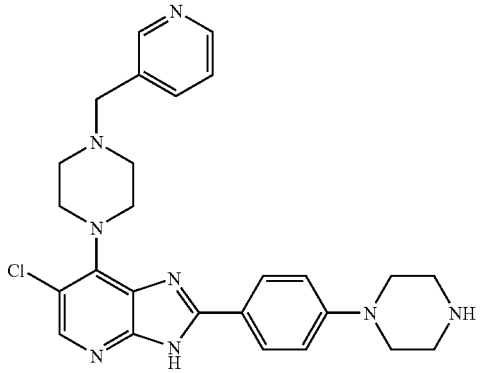

This was prepared using the same procedure as for (4-(6-bromo-7-(4-(pyridin-3-ylmethyl)piperazin-1-yl)-3H-imidazo[4,5-b]pyridin-2-yl)phenyl)methanamine, but here using tert-butyl 4-(4-(6-chloro-7-(4-(pyridin-3-ylmethyl)piperazin-1-yl)-3H-imidazo[4,5-b]pyridin-2-yl)phenyl)piperazine-1-carboxylate (10 mg, 0.0169 mmol), TFA (0.25 mL) and CH$_2$Cl$_2$ (1 mL). The same purification procedure gave the desired product (4 mg, 49%) as a pale yellow solid;

LC (Method A)-MS (ESI, m/z): Rt=2.68 min—489, 491 [(M+H)$^+$, Cl isotopic pattern]. ESI-HRMS: Found: 489.2288, calculated for C$_{26}$H$_{29}$ClN$_8$ (M+H)$^+$: 489.2282.

Example 138

2-(4-((1H-Pyrazol-1-yl)methyl)phenyl)-6-chloro-7-(4-(pyridin-3-ylmethyl)piperazin-1-yl)-3H-imidazo[4,5-b]pyridine

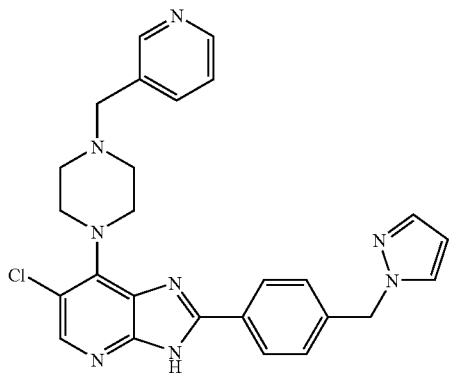

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-chloro-3-nitro-4-(4-(pyridin-3-ylmethyl)piperazin-1-yl)pyridin-2-amine (12.5 mg, 0.036 mmol), DMF (0.10 mL), ethanol (0.70 mL), 1M Na$_2$S$_2$O$_4$ (3 eq, 0.11 mmol, 0.11 mL) and 4-(1H-pyrazol-1-ylmethyl)benzaldehyde (1.1 eq, 0.039 mmol, 8 mg). After 6 h, concentration in vacuo and purification by preparative tlc (CH$_2$Cl$_2$-MeOH, 9:1) gave the product (5 mg, 29%) as a colourless solid; δ$_H$ (500 MHz, DMSO-d$_6$) 2.60 (s, br, 4H, piperazine N(CH$_2$)$_2$), 3.61 (s, 2H, NCH$_2$), 3.70 (s, br, 4H, piperazine N(CH$_2$)$_2$), 5.41 (s, br, 2H, PhCH$_2$), 6.30 (t, J=1.9 Hz, pyrazole H-4), 7.34 (d, J=8.4 Hz, 2H, phenyl H-3 & H-5), 7.37 (dd, J=7.6, 4.6 Hz, 1H, pyridine H-5), 7.49 (s, br, 1H, pyrazole H-3 or H-5), 7.78 (d, br, J=7.5 Hz, 1H, pyridine H-4), 7.86 (d, J=2.0 Hz, 1H, pyrazole H-3 or H-5), 8.11 (d, J=8.5 Hz, 2H, phenyl H-2 & H-6), 8.12 (s, 1H, imidazo[4,5-b]pyridine H-5), 8.49 (dd, J=4.7 Hz, 1H, pyridine H-6), 8.56 (s, br, 1H, pyridine H-2), 13.47 (s, br, 1H, imidazo[4,5-b]pyridine NH);

LC (Method B)-MS (ESI, m/z): Rt=3.02 min—485, 487 [(M+H)$^+$, Cl isotopic pattern]. ESI-HRMS: Found: 485.1969, calculated for C$_{26}$H$_{25}$ClN$_8$ (M+H)$^+$: 485.1969.

Example 139

5-Chloro-3-nitro-4-(4-(pyrimidin-5-ylmethyl)piperazin-1-yl)pyridin-2-amine

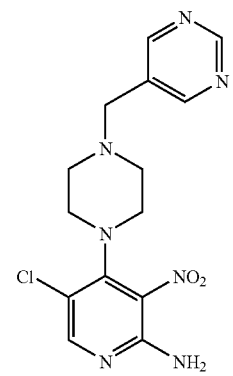

This was prepared using the same procedure as for 5-bromo-3-nitro-4-(4-(1-(pyridin-2-yl)ethyl)piperazin-1-yl)pyridin-2-amine, but here using tert-butyl 4-(pyrimidin-5-ylmethyl)piperazine-1-carboxylate (1.1 eq, 0.13 mmol, 35 mg), TFA (0.25 mL) and CH$_2$Cl$_2$ (1 mL), then 4,5-dichloro-3-nitropyridin-2-amine (37 mg, 0.11 mmol) in $^i$PrOH (1 mL) and DIPEA (0.25 mL). Filtration and washing as previously described gave the product (22 mg, 50% for two steps) as a yellow solid; δ$_H$ (500 MHz, DMSO-d$_6$) 2.52 (s, br, 4H, piperazine N(CH$_2$)$_2$), 3.07 (t, J=4.5 Hz, 4H, piperazine N(CH$_2$)$_2$), 3.60 (s, 2H, CH$_2$), 6.95 (s, br, 2H, NH$_2$), 8.06 (s, 1H, pyridine H-6), 8.75 (s, 2H, pyrimidine H-4 & H-6), 9.10 (s, 1H, pyrimidine H-2);

LC (Method B)-MS (ESI, m/z): Rt=1.89 min—350, 352 [(M+H)$^+$, Cl isotopic pattern]. ESI-HRMS: Found: 350.1133, calculated for C$_{14}$H$_{16}$ClN$_7$O$_2$ (M+H)$^+$: 350.1132.

6-Chloro-2-(4-methoxyphenyl)-7-(4-(pyrimidin-5-ylmethyl)piperazin-1-yl)-3H-imidazo[4,5-b]pyridine

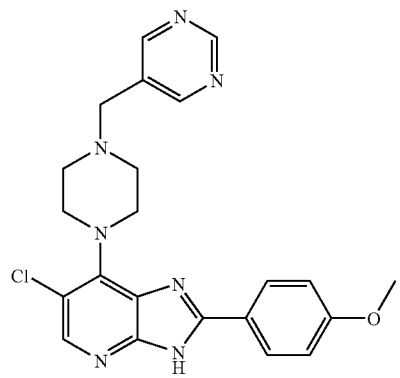

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-chloro-3-nitro-4-(4-(pyrimidin-5-ylmethyl)piperazin-1-yl)pyridin-2-amine (19 mg, 0.054 mmol), DMF (0.15 mL), ethanol (0.85 mL), 1M $Na_2S_2O_4$ (3 eq, 0.16 mmol, 0.16 mL) and 4-methoxybenzene carboxaldehyde (1.1 eq, 0.060 mmol, 8 mg). After 6 h, concentration in vacuo and purification by preparative tlc ($CH_2Cl_2$-MeOH, 95:5) gave the product (9 mg, 38%) as a pale yellow solid; $\delta_H$ (500 MHz, DMSO-$d_6$) 2.63 (s, br, 4H, piperazine $N(CH_2)_2$), 3.64 (s, 2H, $CH_2$), 3.70 (s, br, 4H, piperazine $N(CH_2)_2$), 3.84 (s, 3H, $CH_3$), 7.09 (d, J=8.8 Hz, 2H, methoxyphenyl H-2 & H-6), 8.08 (s, 1H, imidazo[4,5-b]pyridine H-5), 8.12 (d, J=8.8 Hz, 2H, methoxyphenyl H-3 & H-5), 8.80 (s, 2H, pyrimidine H-4 & H-6), 9.12 (s, 1H, pyrimidine H-2), 13.32 (s, br, 1H, imidazo[4,5-b]pyridine NH);

LC (Method A)-MS (ESI, m/z): Rt=4.85 min—436, 438 [(M+H)$^+$, Cl isotopic pattern]. ESI-HRMS: Found: 436.1646, calculated for $C_{22}H_{22}ClN_7O$ (M+H)$^+$: 436.1653.

Example 140 tert-Butyl 4-(4-(6-chloro-7-(4-(pyrimidin-5-ylmethyl)piperazin-1-yl)-3H-imidazo[4,5-b]pyridin-2-yl)benzyl)piperazine-1-carboxylate

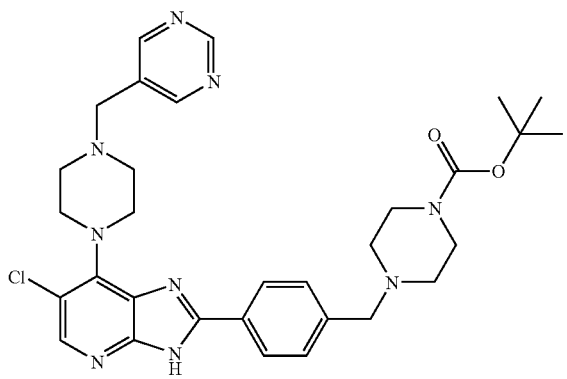

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-chloro-3-nitro-4-(4-(pyrimidin-5-ylmethyl)piperazin-1-yl)pyridin-2-amine (25 mg, 0.071 mmol), DMF (0.15 mL), ethanol (0.85 mL), 1M $Na_2S_2O_4$ (3 eq, 0.21 mmol, 0.21 mL) and tert-butyl 4-(4-formylbenzyl)piperazine-1-carboxylate (1.2 eq, 0.085 mmol, 28 mg). After 6 h, concentration in vacuo and purification by preparative tlc ($CH_2Cl_2$-MeOH, 95:5) gave the product (19 mg, 44%) as a colourless solid; $\delta_H$ (500 MHz, DMSO-$d_6$) 1.39 (s, 9H, $C(CH_3)_3$), 2.34 (t, J=4.9 Hz, 4H, piperazine $N(CH_2)_2$), 2.64 (t, J=4.4 Hz, 4H, piperazine $N(CH_2)_2$), 3.32 (s, br, 4H, piperazine $N(CH_2)_2$), 3.55 (s, 2H, $NCH_2$), 3.65 (s, 2H, $NCH_2$), 3.71 (s, br, 4H, piperazine $N(CH_2)_2$), 7.46 (d, J=8.2 Hz, 2H, phenyl H-3 & H-5), 8.11 (s, 1H, imidazo[4,5-b]pyridine H-5), 8.13 (d, J=8.1 Hz, 2H, phenyl H-2 & H-6), 8.80 (s, 2H, pyrimidine H-4 & H-6), 9.12 (s, 1H, pyrimidine H-2), 13.34 (s, br, 1H, imidazo[4,5-b]pyridine NH);

LC (Method B)-MS (ESI, m/z): Rt=2.65 min—604, 606 [(M+H)$^+$, Cl isotopic pattern]. ESI-HRMS: Found: 604.2919, calculated for $C_{31}H_{38}ClN_9O_2$ (M+H)$^+$: 604.2915.

Example 141

6-Chloro-2-(4-(piperazin-1-ylmethyl)phenyl)-7-(4-(pyrimidin-5-ylmethyl)piperazin-1-yl)-3H-imidazo[4,5-b]pyridine

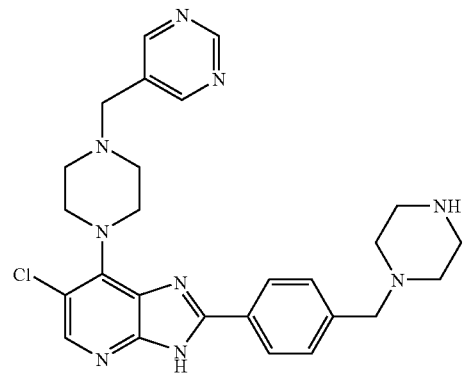

This was prepared using the same procedure as for (4-(6-bromo-7-(4-(pyridin-3-ylmethyl)piperazin-1-yl)-3H-imidazo[4,5-b]pyridin-2-yl)phenyl)methanamine, but here using tert-butyl 4-(4-(6-chloro-7-(4-(pyrimidin-5-ylmethyl)piperazin-1-yl)-3H-imidazo[4,5-b]pyridin-2-yl)benzyl)piperazine-1-carboxylate (15 mg, 0.025 mmol), TFA (0.2 mL) and $CH_2Cl_2$ (1 mL). The same purification procedure gave the desired product (7 mg, 56%) as a pale yellow solid; $\delta_H$ (500 MHz, DMSO-$d_6$) 2.32 (s, br, 4H, piperazine $N(CH_2)_2$), 2.64 (s, br, 4H, piperazine $N(CH_2)_2$), 2.72 (t, J=4.6 Hz, 4H, piperazine $N(CH_2)_2$), 3.50 (s, 2H, $NCH_2$), 3.64 (s, 2H, $NCH_2$), 3.70 (t, J=4.5 Hz, 4H, piperazine $N(CH_2)_2$), 7.45 (d, J=8.2 Hz, 2H, phenyl H-3 & H-5), 8.11 (s, 1H, imidazo[4,5-b]pyridine H-5), 8.12 (d, J=8.3 Hz, 2H, phenyl H-2 & H-6), 8.80 (s, 2H, pyrimidine H-4 & H-6), 9.12 (s, 1H, pyrimidine H-2);

LC (Method B)-MS (ESI, m/z): Rt=1.90 min—504, 506 [(M+H)$^+$, Cl isotopic pattern].

Example 142

5-Chloro-3-nitro-4-(4-(1-(pyridin-4-yl)ethyl)piperazin-1-yl)pyridin-2-amine

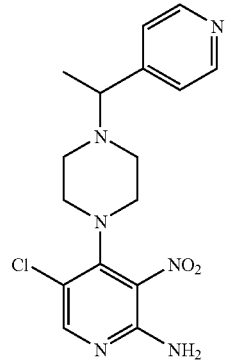

This was prepared using the same procedure as for 2-(4-(2-amino-5-bromo-3-nitropyridin-4-yl)piperazin-1-yl)-N-(thiazol-2-yl)acetamide, but here using 4,5-dichloro-3-nitropyridin-2-amine (22 mg, 0.106 mmol), $^i$PrOH (1 mL), DIPEA (0.2 mL) and 1-(1-(pyridin-4-yl)ethyl)piperazine.3× HCl (1.1 eq, 0.116 mmol, 35 mg). Filtration and washing as previously described gave the product (28 mg, 73%) as a yellow solid; $\delta_H$ (500 MHz, DMSO-$d_6$) 1.30 (d, J=6.7 Hz, 3H, CHCH$_3$), 2.42 (s, br, 2H, piperazine NCH$_2$), 2.53 (s, br, 2H, piperazine NCH$_2$), 3.05 (s, br, 4H, piperazine N(CH$_2$)$_2$), 3.54 (q, J=6.8 Hz, 1H, CHCH$_3$), 6.94 (s, br, 2H, NH$_2$), 7.34 (d, J=6.0 Hz, 2H, pyridine H-2 & H-6), 8.04 (s, 1H, chloropyridine H-6), 8.51 (d, J=6.0 Hz, 2H, pyridine H-3 & H-5);

LC (Method B)-MS (ESI, m/z): Rt=2.00 min—363, 365 [(M+H)$^+$, Cl isotopic pattern]. ESI-HRMS: Found: 363.1336, calculated for $C_{16}H_{19}ClN_6O_2$ (M+H)$^+$: 363.1136.

6-Chloro-2-(4-methoxyphenyl)-7-(4-(1-(pyridin-4-yl)ethyl)piperazin-1-yl)-3H-imidazo[4,5-b]pyridine

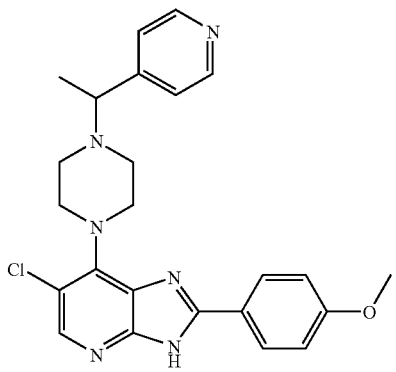

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-chloro-3-nitro-4-(4-(1-(pyridin-4-yl)ethyl)piperazin-1-yl)pyridin-2-amine (19 mg, 0.052 mmol), DMF (0.15 mL), ethanol (0.85 mL), 1M Na$_2$S$_2$O$_4$ (3 eq, 0.16 mmol, 0.16 mL) and 4-methoxybenzene carboxaldehyde (1.1 eq, 0.058 mmol, 8 mg). After 6 h, concentration in vacuo and purification by preparative tlc (CH$_2$Cl$_2$-MeOH, 95:5) gave the product (10 mg, 42%) as a colourless solid; $\delta_H$ (500 MHz, DMSO-$d_6$) 1.35 (d, J=6.7 Hz, 3H, CHCH$_3$), 2.52-2.55 (m, 2H, piperazine NCH$_2$), 2.63-2.66 (m, 2H, piperazine NCH$_2$), 3.58 (q, J=6.7 Hz, CHCH$_3$), 3.68 (s, br, 4H, piperazine N(CH$_2$)$_2$), 3.84 (s, 3H, OCH$_3$), 7.10 (d, J=8.9 Hz, 2H, methoxyphenyl H-2 & H-6), 7.39 (d, J=6.0 Hz, 2H, pyridine H-3 & H-5), 8.06 (s, 1H, imidazo[4,5-b]pyridine H-5), 8.11 (d, J=8.9 Hz, 2H, methoxyphenyl H-3 & H-5), 8.54 (d, J=6.0 Hz, 2H, pyridine H-2 & H-6), 13.30 (s, br, 1H, imidazo[4,5-b]pyridine NH);

LC (Method A)-MS (ESI, m/z): Rt=4.85 min—449, 451 [(M+H)$^+$, Cl isotopic pattern]. ESI-HRMS: Found: 449.1859, calculated for $C_{24}H_{25}ClN_6O$ (M+H)$^+$: 449.1857.

Example 143

5-Chloro-4-(4-ethylpiperazin-1-yl)-3-nitropyridin-2-amine

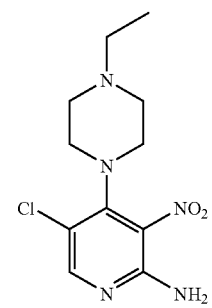

This was prepared using the same procedure as for 2-(4-(2-amino-5-bromo-3-nitropyridin-4-yl)piperazin-1-yl)-N-(thiazol-2-yl)acetamide, but here using 4,5-dichloro-3-nitropyridin-2-amine (75 mg, 0.36 mmol), $^i$PrOH (2 mL), DIPEA (3.5 eq, 1.26 mmol, 0.22 mL) and 1-ethylpiperazine (1.2 eq, 0.43 mmol, 0.05 mL). Concentration in vacuo and purification by preparative tlc (CH$_2$Cl$_2$-MeOH, 95:5) gave the product (32 mg, 31%) as a yellow solid;

LC (Method B)-MS (ESI, m/z): Rt=0.70 min—286, 288 [(M+H)$^+$, Cl isotopic pattern]. ESI-HRMS: Found: 286.1072, calculated for $C_{11}H_{16}ClN_5O_2$ (M+H)$^+$: 286.1071.

2-(4-((1H-pyrazol-1-yl)methyl)phenyl)-6-chloro-7-(4-ethylpiperazin-1-yl)-3H-imidazo[4,5-b]pyridine

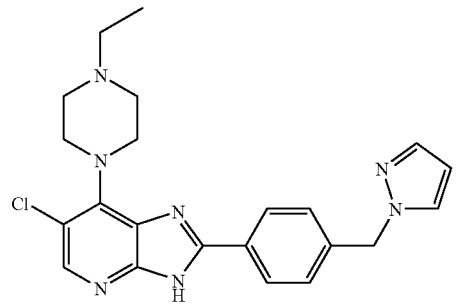

This was prepared using the same procedure as for 4-(6-bromo-2-(4-(dimethylamino)phenyl)-3H-imidazo[4,5-b]pyridin-7-yl)-N-phenylpiperazine-1-carboxamide, but here using 5-chloro-4-(4-ethylpiperazin-1-yl)-3-nitropyridin-2-amine (25 mg, 0.087 mmol), DMF (0.15 mL), ethanol (0.85 mL), 1M Na$_2$S$_2$O$_4$ (3 eq, 0.26 mmol, 0.26 mL) and 4-(1H-pyrazol-1-ylmethyl)benzaldehyde (1.1 eq, 0.096 mmol, 18 mg). After 6 h, concentration in vacuo and purification by preparative tlc (CH$_2$Cl$_2$-MeOH, 9:1) gave the product (9 mg, 24%) as a colourless solid; $\delta_H$ (500 MHz, DMSO-$d_6$) 1.06 (t, J=7.2 Hz, 3H, NCH$_2$CH$_3$), 2.40 (q, J=7.1 Hz, 2H, NCH$_2$CH$_3$), 2.58 (t, br, J=3.8 Hz, 4H, piperazine N(CH$_2$)$_2$), 3.70 (t, J=3.9 Hz, 4H, piperazine N(CH$_2$)$_2$), 5.42 (s, br, 2H, PhCH$_2$), 6.30 (t, J=2.1 Hz, 1H, pyrazole H-4), 7.35 (d, J=8.3 Hz, 2H, phenyl H-2 & H-6), 7.49 (d, J=1.5 Hz, 1H, pyrazole H-3 or H-5), 7.86 (d, J=2.2 Hz, 1H, pyrazole H-3 or H-5), 8.10 (s, 1H, imidazo[4,5-b]pyridine H-5), 8.13 (d, J=8.2 Hz, 2H, phenyl H-3 & H-5);

LC (Method B)-MS (ESI, m/z): Rt=2.72 min—422, 424 [(M+H)$^+$, Cl isotopic pattern].

Example 144 tert-Butyl 4-((2-methylthiazol-4-yl)methyl)piperazine-1-carboxylate

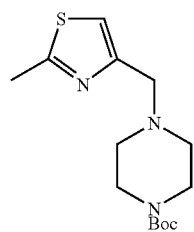

4-(Chloromethyl)-2-methyl-thiazole (0.590 g, 3.18 mmol, 1 eq) was suspended in DCM (5 mL). DIPEA (1.39 mL, 7.95 mmol, 2.5 eq) was added dropwise, followed by N-Boc-piperazine (1.300 g, 7.0 mmol, 2.2 eq). The mixture was stirred at 35° C. for 5 h, then diluted with EtOAc, and washed with H$_2$O and brine. The organic layer was separated, dried (MgSO$_4$) and the solvent removed in vacuo. The crude product was purified by column chromatography on a Biotage SP1 system (DCM/EtOAc; v/v 1:1) to give the title compound (0.940 g, 99%); $^1$H-NMR (500 MHz, CDCl$_3$): δ 1.47 (s, 9H, C(CH$_3$)$_3$), 2.47 (t, 4H, J=4.5 Hz, piperazine N(CH$_2$)$_2$), 2.73 (s, 3H, Me), 3.48 (t, 4H, J=4.5 Hz, piperazine N(CH$_2$)$_2$), 3.64 (s, 2H, NCH$_2$), 6.96 (s, 1H, thiazole 5-H); LC (Method B)-MS (ESI, m/z): Rt=1.96 min—298 [(M+H)$^+$, 100%].

5-Bromo-4-(4-((2-methylthiazol-4-yl)methyl)piperazin-1-yl)-3-nitropyridin-2-amine

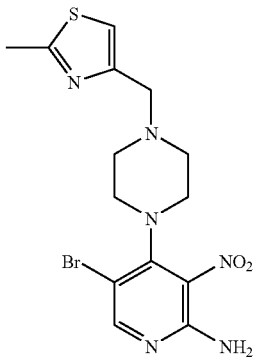

tert-Butyl 4-((2-methylthiazol-4-yl)methyl)piperazine-1-carboxylate (1.00 g, 3.36 mmol, 1.1 eq) was dissolved in DCM (12 mL) and the mixture cooled in a ice-water bath before the dropwise addition of TFA (12 mL). Stirring was continued at this temperature for 1 h and the solvents were removed in vacuo. The resulting crude material was azeotroped with toluene and dried.

LC (Method B)-MS (ESI, m/z): Rt=0.50 min—198 [(M+H)$^+$, 100%]. Half of this material (i.e. 2-methyl-4-(piperazin-1-ylmethyl)thiazole; supposedly 0.331 g, 1.68 mmol, 0.55 eq) was suspended in $^i$PrOH (3.3 mL) and DIPEA (1.3 mL). To this solution, 5-bromo-4-chloro-3-nitropyridin-2-amine (0.390 g, 1.53 mmol, 0.45 eq) was added and the mixture heated and stirred for 17 h at 60° C. The mixture was filtered, washed with $^i$PrOH (3×3 mL), cold H$_2$O (3×3 mL), Et$_2$O (2×3 mL), and dried to give the title compound (0.380 g, 55%); $^1$H-NMR (500 MHz, DMSO-d$_6$): δ 2.50-2.70 (m, 7H, piperazine N(CH$_2$)$_2$ and Me), 3.07 (br s, 4H, piperazine N(CH$_2$)$_2$), 3.60 (s, 2H, NCH$_2$), 6.98 (br s, 2H, NH$_2$), 7.29 (s, 1H. thiazole 5-H), 8.17 (s, 1H, pyridine 6-H); LC (Method B)-MS (ESI, m/z): Rt-2.00 min—413/415 [(M+H$^+$), Br isotopic pattern, 100%].

4-((4-(6-Bromo-2-(4-methoxyphenyl)-3H-imidazo[4,5-b]pyridin-7-yl)piperazin-1-yl)methyl)-2-methylthiazole

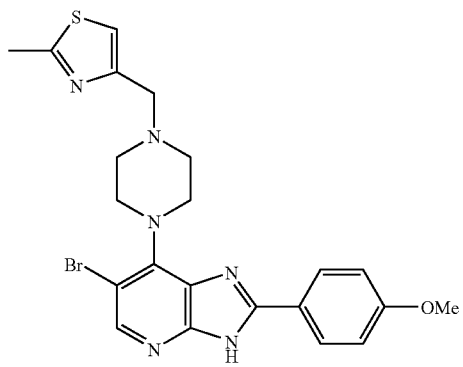

To a mixture of 5-bromo-4-(4-((2-methylthiazol-4-yl)methyl)piperazin-1-yl)-3-nitropyridin-2-amine (0.062 g, 0.15 mmol), ethanol (0.85 mL), DMF (0.15 mL) and 4-methoxybenzaldehyde (0.022 g, 0.165 mmol) was added a freshly prepared aqueous solution of Na$_2$S$_2$O$_4$ (1M; 0.45 mL, 0.45 mmol). The reaction mixture was heated at 85° C. for 17 h, then allowed to cool to room temperature and the solvents were removed in vacuo. The residue was absorbed on preparative silica TLC plates, which were eluted with dichloromethane/methanol (v/v; 9:1). The isolated compound was further purified by column chromatography on a Biotage SP1 system eluting with methanol (2-10%) in dichloromethane. The title compound was obtained as a yellow solid after trituration with diethyl ether (0.010 g, 13%); $^1$H-NMR (500 Mz, DMSO-d$_6$): δ 2.62-2.73 (m, 4H, piperazine N(CH$_2$)$_2$), 3.18 (s, 3H, Me), 3.60-3.74 (m, 4H, piperazine N(CH$_2$)$_2$), 3.85 (s, 3H, OMe), 4.00-4.20 (br s, 2H, NCH$_2$), 7.11 (d, J=8.5 Hz, 2H, ArH), 7.33 (s, 1H, thiazole 5-H), 8.15 (d, J=9.0 Hz, 2H, ArH), 8.21 (s, 1H, imidazo[4,5-b]pyridine 5-H); LC (Method B)-MS (ESI, m/z) 3.14 min—499/501 [(M+H)$^+$, Br isotopic pattern]. ESI-HRMS: Found: 499.0916, calculated for $C_{22}H_{23}BrN_6OS$ (M+H)+: 499.0915.

Example 145 tert-Butyl 4-((2-isopropyloxazol-4-yl)methyl)piperazine-1-carboxylate

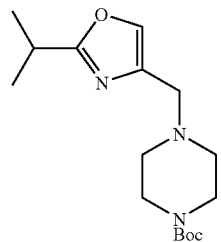

4-(Chloromethyl)-2-isopropyloxazole (0.920 g, 5.75 mmol, 1 eq) was suspended in DCM (9 mL). DIPEA (2.5 mL, 14.4 mmol, 2.5 eq) was added dropwise, followed by N-Boc-piperazine (2.350 g, 12.6 mmol, 2.2 eq). The reaction mixture was stirred at 35° C. for 17 h, then diluted with EtOAc, washed with $H_2O$, and brine. The organic layer was separated, dried (MgSO$_4$) and the solvent removed in vacuo. The crude product was purified by column chromatography on a Biotage SP1 system (DCM/EtOAc; v/v 1:1) to give the title compound (1.760 g, 99%); $^1$H-NMR (500 MHz, CDCl$_3$): δ 1.33 (d, J=5.5 Hz, 6H, $^i$Pr—CH$_3$), 1.45 (s, 9H, C(CH$_3$)$_3$), 2.45 (br t, J=4.8 Hz, 4H, piperazine N(CH$_2$)$_2$), 3.07 (m, 1H, $^i$Pr—CH), 3.41-3.50 (m, 6H, piperazine N(CH$_2$)$_2$ and NCH$_2$), 7.41 (s, 1H, oxazole 5-H); LC (Method B)-MS (ESI, m/z): Rt=2.51 min—310 [(M+H)+, 100%].

5-Bromo-4-(4-((2-isopropyloxazol-4-yl)methyl)piperazin-1-yl)-3-nitropyridin-2-amine

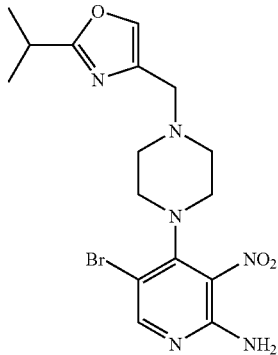

tert-Butyl 4-((2-isopropyloxazol-4-yl)methyl)piperazine-1-carboxylate (0.400 g, 1.29 mmol, 1.1 eq) was dissolved in DCM (5 mL) and the mixture cooled in a ice-water bath before the dropwise addition of TFA (5 mL). Stirring was continued at this temperature for 1 h and the solvents were removed in vacuo. The resulting crude material was azeotroped with toluene and dried. The resulting 2-isopropyl-4-(piperazin-1-ylmethyl)oxazole (supposedly 0.270 g, 1.29 mmol, 1 eq) was suspended in $^i$PrOH (2.5 mL) and DIPEA (1.0 mL). To this solution, the 5-bromo-4-chloro-3-nitropyridin-2-amine (0.300 g, 1.17 mmol, 0.91 eq) was added, and the mixture heated and stirred for 17 h at 60° C. The mixture was filtered, washed with $^i$PrOH (3×3 mL), cold $H_2O$ (3×3 mL), Et$_2$O (2×3 mL) and dried to give the title compound as a bright yellow solid (0.290 g, 53%); $^1$H-NMR (500 MHz, DMSO-d$_6$): δ 1.26 (d, J=7.0 Hz, 6H, $^i$Pr—CH$_3$), 2.52-2.64 (br s, 4H, piperazine N(CH$_2$)$_2$), 2.98-3.12 (m, 5H, piperazine N(CH$_2$)$_2$ and $^i$Pr—CH), 3.40 (s, 2H, NCH$_2$), 6.98 (s, 2H, NH$_2$), 7.84 (s, 1H, oxazole 5-H), 8.16 (s, 1H, pyridine 6-H); LC (Method B)-MS (ESI, m/z): R=2.46 min—425/427 [(M+H)+, Br isotopic pattern, 100%].

4-((4-(6-bromo-2-(4-methoxyphenyl)-3H-imidazo[4,5-b]pyridin-7-yl)piperazin-1-yl)methyl)-2-isopropyloxazole

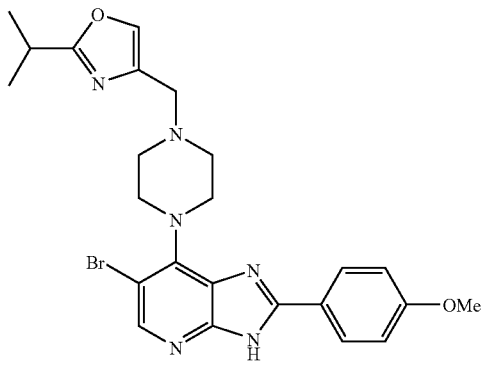

To a mixture of 5-bromo-4-(4-((2-isopropyloxazol-4-yl)methyl)piperazin-1-yl)-3-nitropyridin-2-amine (0.070 g, 0.16 mmol), EtOH (3 mL), and p-anisaldehyde (0.025 g, 0.18 mmol) in EtOH (1 mL) was added followed by a freshly prepared aqueous solution of Na$_2$S$_2$O$_4$ (1M; 0.49 mL, 0.49 mmol). The reaction mixture was heated at 85° C. for 5 h, then allowed to cool to room temperature and the solvents were removed in vacuo. The residue was absorbed on preparative silica TLC plates, which were eluted with dichloromethane/ethyl acetate (v/v; 1:1). The title compound was isolated as a pale yellow solid (0.019 g, 23%) after trituration with diethyl ether; $^1$H-NMR (500 Mz, DMSO-d$_6$): δ 1.27 (d, J=7 Hz, 6H, $^i$Pr—CH$_3$), 2.65 (m, 4H, piperazine N(CH$_2$)$_2$), 3.05 (m, 1H, $^i$Pr—CH), 3.44 (s, 2H, NCH$_2$), 3.65 (m, 4H, piperazine N(CH$_2$)$_2$), 3.84 (s, 3H, OMe), 7.10 (d, J=7.5 Hz, 2H, ArH), 7.86 (s, 1H, oxazole 5-H), 8.13 (d, J=9.0 Hz, 2H, ArH), 8.20 (s, 1H, imidazo[4,5-b]pyridine 5-H), 13.30 (br s, 1H, imidazo[4,5-b]pyridine N—H); LC (Method B)-MS (ESI, m/z) 3.45 min—511/514 [(M+H)$^+$, Br isotopic pattern]. ESI-HRMS: Found: 511.1457, calculated for $C_{24}H_{28}BrN_6O_2$ (M+H)$^+$: 511.1457.

Example 146

4-(4-(6-Bromo-7-(4-((2-isopropyloxazol-4-yl)methyl)piperazin-1-yl)-3H-imidazo[4,5-b]pyridin-2-yl)benzyl)morpholine

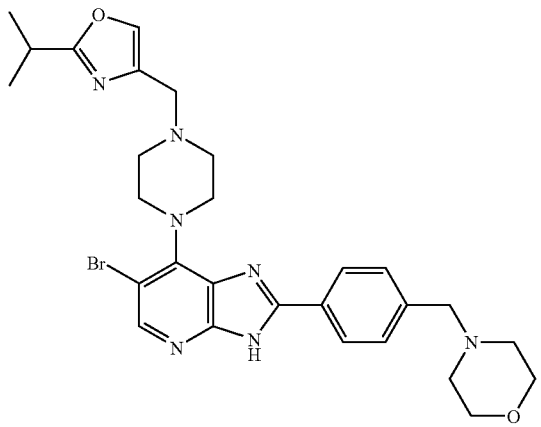

To a mixture of 5-bromo-4-(4-((2-isopropyloxazol-4-yl)methyl)piperazin-1-yl)-3-nitropyridin-2-amine (0.065 g, 0.15 mmol), EtOH (0.85 mL), and DMF (0.15 mL), was added 4-(morpholinomethyl)benzaldehyde (0.040 g, 0.19 mmol) followed by a freshly prepared aqueous solution of $Na_2S_2O_4$ (1M; 0.49 mL, 0.49 mmol). The reaction mixture was heated at 85° C. for 24 h, then allowed to cool to room temperature and the solvents were removed in vacuo. The residue was purified by column chromatography on a Biotage SP1 system eluting with methanol (10-30%) in ethyl acetate. The title compound was isolated as a pale yellow solid (0.002 g, 2.4%) after trituration with ether; $^1$H-NMR (500 Mz, DMSO-d$_6$): δ 1.27 (d, J=7 Hz, 6H, $^i$Pr—CH$_3$), 2.38 (m, 4H), 2.65 (m, 4H), 3.05 (m, 1H, $^i$Pr—CH), 3.44 (s, 2H, NCH$_2$), 3.54 (s, 2H, NCH$_2$), 3.59 (t, J=4.5 Hz, 4H), 3.66 (m, 4H), 7.47 (d, J=7.5 Hz, 2H, ArH), 7.87 (s, 1H, oxazole 5-H), 8.14 (d, J=8.0 Hz, 2H, ArH), 8.23 (s, 1H, imidazo[4,5-b]pyridine 5-H), 13.49 (br s, 1H, imidazo[4,5-b]pyridine N—H); LC (Method B)-MS (ESI, m/z) 2.43 min—580/582 [(M+H)$^+$, Br isotopic pattern]. ESI-HRMS: Found: 580.2036, calculated for $C_{28}H_{35}BrN_7O_2$ (M+H)$^+$: 580.2035.

Example 147

5-Bromo-4-(4-(4-fluorobenzyl)piperazin-1-yl)-3-nitropyridin-2-amine

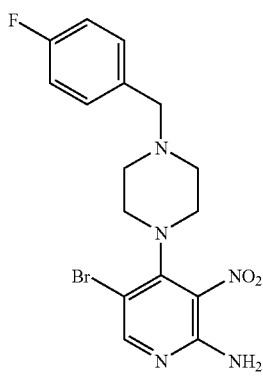

1-(4-Fluorobenzyl)piperazine (0.160 g, 0.81 mmol, 1.05 eq) was suspended in iPrOH (8 mL) and DIPEA (0.72 mL). To this solution, the 5-bromo-4-chloro-3-nitropyridin-2-amine (0.19 g, 0.77 mmol, 1 eq) was added and the reaction mixture was heated and stirred for 17 h at 60° C. The mixture was filtered, washed with $^i$PrOH (3×3 mL), Et$_2$O (2×3 mL) and dried to give the title compound as a bright yellow solid (0.250 g, 75%); $^1$H-NMR (500 MHz, DMSO-d$_6$): δ 2.43-2.55 (m, 4H, piperazine N(CH$_2$)$_2$), 3.05 (m, 4H, piperazine N(CH$_2$)$_2$), 3.51 (s, 2H, NCH$_2$), 6.96 (br s, 2H, NH$_2$), 7.14 (t, J=9.0 Hz, 2H, ArH), 7.35 (dd, J=8.5, 6.0 Hz, 2H, ArH), 8.15 (s, 1H, pyridine 6-H). LC (Method B)-MS (ESI, m/z): Rt=2.52 min—410/412 [(M+H$^+$), Br isotopic pattern, 100%].

6-Bromo-7-(4-(4-fluorobenzyl)piperazin-1-yl)-2-(4-methoxyphenyl)-3H-imidazo[4,5-b]pyridine

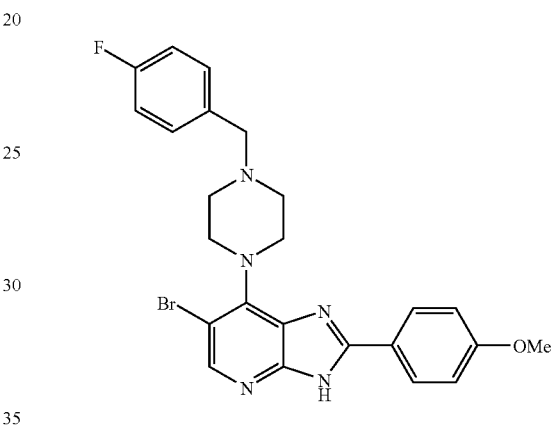

To a mixture of 5-bromo-4-(4-(4-fluorobenzyl)piperazin-1-yl)-3-nitropyridin-2-amine (0.120 g, 0.30 mmol) and EtOH (5 mL), was added p-anisaldehyde (0.045 g, 0.33 mmol) in EtOH (1.8 mL), followed by a freshly prepared aqueous solution of $Na_2S_2O_4$ (1M; 0.9 mL, 0.9 mmol). The reaction mixture was heated at 85° C. for 24 h, then allowed to cool to room temperature and the solvents were removed in vacuo. The residue was absorbed on silica gel and purified by column chromatography on a Biotage SP1 system eluting with methanol (2-10%) in dichloromethane. The title compound was isolated as a pale yellow solid after trituration with diethyl ether (0.010 g, 7%); $^1$H-NMR (500 Mz, DMSO-d$_6$): δ 2.60 (m, 4H, piperazine N(CH$_2$)$_2$), 3.56 (s, 2H, NCH$_2$), 3.65 (m, 4H, piperazine N(CH$_2$)$_2$), 3.84 (s, 3H, OMe), 7.10 (d, J=7.0 Hz, 2H, ArH, C$_6$H$_4$—OMe), 7.17 (br t, J=9.0 Hz, 2H, ArH, C$_6$H$_4$—F), 7.40 (br dd, J=8.5, 6.0 Hz, 2H, ArH, C$_6$H$_4$—F), 8.13 (d, J=9.0 Hz, 2H, ArH, C$_6$H$_4$—OMe), 8.20 (s, 1H, imidazo[4,5-b]pyridine 5-H), 13.34 (br s, 1H, imidazo[4,5-b]pyridine N—H); LC (Method B)-MS (ESI, m/z) 3.58 min—496/498 [(M+H)$^+$, Br isotopic pattern]. ESI-HRMS: Found: 496.1144, calculated for $C_{24}H_{24}BrFN_5O$ (M+H)$^+$: 496.1148.

Example 148

4-(4-(6-Bromo-7-(4-(4-fluorobenzyl)piperazin-1-yl)-3H-imidazo[4,5-b]pyridin-2-yl)benzyl)morpholine

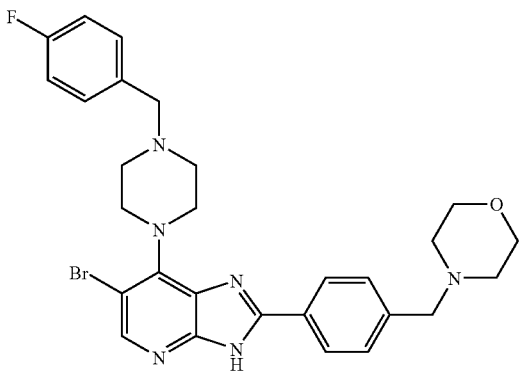

To a mixture of 5-bromo-4-(4-(4-fluorobenzyl)piperazin-1-yl)-3-nitropyridin-2-amine (0.12 g, 0.30 mmol) and EtOH (5 mL), 4-(morpholinomethyl)benzaldehyde (0.068, 0.33 mmol) in EtOH (1.8 mL) was added followed by a freshly prepared aqueous solution of $Na_2S_2O_4$ (1M; 0.9 mL, 0.9 mmol). The reaction mixture was heated at 85° C. for 24 h, then allowed to cool to room temperature and the solvents were removed in vacuo. The residue was absorbed on silica gel and purified by column chromatography on a Biotage SP1 system eluting with methanol (2-10%) in dichloromethane. The title compound was isolated as a pale yellow solid after trituration with diethyl ether (0.013 g, 7.6%); $^1$H-NMR (500 Mz, DMSO-$d_6$): δ 2.38 (m, 4H), 2.60 (m, 4H), 3.54 (s, 2H, NCH$_2$), 3.56 (s, 2H, NCH$_2$), 3.59 (t, J=4.5 Hz, 4H), 3.66 (m, 4H), 7.17 (d, J=8.5 Hz, 2H, ArH, C$_6$H$_4$—F), 7.40 (br dd, J=8.5, 6.0 Hz, 2H, ArH, C$_6$H$_4$—F), 7.47 (d, J=8.0 Hz, 2H, ArH), 8.14 (d, J=8.0 Hz, 2H, ArH), 8.23 (s, 1H, imidazo[4,5-b]pyridine 5-H), 13.47 (br s, 1H, imidazo[4,5-b]pyridine N—H); LC (Method B)-MS (ESI, m/z) 2.33 min—565/567 [(M+H)$^+$, Br isotopic pattern]. ESI-HRMS: Found: 565.1725, calculated for $C_{28}H_{31}BrFN_6O$ (M+H)$^+$: 565.1727.

Example 149 tert-Butyl 4-(cyclobutylmethyl)piperazine-1-carboxylate

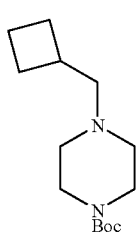

Bromomethylcyclobutane (0.200 g, 1.34 mmol, 1 eq) was suspended in DCM (2 mL). DIPEA (0.59 mL, 3.35 mmol, 2.5 eq) was added dropwise, followed by N-Boc-piperazine (0.550 g, 2.95 mmol, 2.2. eq), and the reaction mixture was stirred at 35° C. for 2 h. The crude product was purified by column chromatography on a Biotage SP1 system (DCM/EtOAc; v/v 1:1) to give the title compound (0.030 g, 8.8%); $^1$H-NMR (500 MHz, CDCl$_3$): δ 1.46 (s, 9H, C(CH$_3$)$_3$), 1.64-1.74 (m, 2H), 1.76-1.96 (m, 2H), 2.02-2.12 (m, 2H), 2.37 (t, J=5.0 Hz, 4H, piperazine N(CH$_2$)$_2$), 2.43 (d, J=7.0 Hz, 2H, NCH$_2$), 2.55 (m, 1H, cyclobutyl CH), 3.43 (t, J=5.0 Hz, 4H, piperazine N(CH$_2$)$_2$); GC-MS (Cl, m/z): Rt=3.77 min—255 [(M+H)$^+$, 100%].

5-Bromo-4-(4-(cyclobutylmethyl)piperazin-1-yl)-3-nitropyridin-2-amine

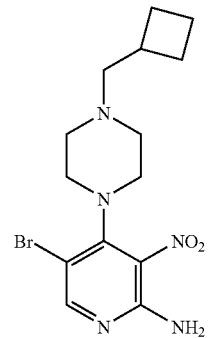

tert-Butyl 4-(cyclobutylmethyl)piperazine-1-carboxylate (0.140 g, 0.56 mmol, 1.0 eq) was dissolved in DCM (2 mL) and the mixture cooled in a ice-water bath before the dropwise addition of TFA (2 mL). Stirring was continued at this temperature for 1 h, and the solvents were removed in vacuo. The resulting crude material was azeotroped with toluene and dried.

The resulting 1-(cyclobutylmethyl)piperazine (supposedly 0.086 g, 0.56 mmol, 1 eq) was suspended in $^i$PrOH (0.55 mL) and DIPEA (0.22 mL). To this solution, 5-bromo-4-chloro-3-nitropyridin-2-amine (0.14 g, 0.56 mmol, 1 eq) was added and the reaction mixture was heated and stirred for 17 h at 60° C. The mixture was filtered, washed with $^i$PrOH (3×3 mL), Et$_2$O (2×3 mL), and dried to give the title compound as a bright yellow powder (0.093 g, 45%); $^1$H-NMR (500 MHz, DMSO-$d_6$): δ 1.73-1.92 (m, 2H), 1.96-2.05 (m, 2H), 2.37 (d, J=7.0 Hz, 2H, piperazine N(CH$_2$)$_2$), 2.41-2.54 (m, 5H), 3.02 (m, 4H), 6.95 (s, 2H, NH$_2$), 8.15 (s, 1H, pyridine 6-H); LC (Method B)-MS (ESI, m/z): Rt=2.02 min—370/372 [(M+H$^+$), Br isotopic pattern, 100%].

6-Bromo-7-(4-(cyclobutylmethyl)piperazin-1-yl)-2-(4-methoxyphenyl)-3H-imidazo[4,5-b]pyridine

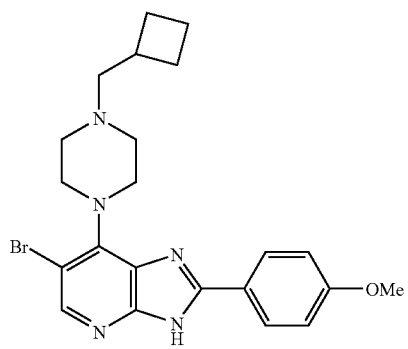

To a mixture of 5-bromo-4-(4-(cyclobutylmethyl)piperazin-1-yl)-3-nitropyridin-2-amine (0.036 g, 0.097 mmol) and EtOH (1 mL) was added p-anisaldehyde (0.015 g, 0.11 mmol) in EtOH (1.2 mL) followed by a freshly prepared aqueous solution of $Na_2S_2O_4$ (1M; 0.29 mL, 0.29 mmol). The reaction mixture was heated at 85° C. for 24 h, then allowed to cool to room temperature and the solvents were removed in vacuo. The residue was absorbed on silica gel and purified by column chromatography on a Biotage SP1 system eluting with methanol (2-10%) in dichloromethane. The title compound was isolated as a pale yellow solid after trituration with diethyl ether (0.016 g, 37%); $^1$H-NMR (500 Mz, DMSO-$d_6$): δ 1.63-1.73 (m, 2H), 1.77-1.93 (m, 2H), 2.00-2.10 (m, 2H), 2.42 (d, J=7.0 Hz, 2H, $NCH_2$), 2.52-2.60 (m, 4H, piperazine $N(CH_2)_2$), 3.62 (m, 4H, piperazine $N(CH_2)_2$), 3.84 (s, 3H, OMe), 7.10 (d, J=9.0 Hz, 2H, ArH, $C_6H_4$—OMe), 8.13 (d, J=8.5 Hz, 2H, ArH, $C_6H_4$—OMe), 8.20 (s, 1H, imidazo[4,5-b]pyridine 5-H), 13.34 (br s, 1H, imidazo[4,5-b]pyridine N—H); LC (Method B)-MS (ESI, m/z) 3.29 min—456/458 [(M+H)$^+$, Br isotopic pattern]. ESI-HRMS: Found: 456.1395, calculated for $C_{22}H_{27}BrN_5O$ (M+H)$^+$: 456.1399.

Example 150

4-(4-(6-Bromo-7-(4-(cyclobutylmethyl)piperazin-1-yl)-3H-imidazo[4,5-b]pyridin-2-yl)benzyl)morpholine

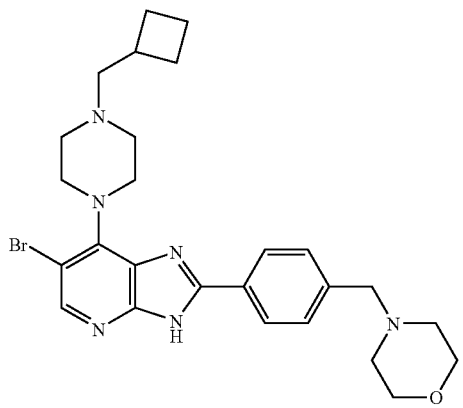

To a mixture of 5-bromo-4-(4-(cyclobutylmethyl)piperazin-1-yl)-3-nitropyridin-2-amine (0.046 g, 0.12 mmol) and EtOH (1.5 mL), was added 4-(morpholinomethyl)benzaldehyde (0.028 g, 0.14 mmol) in EtOH (1.3 mL) followed by a freshly prepared aqueous solution of $Na_2S_2O_4$ (1M; 0.37 mL, 0.37 mmol). The reaction mixture was heated at 85° C. for 24 h, then allowed to cool to room temperature and the solvents were removed in vacuo. The residue was absorbed on silica gel and purified by column chromatography on a Biotage SP1 system eluting with methanol (2-10%) in dichloromethane. The title compound was isolated as a pale yellow solid after trituration with diethyl ether and (0.011 g, 17%); $^1$H-NMR (500 Mz, DMSO-$d_6$): δ 1.61-1.74 (m, 2H), 1.76-1.94 (m, 3H), 2.00-2.10 (m, 2H), 2.33-2.45 (m, 6H), 2.52-2.61 (m, 4H, piperazine $N(CH_2)_2$), 3.54 (s, 2H, $NCH_2$), 3.59 (t, J=4.5 Hz, 4H), 3.64 (m, 4H), 7.48 (d, J=8.5 Hz, 2H, ArH), 8.14 (d, J=8.5 Hz, 2H, ArH), 8.23 (s, 1H, imidazo[4,5-b]pyridine 5-H), 13.47 (br s, 1H, imidazo[4,5-b]pyridine N—H); LC (Method B)-MS (ESI, m/z) 2.67 min—525/527 [(M+H)$^+$, Br isotopic pattern]; ESI-HRMS: Found: 525.1972, calculated for $C_{28}H_{31}BrFN_6O$ (M+H)$^+$: 525.1977.

Example 151 tert-Butyl 4-(thiazol-2-ylmethyl)piperazine-1-carboxylate

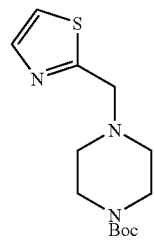

N-Boc-piperazine (1.42 g, 7.6 mmol, 1.1 eq) was dissolved in 1,2-DCE (20 mL). To this solution, 2-thiazolecarboxaldehyde (0.780 g, 6.91 mmol, 1 eq) in 1,2-DCE (4 mL) was added followed by the portionwise addition of sodium triacetoxyborohydride (2.05 g, 9.68 mmol, 1.4 eq). The mixture was stirred at room temperature for 3 h and then washed with an aqueous saturated solution of $NaHCO_3$. The organic layer was dried ($MgSO_4$), the solvent removed in vacuo and the crude product was purified by column chromatography on a Biotage SP1 system (hexanes/EtOAc; v/v 6:4) to give the title compound (1.95 g, 100%); $^1$H-NMR (500 MHz, $CDCl_3$): δ 1.47 (s, 9H, $C(CH_3)_3$), 2.54 (t, 4H, J=4.7 Hz, piperazine $N(CH_2)_2$), 3.48 (t, 4H, J=5.0 Hz, piperazine $N(CH_2)_2$), 3.89 (s, 2H, $NCH_2$), 7.30 (d, J=3.5 Hz, 1H, thiazole 5-H), 7.72 (d, J=3.5 Hz, 1H, thiazole 4-H); LC (Method B)-MS (ESI, m/z): Rt=2.84 min—306 [(M+Na)$^+$, 100%].

5-Bromo-3-nitro-4-(4-(thiazol-2-ylmethyl)piperazin-1-yl)pyridin-2-amine

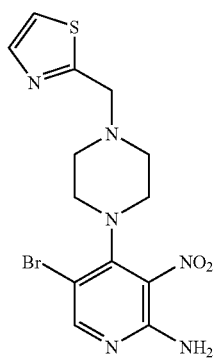

tert-Butyl 4-(thiazol-2-ylmethyl)piperazine-1-carboxylate (0.900 g, 3.18 mmol, 1.0 eq) was dissolved in DCM (10 mL)

and the mixture cooled in a ice-water bath before the dropwise addition of TFA (10 mL). Stirring was continued at this temperature for 1 h, and the solvents were removed in vacuo. The resulting crude material was azeotroped with toluene and dried.

The resulting 2-(piperazin-1-ylmethyl)thiazole (supposedly 0.580 g, 3.18 mmol, 1 eq) was suspended in $^i$PrOH (3.1 mL) and DIPEA (2.2 mL). To this solution, 5-bromo-4-chloro-3-nitropyridin-2-amine (0.800 g, 3.18 mmol, 1 eq) was added and the reaction mixture was heated and stirred for 17 h at 65° C. The mixture was filtered, washed with $^i$PrOH (3×3 mL), Et$_2$O (2×3 mL) and dried to give the title compound as a bright yellow powder (0.750 g, 59%); $^1$H-NMR (500 MHz, DMSO-d$_6$): δ 2.65 (br s, 4H, piperazine N(CH$_2$)$_2$), 3.09 (m, 4H, piperazine N(CH$_2$)$_2$), 3.90 (s, 2H, NCH$_2$), 6.98 (s, 2H, NH$_2$), 7.66 (d, J=3.0 Hz, 1H, thiazole 5-H), 7.72 (d, J=3.0 Hz, 1H, thiazole 4-H), 8.16 (s, 1H, pyridine 6-H); LC (Method B)-MS (ESI, m/z): Rt=2.90 mins—399/401 [(M+H$^+$), Br isotopic pattern, 100%].

2-((4-(6-Bromo-2-(4-methoxyphenyl)-3H-imidazo[4,5-b]pyridin-7-yl)piperazin-1-yl)methyl)thiazole

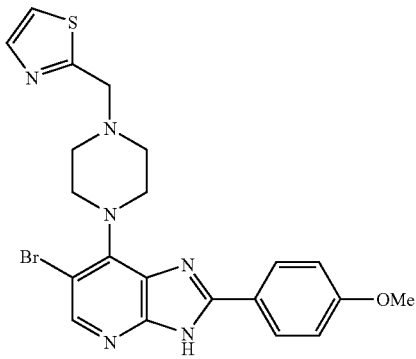

To a mixture of 5-bromo-3-nitro-4-(4-(thiazol-2-ylmethyl)piperazin-1-yl)pyridin-2-amine (0.072 g, 0.18 mmol) and EtOH (2 mL), p-anisaldehyde (0.079 g, 0.20 mmol) in EtOH (2 mL) was added followed by a freshly prepared aqueous solution of Na$_2$S$_2$O$_4$ (1M; 0.54 mL, 0.54 mmol). The reaction mixture was heated at 85° C. for 24 h, then allowed to cool to room temperature and diluted with DCM and a few drops of aqueous NH$_3$ until complete dissolution was observed. This solution was deposited on two preparative silica TLC plates and eluted with DCM/MeOH (v/v; 96:4) to give the title compound as a off-white solid (0.022 g, 25%); $^1$H-NMR (500 Mz, DMSO-d$_6$): δ 2.75 (m, 4H, piperazine N(CH$_2$)$_2$), 3.65-3.73 (m, 4H, piperazine N(CH$_2$)$_2$), 3.84 (s, 3H, OMe), 3.95 (s, 2H, NCH$_2$), 7.11 (d, J=9.0 Hz, 2H, ArH, C$_6$H$_4$—OMe), 7.69 (d, J=3.5 Hz, 1H, thiazole 5-H), 7.75 (d, J=3.0 Hz, 1H, thiazole 4-H), 8.14 (d, J=9.0 Hz, 2H, ArH, C$_6$H$_4$—OMe), 8.21 (s, 1H, imidazo[4,5-b]pyridine 5-H), 13.36 (br s, 1H, imidazo[4,5-b]pyridine N—H); LC (Method B)-MS (ESI, m/z) 4.10 min—485/487 [(M+H)$^+$, Br isotopic pattern]. ESI-HRMS: Found: 485.0759, calculated for C$_{21}$H$_{22}$BrN$_6$OS (M+H)$^+$: 485.0748.

Example 152

4-(4-(6-Bromo-7-(4-(thiazol-2-ylmethyl)piperazin-1-yl)-3H-imidazo[4,5-b]pyridin-2-yl)benzyl)morpholine

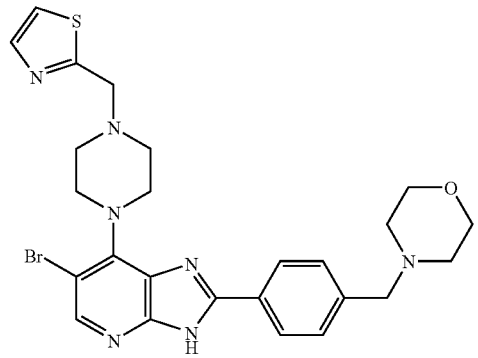

To a mixture of 5-bromo-3-nitro-4-(4-(thiazol-2-ylmethyl)piperazin-1-yl)pyridin-2-amine (0.088 g, 0.22 mmol) and EtOH (2.5 mL), 4-(morpholinomethyl)-benzaldehyde (0.045 g, 0.24 mmol) in EtOH (2.5 mL) was added, followed by a freshly prepared aqueous solution of Na$_2$S$_2$O$_4$ (1M; 0.66 mL, 0.66 mmol). The reaction mixture was heated at 85° C. for 24 h, then allowed to cool to room temperature and diluted with DCM and a few drops of aqueous NH$_3$ until complete dissolution was observed. This solution was deposited on two preparative silica TLC plates and eluted with DCM/MeOH (v/v; 96:4) to give the title compound as a solid (0.049 g, 40%); $^1$H-NMR (500 Mz, DMSO-d$_6$): δ 2.33-2.43 (m, 4H), 2.72-2.79 (m, 4H), 3.54 (s, 2H, NCH$_2$), 3.59 (t, J=4.5 Hz, 4H), 3.70 (t, J=4.5 Hz, 4H), 3.95 (s, 2H, NCH$_2$), 7.48 (d, J=8.5 Hz, 2H, ArH), 7.69 (d, J=3.5 Hz, 1H, thiazole 5-H), 7.75 (d, J=3.0 Hz, 1H, thiazole 4-H), 8.15 (d, J=8.0 Hz, 2H, ArH), 8.24 (s, 1H, imidazo[4,5-b]pyridine 5-H), 13.49 (br s, 1H, imidazo[4,5-b]pyridine N—H); LC (Method B)-MS (ESI, m/z) 2.37 min—554/556 [(M+H)$^+$, Br isotopic pattern]. ESI-HRMS: Found: 554.1341, calculated for C$_{25}$H$_{29}$BrN$_7$OS (M+H)$^+$: 554.1338.

Example 153 tert-Butyl 4-((2-isopropylthiazol-4-yl)methyl)piperazine-1-carboxylate

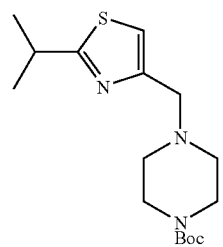

4-(Chloromethyl)-2-isopropyl-thiazole (0.500 g, 2.85 mmol, 1 eq) was suspended in DCM (4.5 mL). DIPEA (1.24 mL, 7.1 mmol, 2.5 eq) was added dropwise, followed by N-Boc-piperazine (1.170 g, 6.3 mmol, 2.2. eq). The reaction mixture was stirred at 35° C. for 5 h, then diluted with EtOAc, and washed with H₂O and brine. The organic layer was separated, dried (MgSO₄) and the solvent removed in vacuo. The crude product was purified by column chromatography on a Biotage SP1 system (DCM/EtOAc; v/v 1:1) to give the title compound as a clear oil (0.600 g, 65%); ¹H-NMR (500 MHz, CDCl₃): δ 1.39 (d, J=7.0 Hz, 6H, $^i$Pr—CH₃), 1.46 (s, 9H, C(CH₃)₃), 2.47 (br t, J=5.0 Hz, 4H, piperazine N(CH₂)₂), 3.34 (m, 1H, $^i$Pr—CH), 3.6 (br t, J=5.0 Hz, 4H, piperazine N(CH₂)₂), 3.66 (s, 2H, NCH₂), 6.98 (s, 1H, thiazole 5-H); LC (Method B)-MS (ESI, m/z): Rt=2.80 min—326 [(M+H)⁺, 100%].

5-Bromo-4-(4-((2-isopropylthiazol-4-yl)methyl)piperazin-1-yl)-3-nitropyridin-2-amine

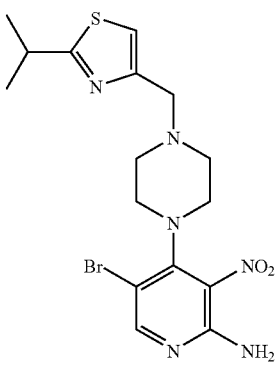

tert-Butyl 4-((2-isopropylthiazol-4-yl)methyl)piperazine-1-carboxylate (0.380 g, 1.15 mmol, 1.0 eq) was dissolved in DCM (3.6 mL) and the mixture cooled in an ice-water bath before the dropwise addition of TFA (3.6 mL). Stirring was continued at this temperature for 1 h and the solvents were removed in vacuo. The resulting crude material was azeotroped with toluene and dried. The resulting 2-isopropyl-4-(piperazin-1-ylmethyl)thiazole (supposedly 0.260 g, 1.15 mmol, 1.1 eq) was suspended in $^i$PrOH (3.5 mL) and DIPEA (0.9 mL). To this solution, 5-bromo-4-chloro-3-nitropyridin-2-amine (0.270 g, 1.05 mmol, 1 eq) was added and the reaction mixture was heated and stirred for 17 h at 65° C. The mixture was filtered, washed with $^i$PrOH (3×3 mL), Et₂O (2×3 mL) and dried to give the title compound as a bright yellow powder (0.300 g, 59%); ¹H-NMR (500 MHz, DMSO-d₆): δ 1.31 (d, J=7.0 Hz, 6H, $^i$Pr—CH₃), 2.53-2.65 (br s, 4H, piperazine N(CH₂)₂), 3.06 (m, 4H, piperazine N(CH₂)₂), 3.20-3.33 (m, 1H, $^i$Pr—CH), 3.61 (s, 2H, NCH₂), 6.96 (s, 2H, NH₂), 7.31 (s, 1H, thiazole 5-H), 8.15 (s, 1H, pyridine 6-H); LC (Method B)-MS (ESI, m/z): Rt=2.81 min—441/443 [(M+H⁺), Br isotopic pattern, 100%].

4-((4-(6-Bromo-2-(4-methoxyphenyl)-3H-imidazo[4,5-b]pyridin-7-yl)piperazin-1-yl)methyl)-2-isopropylthiazole

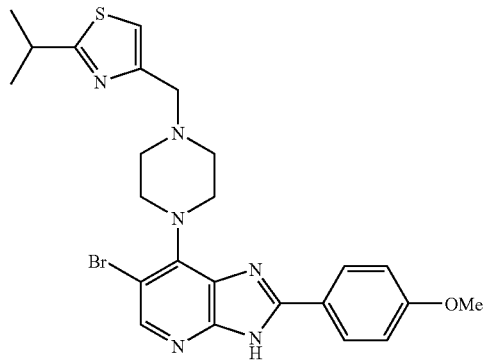

To a mixture of 5-bromo-4-(4-((2-isopropylthiazol-4-yl)methyl)piperazin-1-yl)-3-nitropyridin-2-amine (0.066 g, 0.15 mmol), EtOH (2.6 mL) and DMF (0.35 mL), p-anisaldehyde (0.023 g, 0.165 mmol) was added followed by a freshly prepared aqueous solution of Na₂S₂O₄ (1M; 0.45 mL, 0.45 mmol). The reaction mixture was heated at 85° C. for 24 h, then allowed to cool to room temperature and diluted with DCM and a few drops of aqueous NH₃ until complete dissolution was observed. This solution was deposited on two preparative silica TLC plates and eluted with DCM/MeOH (v/v; 96:4) to give the title compound as a solid (0.019 g, 24%); ¹H-NMR (500 Mz, DMSO-d₆): δ 1.33 (d, J=7.0 Hz, 6H, $^i$Pr—CH₃), 2.68 (m, 4H, piperazine N(CH₂)₂), 3.22-3.34 (m, 1H), 3.62-3.70 (m, 6H, piperazine N(CH₂)₂ and NCH₂), 3.84 (s, 3H, OMe), 7.10 (d, J=9.0 Hz, 2H, ArH, C₆H₄—OMe), 7.35 (s, 1H, thiazole 5-H), 8.14 (d, J=9.0 Hz, 2H, ArH, C₆H₄—OMe), 8.20 (s, 1H, imidazo[4,5-b]pyridine 5-H), 13.33 (br s, 1H, imidazo[4,5-b]pyridine N—H); LC (Method B)-MS (ESI, m/z) 3.71 min—527/529 [(M+H)⁺, Br isotopic pattern]. ESI-HRMS: Found: 527.1232, calculated for C₂₄H₂₈BrN₆OS (M+H)⁺: 527.1229.

Example 154 tert-Butyl 4-(thiazol-4-ylmethyl)piperazine-1-carboxylate

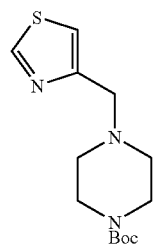

4-(Chloromethyl)thiazole (0.500 g, 2.94 mmol, 1 eq) was suspended in DCM (4.6 mL). DIPEA (1.28 mL, 7.35 mmol, 2.5 eq) was added dropwise, followed by N-Boc-piperazine (1.200 g, 6.47 mmol, 2.2. eq). The mixture was stirred at 35° C. for 5 h, diluted with EtOAc and washed with H$_2$O and brine. The organic layer was separated, dried (MgSO$_4$) and the solvent was removed in vacuo. The crude product was purified by column chromatography on a Biotage SP1 system (DCM/EtOAc; v/v 1:1) to give the title compound as a clear oil (0.160 g, 19%); $^1$H-NMR (500 MHz, CDCl$_3$): δ 1.46 (s, 9H, C(CH$_3$)$_3$), 2.47 (br t, J=4.2 Hz, 4H, piperazine N(CH$_2$)$_2$), 3.46 (br t, J=4.5 Hz, 4H, piperazine N(CH$_2$)$_2$), 3.75 (s, 2H, NCH$_2$), 7.20 (s, 1H, thiazole 5-H), 8.79 (s, 1H, thiazole 2-H); LC (Method B)-MS (ESI, m/z): Rt=1.80 min—284 [(M+H)$^+$, 100%].

5-Bromo-3-nitro-4-(4-(thiazol-4-ylmethyl)piperazin-1-yl)pyridin-2-amine

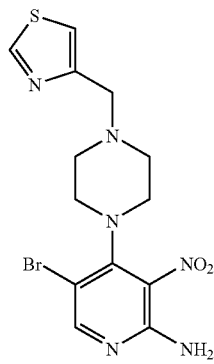

tert-Butyl 4-(thiazol-4-ylmethyl)piperazine-1-carboxylate (0.160 g, 0.56 mmol, 1.0 eq) was dissolved in DCM (1.8 mL) and the reaction mixture cooled in a ice-water bath before the dropwise addition of TFA (1.8 mL). Stirring was continued at this temperature for 1 h, the solvents were removed in vacuo. The resulting crude material was azeotroped with toluene and dried. The resulting 4-(piperazin-1-ylmethyl)thiazole (supposedly 0.10 g, 0.56 mmol, 1.1 eq) was suspended in $^i$PrOH (0.55 mL) and DIPEA (0.22 mL). To this solution, 5-bromo-4-chloro-3-nitropyridin-2-amine (0.130 g, 0.51 mmol, 1 eq) was added and the reaction mixture was heated and stirred for 17 h at 65° C. The mixture was filtered, washed with $^i$PrOH (3×3 mL), Et$_2$O (2×3 mL) and dried to give the title compound as a bright yellow powder (0.120 g, 55%); $^1$H-NMR (500 MHz, DMSO-d$_6$): δ 2.58 (br s, 4H, piperazine N(CH$_2$)$_2$), 3.06 (m, 4H, piperazine N(CH$_2$)$_2$), 3.72 (s, 2H, NCH$_2$), 6.96 (s, 2H, NH$_2$), 7.54 (br d, 1H, J=1.2 Hz, thiazole 5-H), 8.15 (s, 1H, pyridine 6-H), 9.04 (d, 1H, J=1.7 Hz, thiazole 2-H); LC (Method B)-MS (ESI, m/z): Rt=1.83 min—398/400 [(M+H)$^+$, Br isotopic pattern, 100%].

4-((4-(6-Bromo-2-(4-methoxyphenyl)-3H-imidazo[4,5-b]pyridin-7-yl)piperazin-1-yl)methyl)thiazole

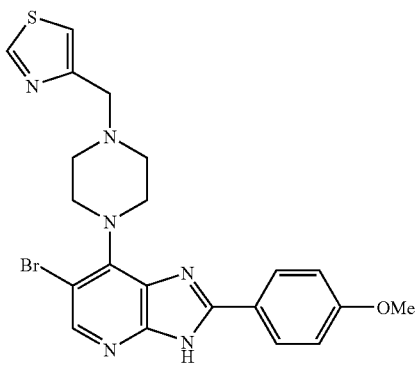

To a mixture of 5-bromo-3-nitro-4-(4-(thiazol-4-ylmethyl) piperazin-1-yl)pyridin-2-amine (0.045 g, 0.11 mmol), EtOH (2.6 mL) and DMF (0.35 mL), p-anisaldehyde (0.017 g, 0.12 mmol) was added followed by a freshly prepared aqueous solution of Na$_2$S$_2$O$_4$ (1M; 0.33 mL, 0.33 mmol). The reaction mixture was heated at 85° C. for 24 h, then allowed to cool to room temperature and diluted with DCM and a few drops of aqueous NH$_3$ until complete dissolution was observed. This solution was deposited on two preparative silica TLC plates and eluted with DCM/MeOH (v/v 96:4) to give the title compound as a white solid (0.026 g, 49%); $^1$H-NMR (500 Mz, DMSO-d$_6$): δ 2.64-2.72 (m, 4H, piperazine N(CH$_2$)$_2$), 3.61-3.70 (m, 4H, piperazine N(CH$_2$)$_2$), 3.77 (br s, 2H, NCH$_2$), 3.84 (s, 3H, OMe), 7.10 (d; J=9.0 Hz, 2H, ArH, C$_6$H$_4$), 7.58 (d, J=2.0 Hz, 1H, thiazole 5-H), 8.14 (d, J=7.0 Hz, 2H, ArH, C$_6$H$_4$), 8.20 (s, 1H, imidazo[4,5-b]pyridine 5-H), 9.07 (d, J=2.0 Hz, 1H, thiazole 2-H), 13.33 (br s, 1H, imidazo[4,5-b]pyridine N—H); LC (Method B)-MS (ESI, m/z) 3.07 min—485/487 [(M+H)$^+$, Br isotopic pattern]. ESI-HRMS: Found: 485.0759, calculated for C$_{21}$H$_{22}$BrN$_6$OS (M+H)$^+$: 485.0742.

Example 55

4-(4-(6-Bromo-7-(4-((2-isopropylthiazol-4-yl)methyl)piperazin-1-yl)-3H-imidazo[4,5-b]pyridin-2-yl)benzyl)morpholine

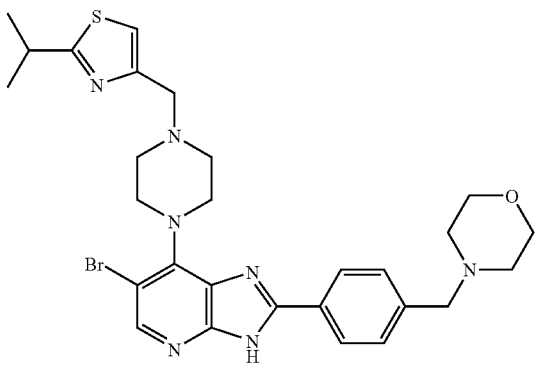

To a mixture of 5-bromo-4-(4-((2-isopropylthiazol-4-yl)methyl)piperazin-1-yl)-3-nitropyridin-2-amine (0.066 g, 0.15 mmol), EtOH (2.6 mL) and DMF (0.35 mL), 4-(morpholinomethyl)-benzaldehyde (0.034 g, 0.165 mmol) was added, followed by a freshly prepared aqueous solution of $Na_2S_2O_4$ (1M; 0.45 mL, 0.45 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 96:4) to give the title compound as a solid (0.035 g, 39%); $^1$H-NMR (500 Mz, DMSO-$d_6$): δ 1.33 (d, J=7.0 Hz, 6H, $^i$Pr—$CH_3$), 2.34-2.42 (m, 4H), 2.68 (m, 4H), 3.22-3.32 (m, 1H), 3.54 (s, 2H), 3.59 (d, J=4.5 Hz, 4H), 3.62-3.70 (m, 6H), 7.35 (s, 1H, thiazole 5-H), 7.47 (d, J=8.5 Hz, 2H, ArH, $C_6H_4$), 8.14 (d, J=8.0 Hz, 2H, ArH, $C_6H_4$), 8.23 (s, 1H, imidazo[4,5-b]pyridine 5-H), 13.47 (br s, 1H, imidazo[4,5-b]pyridine N—H); LC (Method B)-MS (ESI, m/z) 2.55 min—596/598 [(M+H)$^+$, Br isotopic pattern]. ESI-HRMS: Found: 596.18.07, calculated for $C_{28}H_{35}BrN_7OS$ (M+H)$^+$: 596.1793.

Example 156

4-(4-(6-Bromo-7-(4-((2-methylthiazol-4-yl)methyl)piperazin-1-yl)-3H-imidazo[4,5-b]pyridin-2-yl)benzyl)morpholine

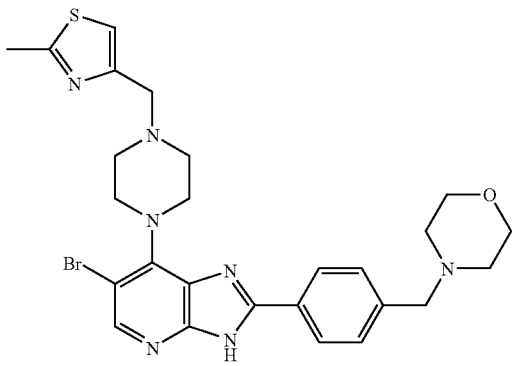

To a mixture of 5-bromo-4-(4-((2-methylthiazol-4-yl)methyl)piperazin-1-yl)-3-nitropyridin-2-amine (0.062 g, 0.15 mmol), EtOH (2.6 mL) and DMF (0.35 mL), 4-(morpholinomethyl)-benzaldehyde (0.034 g, 0.165 mmol) was added followed by a freshly prepared aqueous solution of $Na_2S_2O_4$ (1M; 0.45 mL, 0.45 mmol). The reaction mixture was heated at 85° C. for 24 h, then allowed to cool to room temperature and diluted with DCM, and a few drops of aqueous $NH_3$ until complete dissolution was observed. This solution was deposited on two preparative silica TLC plates and eluted with DCM/MeOH (v/v; 96:4) to give the title compound as a pale yellow solid (0.024 g, 29%); $^1$H-NMR (500 Mz, DMSO-$d_6$): δ 2.33-2.42 (m, 4H), 2.62-2.71 (m, 7H), 3.54 (s, 2H, $NCH_2$), 3.59 (t, J=4.5 Hz, 4H), 3.62-3.74 (m, 6H), 7.32 (s, 1H, thiazole 5-H), 7.47 (d, J=8.0 Hz, 2H, ArH, $C_6H_4$), 8.14 (d, J=8.0 Hz, 2H, ArH, $C_6H_4$), 8.23 (s, 1H, imidazo[4,5-b]pyridine 5-H), 13.51 (br s, 1H, imidazo[4,5-b]pyridine N—H); LC (Method B)-MS (ESI, m/z) 2.12 min—568/570 [(M+H)$^+$, Br isotopic pattern]. ESI-HRMS: Found: 568.1504, calculated for $C_{26}H_{31}N_7BrOS$ (M+H)$^+$: 568.1494.

Example 157 tert-Butyl 4-(4-(6-bromo-7-(4-((2-methylthiazol-4-yl)methyl)piperazin-1-yl)-3H-imidazo[4,5-b]pyridin-2-yl)benzyl)piperazine-1-carboxylate

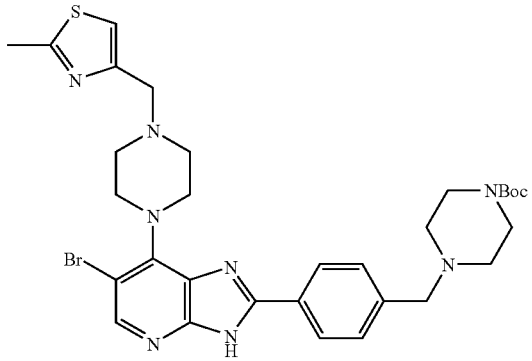

To a mixture of 5-bromo-4-(4-((2-methylthiazol-4-yl)methyl)piperazin-1-yl)-3-nitropyridin-2-amine (0.062 g, 0.15 mmol), EtOH (2.6 mL) and DMF (0.35 mL), tert-butyl-4-(4-formylbenzyl)piperazine-1-carboxylate (0.050 g, 0.165 mmol) was added followed by a freshly prepared aqueous solution of $Na_2S_2O_4$ (1M; 0.45 mL, 0.45 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 96:4) to give the title compound as a solid (0.033 g, 33%); $^1$H-NMR (500 Mz, DMSO-$d_6$): δ 1.39 (s, 9H, $C(CH_3)_3$), 2.34 (t, J=5.0 Hz, 4H), 2.62-2.72 (m, 7H), 3.28-3.36 (m, 4H), 3.55 (s, 2H, $NCH_2$), 3.64 (s, 2H, $NCH_2$), 3.67 (t, J=4.0 Hz, 4H), 7.32 (s, 1H, thiazole 5-H), 7.47 (d, J=8.0 Hz, 2H, ArH, $C_6H_4$), 8.14 (d, J=8.5 Hz, 2H, ArH, $C_6H_4$), 8.23 (s, 1H, imidazo[4,5-b]pyridine 5-H), 13.47 (br s, 1H, imidazo[4,5-b]pyridine N—H); LC (Method B)-MS (ESI, m/z) 2.76 min—667/669 [(M+H)$^+$, Br isotopic pattern]. ESI-HRMS: Found: 667.2190, calculated for $C_{31}H_{40}BrN_8O_2S$ (M+H)$^+$: 667.2178.

Example 158 tert-Butyl 4-(4-(6-bromo-7-(4-((2-methylthiazol-4-yl)methyl)piperazin-1-yl)-3H-imidazo[4,5-b]pyridin-2-yl)phenyl)piperazine-1-carboxylate

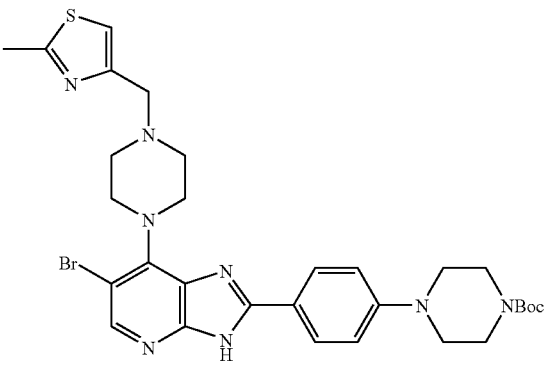

To a mixture of 5-bromo-4-(4-((2-methylthiazol-4-yl)methyl)piperazin-1-yl)-3-nitropyridin-2-amine (0.062 g, 0.15 mmol) in EtOH (2.6 mL) and DMF (0.35 mL), tert-butyl 4-(4-formylphenyl)piperazine-1-carboxylate (0.044 g, 0.165 mmol) was added followed by a freshly prepared aqueous solution of $Na_2S_2O_4$ (1M; 0.45 mL, 0.45 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v 96:4) to give the title compound as a off-white solid (0.043 g, 47%); $^1$H-NMR (500 Mz, DMSO-$d_6$): δ 1.43 (s, 9H, C(CH$_3$)$_3$), 2.61-2.70 (m, 7H), 3.22-3.31 (m, 4H), 3.43-3.52 (m, 4H), 3.60-3.68 (m, 6H), 7.07 (d, J=9.0 Hz, 2H, ArH, C$_6$H$_4$), 7.32 (s, 1H, thiazole 5-H), 8.04 (d, J=8.5 Hz, 2H, ArH, C$_6$H$_4$), 8.23 (s, 1H, imidazo[4,5-b]pyridine 5-H), 13.22 (br s, 1H, imidazo[4,5-b]pyridine N—H); LC (Method B)-MS (ESI, m/z) 4.01 min—653/655 [(M+H)$^+$, Br isotopic pattern]. ESI-HRMS: Found: 653.2022, calculated for $C_{30}H_{38}BrN_8O_2S$ (M+H)$^+$: 653.2019.

Example 159

4-(4-(6-Bromo-7-(4-((2-methylthiazol-4-yl)methyl)piperazin-1-yl)-3H-imidazo[4,5-b]pyridin-2-yl)phenyl)morpholine

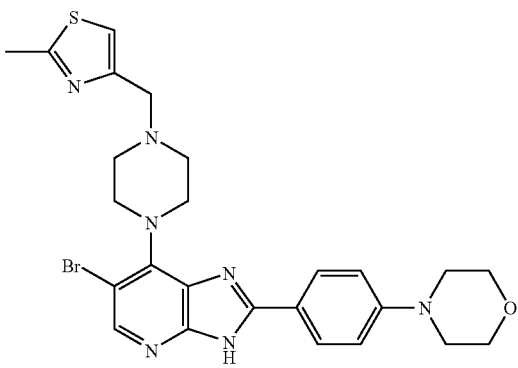

To a mixture of 5-bromo-4-(4-((2-methylthiazol-4-yl)methyl)piperazin-1-yl)-3-nitropyridin-2-amine (0.041 g, 0.10 mmol), EtOH (2.6 mL) and DMF (0.35 mL), 4-morpholin-4-yl-benzaldehyde (0.021 g, 0.11 mmol) was added followed by a freshly prepared aqueous solution of $Na_2S_2O_4$ (1M; 0.30 mL, 0.3 mmol). The reaction mixture was heated at 85° C. for 24 h, then allowed to cool to room temperature and diluted with DCM, and a few drops of aqueous $NH_3$ until complete dissolution was observed. This solution was deposited on two preparative silica TLC plates and eluted with DCM/MeOH (v/v; 96:4) to give the title compound as a solid (0.017 g, 30%); $^1$H-NMR (500 Mz, DMSO-$d_6$): δ 2.63-2.70 (m, 7H), 3.21-3.27 (m, 4H), 3.60-3.68 (m, 6H), 3.76 (m, 4H), 7.07 (d, J=9.0 Hz, 2H, ArH, C$_6$H$_4$), 7.31 (s, 1H, thiazole 5-H), 8.05 (d, J=8.0 Hz, 2H, ArH, C$_6$H$_4$), 8.17 (s, 1H, imidazo[4,5-b]pyridine 5-H), 13.22 (br s, 1H, imidazo[4,5-b]pyridine N—H); LC (Method B)-MS (ESI, m/z) 3.29 min—554/556 [(M+H)$^+$, Br isotopic pattern]. ESI-HRMS: Found: 554.1345, calculated for $C_{25}H_{29}BrN_7OS$ (M+H)$^+$: 554.1338.

Example 160

4-(4-(6-Bromo-7-(4-(thiazol-4-ylmethyl)piperazin-1-yl)-3H-imidazo[4,5-b]pyridin-2-yl)benzyl)morpholine

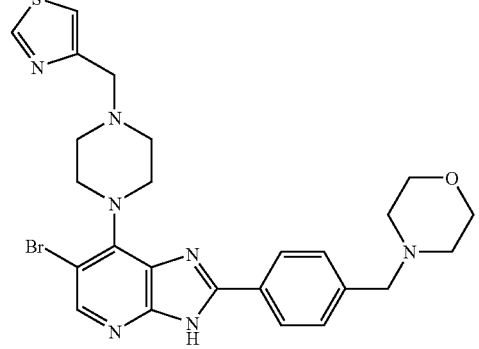

To a mixture of 5-bromo-3-nitro-4-(4-(thiazol-4-ylmethyl)piperazin-1-yl)pyridin-2-amine (0.045 g, 0.11 mmol), EtOH (2.6 mL) and DMF (0.35 mL), 4-(morpholinomethyl)-benzaldehyde (0.025 g, 0.12 mmol) was added followed by a freshly prepared aqueous solution of $Na_2S_2O_4$ (1M; 0.33 mL, 0.33 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 96:4) to give the title compound as a off-white solid (0.012 g, 20%); $^1$H-NMR (500 Mz, DMSO-$d_6$): δ 2.33-2.43 (m, 4H), 2.65-2.73 (m, 4H), 3.54 (s, 2H, NCH$_2$), 3.59 (t, J=4.5 Hz, 4H), 3.64-3.72 (m, 4H), 3.77 (s, 2H, NCH$_2$), 7.47 (d, J=8.0 Hz, 2H, ArH, C$_6$H$_4$), 7.58 (d, J=2.0 Hz, 1H, thiazole 5-H), 8.14 (d, J=8.0 Hz, 2H, ArH, C$_6$H$_4$), 8.23 (s, 1H, imidazo[4,5-b]pyridine 5-H), 9.07 (d, J=2.0 Hz, 1H, thiazole 2-H), 13.46 (br s, 1H, imidazo[4,5-b]pyridine N—H); LC (Method B)-MS (ESI, m/z) 1.95 min—554/556 [(M+H)$^+$, Br isotopic pattern]. ESI-HRMS: Found: 554.1338, calculated for $C_{25}H_{29}N_7OSBr$ (M+H)$^+$: 554.1339.

Example 161

4-((4-(2-(4-(1H-Pyrazol-1-yl)phenyl)-6-bromo-3H-imidazo[4,5-b]pyridin-7-yl)piperazin-1-yl)methyl)-2-methylthiazole

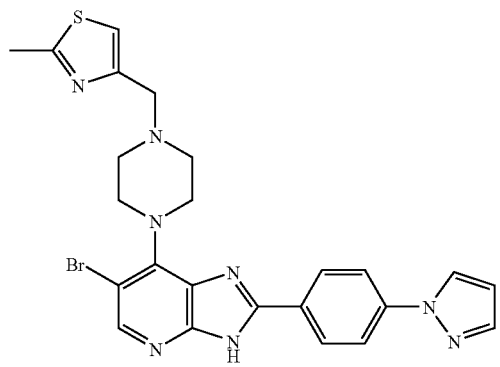

To a mixture of 5-bromo-4-(4-((2-methylthiazol-4-yl)methyl)piperazin-1-yl)-3-nitropyridin-2-amine (0.050 g, 0.12 mmol), EtOH (2.3 mL) and DMF (0.2 mL), 4-(1H-pyrazol-1-yl)-benzaldehyde (0.023 g, 0.13 mmol) was added followed by a freshly prepared aqueous solution of Na$_2$S$_2$O$_4$ (1M; 0.36 mL, 0.36 mmol). The reaction mixture was heated at 85° C. for 24 h, then allowed to cool to room temperature and diluted with DCM and a few drops of aqueous NH$_3$ until complete dissolution was observed. This solution was deposited on two preparative silica TLC plates and eluted with DCM/MeOH v/v 96:4 to give the title compound as a off-white solid (0.016 g, 25%); $^1$H-NMR (500 Mz, DMSO-d$_6$): δ 2.63-2.71 (m, 7H), 3.65 (s, 2H, NCH$_2$), 3.66-3.72 (m, 4H), 6.59-6.62 (m, 1H), 7.33 (s, 1H, thiazole 5-H), 7.81 (d, J=2.0 Hz, 1H), 8.03 (d, J=9.0 Hz, 2H, ArH, C$_6$H$_4$), 8.25 (s, 1H, imidazo[4,5-b]pyridine 5-H), 8.30 (d, J=8.5 Hz, 2H, ArH, C$_6$H$_4$), 8.61 (d, J=2.5 Hz, 1H), 13.54 (br s, 1H, imidazo[4,5-b]pyridine N—H); LC (Method B)-MS (ESI, m/z) 3.41 min—535/537 [(M+H)$^+$, Br isotopic pattern]. ESI-HRMS: Found: 535.1028, calculated for C$_{24}$H$_{24}$BrN$_8$S (M+H)$^+$: 535.1039.

Example 162

4-((4-(2-(4-((1H-Pyrazol-1-yl)methyl)phenyl)-6-bromo-3H-imidazo[4,5-b]pyridin-7-yl)piperazin-1-yl)methyl)-2-methylthiazole

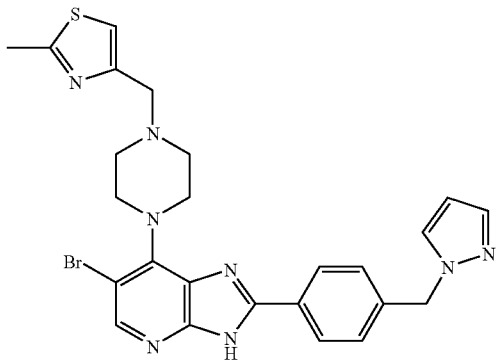

To a mixture of 5-bromo-4-(4-((2-methylthiazol-4-yl)methyl)piperazin-1-yl)-3-nitropyridin-2-amine (0.050 g, 0.12 mmol), EtOH (2.3 mL) and DMF (0.2 mL), 4-(1H-pyrazol-1-ylmethyl)-benzaldehyde (0.025 g, 0.13 mmol) was added followed by a freshly prepared aqueous solution of Na$_2$S$_2$O$_4$ (1M; 0.36 mL, 0.36 mmol). The reaction mixture was heated at 85° C. for 24 h, then allowed to cool to room temperature and diluted with DCM and a few drops of aqueous NH$_3$ until complete dissolution was observed. This solution was deposited on two preparative silica TLC plates and eluted with DCM/MeOH (v/v; 96:4). The title compound was obtained after trituration with ether as a white solid (0.033 g, 49%); $^1$H-NMR (500 Mz, DMSO-d$_6$): δ 2.62-2.70 (m, 7H), 3.64 (s, 2H, NCH$_2$), 3.65-3.70 (m, 4H), 5.42 (s, 2H, NCH$_2$), 6.30 (t, J=2.5 Hz, 1H), 7.32 (s, 1H, thiazole 5-H), 7.34 (d, J=8.0 Hz, 1H), 7.48-7.51 (m, 1H), 7.86 (d, J=2.0 Hz, 1H), 8.13 (d, J=8.0 Hz, 2H), 8.23 (s, 1H, imidazo[4,5-b]pyridine 5-H), 13.49 (br s, 1H, imidazo[4,5-b]pyridine N—H); LC (Method B)-MS (ESI, m/z) 3.17 min—549/551 [(M+H)$^+$, Br isotopic pattern]. ESI-HRMS: Found: 549.1176, calculated for C$_{25}$H$_{26}$N$_8$SBr (M+H)$^+$: 549.1185.

Example 163

4-((4-(6-Bromo-2-(4-(piperazin-1-yl)phenyl)-3H-imidazo[4,5-b]pyridin-7-yl)piperazin-1-yl)methyl)-2-methylthiazole

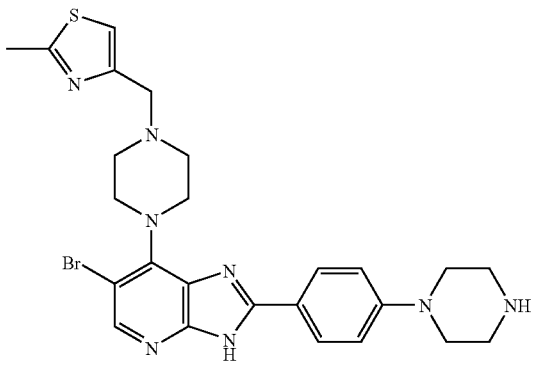

tert-Butyl-4-(4-(6-bromo-7-(4-((2-methylthiazol-4-yl)methyl)piperazin-1-yl)-3H-imidazo[4,5-b]pyridin-2-yl)phenyl)piperazine-1-carboxylate (0.022 g, 0.033 mmol) was suspended in DCM (2.0 mL) and the mixture cooled in an ice bath. TFA (0.5 mL) was added and the resulting solution was allowed to warm up to room temperature and stirred for 2 h. The mixture was passed through an SCX column (5 g), the filtrate collected and the solvent removed in vacuo to give the title compound as a solid (0.016 g, 86%); $^1$H-NMR (500 Mz, DMSO-d$_6$): δ 2.61-2.70 (m, 7H), 2.81-2.89 (m, 4H), 3.15-3.22 (m, 4H), 3.60-3.68 (m, 6H), 7.03 (d, J=9.0 Hz, 2H, ArH, C$_6$H$_4$), 7.32 (s, 1H, thiazole 5-H), 8.02 (d, J=9.0 Hz, 2H, ArH, C$_6$H$_4$), 8.17 (s, 1H, imidazo[4,5-b]pyridine 5-H); LC (Method B)-MS (ESI, m/z) 2.23 min—553/555 [(M+H)$^+$, Br isotopic pattern]. ESI-HRMS: Found: 553.1522, calculated for C$_{25}$H$_{30}$BrN$_8$S (M+H)$^+$: 553.1498.

Example 164

4-((4-(6-Bromo-2-(4-(piperazin-1-ylmethyl)phenyl)-3H-imidazo[4,5-b]pyridin-7-yl)piperazin-1-yl)methyl)-2-methylthiazole

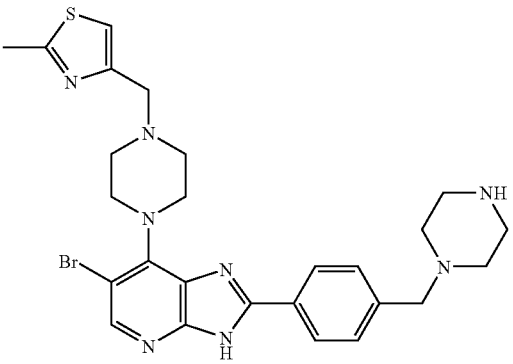

tert-Butyl-4-(4-(6-bromo-7-(4-((2-methylthiazol-4-yl)methyl)piperazin-1-yl)-3H-imidazo[4,5-b]pyridin-2-yl)benzyl)piperazine-1-carboxylate (0.022 g, 0.033 mmol) was suspended in DCM (2.0 mL) and the mixture cooled in an ice bath. TFA (0.5 mL) was added and the resulting solution was allowed to warm up to room temperature and stirred for 2 h. The mixture was passed through an SCX column (5 g), washed with methanol and then eluted with ammonia (0.2M) in methanol. The filtrate was collected and the solvent removed in vacuo to give the title compound as a off-white solid (0.017 g, 91%); $^1$H-NMR (500 Mz, DMSO-$d_6$): δ 2.26-2.36 (m, 4H), 2.61-2.75 (m, 11H), 3.50 (s, 2H, NCH$_2$), 3.61-3.70 (m, 6H), 7.32 (s, 1H, thiazole 5-H), 7.45 (d, J=8.5 Hz, 2H, ArH, C$_6$H$_4$), 8.13 (d, J=8.05 Hz, 2H, ArH, C$_6$H$_4$), 8.23 (s, 1H, imidazo[4,5-b]pyridine 5-H); LC (Method B)-MS (ESI, m/z) 2.19 min—567/569 [(M+H)$^+$, Br isotopic pattern]; ESI-HRMS: Found: 567.1634, calculated for C$_{26}$H$_{32}$N$_8$SBr (M+H)$^+$: 567.1654.

Example 165 tert-Butyl 4-((1-methyl-1H-imidazol-5-yl)methyl)piperazine-1-carboxylate

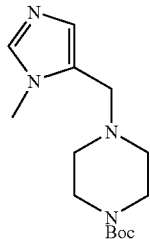

N-Boc-piperazine (0.930 g, 5.0 mmol, 1.1 eq) was dissolved in 1,2-DCE (14 mL). To this solution, 1-methyl-1H-imidazole-5-carboxaldehyde (0.500 g, 4.54 mmol, 1 eq) was added followed by the portionwise addition of sodium triacetoxyborohydride (1.35 g, 6.36 mmol, 1.4 eq). The mixture was stirred at room temperature for 4 h and was then washed with a saturated aqueous solution of NaHCO$_3$. The organic layer was dried (MgSO$_4$), and the solvent removed in vacuo. The crude mixture was redissolved in 18 mL of DCM and gently stirred overnight in the presence of PS-isocyanate (2 g, loading: 1.58 mmol/g). The mixture was filtered off, and the resin washed with DCM (2×10 mL). The solvent was removed in vacuo and the resulting mixture was purified by column chromatography on a Biotage SP1 system eluting with methanol (2-10%) in dichloromethane to give the title compound (0.280 g, 22%); $^1$H-NMR (500 MHz, CDCl$_3$): δ 1.45 (s, 9H, C(CH$_3$)$_3$), 2.28-2.40 (m, 4H, piperazine N(CH$_2$)$_2$), 3.38 (m, 4H, piperazine N(CH$_2$)$_2$), 3.44 (s, 2H, NCH$_2$), 3.66 (s, 3H, imidazole Me), 6.87 (s, 1H, imidazole 4-H), 7.40 (s, 1H, imidazole 2-H); GC-MS (Cl, m/z): Rt=4.89 min—281 [(M+H)$^+$, 100%].

5-Bromo-4-(4-((1-methyl-1H-imidazol-5-yl)methyl)piperazin-1-yl)-3-nitropyridin-2-amine

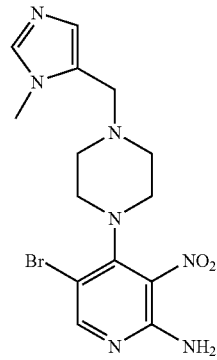

tert-Butyl 4-((1-methyl-1H-imidazol-5-yl)methyl)piperazine-1-carboxylate (0.150 g, 0.54 mmol, 1.1 eq) was dissolved in DCM (1.7 mL) and the mixture cooled in a ice-water bath before the dropwise addition of TFA (1.7 mL). Stirring was continued at this temperature for 1 h and the solvents were removed in vacuo. The resulting crude material was azeotroped with toluene and dried. The resulting 1-((1-methyl-1H-imidazol-5-yl)methyl)piperazine (supposedly 0.097 g, 0.54 mmol, 1 eq) was suspended in $^i$PrOH (1.6 mL) and DIPEA (0.42 mL). To this solution, 5-bromo-4-chloro-3-nitropyridin-2-amine (0.120 g, 0.49 mmol, 1 eq) was added and the mixture heated and stirred for 17 h at 65° C. The mixture was filtered, washed with $^i$PrOH (3×3 mL), Et$_2$O (2×3 mL) and dried to give the title compound as a bright yellow powder (0.070 g, 33%); $^1$H-NMR (500 MHz, DMSO-$d_6$): δ 3.03 (br s, 4H, piperazine N(CH$_2$)$_2$), 3.49 (s, 2H, NCH$_2$), 3.62 (s, 3H, imidazole Me), 6.76 (s, 1H, imidazole H-4), 6.96 (s, 2H, NH$_2$), 7.54 (s, 1H, imidazole H-2), 8.16 (s, 1H, pyridine 6-H); LC (Method B)-MS (ESI, m/z): Rt=1.56 min—396/398 [(M+H$^+$), Br isotopic pattern, 100%].

6-Bromo-2-(4-methoxyphenyl)-7-(4-((1-methyl-1H-imidazol-5-yl)methyl)piperazin-1-yl)-3H-imidazo[4,5-b]pyridine

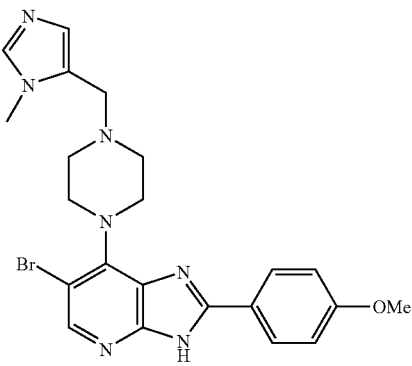

To a mixture of 5-bromo-4-(4-((1-methyl-1H-imidazol-5-yl)methyl)piperazin-1-yl)-3-nitropyridin-2-amine (0.030 g, 0.076 mmol, 1 eq), EtOH (1.95 mL) and DMF (0.29 mL), p-anisaldehyde (0.011 g, 0.083 mmol, 1.1 eq) was added followed by a freshly prepared aqueous solution of $Na_2S_2O_4$ (1M; 0.23 mL, 0.23 mmol). The reaction mixture was heated at 85° C. for 24 h, then allowed to cool to room temperature and diluted with DCM and a few drops of aq $NH_3$ until complete dissolution was observed. This solution was deposited on two preparative silica TLC plates and eluted with DCM/MeOH (v/v; 94:6). The title compound was obtained as a solid after trituration with diethyl ether (0.009 g, 23%); $^1$H-NMR (500 Mz, DMSO-$d_6$): δ 2.55-2.62 (m, 4H, piperazine N(CH$_2$)$_2$), 3.54 (s, 2H, NCH$_2$), 3.60-3.66 (m, 4H, piperazine N(CH$_2$)$_2$), 3.68 (s, 3H, imidazole Me), 3.84 (s, 3H, OMe), 6.80 (s, 1H, imidazole 4-H), 7.09 (d, J=9.0 Hz, 2H, ArH, C$_6$H$_4$), 7.57 (s, 1H, imidazole 2-H), 8.13 (d, J=9.0 Hz, 2H, ArH, C$_6$H$_4$), 8.20 (s, 1H, imidazo[4,5-b]pyridine 5-H), 13.35 (br s, 1H, imidazo[4,5-b]pyridine N—H); LC (Method B)-MS (ESI, m/z): Rt=2.78 min—482/484 [(M+H$^+$), Br isotopic pattern, 100%]. ESI-HRMS: Found: 482.1295, calculated for $C_{22}H_{25}BrN_7O$ (M+H)$^+$: 482.1304.

Example 166 tert-Butyl 4-((1-methyl-1H-imidazol-2-yl)methyl)piperazine-1-carboxylate

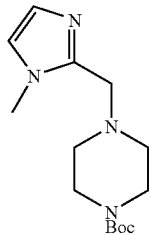

N-Boc-piperazine (0.930 g, 5.0 mmol, 1.1 eq) was dissolved in 1,2-DCE (14 mL). To this solution, 1-methyl-2-imidazolecarboxy aldehyde (0.50 g, 4.54 mmol, 1 eq) was added followed by the portionwise addition of sodium triacetoxyborohydride (1.350 g, 6.36 mmol, 1.4 eq). The mixture was stirred at room temperature for 4 h and was then washed with a saturated aqueous solution of NaHCO$_3$. The organic layer was dried (MgSO$_4$), and the solvent removed in vacuo. The crude mixture was redissolved in 18 mL of DCM and gently stirred overnight in the presence of PS-isocyanate (2 g, loading: 1.58 mmol/g). The mixture was filtered off, and the resin washed with DCM (2×10 mL). The solvent was removed in vacuo and the resulting mixture was purified by column chromatography on a Biotage SP1 system eluting with methanol (1-8%) in dichloromethane to give the title compound as a off-white solid (0.450 g, 32%); $^1$H-NMR (500 MHz, CDCl$_3$): δ 1.40 (s, 9H, C(CH$_3$)$_3$), 2.30-2.40 (m, 4H, piperazine N(CH$_2$)$_2$), 3.30-3.38 (m, 4H, piperazine N(CH$_2$)$_2$), 3.66 (s, 2H, NCH$_2$), 3.67 (s, 3H, imidazole Me), 6.81 (s, 1H, imidazole 4-H), 6.90 (s, 1H, imidazole 5-H); GC-MS (ESI, m/z): Rt=4.62 min, 281.1-[(M+H)$^+$, 100%].

5-Bromo-4-(4-((1-methyl-1H-imidazol-2-yl)methyl) piperazin-1-yl)-3-nitropyridin-2-amine

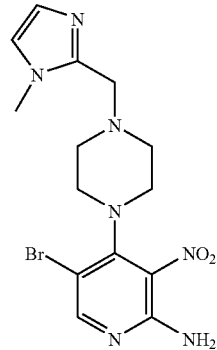

tert-Butyl 4-((1-methyl-1H-imidazol-2-yl)methyl)piperazine-1-carboxylate (0.500 g, 1.78 mmol, 1.1 eq) was dissolved in DCM (5.6 mL) and the mixture cooled in a ice-water bath before the dropwise addition of TFA (5.6 mL). Stirring was continued at this temperature for 1 h. The solvents were removed in vacuo, the resulting crude material was azeotroped with toluene and dried.

The resulting 1-((1-methyl-1H-imidazol-2-yl)methyl)piperazine (supposedly 0.320 g, 1.78 mmol, 1 eq) was suspended in $^i$PrOH (5.4 mL) and DIPEA (1.4 mL). To this solution, 5-bromo-4-chloro-3-nitropyridin-2-amine (0.400 g, 1.62 mmol, 1 eq) was added and the mixture heated and stirred for 17 h at 65° C. The mixture was filtered, washed with $^i$PrOH (3×6 mL), Et$_2$O (2×6 mL) and dried to give the title compound as a bright yellow powder (0.370 g, 51%); $^1$H-NMR (500 MHz, DMSO-$d_6$): δ 2.97-3.08 (br s, 4H, piperazine N(CH$_2$)$_2$), 3.57 (s, 2H, NCH$_2$), 3.66 (s, 3H, imidazole Me), 6.75 (s, 1H, imidazole H-4), 6.96 (s, 2H, NH$_2$), 7.08 (s, 1H, imidazole H-5), 8.16 (s, 1H, pyridine 6-H); LC (Method B)-MS (ESI, m/z): Rt=2.07 min—396/398 [(M+H$^+$), Br isotopic pattern, 100%].

4-(4-(6-Bromo-7-(4-((1-methyl-1H-imidazol-2-yl) methyl)piperazin-1-yl)-3H-imidazo[4,5-b]pyridin-2-yl)benzyl)morpholine

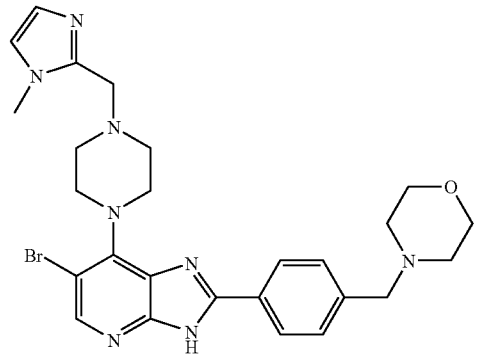

To a mixture of 5-bromo-4-(4-((1-methyl-1H-imidazol-2-yl)methyl)piperazin-1-yl)-3-nitropyridin-2-amine (0.105 g, 0.26 mmol, 1 eq) in EtOH (6 mL) and DMF (0.9 mL), 4-(morpholinomethyl)-benzaldehyde (0.060 g, 0.29 mmol, 1.1 eq) was added followed by a freshly prepared aqueous solution of Na$_2$S$_2$O$_4$ (1M; 0.78 mL, 0.78 mmol). The reaction mixture was heated at 85° C. for 24 h, then allowed to cool to room temperature, and diluted with DCM and a few drops of aqueous NH$_3$ until complete dissolution was observed. This solution was deposited on two preparative silica TLC plates and eluted with DCM/MeOH (v/v; 92:8). The title compound was obtained as a solid after trituration with diethyl ether (0.027 g, 18%); $^1$H-NMR (500 Mz, DMSO-d$_6$): δ 2.34-2.42 (m, 4H), 2.56-2.64 (m, 4H), 3.53 (s, 2H, morpholine N(CH$_2$)$_2$), 3.56-3.68 (m, 10H), 3.72 (s, 3H, imidazole Me), 6.78 (d, J=1.5 Hz, 1H, imidazole 4-H), 7.11 (d, J=1.5 Hz, 1H, imidazole 5-H), 7.47 (d, J=8.0 Hz, 2H, ArH), 8.13 (d, J=8.0 Hz, 2H, ArH), 8.23 (s, 1H, imidazo[4,5-b]pyridine 5-H), 13.47 (br s, 1H, imidazo[4,5-b]pyridine N—H); LC (Method B)-MS (ESI, m/z): Rt=2.23 min—551/553 [(M+H$^+$), Br isotopic pattern, 100%]. ESI-HRMS: Found: 551.1884, calculated for C$_{26}$H$_{32}$BrN$_8$O (M+H)$^+$: 551.1882.

Example 167

6-Bromo-2-(4-methoxyphenyl)-7-(4-((1-methyl-1H-imidazol-2-yl)methyl)piperazin-1-yl)-3H-imidazo[4,5-b]pyridine

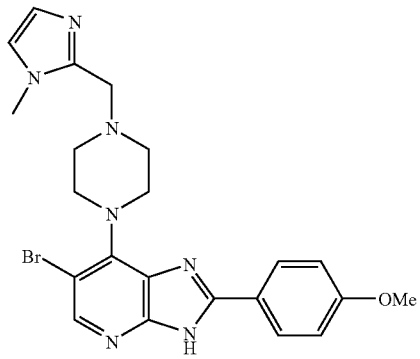

To a mixture of 5-bromo-4-(4-((1-methyl-1H-imidazol-2-yl)methyl)piperazin-1-yl)-3-nitropyridin-2-amine (0.035 g, 0.088 mmol, 1 eq), EtOH (2 mL) and DMF (0.3 mL), p-anisaldehyde (0.013 g, 0.097 mmol, 1.1 eq) was added followed by a freshly prepared aqueous solution of Na$_2$S$_2$O$_4$ (1M; 0.26 mL, 0.26 mmol). The reaction mixture was heated at 85° C. for 24 h, then allowed to cool to room temperature, and diluted with DCM and a few drops of aqueous NH$_3$ until complete dissolution was observed. This solution was deposited on two preparative silica TLC plates and eluted with DCM/MeOH (v/v; 94:6). The title compound was obtained after trituration with diethyl ether as a dark yellow solid (0.009 g, 21%); $^1$H-NMR (500 Mz, DMSO-d$_6$): δ 2.55-2.63 (m, 4H, piperazine N(CH$_2$)$_2$), 3.58-3.67 (m, 6H, piperazine N(CH$_2$)$_2$ and NCH$_2$), 3.72 (s, 3H, imidazole Me), 3.84 (s, 3H, OMe), 6.77 (d, 1H, J=1.0 Hz, imidazole 4-H), 7.07-7.13 (m, 3H), 8.13 (d, J=8.5 Hz, 2H), 8.20 (s, 1H, imidazo[4,5-b]pyridine 5-H), 13.34 (br s, 1H, imidazo[4,5-b]pyridine N—H); LC (Method B)-MS (ESI, m/z): Rt=3.33 min—482/484 [(M+H$^+$), Br isotopic pattern, 100%]. ESI-HRMS: Found: 482.1297, calculated for C$_{22}$H$_{25}$BrN$_7$O (M+H)$^+$: 482.1304.

Example 168 tert-Butyl 4-((1-methyl-1H-imidazol-4-yl)methyl)piperazine-1-carboxylate

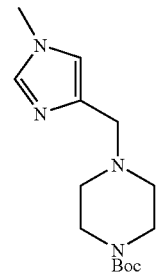

N-Boc-piperazine (0.470 g, 2.50 mmol, 1.1 eq) was dissolved in DCM (6.2 mL). To this solution, 1-methyl-1H-imidazole-4-carboxaldehyde (0.250 g, 2.27 mmol, 1 eq) was added followed by chlorotitanium triisopropoxide (1.19 mL, 5.0 mmol, 2.2 eq). The resulting solution was stirred at room temperature for 10 min before the addition of sodium triacetoxyborohydride (2.40 g, 11.3 mmol, 5 eq). The mixture was stirred at room temperature for 17 h and was diluted with EtOAc (12 mL). It was then poured into ammonia (35% sol. in H$_2$O, 6 mL) and the resulting mixture filtered and washed with EtOAc. The organic phase was washed with H$_2$O dried (MgSO$_4$) and the solvent removed in vacuo. The crude material was purified by column chromatography on a Biotage SP1 system eluting with methanol (1-8%) in dichloromethane to give the title compound as a clear oil (0.390 g, 62%); $^1$H-NMR (500 MHz, CDCl$_3$): δ 1.46 (s, 9H, C(CH$_3$)$_3$), 2.48 (t, J=5.0 Hz, 4H, piperazine N(CH$_2$)$_2$), 3.45 (t, J=5.0 Hz, 4H, piperazine N(CH$_2$)$_2$), 3.52 (s, 2H, NCH$_2$), 3.66 (s, 3H, imidazole Me), 6.80 (s, 1H, imidazole 5-H), 7.38 (s, 1H, imidazole 2-H); LC (Method B)-MS (ESI, m/z): 281 [(M+H$^+$)].

5-Bromo-4-(4-((1-methyl-1H-imidazol-4-yl)methyl)piperazin-1-yl)-3-nitropyridin-2-amine

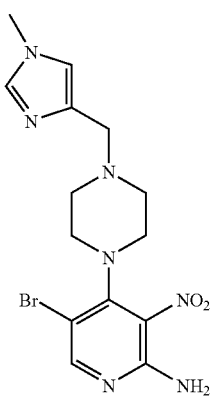

tert-Butyl 4-((1-methyl-1H-imidazol-4-yl)methyl)piperazine-1-carboxylate (0.130 g, 0.46 mmol, 1.1 eq) was dissolved in DCM (1.45 mL) and the mixture cooled in a ice-water bath before the dropwise addition of TFA (1.45 mL). Stirring was continued at this temperature for 1 h. The solvents were removed in vacuo, the resulting crude material was azeotroped with toluene and dried. The resulting 1-((1-methyl-1H-imidazol-4-yl)methyl)piperazine (supposedly 0.083 g, 0.46 mmol, 1 eq) was suspended in $^i$PrOH (1.4 mL) and DIPEA (0.35 mL). To this solution, 5-bromo-4-chloro-3-nitropyridin-2-amine (0.100 g, 0.42 mmol, 1 eq) was added and the mixture heated and stirred for 17 h at 65° C. The mixture was filtered, washed with iPrOH (3×3 mL), Et$_2$O (2×3 mL) and dried to give the title compound as a bright yellow powder (0.085 g, 47%); $^1$H-NMR (500 MHz, DMSO-d$_6$): δ 2.50-2.58 (br s, 4H, piperazine N(CH$_2$)$_2$), 3.03 (m, 4H, piperazine N(CH$_2$)$_2$), 3.39 (s, 2H, NCH$_2$), 3.60 (s, 3H, imidazole Me), 6.95 (s) and 6.97 (s), (3H, NH$_2$ and 6-H), 7.46 (s, 1H), 8.14 (s, 1H, pyridine 6-H); LC (Method B)-MS (ESI, m/z): Rt=1.25 min—396/398 [(M+H$^+$), Br isotopic pattern, 100%].

6-Bromo-2-(4-methoxyphenyl)-7-(4-((1-methyl-1H-imidazol-4-yl)methyl)piperazin-1-yl)-3H-imidazo[4,5-b]pyridine

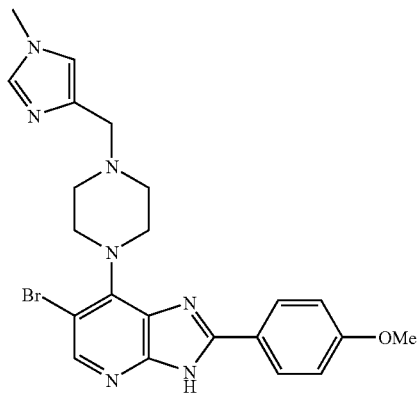

To a mixture of 5-bromo-4-(4-((1-methyl-1H-imidazol-4-yl)methyl)piperazin-1-yl)-3-nitropyridin-2-amine (0.035 g, 0.088 mmol, 1 eq), EtOH (2 mL) and DMF (0.3 mL), p-anisaldehyde (0.013 g, 0.097 mmol, 1.1 eq) was added followed by a freshly prepared aqueous solution of Na$_2$S$_2$O$_4$ (1M; 0.26 mL, 0.26 mmol). The reaction mixture was heated at 85° C. for 24 h, then allowed to cool to room temperature and diluted with DCM and a few drops of aqueous NH$_3$ until complete dissolution was observed. This solution was deposited on two preparative silica TLC plates and eluted with DCM/MeOH (v/v; 94:6). The title compound was obtained as a solid after trituration with diethyl ether (0.011 g, 26%); $^1$H-NMR (500 Mz, DMSO-d$_6$): δ 2.59-2.68 (m, 4H, piperazine N(CH$_2$)$_2$), 3.43 (s, 2H, NCH$_2$), 3.60-3.66 (m, 7H, piperazine N(CH$_2$)$_2$ and imidazole Me), 3.84 (s, 3H, OMe), 7.00 (d, J=1.0 Hz, 1H, imidazole 5-H), 7.10 (d, J=9.0 Hz, 2H, ArH, C$_6$H$_4$), 7.47 (d, J=1.0 Hz, 1H, imidazole 2-H), 8.13 (d, J=9.0 Hz, 2H, ArH, C$_6$H$_4$), 8.19 (s, 1H, imidazo[4,5-b]pyridine 5-H), 13.34 (br s, 1H, imidazo[4,5-b]pyridine N—H); LC (Method B)-MS (ESI, m/z): Rt=2.87 min—482/484 [(M+H$^+$), Br isotopic pattern, 100%]; ESI-HRMS: Found: 482.1300, calculated for C$_{22}$H$_{25}$BrN$_7$O (M+H)$^+$: 482.1304.

Example 169

4-(4-(6-Bromo-7-(4-((1-methyl-1H-imidazol-5-yl)methyl)piperazin-1-yl)-3H-imidazo[4,5-b]pyridin-2-yl)benzyl)morpholine

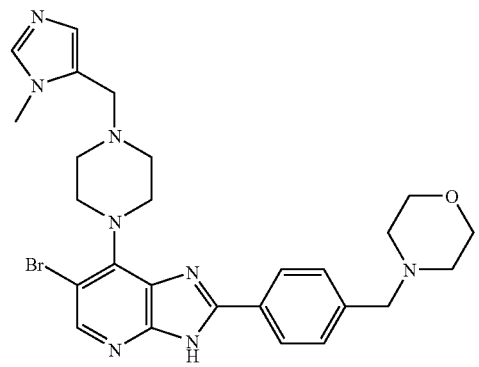

To a mixture of 5-bromo-4-(4-((1-methyl-1H-imidazol-5-yl)methyl)piperazin-1-yl)-3-nitropyridin-2-amine (0.030 g, 0.076 mmol, 1 eq), EtOH (1.95 mL) and DMF (0.29 mL), 4-(morpholinomethyl)-benzaldehyde (0.017 g, 0.083 mmol, 1.1 eq) was added followed by a freshly prepared aqueous solution of Na$_2$S$_2$O$_4$ (1M; 0.23 mL, 0.23 mmol). The reaction mixture was heated at 85° C. for 24 h, then allowed to cool to room temperature and diluted with DCM and a few drops of aqueous NH$_3$ until complete dissolution was observed. This solution was deposited on two preparative silica TLC plates and eluted with DCM/MeOH (v/v; 94:6). The title compound was obtained after trituration with diethyl ether as a yellow solid (0.005 g, 14.7%); $^1$H-NMR (500 Mz, DMSO-d$_6$): δ 2.35-2.41 (m, 4H), 2.55-2.62 (m, 4H), 3.52-3.55 (2 s, 4H, 2NCH$_2$), 3.59 (t, J=4.5 Hz, 4H), 3.62-3.67 (m, 4H), 3.68 (m, 3H, imidazole Me), 6.80 (s, 1H, imidazole 4-H), 7.46 (d, J=8.0 Hz, 2H, ArH, C$_6$H$_4$), 7.57 (s, 1H, imidazole 2-H), 8.13 (d, J=8.0 Hz, 2H, ArH, C$_6$H$_4$), 8.23 (s, 1H, imidazo[4,5-b]pyridine 5-H), 13.47 (br s, 1H, imidazo[4,5-b]pyridine N—H); LC (Method B)-MS (ESI, m/z): R=1.79 min—551/553 [(M+H$^+$), Br isotopic pattern, 100%]; ESI-HRMS: Found: 551.1882, calculated for C$_{26}$H$_{32}$N$_8$OBr (M+H)$^+$: 551.1882.

Example 170 tert-Butyl 4-(thiazol-5-ylmethyl)piperazine-1-carboxylate

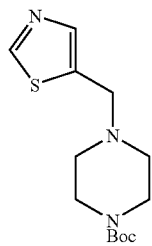

N-Boc-piperazine (0.900 g, 4.86 mmol, 1.1 eq) was dissolved in 1,2-DCE (12 mL). To this solution, 5-thiazolecarboxaldehyde (0.500 g, 4.42 mmol, 1 eq) in 1,2-DCE (2 mL) was added followed by the portionwise addition of sodium triacetoxyborohydride (1.310 g, 6.19 mmol, 1.4 eq). The reaction mixture was stirred at room temperature for 17 h and then washed with a saturated aqueous solution of NaHCO$_3$. The organic layer was dried (MgSO$_4$), the solvent removed in vacuo and the crude product was purified by column chromatography on a Biotage SP1 system (DCM/EtOAc; v/v 1:1) to give the title compound as a light yellow oil (0.640 g, 51%); $^1$H-NMR (500 MHz, CDCl$_3$): δ 1.46 (s, 9H, C(CH$_3$)$_3$), 2.43 (t, J=4.5 Hz, 4H, piperazine N(CH$_2$)$_2$), 3.44 (t, J=5.0 Hz, 4H, piperazine N(CH$_2$)$_2$), 3.77 (s, 2H, NCH$_2$), 7.72 (s, 1H, thiazole 4-H), 8.76 (s, 1H, thiazole 2-H); LC (Method B)-MS (ESI, m/z): Rt=2.04 min—284 [(M+H)$^+$, 100%].

5-Bromo-3-nitro-4-(4-(thiazol-5-ylmethyl)piperazin-1-yl)pyridin-2-amine

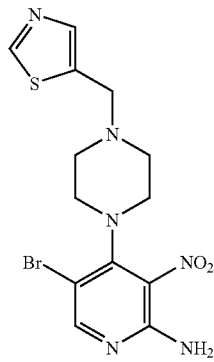

tert-Butyl 4-(thiazol-5-ylmethyl)piperazine-1-carboxylate (0.350 g, 1.23 mmol, 1.1 eq) was dissolved in DCM (3.9 mL) and the mixture cooled in a ice-water bath before the dropwise addition of TFA (3.9 mL). Stirring was continued at this temperature for 1 h. Solvents were removed in vacuo and the resulting crude material was azeotroped with toluene and dried. The resulting 5-(piperazin-1-ylmethyl)thiazole (supposedly 0.230 g, 1.23 mmol, 1 eq) was suspended in $^i$PrOH (2.4 mL) and DIPEA (0.70 mL). To this solution, 5-bromo-4-chloro-3-nitropyridin-2-amine (0.280 g, 1.12 mmol, 1 eq) was added and the mixture was heated and stirred for 17 h at 65° C. The mixture was filtered, washed with $^i$PrOH (3×3 mL), Et$_2$O (2×3 mL) and dried to give the title compound as a bright yellow powder (0.330 g, 67%); $^1$H-NMR (500 MHz, DMSO-d$_6$): δ 2.51-2.58 (br s, 4H, piperazine N(CH$_2$)$_2$), 3.01-3.10 (m, 4H, piperazine N(CH$_2$)$_2$), 3.82 (s, 2H, NCH$_2$), 6.98 (s, 2H, NH$_2$), 7.78 (s, 1H, thiazole 4-H), 8.16 (s, 1H, pyridine 6-H), 9.03 (s, 1H, thiazole 2-H); LC (Method B)-MS (ESI, m/z): Rt=2.17 min—399/401 [(M+H$^+$), Br isotopic pattern, 100%].

5-((4-(6-Bromo-2-(4-methoxyphenyl)-3H-imidazo[4,5-b]pyridin-7-yl)piperazin-1-yl)methyl)thiazole

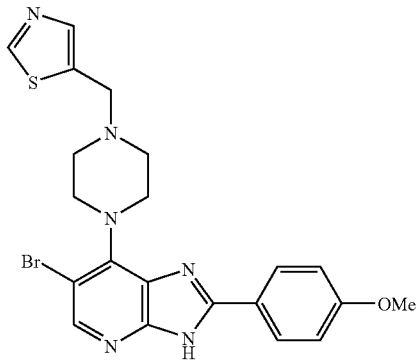

To a mixture of 5-bromo-3-nitro-4-(4-(thiazol-5-ylmethyl)piperazin-1-yl)pyridin-2-amine (0.060 g, 0.15 mmol, 1 eq), EtOH (2.6 mL) and DMF (0.35 mL), p-anisaldehyde (0.022 g, 0.165 mmol, 1.1 eq) was added followed by a freshly prepared aqueous solution of Na$_2$S$_2$O$_4$ (1M; 0.45 mL, 0.45 mmol). The reaction mixture was heated at 85° C. for 24 h, then allowed to cool to room temperature and diluted with DCM and a few drops of aq NH$_3$ until complete dissolution was observed. This solution was deposited on two preparative silica TLC plates and eluted with DCM/MeOH (v/v 94:6). The title compound was obtained after trituration with diethyl ether as a off-white solid (0.02 g, 27%); $^1$H-NMR (500 Mz, DMSO-d$_6$): δ 2.61-2.69 (m, 4H, piperazine N(CH$_2$)$_2$), 3.61-3.67 (m, 4H, piperazine N(CH$_2$)$_2$), 3.84 (s, 3H, OMe), 3.86 (s, 2H, NCH$_2$), 7.10 (d, J=9.0 Hz, 2H, ArH, C$_6$H$_4$), 7.82 (s, 1H, thiazole 4-H), 8.13 (d, J=9.0 Hz, 2H, ArH, C$_6$H$_4$), 8.20 (s, 1H, imidazo[4,5-b]pyridine 5-H), 9.05 (s, 1H, thiazole 2-H), 13.20-13.50 (br s, 1H, imidazo[4,5-b]pyridine N—H); LC (Method B)-MS (ESI, m/z): Rt=3.34 min—485/487 [(M+H$^+$), Br isotopic pattern, 100%]. ESI-HRMS: Found: 485.0760, calculated for C$_{21}$H$_{22}$BrN$_6$OS (M+H)$^+$: 485.0759.

Example 171

4-(4-(6-Bromo-7-(4-(thiazol-5-ylmethyl)piperazin-1-yl)-3H-imidazo[4,5-b]pyridin-2-yl)benzyl)morpholine

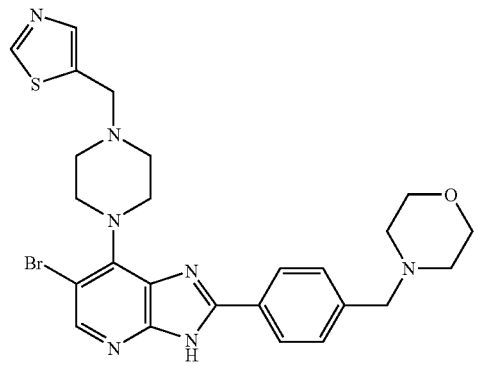

To a mixture of 5-bromo-3-nitro-4-(4-(thiazol-5-ylmethyl)piperazin-1-yl)pyridin-2-amine (0.030 g, 0.076 mmol, 1 eq), EtOH (1.95 mL) and DMF (0.29 mL), 4-(morpholinomethyl)-benzaldehyde (0.017 g, 0.083 mmol, 1.1 eq) was added followed by a freshly prepared aqueous solution of $Na_2S_2O_4$ (1M; 0.23 mL, 0.23 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 94:6). The title compound was obtained as a solid after trituration with diethyl ether (0.022 g, 26%); $^1$H-NMR (500 Mz, DMSO-$d_6$): δ 2.35-2.41 (m, 4H), 2.61-2.67 (m, 4H), 3.54 (s, 2H, $NCH_2$), 3.59 (t, J=4.8 Hz, 4H), 3.63-3.69 (m, 4H), 3.87 (s, 2H, $NCH_2$), 7.48 (d, J=8.0 Hz, 2H, ArH, $C_6H_4$), 7.82 (s, 1H, thiazole H-4), 8.14 (d, J=8.0 Hz, 2H, ArH, $C_6H_4$), 8.24 (s, 1H, imidazo[4,5-b]pyridine 5-H), 9.05 (s, 1H, thiazole H-2), 13.47 (br s, 1H, imidazo[4,5-b]pyridine N—H); LC (Method B)-MS (ESI, m/z): Rt=2.10 min—554/556 [(M+H$^+$), Br isotopic pattern, 100%]. ESI-HRMS: Found: 554.1342, calculated for $C_{25}H_{29}BrN_7OS$ (M+H)$^+$: 554.1338.

Example 172

5-Chloro-4-(4-((2-methylthiazol-4-yl)methyl)piperazin-1-yl)-3-nitropyridin-2-amine

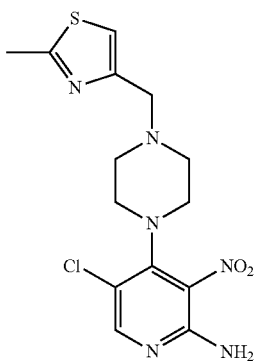

tert-Butyl 4-((2-methylthiazol-4-yl)methyl)piperazine-1-carboxylate (0.380 g, 1.28 mmol, 1.1 eq) was dissolved in DCM (4 mL) and the mixture cooled in a ice-water bath before the dropwise addition of TFA (4 mL). Stirring was continued at this temperature for 1 h. Solvents were removed in vacuo and the resulting crude material was azeotroped with toluene and dried. 2-Methyl-4-(piperazin-1-ylmethyl)thiazole (supposedly 0.250 g, 1.28 mmol, 1.1 eq) was suspended in $^i$PrOH (3.9 mL) and DIPEA (1 mL). To this solution, the 4,5-dichloro-3-nitropyridin-2-amine (0.240 g, 1.16 mmol, 1 eq) was added and the mixture heated and stirred for 17 h at 65° C. The mixture was filtered, washed with $^i$PrOH (3×3 mL), $Et_2O$ (2×3 mL) and dried to give the title compound as a bright yellow powder (0.210 g, 44%); $^1$H-NMR (500 MHz, DMSO-$d_6$): δ 2.52-2.59 (m, 4H, piperazine $N(CH_2)_2$), 2.63 (s, 3H, thiazole Me), 3.06 (m, 4H, piperazine $N(CH_2)_2$), 3.59 (s, 2H, $NCH_2$), 6.94 (s, 2H, $NH_2$), 7.28 (s, 1H, thiazole 5-H), 8.05 (s, 1H, pyridine 6-H); LC (Method B)-MS (ESI, m/z): R=2.06 min—369/371 [(M+H)$^+$, Cl isotopic pattern].

4-(4-(6-Chloro-7-(4-((2-methylthiazol-4-yl)methyl)piperazin-1-yl)-3H-imidazo[4,5-b]pyridin-2-yl)benzyl)morpholine

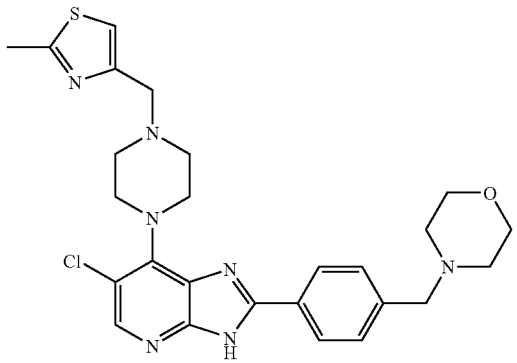

To a mixture of 5-chloro-4-(4-((2-methylthiazol-4-yl)methyl)piperazin-1-yl)-3-nitropyridin-2-amine (0.06 g, 0.19 mmol, 1 eq), EtOH (3.3 mL), and DMF (0.44 mL), 4-(morpholinomethyl)-benzaldehyde (0.043 g, 0.21 mmol, 1.1 eq) was added followed by a freshly prepared aqueous solution of $Na_2S_2O_4$ (1M; 0.57 mL, 0.57 mmol). The reaction mixture was heated at 85° C. for 24 h, allowed to cool to room temperature, and diluted with DCM and a few drops of aqueous $NH_3$ until complete dissolution was observed. This solution was deposited on two preparative silica TLC plates and eluted with DCM/MeOH (v/v; 92:8). The title compound was obtained after trituration with diethyl ether as a yellow solid (0.018 g, 18%); $^1$H-NMR (500 Mz, DMSO-$d_6$): δ 2.35-2.42 (m, 4H), 2.63-2.70 (m, 7H), 3.54 (s, 2H, $NCH_2$), 3.59 (t, J=4.8 Hz, 4H), 3.64 (s, 2H, $NCH_2$), 3.68-3.74 (m, 4H), 7.32 (s, 1H, thiazole 5-H), 7.47 (d, J=8.5 Hz, 2H, ArH, $C_6H_4$), 8.10 (s, 1H, imidazo[4,5-b]pyridine 5-H), 8.13 (d, J=8.0 Hz, 2H, ArH, $C_6H_4$), 13.43 (br s, 1H, imidazo[4,5-b]pyridine N—H); LC (Method B)-MS (ESI, m/z): Rt=2.25 min—524/526 [(M+H)$^+$, Cl isotopic pattern]; ESI-HRMS: Found: 524.1999, calculated for $C_{26}H_{31}ClN_7OS$ (M+H)$^+$: 524.1999;

Example 173

4-((4-(2-(4-((1H-Pyrazol-1-yl)methyl)phenyl)-6-chloro-3H-imidazo[4,5-b]pyridin-7-yl)piperazin-1-yl)methyl)-2-methylthiazole

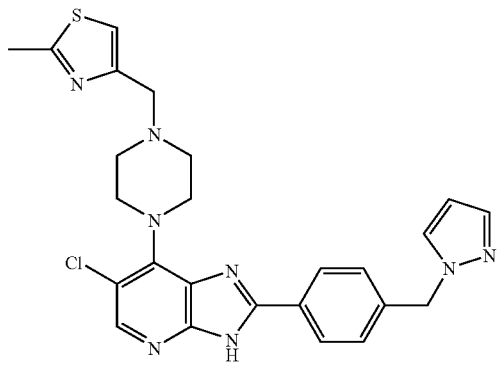

To a mixture of 5-chloro-4-(4-((2-methylthiazol-4-yl)methyl)piperazin-1-yl)-3-nitropyridin-2-amine (0.060 g, 0.19 mmol), EtOH (3.3 mL) and DMF (0.44 mL), 4-(1H-pyrazol-1-ylmethyl)-benzaldehyde (0.039 g, 0.21 mmol) was added followed by a freshly prepared aqueous solution of $Na_2S_2O_4$ (1M; 0.57 mL, 0.57 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 92:8). The title compound was obtained after trituration with diethyl ether as a off-white solid (0.036 g, 37%); $^1$H-NMR (500 Mz, DMSO-$d_6$): δ 2.62-2.69 (m, 7H), 3.63 (s, 2H, $NCH_2$), 3.66-3.74 (m, 4H), 5.42 (s, 2H, $NCH_2$), 6.30 (t, J=2.0 Hz, 1H), 7.31 (s, 1H, thiazole 5-H), 7.34 (d, J=8.0 Hz, 2H, ArH), 7.48-7.51 (m, 1H), 7.86 (m, 1H), 8.08-8.15 (m, 3H, 2ArH and imidazo[4,5-b]pyridine 5-H), 13.46 (br s, 1H, imidazo[4,5-b]pyridine N—H); LC (Method B)-MS (ESI, m/z) 3.16 min—505/507 [(M+H)$^+$, Cl isotopic pattern]. ESI-HRMS: Found: 505.1687, calculated for $C_{25}H_{26}N_8SCl$ (M+H)$^+$: 505.1690.

Example 174 tert-Butyl 4-(4-(6-Chloro-7-(4-((2-methylthiazol-4-yl)methyl)piperazin-1-yl)-3H-imidazo[4,5-b]pyridin-2-yl)benzyl)piperazine-1-carboxylate

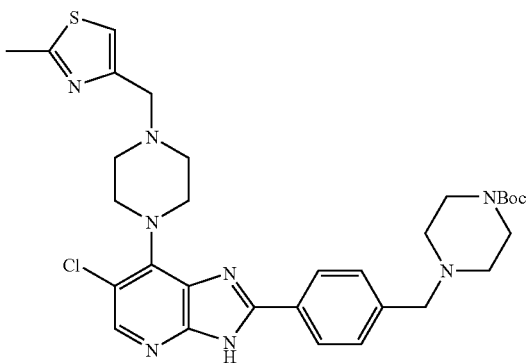

To a mixture of 5-chloro-4-(4-((2-methylthiazol-4-yl)methyl)piperazin-1-yl)-3-nitropyridin-2-amine (0.028 g, 0.076 mmol), EtOH (1.3 mL) and DMF (0.18 mL), tert-butyl-4-(4-formylbenzyl)piperazine-1-carboxylate (0.025 g, 0.083 mmol) was added followed by a freshly prepared aqueous solution of $Na_2S_2O_4$ (1M; 0.23 mL, 0.23 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 92:8) to give the title compound as a solid (0.009 g, 18%); $^1$H-NMR (500 Mz, DMSO-$d_6$): δ 1.39 (s, 9H, C(CH$_3$)$_3$), 2.34 (t, J=5.0 Hz, 4H), 2.62-2.70 (m, 7H), 3.29-3.35 (m, 4H), 3.55 (s, 2H, $NCH_2$), 3.64 (s, 2H, $NCH_2$), 3.67-3.74 (m, 4H), 7.32 (s, 1H, thiazole 5-H), 7.46 (d, J=8.0 Hz, 2H, ArH, $C_6H_4$), 8.10 (s, 1H, imidazo[4,5-b]pyridine 5-H), 8.13 (d, J=8.0 Hz, 2H, ArH, $C_6H_4$), 13.44 (br s, 1H, imidazo[4,5-b]pyridine N—H); LC (Method B)-MS (ESI, m/z) 2.66 min—623/625 [(M+H)$^+$, Cl isotopic pattern]. ESI-HRMS: Found: 623.2680, calculated for $C_{31}H_{40}ClN_8O_2S$ (M+H)$^+$: 623.2683.

Example 175

4-((4-(6-Chloro-2-(4-(piperazin-1-ylmethyl)phenyl)-3H-imidazo[4,5-b]pyridin-7-yl)piperazin-1-yl)methyl)-2-methylthiazole

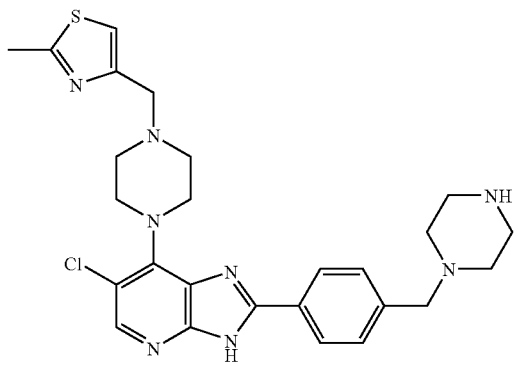

tert-Butyl 4-(4-(6-chloro-7-(4-((2-methylthiazol-4-yl)methyl)piperazin-1-yl)-3H-imidazo[4,5-b]pyridin-2-yl)benzyl)piperazine-1-carboxylate (0.009 g, 0.036 mmol) was suspended in DCM (1.0 mL) and the mixture cooled in an ice bath. TFA (0.3 mL) was added and the resulting solution was allowed to warm up to room temperature and stirred for 2 h. The mixture was passed through an SCX column (2 g), washed with methanol and further eluted with ammonia (35% solution in water, 0.2M). The filtrate was collected and the solvent removed in vacuo to give the title compound as a solid (0.004 g, 21%); $^1$H-NMR (500 Mz, DMSO-$d_6$): δ 2.41-2.49 (m, 4H), 2.62-2.70 (m, 7H), 2.87-2.94 (m, 4H), 3.56 (s, 2H, $NCH_2$), 3.64 (s, 2H, $NCH_2$), 3.67-3.74 (m, 4H), 7.32 (s, 1H, thiazole 5-H), 7.47 (d, J=8.0 Hz, 2H, ArH, $C_6H_4$), 8.11 (s, 1H, imidazo[4,5-b]pyridine 5-H), 8.13 (d, J=8.0 Hz, 2H, ArH, $C_6H_4$); LC (Method B)-MS (ESI, m/z) 2.09 min—523/525 [(M+H)$^+$, Cl isotopic pattern]. ESI-HRMS: Found: 523.2155, calculated for $C_{26}H_{32}ClN_8S$ (M+H)$^+$: 523.2159;

Example 176

5-Chloro-3-nitro-4-(4-phenethylpiperazin-1-yl)pyridin-2-amine

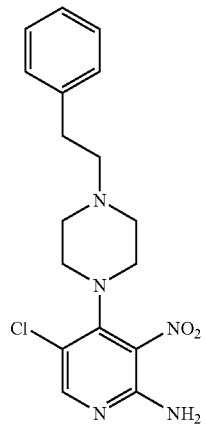

1-Phenethylpiperazine (0.100 g, 0.52 mmol, 1.1 eq) was suspended in $^i$PrOH (1 mL). DIPEA (0.13 mL, 0.79 mmol, 1.5 eq) was added followed by 4,5-dichloro-3-nitropyridin-2-amine (0.099 g, 0.48 mmol, 1 eq). The mixture was heated and stirred at 65° C. overnight. The mixture was cooled to room temperature and filtered. The bright yellow solid was washed with $^i$PrOH (3×2 mL), Et$_2$O (2×2 mL) and dried to give the title compound as a bright yellow solid (0.112 g, 64%); $^1$H-NMR (500 MHz, DMSO-d$_6$): δ 2.53-2.63 (m, 6H), 2.71-2.78 (m, 2H), 3.06 (m, 4H, piperazine N(CH$_2$)$_2$), 6.95 (s, 2H, NH$_2$), 7.15-7.21 (m, 1H), 7.22-7.31 (m, 4H), 8.06 (s, 1H, pyridine 6-H); LC (Method B)-MS (ESI, m/z): Rt=2.31 min—362/364 [(M+H)$^+$, Cl isotopic pattern].

4-(6-Chloro-7-(4-phenethylpiperazin-1-yl)-3H-imidazo[4,5-b]pyridin-2-yl)-N,N-dimethylaniline

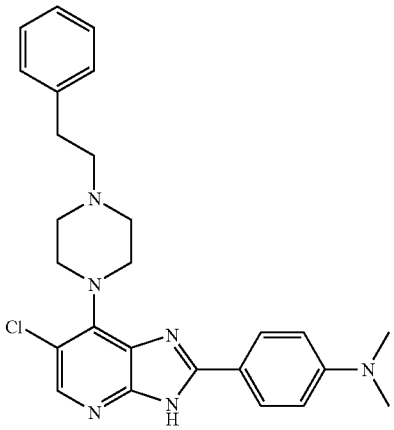

To a mixture of 5-chloro-3-nitro-4-(4-phenethylpiperazin-1-yl)pyridin-2-amine (0.058 g, 0.16 mmol) in EtOH (2.8 mL) and DMF (0.37 mL), 4-(dimethylamino)benzaldehyde (0.026 g, 0.18 mmol, 1.1 eq) was added followed by a freshly prepared aqueous solution of Na$_2$S$_2$O$_4$ (1M; 0.48 mL, 0.48 mmol). The reaction mixture was heated at 85° C. for 24 h, then allowed to cool to room temperature and diluted with DCM and a few drops of aqueous NH$_3$ until complete dissolution was observed. This solution was deposited on two preparative silica TLC plates and eluted with DCM/MeOH (v/v; 99:1) to give the title compound as a solid (0.0012 g, 16%); $^1$H-NMR (500 Mz, DMSO-d$_6$): δ 2.57-2.64 (m, 2H), 2.64-2.70 (m, 4H, piperazine N(CH$_2$)$_2$), 2.77-2.83 (m, 2H), 3.00 (s, 6H, NMe$_2$), 3.65-3.70 (m, 4H piperazine N(CH$_2$)$_2$), 6.82 (d, J=9.0 Hz, 2H, ArH), 7.16-7.22 (m, 1H, ArH, C$_6$H$_5$), 7.25-7.32 (m, 4H, ArH), 7.98-8.04 (m, 3H, imidazo[4,5-b]pyridine 5-H and ArH), 13.09 (br s, 1H, imidazo[4,5-b]pyridine N—H); LC (Method B)-MS (ESI, m/z): Rt=3.59 min— 461/463 [(M+H)$^+$, Cl isotopic pattern]. ESI-HRMS: Found: 461.2214, calculated for C$_{26}$H$_{30}$ClN$_6$ (M+H)$^+$: 461.2220;

Example 177

5-Chloro-3-nitro-4-(4-(thiazol-4-ylmethyl)piperazin-1-yl)pyridin-2-amine

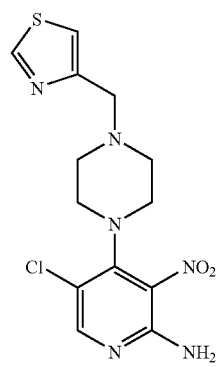

tert-Butyl 4-(thiazol-4-ylmethyl)piperazine-1-carboxylate (0.220 g, 0.79 mmol, 1.1 eq) was dissolved in DCM (2 mL) and the mixture cooled in a ice-water bath before the dropwise addition of TFA (2 mL). Stirring was continued at this temperature for 1 h. The solvents were removed in vacuo and the resulting crude material was azeotroped with toluene and dried. 4-(piperazin-1-ylmethyl)thiazole (supposedly 0.140 g, 0.79 mmol, 1.1 eq) was suspended in $^i$PrOH (0.8 mL) and DIPEA (0.3 mL). To this solution, 4,5-dichloro-3-nitropyridin-2-amine (0.15 g, 0.72 mmol, 1 eq) was added and the mixture was heated and stirred for 17 h at 65° C. The mixture was filtered, washed with $^i$PrOH (3×3 mL), Et$_2$O (2×3 mL) and dried to give the title compound as a bright yellow powder (0.080 g, 27%); $^1$H-NMR (500 MHz, DMSO-d$_6$): δ 2.52-2.60 (m, 4H, piperazine N(CH$_2$)$_2$), 3.07 (m, 4H, piperazine N(CH$_2$)$_2$), 3.72 (s, 2H, NCH$_2$), 6.94 (s, 2H, NH$_2$), 7.54 (s, 1H, thiazole 5-H), 8.05 (s, 1H, pyridine 6-H), 9.04 (s, 1H, thiazole 2-H); LC (Method B)-MS (ESI, m/z): Rt=1.71 min—355/357 [(M+H)$^+$, Cl isotopic pattern].

4-(4-(6-Chloro-7-(4-(thiazol-4-ylmethyl)piperazin-1-yl)-3H-imidazo[4,5-b]pyridin-2-yl)benzyl)morpholine

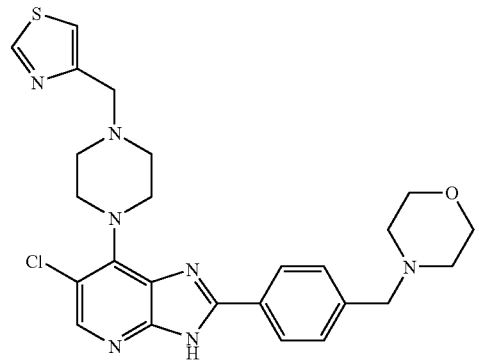

To a mixture of 5-chloro-3-nitro-4-(4-(thiazol-4-ylmethyl) piperazin-1-yl)pyridin-2-amine (0.076 g, 0.21 mmol), EtOH (3.6 mL) and DMF (0.49 mL), 4-(morpholinomethyl)benzaldehyde (0.047 g, 0.23 mmol, 1.1 eq) was added followed by a freshly prepared aqueous solution of $Na_2S_2O_4$ (1M; 0.64 mL, 0.64 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 92:8). The title compound was obtained as a solid after trituration with diethyl ether (0.045 g, 42%); $^1$H-NMR (500 Mz, DMSO-$d_6$): δ 2.38 (m, 4H), 2.68 (m, 4H), 3.53 (s, 2H, $NCH_2$), 3.59 (t, J=4.5 Hz, 4H), 3.71 (m, 4H), 3.76 (s, 2H, $NCH_2$), 7.47 (d, J=8.5 Hz, 2H, ArH, $C_6H_4$), 7.58 (d, J=2.0 Hz, 1H, thiazole 5-H), 8.10 (s, 1H, pyridine 6-H), 8.13 (d, J=8.0 Hz, 2H, ArH, $C_6H_4$), 9.07 (d, J=2.0 Hz, 1H, thiazole 2-H), 13.44 (br s, 1H, imidazo[4,5-b]pyridine N—H); LC (Method B)-MS (ESI, m/z): Rt=1.85 min—510/512 [(M+H)$^+$, Cl isotopic pattern]; ESI-HRMS: Found: 510.1866, calculated for $C_{25}H_{29}ClN_7OS$ (M+H)$^+$: 510.1843.

Example 178 tert-Butyl 4-(4-(6-bromo-7-(4-(thiazol-4-ylmethyl) piperazin-1-yl)-3H-imidazo[4,5-b]pyridin-2-yl)benzyl)piperazine-1-carboxylate

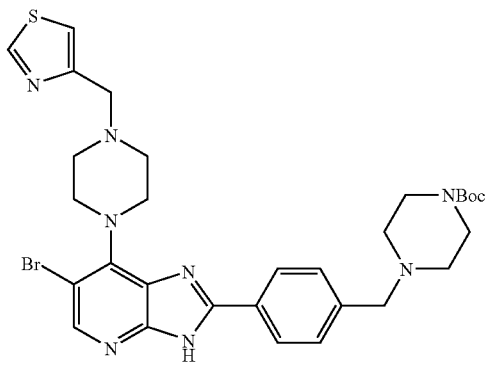

To a mixture of 5-bromo-3-nitro-4-(4-(thiazol-4-ylmethyl) piperazin-1-yl)pyridin-2-amine (0.054 g, 0.13 mmol), EtOH (2.3 mL) and DMF (0.31 mL), tert-butyl-4-(4-formylbenzyl) piperazine-1-carboxylate (0.045 g, 0.15 mmol, 1.1 eq) was added followed by a freshly prepared aqueous solution of $Na_2S_2O_4$ (1M; 0.40 mL, 0.40 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 92:8). The title compound was obtained as a solid after trituration with diethyl ether (0.031 g, 35%); $^1$H-NMR (500 Mz, DMSO-$d_6$): δ 1.39 (s, 9H, $C(CH_3)_3$), 2.34 (t, J=4.8 Hz, 4H), 2.65-2.72 (m, 4H), 3.30-3.36 (m, 4H), 3.55 (s, 2H, $NCH_2$), 3.68 (m, 4H), 3.77 (s, 2H, $NCH_2$), 7.47 (d, J=8.0 Hz, 2H, ArH, $C_6H_4$), 7.58 (d, J=2.0 Hz, 1H, thiazole 5-H), 8.14 (d, J=8.5 Hz, 2H, ArH, $C_6H_4$), 8.23 (s, 1H, imidazo[4,5-b]pyridine 5-H), 9.07 (d, J=2.0 Hz, 1H, thiazole 2-H), 13.47 (br s, 1H, imidazo[4,5-b]pyridine N—H); LC (method B)-MS (ESI, m/z) 2.50 min—653/655 [(M+H)$^+$], Br isotopic pattern]. ESI-HRMS: Found: 653.2023, calculated for $C_{30}H_{38}BrN_8O_2S$ (M+H)$^+$: 653.2022.

Example 179

4-((4-(6-Bromo-2-(4-(piperazin-1-ylmethyl)phenyl)-3H-imidazo[4,5-b]pyridin-7-yl)piperazin-1-yl)methyl)thiazole

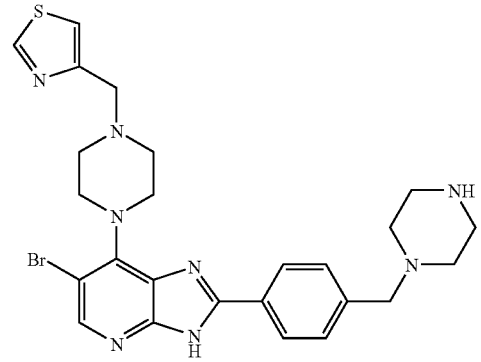

4-((4-(6-Bromo-2-(4-(piperazin-1-ylmethyl)phenyl)-3H-imidazo[4,5-b]pyridin-7-yl)piperazin-1-yl)methyl)thiazole (0.025 g, 0.038 mmol) was suspended in DCM (2 mL) and the mixture cooled in an ice bath. TFA (0.5 mL) was added and the resulting solution was allowed to warm up to room temperature and stirred for 2 h. The mixture was passed through an SCX column (2 g), washed with methanol and further eluted with ammonia (35% solution in water, 0.2M). The filtrate was collected and the solvent removed in vacuo to give the title compound as a yellow solid (0.020 g, 95%); $^1$H-NMR (500 Mz, DMSO-$d_6$): 2.40-2.46 (m, 4H), 2.65-2.72 (m, 4H), 2.88 (t, J=4.5 Hz, 4H), 3.55 (s, 2H, $NCH_2$), 3.64-3.70 (m, 4H), 3.77 (s, 2H, $NCH_2$), 7.46 (d, J=8.5 Hz, 2H, ArH, $C_6H_4$), 7.58 (d, J=2.0 Hz, 1H, thiazole 5-H), 8.14 (d, J=8.5 Hz, 2H, ArH, $C_6H_4$), 8.23 (s, 1H, imidazo[4,5-b]pyridine 5-H), 9.07 (d, J=2.0 Hz, 1H, thiazole 2-H); LC (method B)-MS (ESI, m/z) 1.91 min—553/555 [(M+H)$^+$], Br isotopic pattern]; ESI-HRMS: Found: 553.1500, calculated for $C_{25}H_{30}N_8SBr$ (M+H)$^+$: 553.1498.

Example 180 tert-Butyl 4-(4-(6-bromo-7-(4-((1-methyl-1H-imidazol-5-yl)methyl)piperazin-1-yl)-3H-imidazo[4,5-b] pyridin-2-yl)benzyl)piperazine-1-carboxylate

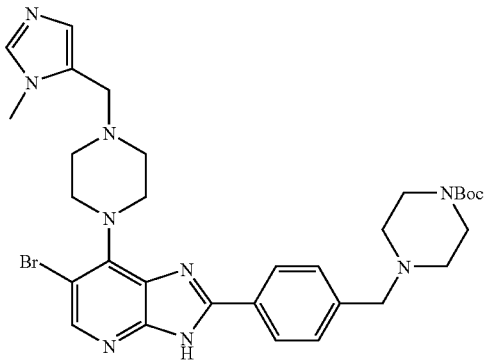

To a mixture of 5-bromo-4-(4-((1-methyl-1H-imidazol-5-yl)methyl)piperazin-1-yl)-3-nitropyridin-2-amine (0.050 g, 0.13 mmol, 1 eq) in EtOH (2.2 mL) and DMF (0.3 mL), tert-butyl-4-(4-formylbenzyl)piperazine-1-carboxylate (0.042 g, 0.14 mmol, 1.1 eq) was added followed by a freshly prepared aqueous solution of $Na_2S_2O_4$ (1M; 0.38 mL, 0.38 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 92:8) to give the title compound as a solid (0.032 g, 39%); $^1$H-NMR (500 Mz, DMSO-$d_6$): 1.39 (s, 9H, C(CH$_3$)$_3$), 2.34 (t, J=5.0 Hz, 4H), 2.56-2.62 (m, 4H), 3.29-3.35 (m, 4H), 3.54 (s, 2H, NCH$_2$), 3.55 (s, 2H, NCH$_2$), 3.61-3.66 (m, 4H), 3.68 (s, 3H, CH$_3$), 6.80 (s, 1H, imidazole 4-H), 7.46 (d, J=8.0 Hz, 2H, ArH, C$_6$H$_4$), 7.57 (s, 1H, imidazole 2-H), 8.14 (d, J=8.5 Hz, 2H, ArH, C$_6$H$_4$), 8.23 (s, 1H, imidazo[4,5-b]pyridine 5-H); LC (Method B)-MS (ESI, m/z) 2.33 min—650/652 [(M+H)$^+$], Br isotopic pattern]. ESI-HRMS: Found: 650.2565, calculated for $C_{31}H_{41}BrN_9O_2$ (M+H)$^+$: 650.2567.

Example 181

6-bromo-7-(4-((1-methyl-1H-imidazol-5-yl)methyl)piperazin-1-yl)-2-(4-(piperazin-1-ylmethyl)phenyl)-3H-imidazo[4,5-b]pyridine

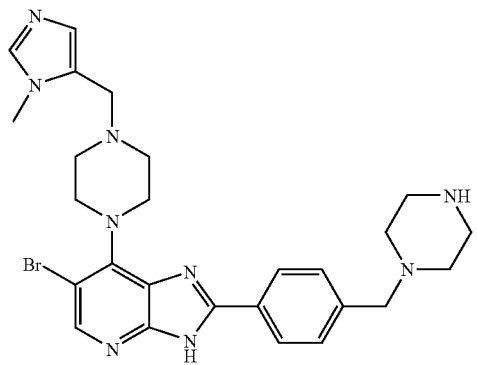

tert-Butyl 4-(4-(6-bromo-7-(4-((1-methyl-1H-imidazol-5-yl)methyl)piperazin-1-yl)-3H-imidazo[4,5-b]pyridin-2-yl)benzyl)piperazine-1-carboxylate (0.028 g, 0.043 mmol) was suspended in DCM (2.3 mL) and the mixture cooled in an ice bath. TFA (0.56 mL) was added and the resulting solution was allowed to warm up to room temperature and stirred for 2 h. The mixture was passed through an SCX column (2 g), the filtrate collected and the solvent removed in vacuo to give the title compound as a off-white solid (0.021 g, 89%); $^1$H-NMR (500 Mz, DMSO-$d_6$): 2.27-2.36 (m, 4H), 2.55-2.62 (m, 4H), 2.72 (t, J=4.8 Hz, 4H), 3.50 (s, 2H, NCH$_2$), 3.54 (s, 2H, NCH$_2$), 3.61-3.66 (m, 4H), 3.68 (s, 3H, imidazole Me), 6.80 (s, 1H, imidazole 4-H), 7.45 (d, J=8.0 Hz, 2H, ArH, C$_6$H$_4$), 7.57 (s, 1H, imidazole 2-H), 8.14 (d, J=8.5 Hz, 2H, ArH, C$_6$H$_4$), 8.23 (s, 1H, imidazo[4,5-b]pyridine 5-H); LC (Method B)-MS (ESI, m/z) 1.66 min—550/552 [(M+H)$^+$], Br isotopic pattern]; ESI-HRMS: Found: 550.2044, calculated for $C_{26}H_{33}BrN_9$ (M+H)$^+$: 550.2042.

Example 182

2-(4-((1H-Pyrazol-1-yl)methyl)phenyl)-6-bromo-7-(4-((1-methyl-1H-imidazol-5-yl)methyl)piperazin-1-yl)-3H-imidazo[4,5-b]pyridine

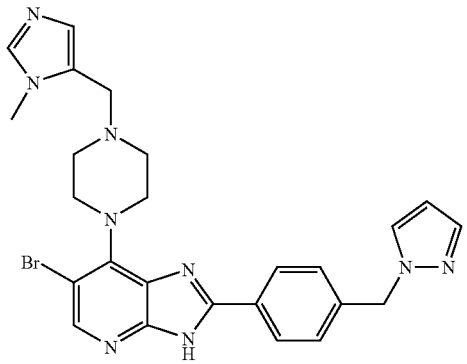

To a mixture of 5-bromo-4-(4-((1-methyl-1H-imidazol-5-yl)methyl)piperazin-1-yl)-3-nitropyridin-2-amine (0.050 g, 0.126 mmol, 1 eq), EtOH (2.2 mL), and DMF (0.3 mL), 4-(1H-pyrazol-1-ylmethyl)-benzaldehyde (0.026 g, 0.14 mmol, 1.1 eq) was added followed by a freshly prepared aqueous solution of $Na_2S_2O_4$ (1M; 0.38 mL, 0.38 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 92:8). The title compound was obtained as a solid after trituration with diethyl ether (0.008 g, 12%); $^1$H-NMR (500 Mz, DMSO-$d_6$): 2.55-2.62 (m, 4H, piperazine N(CH$_2$)$_2$), 3.53 (s, 2H, NCH$_2$), 3.61-3.67 (m, 4H, piperazine N(CH$_2$)$_2$), 3.68 (s, 3H, imidazole Me), 5.41 (s, 2H, NCH$_2$), 6.30 (t, J=2.0 Hz, 1H, pyrazole H-4), 6.81 (s, 1H, imidazole H-4), 7.34 (d, J=8.0 Hz, 2H, ArH, C$_6$H$_4$), 7.49 (d, J=1.5 Hz, 1H, pyrazole H-3), 7.58 (s, 1H, imidazole 2-H), 7.85 (d, J=2.0 Hz, 1H, pyrazole H-3), 8.13 (d, J=8.5 Hz, 2H, ArH, C$_6$H$_4$), 8.23 (s, 1H, imidazo[4,5-b]pyridine 5-H); LC (Method B)-MS (ESI, m/z) 2.71 min—532/534 [(M+H)$^+$], Br isotopic pattern]. ESI-HRMS: Found: 532.1567, calculated for $C_{25}H_{27}BrN_9$ (M+H)$^+$: 532.1573.

Example 183

2-(4-(6-Chloro-2-(4-(2-hydroxyethoxy)phenyl)-3H-imidazo[4,5-b]pyridin-7-yl)piperazin-1-yl)-N-(thiazol-2-yl)acetamide

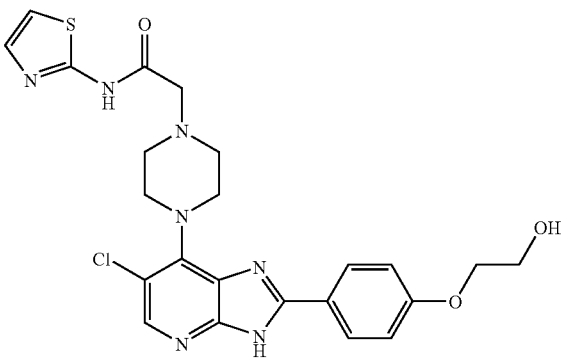

To a mixture of 2-(4-(2-amino-5-chloro-3-nitropyridin-4-yl)piperazin-1-yl)-N-(thiazol-2-yl)acetamide (0.060 g, 0.15 mmol, 1 eq), EtOH (2.6 mL) and DMF (0.35 mL), 4-(2-hydroxyethoxy)benzaldehyde (0.028 g, 0.17 mmol, 1.1 eq) was added followed by a freshly prepared aqueous solution of $Na_2S_2O_4$ (1M; 0.45 mL, 0.45 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 94:6). The title compound was obtained after trituration with diethyl ether as a off-white solid (0.021 g, 27%); $^1$H-NMR (500 Mz, DMSO-$d_6$): 2.74-2.81 (m, 4H, piperazine N($CH_2$)$_2$), 3.40 (s, 2H, $NCH_2$), 3.69-3.79 (m, 6H, piperazine N($CH_2$)$_2$ and $OCH_2$), 4.07 (t, J=5.0 Hz, 2H, $OCH_2$), 4.88 (t, J=5.5 Hz, 1H, OH), 7.10 (d, J=9.0 Hz, 2H, ArH, $C_6H_4$), 7.23 (d, J=3.5 Hz, 1H) and 7.49 (d, J=3.5 Hz, 1H) (thiazole H-4, H-5), 8.08 (s, 1H, imidazo[4,5-b]pyridine 5-H), 8.12 (d, J=9.0 Hz, 2H, ArH, $C_6H_4$); LC (Method B)-MS (ESI, m/z) 3.69 min—514/516 [(M+H)$^+$, Cl isotopic pattern].

Example 184

2-(4-(6-Chloro-2-(4-(4-hydroxypiperidin-1-yl)phenyl)-3H-imidazo[4,5-b]pyridin-7-yl)piperazin-1-yl)-N-(thiazol-2-yl)acetamide

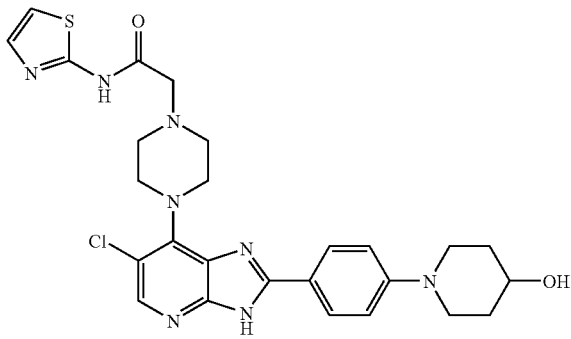

To a mixture of 2-(4-(2-amino-5-chloro-3-nitropyridin-4-yl)piperazin-1-yl)-N-(thiazol-2-yl)acetamide (0.060 g, 0.15 mmol, 1 eq), EtOH (2.6 mL) and DMF (0.35 mL), 4-(4-hydroxypiperidin-1-yl)benzaldehyde (0.034 g, 0.17 mmol, 1.1 eq) was added followed by a freshly prepared aqueous solution of $Na_2S_2O_4$ (1M; 0.45 mL, 0.45 mmol). The reaction mixture was heated at 85° C. for 24 h, then allowed to cool to room temperature and diluted with DCM and a few drops of aq $NH_3$ until complete dissolution was observed. This solution was deposited on two preparative silica TLC plates and eluted with DCM/MeOH (v/v; 94:6). The title compound was obtained after trituration with diethyl ether as a yellow solid (0.011 g, 13%); $^1$H-NMR (500 Mz, DMSO-$d_6$): 1.40-1.50 (m, 2H), 1.77-1.87 (m, 2H), 2.60-2.92 (br s, 4H, piperazine N($CH_2$)$_2$), 2.95-3.05 (m, 2H), 3.63-3.85 (m, 7H), 4.61-4.75 (br s, 1H, CHOH), 7.04 (d, J=9.0 Hz, 2H, ArH, $C_6H_4$), 7.24-7.29 (m, 1H) and 7.50 (d, J=3.5 Hz, 1H) thiazole H-4, H-5), 8.01 (d, J=8.5 Hz, 2H, ArH, $C_6H_4$), 8.07 (s, 1H, imidazo[4, 5-b]pyridine 5-H); LC (Method B)-MS (ESI, m/z) 3.69 min—514/516 [(M+H)$^+$, Cl isotopic pattern].

Example 185

2-(4-(6-Chloro-2-(3-(2-morpholinoethoxy)phenyl)-3H-imidazo[4,5-b]pyridin-7-yl)piperazin-1-yl)-N-(thiazol-2-yl)acetamide

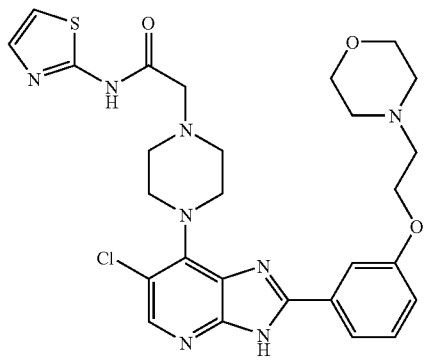

To a mixture of 2-(4-(2-amino-5-chloro-3-nitropyridin-4-yl)piperazin-1-yl)-N-(thiazol-2-yl)acetamide (0.060 g, 0.15 mmol, 1 eq) in EtOH (2.6 mL) and DMF (0.35 mL), 3-(2-morpholin-4-ylethoxy)benzaldehyde (0.039 g, 0.17 mmol, 1.1 eq) was added followed by a freshly prepared aqueous solution of $Na_2S_2O_4$ (1M; 0.45 mL, 0.45 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 94:6). The title compound was obtained after trituration with diethyl ether as a pale yellow solid (0.018 g, 21%); $^1$H-NMR (500 Mz, DMSO-$d_6$): 2.68-2.85 (m, 6H), 3.41 (s, 2H, $NCH_2CO$), 3.55-3.65 (m, 4H), 3.71-3.80 (m, 4H), 4.12-4.25 (s, 2H), 7.06-7.12 (m, 1H), 7.23 (d, J=3.5 Hz, 1H, thiazole H-5 or thiazole H-4), 7.40-7.50 (m, 2H, thiazole H-4 or thiazole H-4 and ArH), 7.75-7.82 (m, 2H, ArH), 8.13 (s, 1H, imidazo[4,5-b]pyridine 5-H), 11.70-12.10 (br s, 1H, NHCO), 13.18 (br s, 1H, imidazo[4,5-b]pyridine N—H); LC (Method B)-MS (ESI, m/z) 2.62 min—583/585 [(M+H)$^+$, Cl isotopic pattern].

Example 186

2-(4-(6-Chloro-2-(4-(2-(dimethylamino)ethoxy)phenyl)-3H-imidazo[4,5-b]pyridin-7-yl)piperazin-1-yl)-N-(thiazol-2-yl)acetamide

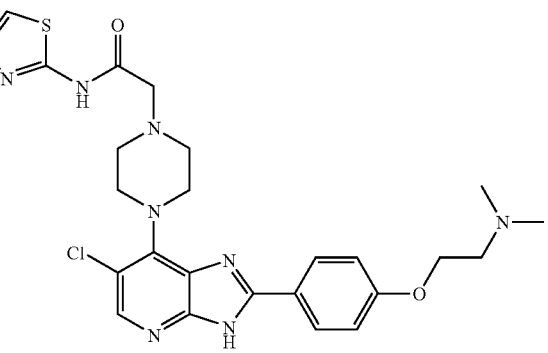

To a mixture of 2-(4-(2-amino-5-chloro-3-nitropyridin-4-yl)piperazin-1-yl)-N-(thiazol-2-yl)acetamide (0.050 g, 0.13 mmol, 1 eq), EtOH (2.2 mL) and DMF (0.29 mL), 4-(2-dimethylaminoethoxy)benzaldehyde (0.027 g, 0.14 mmol, 1.1 eq) was added followed by a freshly prepared aqueous solution of $Na_2S_2O_4$ (1M; 0.38 mL, 0.38 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v; 92:8). The title compound was obtained after trituration with diethyl ether as a pale yellow solid (0.010 g, 15%); $^1$H-NMR (500 Mz, DMSO-$d_6$): 2.24 (s, 6H, $NMe_2$), 2.66 (t, J=5.5 Hz, 2H, $CH_2NMe_2$), 2.75-2.80 (m, 4H, piperazine $N(CH_2)_2$), 3.40 (s, 2H, $NCH_2CO$), 3.70-3.76 (m, 4H), 4.13 (t, J=5.8 Hz, 2H, $CH_2O$), 7.10 (d, J=8.5 Hz, 2H, ArH $C_6H_4$), 7.23 (d, J=4.0 Hz, 1H) and 7.49 (d, J=3.50 Hz, 1H) (thiazole H-4, H-5), 8.04-8.11 (m, 3H, imidazo[4,5-b]pyridine 5-H and ArH $C_6H_4$), 11.88 (br s, 1H, NHCO), 13.24 (br s, 1H, imidazo[4,5-b]pyridine N—H); LC (Method B)-MS (ESI, m/z) 3.63 min—587/589 [(M+H)$^+$, Cl isotopic pattern].

Example 187

2-(4-(6-Chloro-2-(4-(1,1-dioxothiomorpholino)phenyl)-3H-imidazo[4,5-b]pyridin-7-yl)piperazin-1-yl)-N-(thiazol-2-yl)acetamide

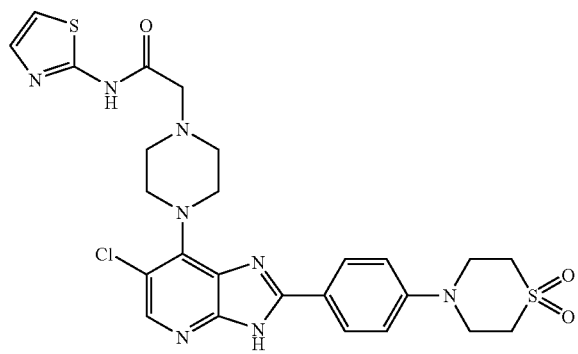

To a mixture of 2-(4-(2-amino-5-chloro-3-nitropyridin-4-yl)piperazin-1-yl)-N-(thiazol-2-yl)acetamide (0.050 g, 0.13 mmol, 1 eq), EtOH (2.2 mL) and DMF (0.29 mL), 4-(1,1-dioxothiomorpholino)benzaldehyde (0.033 g, 0.14 mmol, 1.1 eq) was added followed by a freshly prepared aqueous solution of $Na_2S_2O_4$ (1M; 0.38 mL, 0.38 mmol). The reaction mixture was heated at 85° C. for 24 h, then allowed to cool to room temperature and diluted with DCM and a few drops of aqueous $NH_3$ until complete dissolution was observed. This solution was deposited on two preparative silica TLC plates and eluted with DCM/MeOH (v/v, 92:8) and washed with DCM/MeOH (1 mL, 1/1) to give the title compound as a pale yellow solid (0.010 g, 13%); $^1$H-NMR (500 Mz, DMSO-$d_6$): 2.72-2.83 (m, 4H, piperazine $N(CH_2)_2$), 3.08-3.17 (m, 4H, piperazine $N(CH_2)_2$), 3.40 (s, 2H, $NCH_2CO$), 3.66-3.77 (m, 4H, dithioxomorpholino $SO_2(CH_2)_2$), 3.85-3.95 (m, 4H, dithioxomorpholino $SO_2(CH_2)_2$), 7.17 (d, J=8.5 Hz, 2H, ArH $C_6H_4$), 7.23 (d, J=3.5 Hz, 1H) and 7.49 (d, J=3.5 Hz, 1H) (thiazole H-4, H-5), 8.08 (s, 1H, imidazo[4,5-b]pyridine 5-H), 8.12 (d, J=8.5 Hz, 1H, ArH, $C_6H_4$), 11.88 (br s, 1H, NHCO), 13.31 (br s, 1H, imidazo[4,5-b]pyridine N—H); LC (Method B)-MS (ESI, m/z) 2.47 min—541/543 [(M+H)$^+$, Cl isotopic pattern].

The compounds of the above examples were tested in the assays described below and shown to have Aurora-A and/or Aurora-B and/or Aurora-C inhibitory activity.

Flashplate® Assay for Identification and Evaluation of Aurora-A Inhibitors

On this assay 384-well Basic Flashplate® (SMP400E, PerkinElmer) as solid assay platform was used. The plates were coated overnight at 4° C. with dithiothreitol (DTT) (M1891, SIGMA) at 100 µg/ml in PBS buffer and used after being washed twice with PBS. 5 µl of compound in 2% DMSO was added to each well followed by 15 µl master mix of kinase buffer (50 mM Tris pH 7.5, 10 mM NaCl, 2.5 mM $MgCl_2$, 1 mM myelin basic protein (MBP), 20 µM ATP, and 0.025 µCi/µl $^{33}$P-ATP). Finally, 250 ng per well of Aurora-A enzyme was added. The plate was shaken for approximately 2 min on a flat-bed plate shaker (Wellmix, Denley, UK) and incubated for 2 hours at room temperature. The reaction was stopped by washing the plate twice on a 16-pin wash (ELX50 BioTek Instruments Ltd., Northstar, Bedford, UK) with 10 mM sodium pyrophosphate. The plate was then read on a TopCount-NX™ (PerkinElmer Life Sciences UK Ltd., Hounslow, UK).

Flashplate® Assay for Identification and Evaluation of Aurora-B and Aurora-C Inhibitors For the determination of the inhibitory activity against Aurora-B or Aurora-C, the same conditions were followed in the assay using Aurora-B or Aurora-C enzymes.

Filterplate Assay for Identification and Evaluation of Aurora-A Inhibitors

40 µl master mix of kinase buffer (50 mM Tris pH 7.5, 10 mM NaCl, 2.5 mM $MgCL_2$, 1 mM DTT, 20 µM ATP, 0.025 µCi/µl $^{33}$P-ATP, and 100 µg/ml MBP was added to a 96-well plate followed by addition of 250 ng of Aurora-A enzyme per well. The plate was shaken for approximately 2 min on a flat-bed plate shaker (Wellmix, Denley, UK) and incubated for 2 hours at room temperature. The reaction was stopped by the addition of 30 µl of 2% orthophosphoric acid. The reaction mixture was then transferred and filtered on the 96-well Multi-Screening Filter Plate (MATAH0P00, MILLIPORE), pre-treated with 50 µl per well of 0.5% orthophosphoric acid. The plate was washed twice with 200 µl of 0.5% orthophosphoric acid and vacuum-dried. 25 µl of scintillant (Microscint™20, PerkinElmer) per well was added and the plate was shaken for 10 min. Finally, the plate was re-sealed with TopSealA and the signal from the filter-bound component was read on TopCount-NXT™ (PerkinElmer Life Sciences UK Ltd., Hounslow, UK).

Filterplate Assay for Identification and Evaluation of Aurora-B and Aurora-C Inhibitors For the determination of the inhibitory activity against Aurora-B or Aurora-C, the same conditions were followed in the assay using Aurora-B or Aurora-C enzymes.

Results

By way of example only, the $IC_{50}$ values (nM) against Aurora-A, Aurora-B and Aurora-C for two of the compounds of the examples above were found to be as follows:

| Compound | Aurora-A* | Aurora-B** | Aurora-C** |
|---|---|---|---|
| Example 2 | 70 | 410 | 530 |
| Example 1 | 80 | 110 | 362 |

*Filterplate assay
**Flashplate assay

Cell Viability Assay: Determination of $IC_{50}$ of Aurora Inhibitors in HCT116 Cell Line Using MTT Assay.

The effects of compounds of the Examples on cellular proliferation were determined using the MTT assay according to manufacturer's instructions (Sigma). Briefly, the human colon tumour cells HCT116, were seeded in triplicate into 96-well plates at 2500 cells/well 24 hours before treatment with a range of concentrations of Aurora inhibitors (0-50 μM). After 72 hrs, 15 μl/well of 0.5% 3-(4,5-dimethylthiazol-2-yl)-2,5-diphenyltetrazolium bromide (MTT) was added to the cells for 4 hrs at 37° C., the dye-stained viable cells were extracted by adding 150 μl/well of dimethyl sulphoxide (DMSO). The optical density was measured at 570 nm using the Wallac VICTOR²™ 1420 Multilabel Counter (PerkinElmer). The $IC_{50}$ was calculated using the Prism software.

The Table below summarises the results of testing compounds of the invention in the Flashplate Aurora A enzyme inhibition assay, and in the cell viability assay described above:

$IC_{50}$ results were allocated to one of 3 ranges as follows:
Range A: $IC_{50}$<500 nM,
Range B: $IC_{50}$ from 500 nM to 2000 nM,
Range C: $IC_{50}$>2000 nM to 10000 for the enzyme inhibition assay and from 2000 nM to 50000 nm for the cell viability assay.

Results Table

| Example No | Aurora-A inhibition | HCT116 cell growth inhibition |
|---|---|---|
| 1 | A | A |
| 2 | A | A |
| 3 | A | C |
| 4 | A | B |
| 5 | A | C |
| 6 | B | Not tested |
| 7 | A | B |
| 8 | A | B |
| 9 | A | Not tested |
| 10 | B | C |
| 11 | A | B |
| 12 | A | C |
| 13 | A | B |
| 14 | Not tested | Not tested |
| 15 | A | Not tested |
| 16 | B | Not tested |
| 17 | A | B |
| 18 | C | Not tested |
| 19 | A | B |
| 20 | A | B |
| 21 | A | B |
| 22 | A | C |
| 23 | A | B |
| 24 | A | C |
| 25 | A | C |
| 26 | A | A |
| 27 | A | B |
| 28 | A | B |
| 29 | A | B |
| 30 | A | C |
| 31 | A | B |
| 32 | A | B |
| 33 | Not tested | Not tested |
| 34 | A | C |
| 35 | A | B |
| 36 | A | A |
| 37 | A | C |
| 38 | A | B |
| 39 | A | Not tested |
| 40 | Not tested | Not tested |
| 41 | A | Not tested |
| 42 | A | C |
| 43 | A | Not tested |
| 44 | A | B |
| 45 | B | Not tested |
| 46 | B | C |
| 47 | B | Not tested |
| 48 | A | Not tested |
| 49 | A | B |
| 50 | A | B |
| 51 | Not tested | Not tested |
| 52 | A | B |
| 53 | A | B |
| 54 | A | A |
| 55 | B | Not tested |
| 56 | A | C |
| 57 | A | C |
| 58 | A | B |
| 59 | A | C |
| 60 | A | B |
| 61 | A | B |
| 62 | A | B |
| 63 | A | B |
| 64 | A | B |
| 65 | A | A |
| 66 | A | A |
| 67 | A | A |
| 68 | A | A |
| 69 | A | B |
| 70 | A | B |
| 71 | A | A |
| 72 | A | A |
| 73 | B | B |
| 74 | A | A |
| 75 | A | A |
| 76 | A | A |
| 77 | A | A |
| 78 | A | A |
| 79 | A | A |
| 80 | A | B |
| 81 | A | B |
| 82 | A | A |
| 83 | A | A |
| 84 | A | A |
| 85 | A | A |
| 86 | A | A |
| 87 | A | B |
| 88 | A | Not tested |
| 89 | A | A |
| 90 | A | B |
| 91 | A | Not tested |
| 92 | A | B |
| 94 | A | C |
| 95 | A | B |
| 96 | A | B |
| 97 | A | C |
| 98 | C | C |
| 99 | C | C |
| 100 | C | C |
| 101 | A | B |
| 102 | A | A |
| 103 | A | Not tested |
| 104 | A | A |
| 105 | A | B |
| 106 | A | A |
| 107 | A | B |

Results Table

| Example No | Aurora-A inhibition | HCT116 cell growth inhibition |
| --- | --- | --- |
| 108 | A | B |
| 109 | A | B |
| 110 | A | B |
| 111 | A | A |
| 112 | A | B |
| 113 | A | A |
| 114 | A | A |
| 115 | A | B |
| 116 | A | B |
| 117 | A | B |
| 118 | A | A |
| 119 | A | A |
| 120 | A | C |
| 121 | A | A |
| 122 | A | A |
| 123 | A | B |
| 124 | A | B |
| 125 | A | A |
| 126 | A | Not tested |
| 127 | A | B |
| 128 | A | A |
| 129 | A | A |
| 130 | A | B |
| 131 | A | A |
| 132 | A | C |
| 133 | A | B |
| 134 | A | A |
| 135 | A | B |
| 136 | B | C |
| 137 | A | B |
| 138 | A | B |
| 139 | A | B |
| 140 | A | A |
| 141 | A | B |
| 142 | A | A |
| 143 | A | A |
| 144 | A | A |
| 145 | A | A |
| 146 | A | Not tested |
| 147 | A | C |
| 148 | A | B |
| 149 | A | A |
| 150 | A | A |
| 151 | A | Not tested |
| 152 | A | B |
| 153 | A | Not tested |
| 154 | A | A |
| 155 | A | C |
| 156 | A | A |
| 157 | A | Not tested |
| 158 | A | Not tested |
| 159 | A | B |
| 160 | A | A |
| 161 | A | C |
| 162 | A | A |
| 163 | A | A |
| 163 | A | A |
| 164 | A | A |
| 165 | A | B |
| 166 | A | B |
| 167 | A | B |
| 168 | A | C |
| 169 | A | B |
| 170 | A | B |
| 171 | A | B |
| 172 | A | B |
| 173 | A | A |
| 174 | Not tested | Not tested |
| 175 | A | A |
| 176 | B | C |
| 177 | A | B |
| 178 | Not tested | Not tested |
| 179 | A | B |
| 180 | Not tested | Not tested |
| 181 | A | C |
| 182 | A | B |
| 183 | A | B |
| 184 | A | B |
| 185 | A | A |
| 186 | A | A |
| 187 | A | B |

The compounds of Examples 65, 75, 77, 106, 122 and 162 were tested in the filterplate assay above. All and had $IC_{50}$s in the range A in respect of Aurora-C. Examples 75, 77 and 122 had $IC_{50}$s in the range A in respect of Aurora-B and Examples 65, 106 and 162 had $IC_{50}$s in the range B in respect of Aurora-B.

The invention claimed is:

1. A compound of formula (I), or a salt or N-oxide thereof:

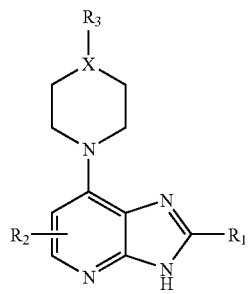

(I)

wherein
X is —N—, —CH$_2$—N—, —CH$_2$—CH—, or —CH—;
R$_1$ is a radical of formula (IA)

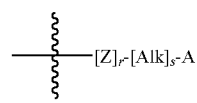

(IA)

wherein
Z is —CH$_2$—, —NH—, —O—, —S(O)—, —S—, —S(O)$_2$ or a divalent monocyclic carbocyclic or heterocyclic radical having 3-7 ring atoms;
Alk is an optionally substituted divalent C$_1$-C$_6$ alkylene radical;
A is hydrogen or an optionally substituted monocyclic carbocyclic or heterocyclic ring having 5-7 ring atoms;
r and s are independently 0 or 1, provided that when A is hydrogen then at least one of r and s is 1;
R$_2$ is halogen, —CN, —CF$_3$, —OCH$_3$, or cyclopropyl; and
R$_3$ is a radical of formula (IB)

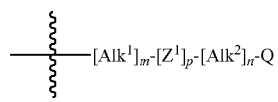

(IB)

wherein

Q is optionally substituted phenyl, pyridyl, pyrimidinyl, triazinyl, thienyl, furanyl, thiazolyl, oxazolyl, isoxazolyl, thiadiazolyl, or oxadiazolyl;

$Z^1$ is —S—, —S(O)—, —S(O)$_2$—, —O—, —SO$_2$NH—, —NHSO$_2$—, NHC(=O)NH, —NH(C=S)NH—, or —N(R$_4$)— wherein R$_4$ is hydrogen, C$_1$-C$_3$ alkyl, cycloalkyl, or benzyl; and Alk$^1$ and Alk$^2$ are, independently, optionally substituted divalent C$_1$-C$_3$ alkylene radicals; and m, n and p are independently 0 or 1.

2. A compound as claimed in claim 1 wherein, in R$_3$, Alk$^1$ and Alk$^2$ are independently selected from optionally substituted —CH$_2$—, —CH$_2$CH$_2$— and —CH$_2$CH$_2$CH$_2$—.

3. A compound as claimed in claim 1, in R$_3$, Z$^1$ is —NH— or —N(CH$_3$)— and an adjacent carbon atom of Alk$^1$ or Alk$^2$ is substituted by oxo, whereby R$_3$ includes an amido or reverse amido link.

4. A compound as claimed in claim 1 wherein X is nitrogen.

5. A compound as claimed in claim 1 wherein radical R$_3$ has formula (IB):

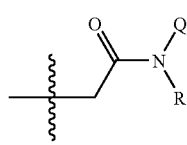

(IB)

wherein Q is as defined in claim 1 and R is hydrogen or methyl.

6. A compound as claimed in claim 1 wherein radical R$_3$ has formula (IC):

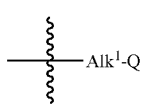

(IC)

wherein Alk$^1$ and Q are as defined in claim 1.

7. A compound as claimed in claim 6 wherein Alk$^1$ is —CH(R)—, —CH(R)CH(R)— or —CH(R)CH(R)CH(R)— wherein each R is independently hydrogen or methyl.

8. A compound as claimed in claim 6 wherein Alk$^1$ is —CH$_2$—, —CH$_2$CH$_2$— or —CH(CH$_3$)—.

9. A compound as claimed in claim 1 wherein Q is selected from optionally substituted phenyl, thiazolyl, isothiazolyl, oxazolyl, isoxazolyl, and pyridyl.

10. A compound as claimed in claim 5 wherein Q is thiazol-2-yl, 3-methylisoxazol-5-yl, 4-methylthiazol-2-yl, phenyl or 3-chlorophenyl.

11. A compound as claimed in claim 7 wherein Q is phenyl, 4-chlorophenyl, 5-methyl-isoxazol-3-yl, pyrid-3-yl or pyrid-4-yl, pyrimidin-5-yl or 2-methylthiazol-4-yl.

12. A compound as claimed in claim 1 wherein, in R$_1$, Z is selected from

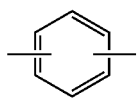 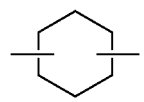 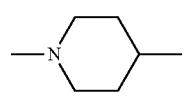

-continued

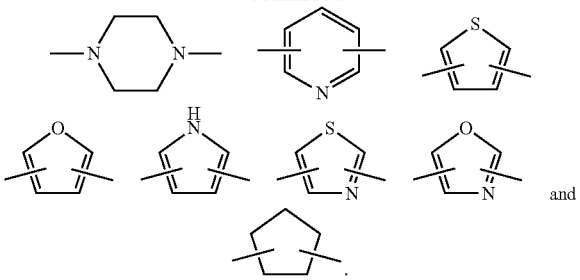 and

13. A compound as claimed in claim 1 wherein, in R$_1$, Alk is optionally substituted —CH$_2$—, —CH$_2$CH$_2$— or —CH$_2$CH$_2$CH$_2$—.

14. A compound as claimed in claim 13 wherein Alk is substituted by a primary, secondary or cyclic amino group.

15. A compound as claimed in claim 14 wherein, in R$_1$, r is 0 or 1, s is 1 and A is hydrogen.

16. A compound as claimed in claim 15 wherein Alk is substituted on a terminal carbon by a primary, secondary or cyclic amino group.

17. A compound as claimed in claim 15 wherein Alk is substituted by —NR$_5$R$_6$ wherein R$_5$ and R$_6$ are independently hydrogen or C$_1$-C$_3$ alkyl, or R$_5$ and R$_6$ taken together with the nitrogen to which they are attached form a 3-7 membered ring.

18. A compound as claimed in claim 17 wherein R$_5$ and R$_6$ taken together with the nitrogen to which they are attached form a piperidine, piperazine, N-methylpiperazine, or morpholine ring.

19. A compound as claimed in claim 1 wherein R$_1$ is optionally substituted phenyl, or optionally substituted heteroaryl having 5 or 6 ring atoms.

20. A compound as claimed in claim 19 wherein the phenyl or heteroaryl ring A is substituted by a group —(CH$_2$)$_v$NR$_5$R$_6$ wherein v is 0, 1, 2, 3 or 4, and R$_5$ and R$_6$ are independently hydrogen or C$_1$-C$_3$ alkyl, or R$_5$ and R$_6$ taken together with the nitrogen to which they are attached form an optionally substituted 3-7 membered ring.

21. A compound as claimed in claim 19 wherein the phenyl or heteroaryl ring A is substituted by a group —O(CH$_2$)$_v$NR$_5$R$_6$ wherein v is 0, 1, 2, 3 or 4, and R$_5$ and R$_6$ are independently hydrogen or C$_1$-C$_3$ alkyl, or R$_5$ and R$_6$ taken together with the nitrogen to which they are attached form an optionally substituted 3-7 membered ring.

22. A compound as claimed in claim 20 wherein R$_5$ and R$_6$ taken together with the nitrogen to which they are attached form an optionally substituted piperidine, piperazine, morpholine or pyrazolyl ring.

23. A compound as claimed in claim 1 wherein R$_2$ is attached to the non-bridging carbon atom adjacent the group:

24. A compound as claimed in claim 1 wherein R$_2$ is —Cl, or —Br.

25. A compound as claimed in claim 1 having formula (ID):

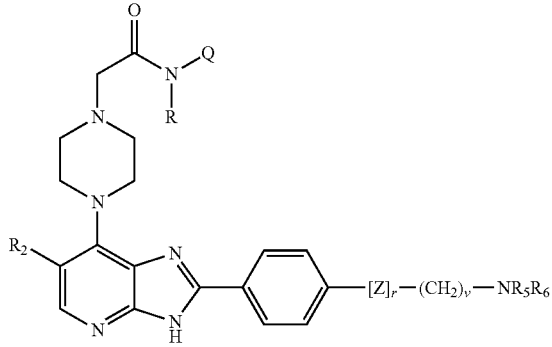

(ID)

wherein R is hydrogen or methyl; $R_2$ is chloro or bromo; Q is thiazol-2-yl, 3-methylisoxazol-5-yl, 4-methylthiazol-2-yl, phenyl or 3-chlorophenyl; Z is —O—; r is 0 or 1; v is 1, 2, or 3; and $R_5$ and $R_6$ are independently hydrogen, methyl or ethyl, or $R_5$ and $R_6$ taken together with the nitrogen to which they are attached form a piperidinyl, morpholinyl, pyrazolyl or piperazinyl ring, the latter being optionally substituted on the second nitrogen.

26. A compound as claimed I claim 1 having formula (IE):

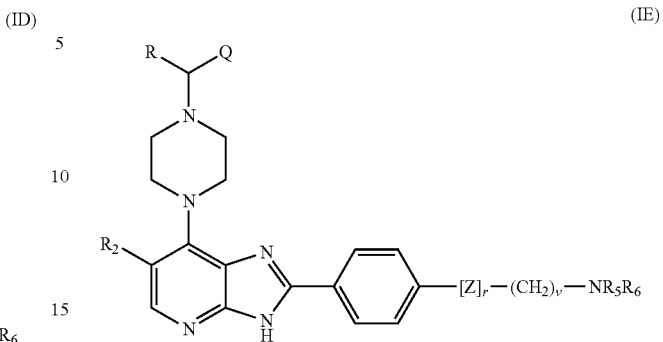

(IE)

wherein R is hydrogen or methyl; $R_2$ is chloro or bromo; r is 0 or 1; v is 1, 2, or 3; and $R_5$ and $R_6$ are independently hydrogen, methyl or ethyl, or $R_5$ and $R_6$ taken together with the nitrogen to which they are attached form a piperidinyl, morpholinyl, pyrazolyl or piperazinyl ring, the latter being optionally substituted on the second nitrogen; and Q is phenyl, 4-chlorophenyl, 5-methyl-isoxazol-3-yl, pyrid-3-yl or pyrid-4-yl, pyrimidin-5-yl or 2-methylthiazol-4-yl.

27. A pharmaceutical composition comprising a compound as claimed in claim 1, together with a pharmaceutically acceptable carrier.

\* \* \* \* \*